US010524696B2

(12) United States Patent
Tzvieli et al.

(10) Patent No.: US 10,524,696 B2
(45) Date of Patent: Jan. 7, 2020

(54) VIRTUAL COACHING BASED ON RESPIRATION SIGNALS

(71) Applicant: Facense Ltd., Kiryat Tivon (IL)

(72) Inventors: Arie Tzvieli, Berkeley, CA (US); Gil Thieberger, Kiryat Tivon (IL); Ari M Frank, Haifa (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 16/156,586

(22) Filed: Oct. 10, 2018

(65) Prior Publication Data

US 2019/0038180 A1     Feb. 7, 2019

Related U.S. Application Data

(63) Continuation-in-part of application No. 15/722,434, filed on Oct. 2, 2017, and a continuation-in-part of (Continued)

(51) Int. Cl.
  *H04N 5/33*   (2006.01)
  *A61B 5/08*   (2006.01)
  (Continued)

(52) U.S. Cl.
  CPC ............ *A61B 5/0816* (2013.01); *A61B 3/113* (2013.01); *A61B 5/015* (2013.01);
  (Continued)

(58) Field of Classification Search
  CPC ..... A61B 5/015; A61B 5/0077; A61B 5/6803; A61B 5/0075; A61B 5/6814; A61B 5/7282; G01J 5/0265; G01J 5/12
  See application file for complete search history.

(56) References Cited

U.S. PATENT DOCUMENTS

| 5,664,578 A | 9/1997 | Boczan |
| 6,121,953 A | 9/2000 | Walker |

(Continued)

FOREIGN PATENT DOCUMENTS

| CN | 104771171 A | 7/2015 |
| WO | WO 2012/117376 | 9/2012 |

(Continued)

OTHER PUBLICATIONS

Al-Khalidi, F. Q., Saatchi, R., Burke, D., Elphick, H., & Tan, S. (2011). Respiration rate monitoring methods: A review. Pediatric pulmonology, 46(6), 523-529.

(Continued)

*Primary Examiner* — David P Porta
*Assistant Examiner* — Fani Boosalis
(74) *Attorney, Agent, or Firm* — Active Knowledge Ltd.

(57) ABSTRACT

Disclosed herein are embodiments of an athletic coaching system that includes at least one inward-facing head-mounted thermal camera (CAM) and a computer. Each CAM from among the at least one CAM is configured to take thermal measurements of a region below the nostrils (denoted $TH_{RBN}$) of a user. $TH_{RBN}$ are indicative of an exhale stream of the user (e.g., an exhale stream from a nostril and/or from the mouth). The computer is configured to: receive measurements of movements ($M_{move}$) involving the user; generate, based on $TH_{RBN}$ and $M_{move}$, a coaching indication; and present, via a user interface, the coaching indication to the user. In one example, the coaching indication is indicative of a change the user should make to one or more of the following: cadence of movements, stride length, breathing rate, breathing type (mouth or nasal), and duration of exhales.

20 Claims, 24 Drawing Sheets

Related U.S. Application Data application No. 15/182,592, filed on Jun. 14, 2016, now Pat. No. 10,165,949, said application No. 15/722,434 is a continuation-in-part of application No. 15/231,276, filed on Aug. 8, 2016, said application No. 15/722,434 is a continuation-in-part of application No. 15/284,528, filed on Oct. 3, 2016, now Pat. No. 10,113,913, application No. 16/156,586, which is a continuation-in-part of application No. 15/635,178, filed on Jun. 27, 2017, now Pat. No. 10,136,856, and a continuation-in-part of application No. 15/231,276, filed on Aug. 8, 2016, application No. 16/156,586, which is a continuation-in-part of application No. 15/832,815, filed on Dec. 6, 2017, now Pat. No. 10,136,852, and a continuation-in-part of application No. 15/182,592, filed on Jun. 14, 2016, now Pat. No. 10,165,949, and a continuation-in-part of application No. 15/231,276, filed on Aug. 8, 2016, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017, and a continuation-in-part of application No. 15/182,566, filed on Jun. 14, 2016, now Pat. No. 9,867,546, application No. 16/156,586, which is a continuation-in-part of application No. 15/859,772, filed on Jan. 2, 2018, now Pat. No. 10,159,411, which is a continuation-in-part of application No. 15/182,592, filed on Jun. 14, 2016, now Pat. No. 10,165,949, and a continuation-in-part of application No. 15/231,276, filed on Aug. 8, 2016, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017.

(60) Provisional application No. 62/408,677, filed on Oct. 14, 2016, provisional application No. 62/456,105, filed on Feb. 7, 2017, provisional application No. 62/480,496, filed on Apr. 2, 2017, provisional application No. 62/175,319, filed on Jun. 14, 2015, provisional application No. 62/202,808, filed on Aug. 8, 2015, provisional application No. 62/236,868, filed on Oct. 3, 2015, provisional application No. 62/354,833, filed on Jun. 27, 2016, provisional application No. 62/372,063, filed on Aug. 8, 2016, provisional application No. 62/652,348, filed on Apr. 4, 2018, provisional application No. 62/667,453, filed on May 5, 2018, provisional application No. 62/566,572, filed on Oct. 2, 2017.

(51) Int. Cl.
*A61B 5/01* (2006.01)
*G02B 27/01* (2006.01)
*A61B 5/00* (2006.01)
*A61B 5/024* (2006.01)
*A61B 3/113* (2006.01)
*A61B 5/087* (2006.01)
*A61B 5/11* (2006.01)
*A61B 5/16* (2006.01)
*G16H 50/20* (2018.01)
*G02B 7/00* (2006.01)
*G02B 13/14* (2006.01)
*G02B 27/00* (2006.01)
*A61B 5/0205* (2006.01)
*A63B 71/06* (2006.01)
*A63B 23/18* (2006.01)
*A63B 23/00* (2006.01)

(52) U.S. Cl.
CPC ........ *A61B 5/02438* (2013.01); *A61B 5/0873* (2013.01); *A61B 5/112* (2013.01); *A61B 5/163* (2017.08); *A61B 5/165* (2013.01); *A61B 5/411* (2013.01); *A61B 5/6803* (2013.01); *A61B 5/6821* (2013.01); *A61B 5/7267* (2013.01); *A61B 5/7275* (2013.01); *A61B 5/742* (2013.01); *G02B 7/002* (2013.01); *G02B 13/14* (2013.01); *G02B 27/0093* (2013.01); *G02B 27/0172* (2013.01); *G16H 50/20* (2018.01); *H04N 5/33* (2013.01); *A61B 5/0002* (2013.01); *A61B 5/0205* (2013.01); *A61B 5/02405* (2013.01); *A61B 5/02416* (2013.01); *A61B 5/08* (2013.01); *A61B 5/1118* (2013.01); *A61B 5/1123* (2013.01); *A61B 5/168* (2013.01); *A61B 5/486* (2013.01); *A61B 2503/08* (2013.01); *A61B 2503/10* (2013.01); *A63B 23/00* (2013.01); *A63B 23/18* (2013.01); *A63B 71/0619* (2013.01); *A63B 71/0686* (2013.01); *G02B 2027/0138* (2013.01); *G02B 2027/0178* (2013.01)

(56) References Cited

U.S. PATENT DOCUMENTS

| | | | |
|---|---|---|---|
| 6,996,256 | B2 | 2/2006 | Pavlidis |
| 7,027,621 | B1 | 4/2006 | Prokoski |
| 7,543,934 | B2 | 6/2009 | Howell et al. |
| 7,602,301 | B1 | 10/2009 | Stirling et al. |
| 8,033,959 | B2 | 10/2011 | Oleson et al. |
| 8,149,273 | B2 | 4/2012 | Liu et al. |
| 8,172,459 | B2 * | 5/2012 | Abreu .................. A61B 5/0002 374/208 |
| 8,200,323 | B2 | 6/2012 | Dibenedetto et al. |
| 8,289,443 | B2 | 10/2012 | MacKenzie |
| 8,334,872 | B2 | 12/2012 | Epps et al. |
| 8,485,982 | B2 | 7/2013 | Gavish et al. |
| 8,573,866 | B2 | 11/2013 | Bond et al. |
| 8,786,698 | B2 | 7/2014 | Chen et al. |
| 9,020,185 | B2 | 4/2015 | Mestha et al. |
| 9,211,069 | B2 | 12/2015 | Larsen et al. |
| 2005/0083248 | A1 | 4/2005 | Biocca et al. |
| 2009/0221888 | A1 | 9/2009 | Wijesiriwardana |
| 2010/0240945 | A1 | 9/2010 | Bikko |
| 2010/0280334 | A1 | 11/2010 | Carlson et al. |
| 2011/0130643 | A1 | 6/2011 | Derchak et al. |
| 2012/0062719 | A1 | 3/2012 | Debevec et al. |
| 2012/0197093 | A1 | 8/2012 | LeBoeuf et al. |
| 2014/0155773 | A1 | 6/2014 | Stamatopoulos et al. |
| 2014/0347265 | A1 | 11/2014 | Aimone et al. |
| 2015/0087924 | A1 | 3/2015 | Li et al. |
| 2015/0126872 | A1 * | 5/2015 | Dubielczyk ............. G06F 19/00 600/473 |
| 2015/0310263 | A1 | 10/2015 | Zhang et al. |
| 2016/0170996 | A1 | 6/2016 | Frank et al. |

FOREIGN PATENT DOCUMENTS

| | | |
|---|---|---|
| WO | WO 2013/093666 | 6/2013 |
| WO | WO 2016/074042 | 5/2016 |

OTHER PUBLICATIONS

Altini, M., Penders, J. and Amft, O., 2016. Estimating oxygen uptake during nonsteady-state activities and transitions using wear-

(56) References Cited

OTHER PUBLICATIONS able sensors. IEEE journal of biomedical and health informatics, 20(2), pp. 469-475.

Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.

Cardone, D., Pinti, P., & Merla, A. (2015). Thermal infrared imaging-based computational psychophysiology for psychometrics. Computational and mathematical methods in medicine, 2015.

Carey, Daniel G., et al. "Respiratory rate is a valid arid reliable marker for the anaerobic threshold: implications for measuring change in fitness." Journal of sports science & medicine 4.4 (2005): 482.

Carine Collé, Re-Experience Big-Data, 3 months group project with Sanya Rai Gupta and Florian Puech, UK, London, RCA, IDE, 2014, Amoeba.

Charlot, Keyne, et al. "Improvement of energy expenditure prediction from heart rate during running." Physiological measurement 35.2 (2014): 253.

Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.

Fei, J., & Pavlidis, I. (2010). Thermistor at a distance: unobtrusive measurement of breathing. IEEE Transactions on Biomedical Engineering, 57(4), 988-998.

Fernández-Cuevas, I., Marins, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.

Firstbeat Technologies Ltd. An Energy Expenditure Estimation Method Based on Heart Rate Measurement (2012). https://www.firstbeat.com/en/energy-expenditure-estimation-firstbeat-white-paper/.

VO2MAX, I. O. A. F. (2014). Automated Fitness Level (VO2max) Estimation with Heart Rate and Speed Data.

Izhar, L. I., & Petrou, M. (2012). Thermal imaging in medicine. In Advances in Imaging and Electron Physics (vol. 171, pp. 41-114). Elsevier.

Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE vol. (vol. 7486, pp. 74860I-1).

Ioannou, S., Gallese, V., & Merla, A. (2014). Thermal infrared imaging in psychophysiology: potentialities and limits. Psychophysiology, 51(10), 951-963.

Johnson, M. L., Price, P. A., & Jovanov, E. (Aug. 2007). A new method for the quantification of breathing. In Engineering in Medicine and Biology Society, 2007. EMBS 2007. 29th Annual International Conference of the IEEE (pp. 4568-4571). IEEE.

Jovanov, E., Raskovic, D., & Hormigo, R. (2001). Thermistor-based breathing sensor for circadian rhythm evaluation. Biomedical sciences instrumentation, 37, 493-498.

Lewis, G. F., Gatto, R. G., & Porges, S. W. (2011). A novel method for extracting respiration rate and relative tidal volume from infrared thermography. Psychophysiology, 48(7), 877-887.

Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.

Murthy, R., & Pavlidis, I. (2006). Noncontact measurement of breathing function. IEEE Engineering in Medicine and Biology Magazine, 25(3), 57-67.

Murthy, R., Pavlidis, I., & Tsiamyrtzis, P. (Sep. 2004). Touchless monitoring of breathing function. In Engineering in Medicine and Biology Society, 2004. IEMBS'04. 26th Annual International Conference of the IEEE (vol. 1, pp. 1196-1199). IEEE.

Nhan, B. R., & Chau, T. (2010). Classifying affective states using thermal infrared imaging of the human face. IEEE Transactions on Biomedical Engineering, 57(4), 979-987.

Pavlidis, I., Dowdall, J., Sun, N., Puri, C., Fei, J., & Garbey, M. (2007). Interacting with human physiology. Computer Vision and Image Understanding, 108(1), 150-170.

Shastri, D., Papadakis, M., Tsiamyrtzis, P., Bass, B., & Pavlidis, I. (2012). Perinasal imaging of physiological stress and its affective potential. IEEE Transactions on Affective Computing, 3(3), 366-378.

Smolander, Juhani, et al. "A new heart rate variability-based method for the estimation of oxygen consumption without individual laboratory calibration: application example on postal workers." Applied ergonomics 39.3 (2008): 325-331.

Yang, M., Liu, Q., Turner, T., & Wu, Y. (Jan. 2008). Vital sign estimation from passive thermal video. In Computer Vision and Pattern Recognition, 2008. CVPR 2008. IEEE Conference on (pp. 1-8). IEEE.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE RAS & EMBS International Conference on (pp. 276-280). IEEE.

\* cited by examiner

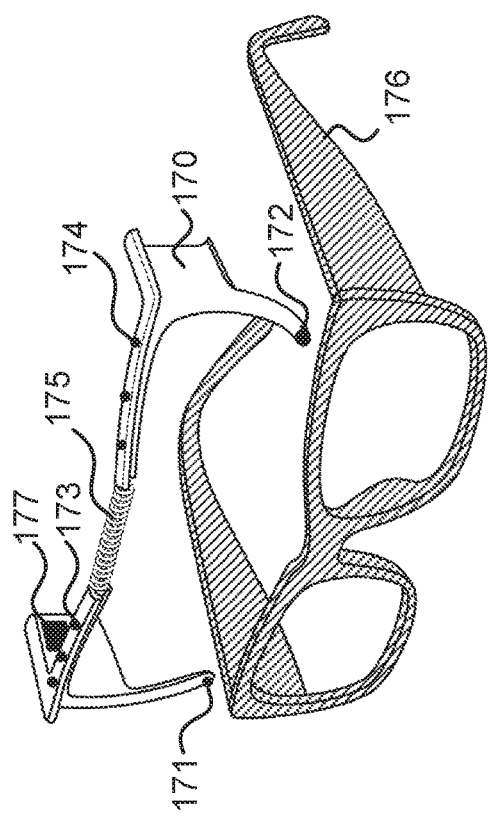
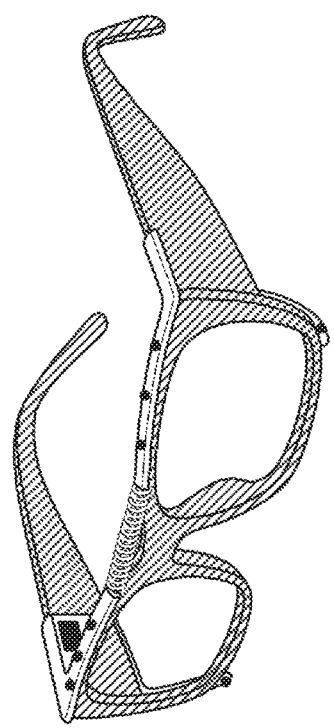
FIG. 16a  FIG. 16b
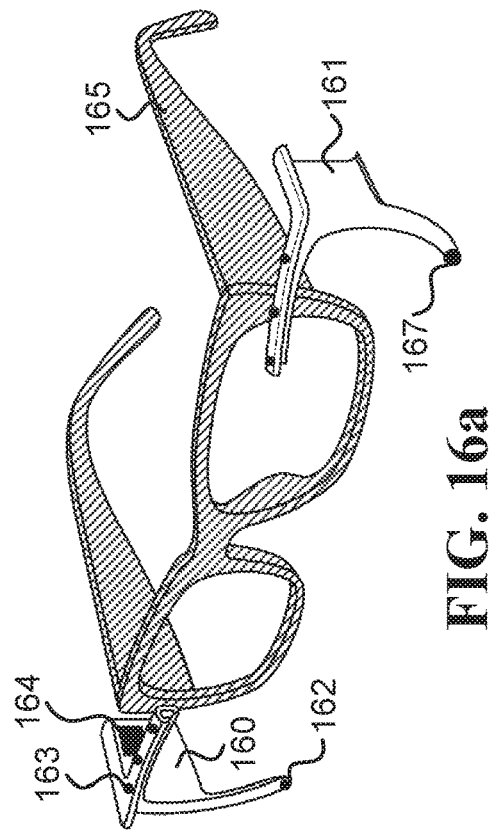
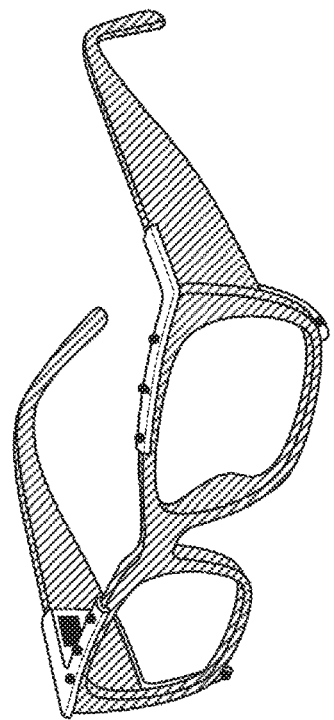
FIG. 17a  FIG. 17b

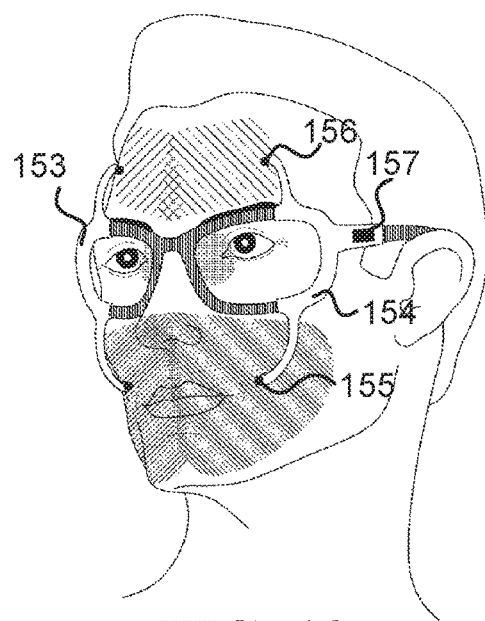
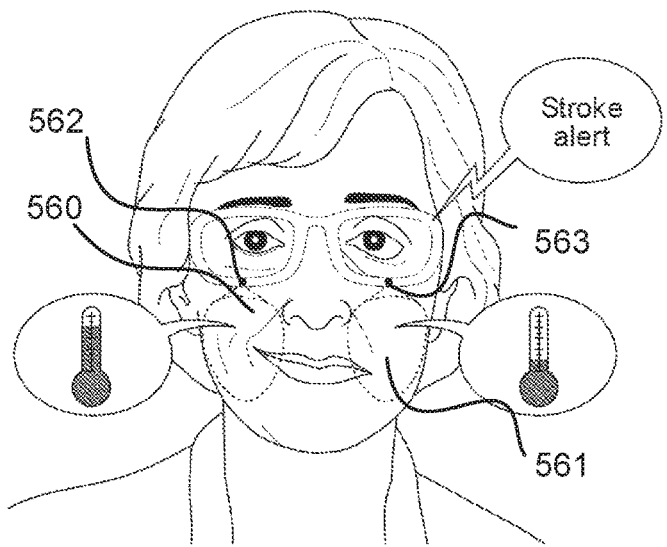
FIG. 18    FIG. 19
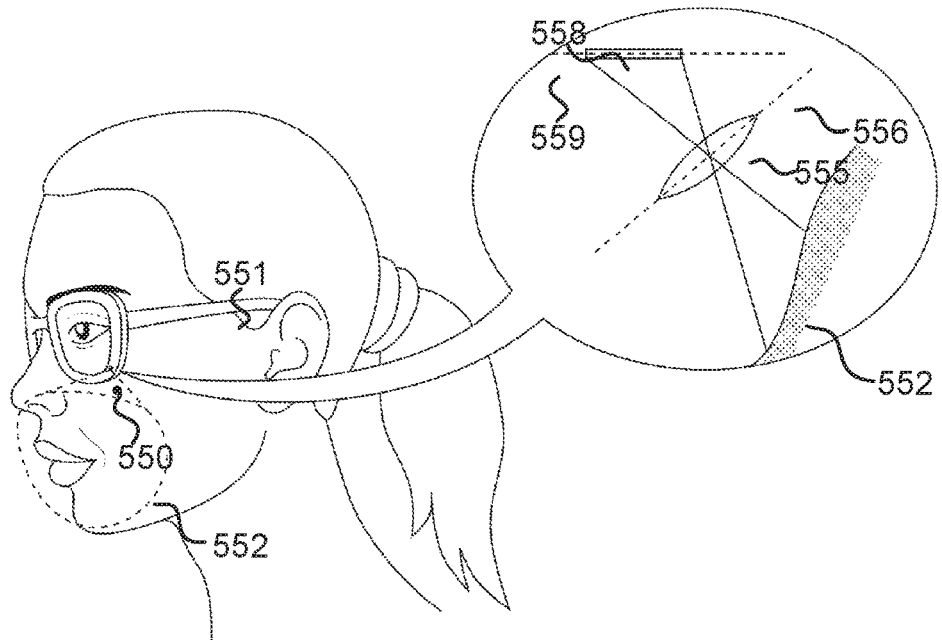
FIG. 20a
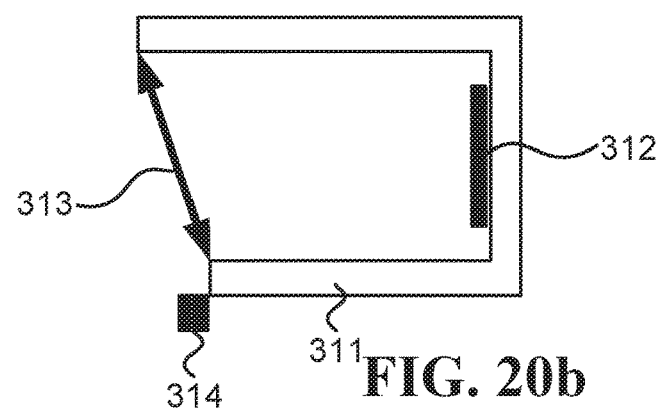
FIG. 20b

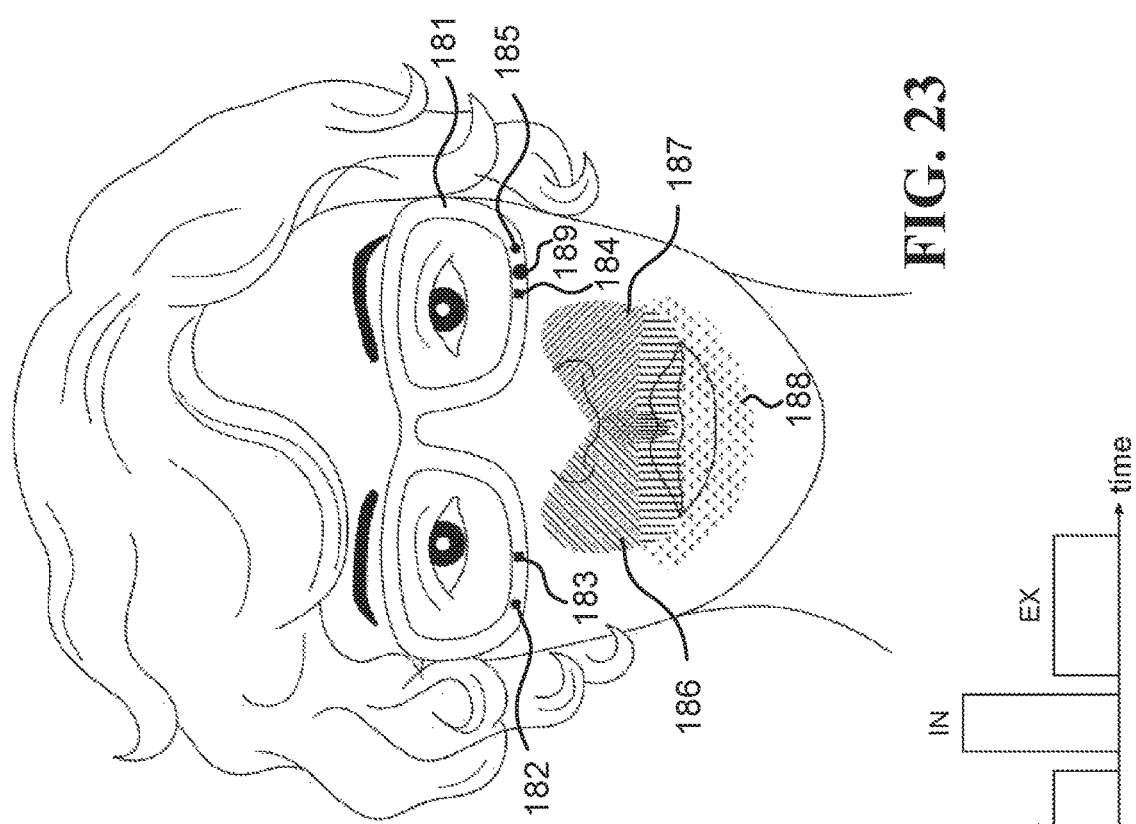
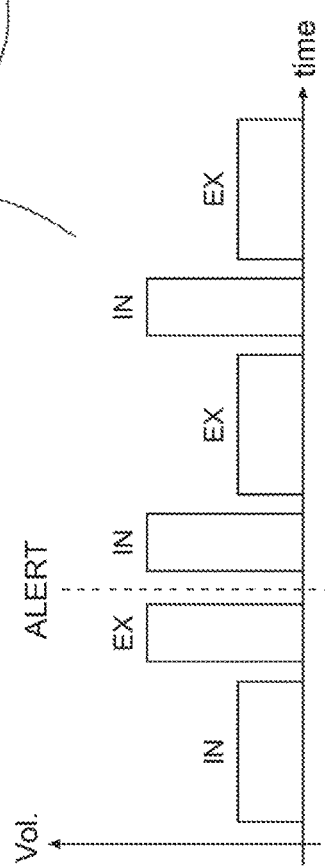
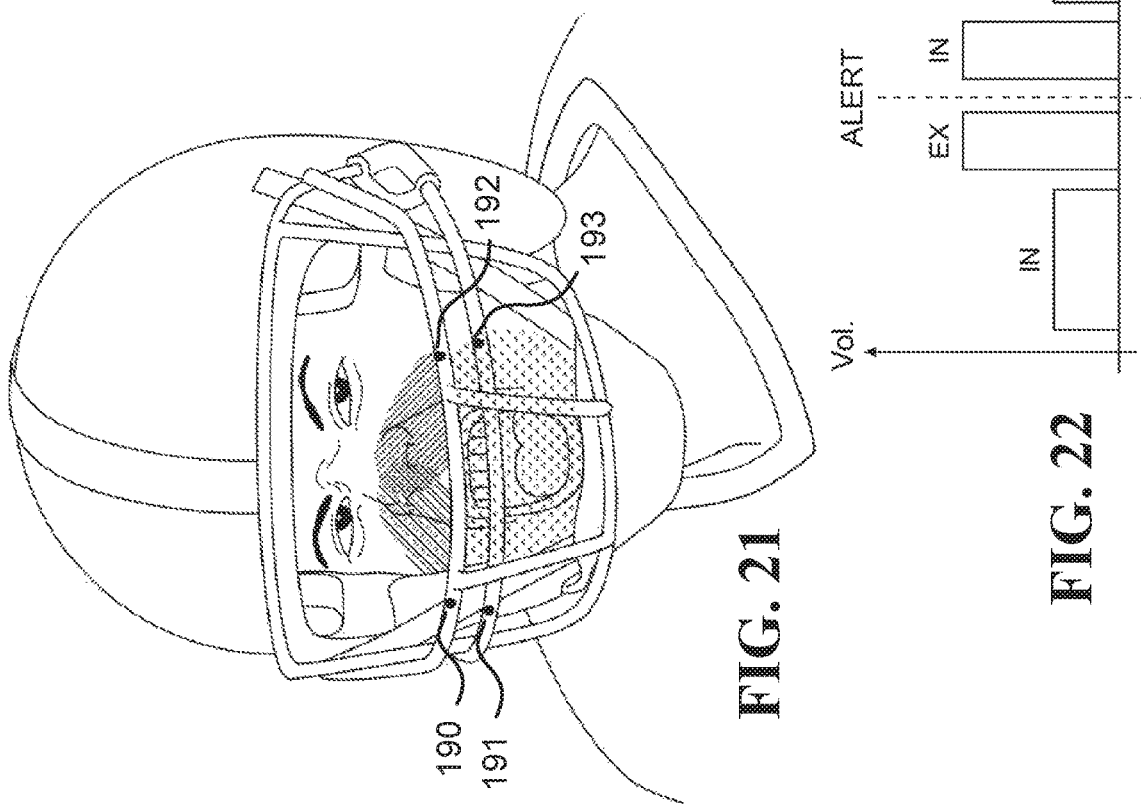
FIG. 21
FIG. 22
FIG. 23

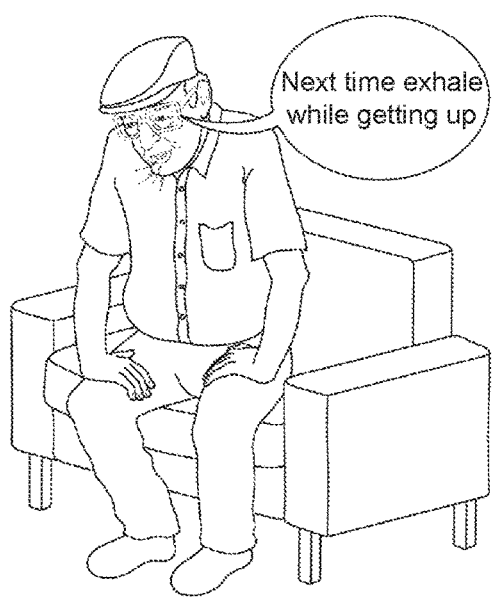 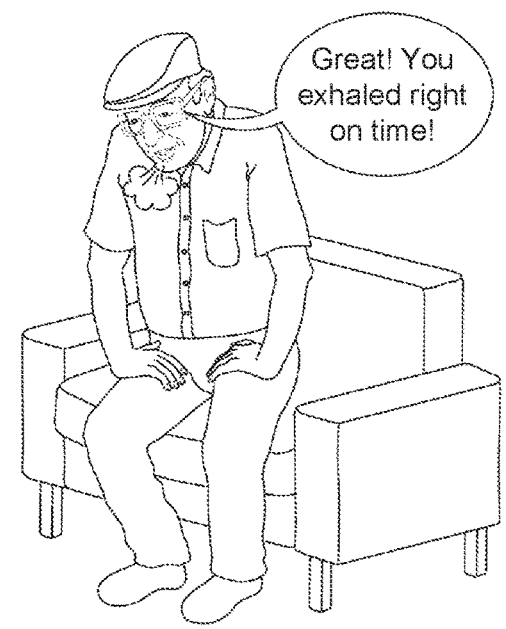
FIG. 24a  FIG. 24b
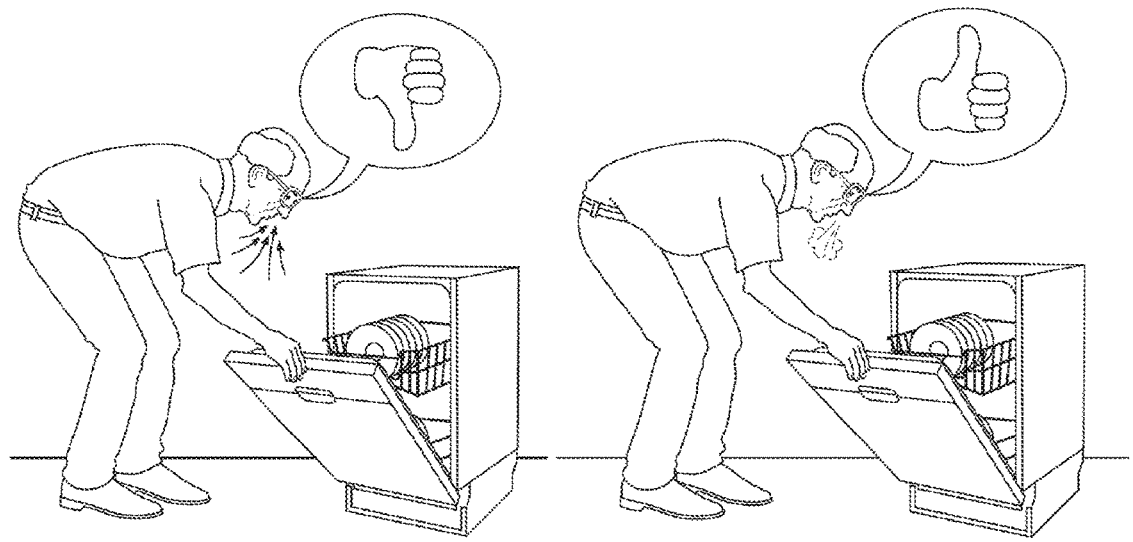
FIG. 25a  FIG. 25b
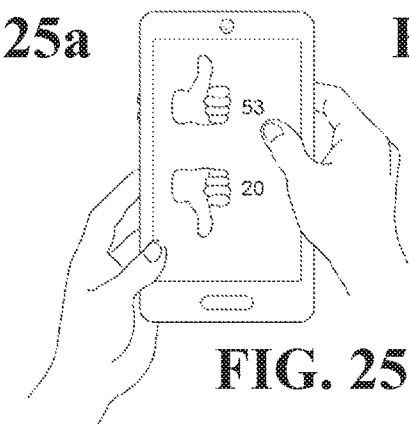
FIG. 25c

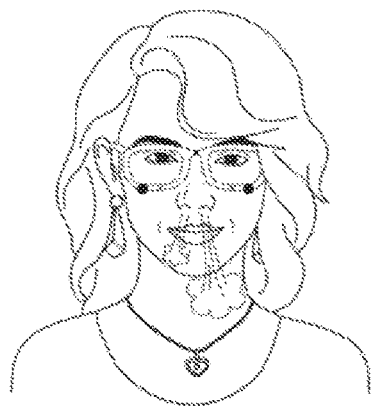
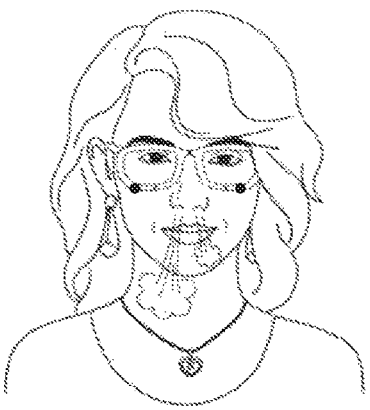
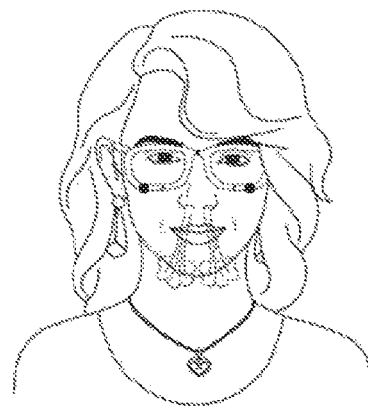
FIG. 32a  FIG. 32b  FIG. 32c
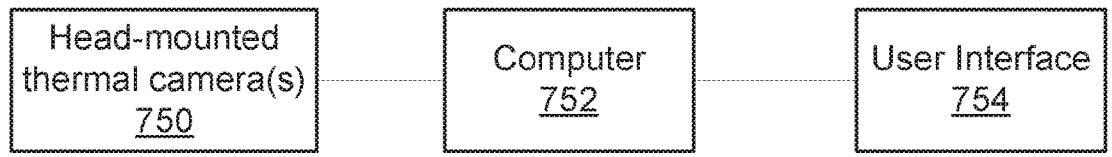
FIG. 33
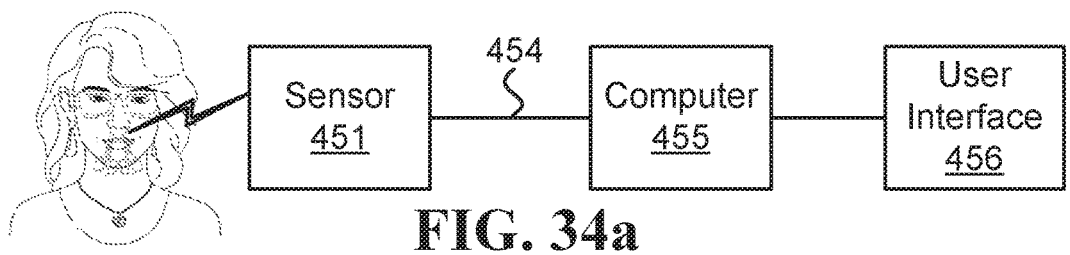
FIG. 34a
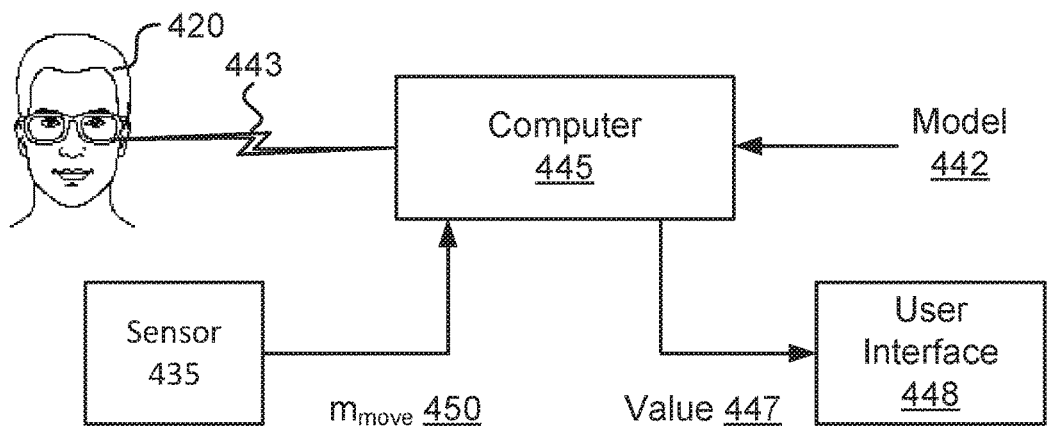
FIG. 34b

VIRTUAL COACHING BASED ON RESPIRATION SIGNALS

CROSS-REFERENCE TO RELATED APPLICATIONS

This Application claims priority to U.S. Provisional Patent Application No. 62/652,348, filed Apr. 4, 2018, and U.S. Provisional Patent Application No. 62/667,453, filed May 5, 2018.

This application is also a Continuation-In-Part of U.S. application Ser. No. 15/722,434, filed Oct. 2, 2017, which claims priority to U.S. Provisional Patent Application No. 62/408,677, filed Oct. 14, 2016, and U.S. Provisional Patent Application No. 62/456,105, filed Feb. 7, 2017, and U.S. Provisional Patent Application No. 62/480,496, filed Apr. 2, 2017. U.S. Ser. No. 15/722,434 is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015. U.S. Ser. No. 15/722,434 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015. And U.S. Ser. No. 15/722,434 is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

This Application is also a Continuation-In-Part of U.S. application Ser. No. 15/635,178, filed Jun. 27, 2017, which claims priority to U.S. Provisional Patent Application No. 62/354,833, filed Jun. 27, 2016, and U.S. Provisional Patent Application No. 62/372,063, filed Aug. 8, 2016.

This Application is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

This Application is also a Continuation-In-Part of U.S. application Ser. No. 15/832,815, filed Dec. 6, 2017, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 15/832,815 is a Continuation-In-Part of U.S. application Ser. No. 15/182,592, filed Jun. 14, 2016, a Continuation-In-Part of U.S. application Ser. No. 15/231,276, filed Aug. 8, 2016, a Continuation-In-Part of U.S. application Ser. No. 15/284,528, filed Oct. 3, 2016, a Continuation-In-Part of U.S. application Ser. No. 15/635,178, filed Jun. 27, 2017, and a Continuation-In-Part of U.S. application Ser. No. 15/722,434, filed Oct. 2, 2017.

U.S. Ser. No. 15/832,815 is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/182,592, filed Jun. 14, 2016, now U.S. Pat. No. 10,165,949, claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/284,528, filed Oct. 3, 2016, now U.S. Pat. No. 10,113,913, claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

This application is also a Continuation-In-Part of U.S. application Ser. No. 15/859,772, filed Jan. 2, 2018. U.S. Ser. No. 15/859,772 is a Continuation-In-Part of U.S. application Ser. No. 15/182,592, filed Jun. 14, 2016, a Continuation-In-Part of U.S. application Ser. No. 15/231,276, filed Aug. 8, 2016, a Continuation-In-Part of U.S. application Ser. No. 15/284,528, filed Oct. 3, 2016, a Continuation-In-Part of U.S. application Ser. No. 15/635,178, filed Jun. 27, 2017, and a Continuation-In-Part of U.S. application Ser. No. 15/722,434, filed Oct. 2, 2017.

ACKNOWLEDGMENTS

Gil Thieberger would like to thank his holy and beloved teacher, Lama Dvora-hla, for her extraordinary teachings and manifestation of wisdom, love, compassion and morality, and for her endless efforts, support, and skills in guiding him and others on their paths to freedom and ultimate happiness. Gil would also like to thank his beloved parents for raising him exactly as they did.

BACKGROUND

Respiration has an important role in athletic performance. To achieve higher performance the body needs more oxygen. Thus, it is important to breathe correctly when exercising. Additionally, when performing certain sequences of movements such as lifting weights, swinging a golf club, or hitting a ball with a racket, breathing in certain patterns that are synchronized with the movements can help improve factors such as posture, coordination and the effect of the movements on the muscles.

The process of respiration is under both conscious and unconscious control. Thus, if proper coaching and guidance is provided, breathing may be corrected while performing athletic activities. However, keeping track of breathing while conducting athletic activities is difficult. Additionally, it may not be possible for a person exercising to translate the information about breathing into actionable instructions that may be used to improve athletic performance. Thus, there is a need for a way to track a user's breathing while performing athletic activities, and to use this information to help the user improve his/her performance.

SUMMARY

Collecting thermal measurements of various regions of a user's face can have many health-related (and other) applications. In particular, thermal measurements of regions below the nostrils can enable monitoring of the user's respiration. However, movements of the user and/or of the user's head can make acquiring this data difficult with many of the known approaches. Some embodiments described herein utilize various combinations of head-mounted thermal cameras, which may be physically coupled to a frame worn on the user's head, in order to collect thermal measurements indicative of the user's respiration.

One aspect of disclosure involves an athletic coaching system that includes at least one inward-facing head-mounted thermal camera (CAM) and a computer. Each CAM from among the at least one CAM is configured to take thermal measurements of a region below the nostrils (denoted $TH_{RBN}$) of a user. $TH_{RBN}$ are indicative of an exhale stream of the user (e.g., an exhale stream from a nostril and/or from the mouth). The computer is configured to: receive measurements of movements ($M_{move}$) involving the user, generate, based on $TH_N$ and $M_{move}$, a coaching indication and present, via a user interface, the coaching indication to the user.

In one embodiment, the coaching indication is indicative of a change the user should make to one or more of the following: cadence of movements, stride length, breathing rate, breathing type (mouth or nasal), and duration of exhales.

In another embodiment, the computer is further configured to calculate a target breathing rate based on data comprising at least one of $TH_{RBN}$ and $M_{move}$, and to include in the coaching indication breathing cues that correspond to the target breathing rate. Optionally, the computer is further configured to receive a value indicative of the heart rate (HR) of the user, and to calculate the target breathing rate based on HR (in addition to at least one of $TH_{RBN}$ and $M_{move}$).

In yet another embodiment, the coaching indication is indicative of synchronization of a breathing pattern of the user with a sequence of movements of the user. In one example, the sequence of movements of the user corresponds to a pressing motion of weights or a barbell, and the coaching indication indicates to inhale in the concentric phase of the press and exhale in the eccentric phase of the press. In another example, the sequence of movements of the user corresponds to swinging a racket in order to hit a ball with the racket, and the coaching indication indicates to exhale while hitting the ball. In yet another example, the sequence of movements of the user corresponds to making a drive shot in golf, and the coaching indication indicates to: exhale at address, inhale during the backswing, and exhale again on the downswing.

In some embodiments, the athletic coaching system may include a frame configured to be worn on the user's head. Optionally, each CAM, from among the at least one CAM, is physically coupled to the frame and weighs below 10 g. The frame is further configured to hold each CAM, from among the at least one CAM, less than 15 cm from the user's face and above the user's upper lip. Optionally, the at least one CAM comprises at least first and second inward-facing head-mounted thermal cameras that are physically coupled to the right and left sides of the frame, respectively, at a distance that is less than 15 cm from the user's face.

BRIEF DESCRIPTION OF THE DRAWINGS

The embodiments are herein described by way of example only, with reference to the following drawings:

FIG. 16a and FIG. 16b illustrate embodiments of right and left clip-on devices that are configured to be attached behind an eyeglasses frame:

FIG. 17a and FIG. 17b illustrate an embodiment of a single-unit clip-on device that is configured to be attached behind an eyeglasses frame:

FIG. 18 illustrates embodiments of right and left clip-on devices, which are configured to be attached/detached from an eyeglasses frame, and have protruding arms to hold inward-facing head-mounted cameras;

FIG. 19 illustrates a scenario in which an alert regarding a possible stroke is issued;

FIG. 20a is a schematic illustration of an inward-facing head-mounted camera embedded in an eyeglasses frame, which utilizes the Scheimpflug principle:

FIG. 20b is a schematic illustration of a camera that is able to change the relative tilt between its lens and sensor planes according to the Scheimpflug principle;

FIG. 21 illustrates an embodiment of a system that collects thermal measurements related to respiration, in which four inward-facing head-mounted thermal cameras (CAMs) are coupled to a football helmet:

FIG. 22 illustrates a situation in which an alert is issued to a user when it is detected that the ratio the duration of exhaling and inhaling is too low:

FIG. 23 illustrates an embodiment of a system that collects thermal measurements related to respiration, in which four CAMs are coupled to the bottom of an eyeglasses frame:

FIG. 24a. FIG. 24b. FIG. 25a, FIG. 25b and FIG. 25c illustrate how embodiments described herein may help train an elderly user to exhale during effort;

FIG. 32a is a schematic illustration of a left dominant nostril;

FIG. 32b is a schematic illustration of a right dominant nostril;

FIG. 32c is a schematic illustration of balanced breathing;

FIG. 33 is a schematic illustration of an embodiment of a system that identifies the dominant nostril;

FIG. 34a illustrates an embodiment of a system that suggests activities according to the dominant nostril;

FIG. 34b illustrates an embodiment of a system for calculating a respiratory parameter;

DETAILED DESCRIPTION

Figure 1A:
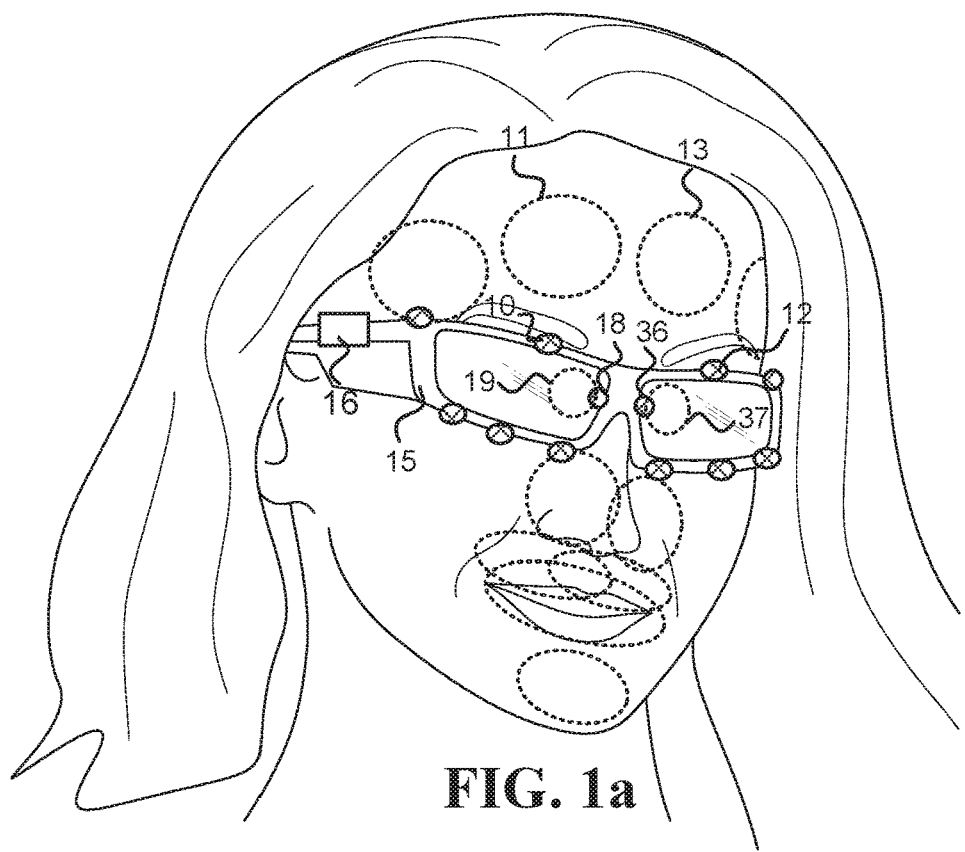
FIG. 1a and FIG. 1b illustrate various inward-facing head-mounted cameras coupled to an eyeglasses frame.

A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

Sentences in the form of "thermal measurements of an ROI" (usually denoted $TH_{ROI}$ or some variant thereof) refer to at least one of: (i) temperature measurements of the ROI ($T_{ROI}$), such as when using thermopile or microbolometer sensors, and (ii) temperature change measurements of the ROI ($\Delta T_{ROI}$), such as when using a pyroelectric sensor or when deriving the temperature changes from temperature measurements taken at different times by a thermopile sensor or a microbolometer sensor.

In some embodiments, a device, such as a thermal camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 7, FIG. 11 and FIG. 19. Sentences in the form of "the system/camera occludes the ROI" indicate that some of the ROIs cannot be observed directly by that third person, such as ROIs 19 and 37 that are occluded by the lenses in FIG. 1a, and ROIs 97 and 102 that are occluded by cameras 91 and 96, respectively, in FIG. 9.

Although many of the disclosed embodiments can use occluding thermal cameras successfully, in certain scenarios, such as when using an HMS on a daily basis and/or in a normal day-to-day setting, using thermal cameras that do not occlude their ROIs on the face may provide one or more advantages to the user, to the HMS, and/or to the thermal cameras, which may relate to one or more of the following: esthetics, better ventilation of the face, reduced weight, simplicity to wear, and reduced likelihood to being tarnished.

A "Visible-light camera" refers to a non-contact device designed to detect at least some of the visible spectrum, such as a camera with optical lenses and CMOS or CCD sensor. The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame. The abbreviation "CAM" denotes "inward-facing head-mounted thermal camera", the abbreviation "$CAM_{out}$" denotes "outward-facing head-mounted thermal camera", the abbreviation "VCAM" denotes "inward-facing head-mounted visible-light camera", and the abbreviation "VCAM$_{out}$" denotes "outward-facing head-mounted visible-light camera".

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge: the frame in Oculus Rift™ includes the foam placed on the user's face and the straps: and the frames in Google Glass™ and Spectacles by Snap Inc, are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a thermal camera is inward-facing and head-mounted, challenges faced by systems known in the art that are used to acquire thermal measurements, which include non-head-mounted thermal cameras, may be simplified and even eliminated with some of the embodiments described herein. Some of these challenges may involve dealing with complications caused by movements of the user, image registration. ROI alignment, tracking based on hot spots or markers, and motion compensation in the IR domain.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 15 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 1B:
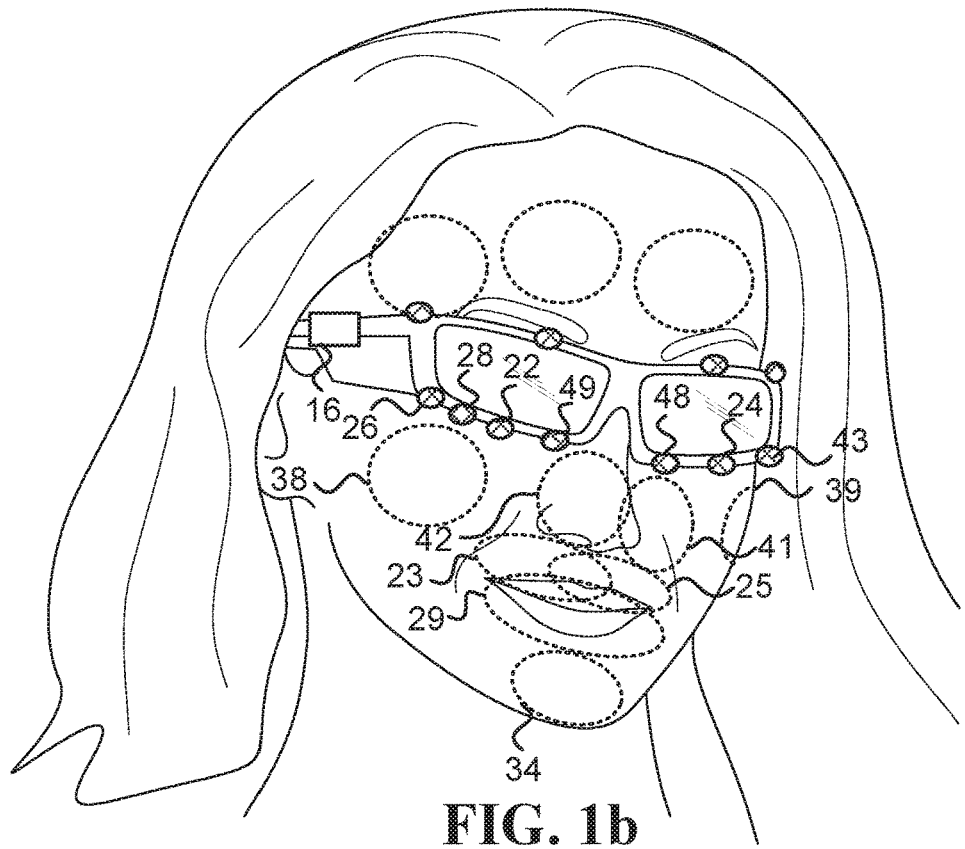

The following figures show various examples of HMSs equipped with head-mounted cameras. FIG. 1a illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 1b illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

Figure 2:
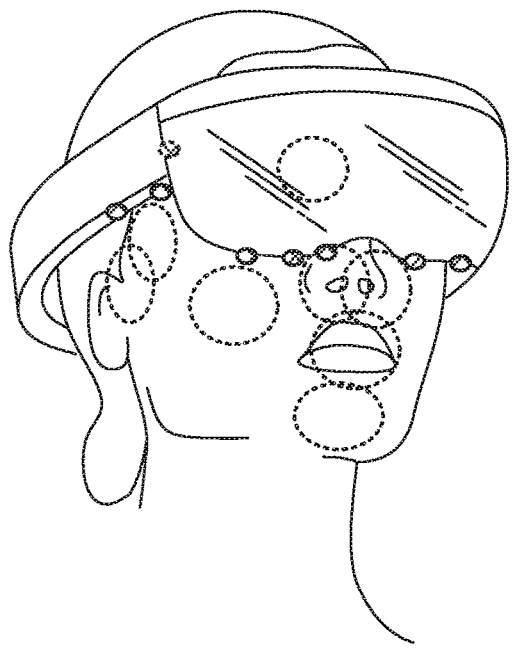
FIG. 2 illustrates inward-facing head-mounted cameras coupled to an augmented reality device.
Figure 3:
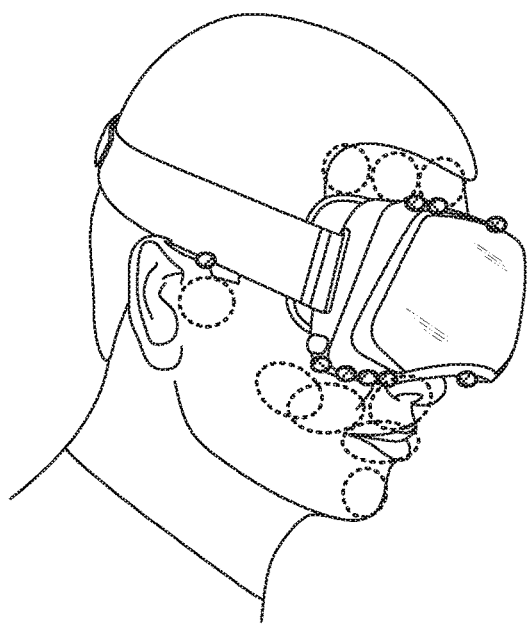
FIG. 3 illustrates head-mounted cameras coupled to a virtual reality device.
Figure 4:
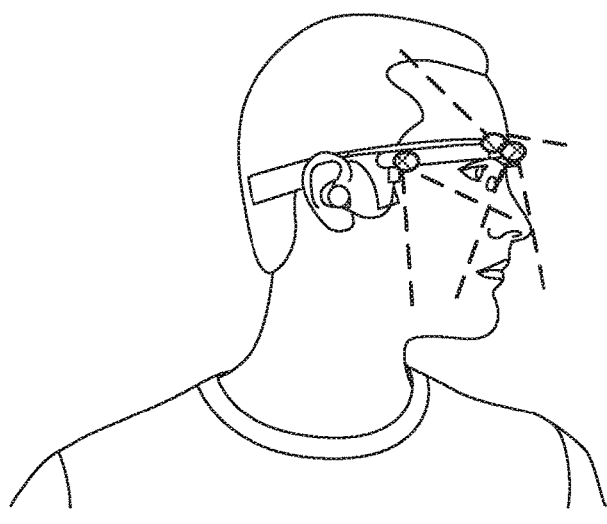
FIG. 4 illustrates a side view of head-mounted cameras coupled to an augmented reality device.
Figure 5:
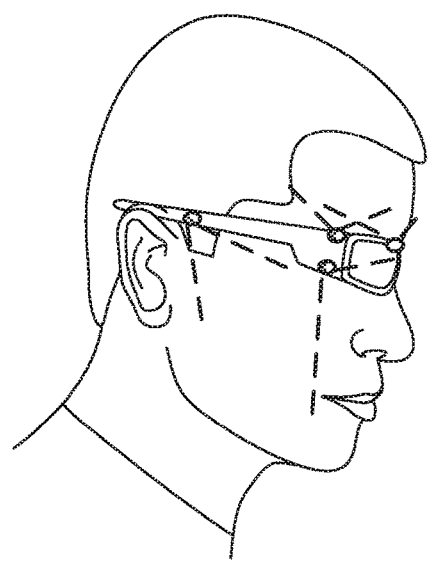
FIG. 5 illustrates a side view of head-mounted cameras coupled to a sunglasses frame.

FIG. 2 illustrates inward-facing head-mounted cameras coupled to an augmented reality device such as Microsoft HoloLens™. FIG. 3 illustrates head-mounted cameras coupled to a virtual reality device such as Facebook's Oculus Rift™. FIG. 4 is a side view illustration of head-mounted cameras coupled to an augmented reality device such as Google Glass™. FIG. 5 is another side view illustration of head-mounted cameras coupled to a sunglasses frame.

Figure 6:
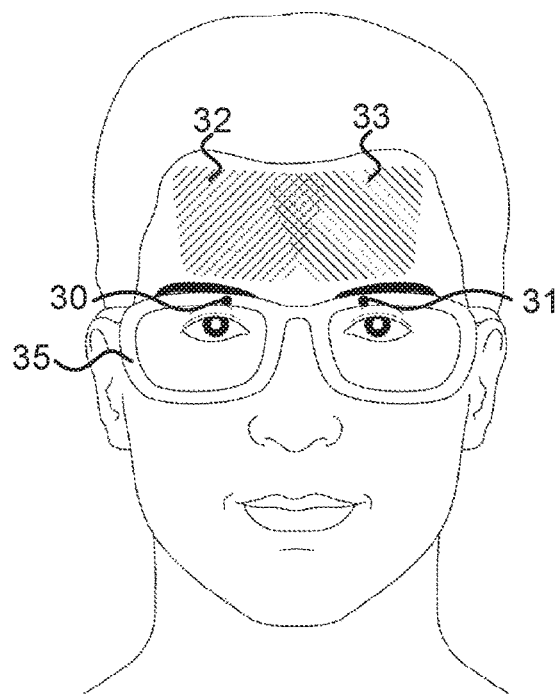
FIG. 6, FIG. 7, FIG. 8 and FIG. 9 illustrate head-mounted systems (HMSs) configured to measure various ROIs relevant to some of the embodiments describes herein.
Figure 7:
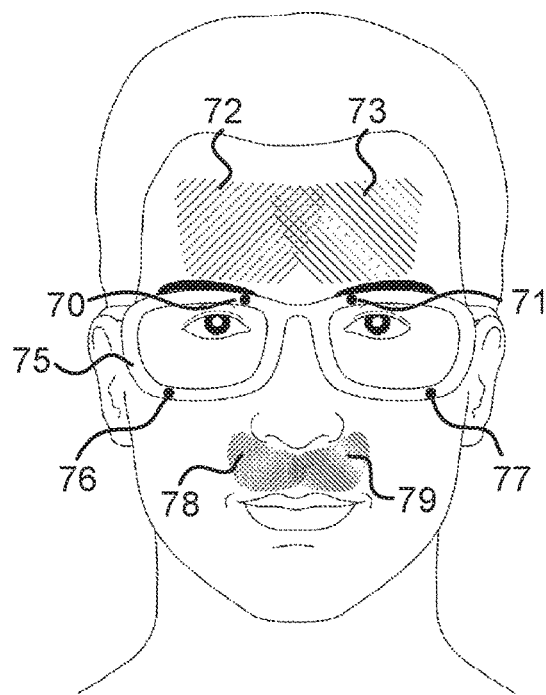
Figure 8:
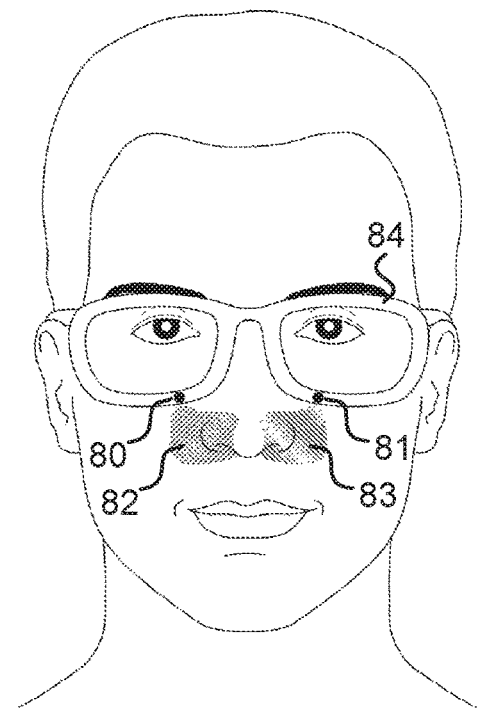
Figure 9:
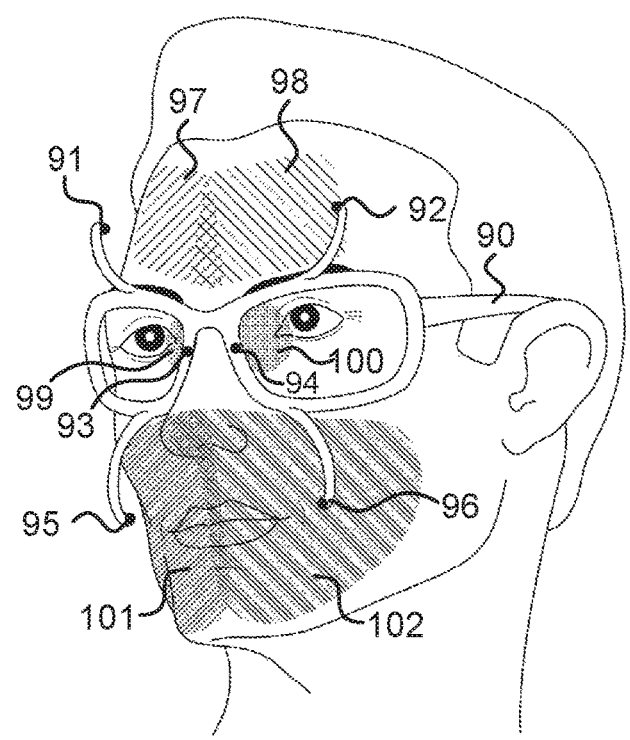

FIG. 6 to FIG. 9 illustrate HMSs configured to measure various ROIs relevant to some of the embodiments describes herein FIG. 6 illustrates a frame 35 that mounts inward-facing head-mounted cameras 30 and 31 that measure regions 32 and 33 on the forehead, respectively. FIG. 7 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 8 illustrates a frame 84 that mounts inward-facing head-mounted cameras 80 and 81 that measure regions 82 and 83 on the sides of the nose, respectively. And FIG. 9 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 10:
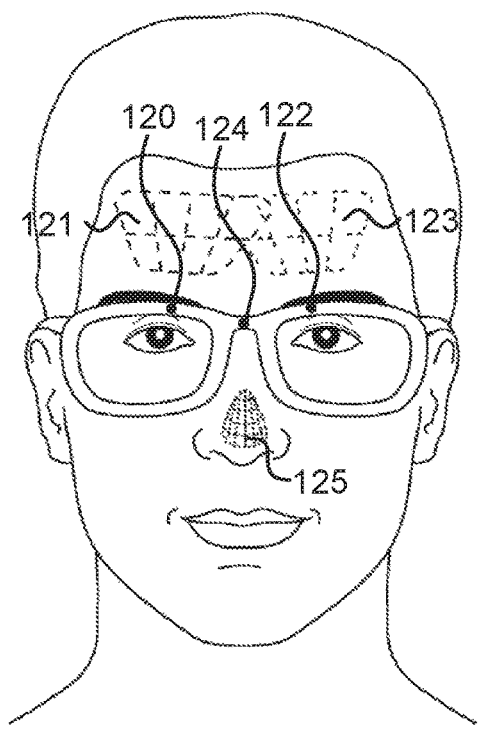
FIG. 10, FIG. 11, FIG. 12 and FIG. 13 illustrate various embodiments of systems that include inward-facing head-mounted cameras having multi-pixel sensors (FPA sensors)
Figure 11:
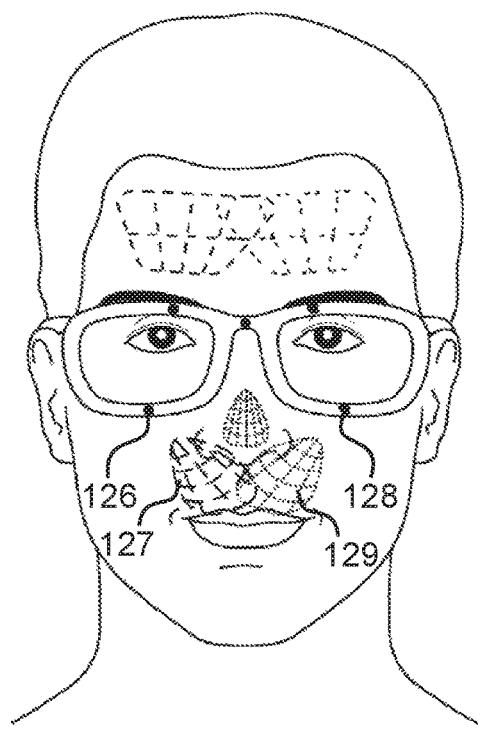
Figure 12:
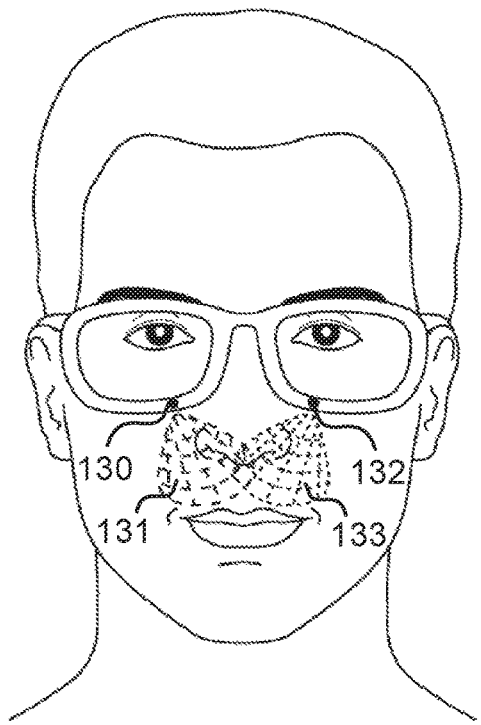
Figure 13:
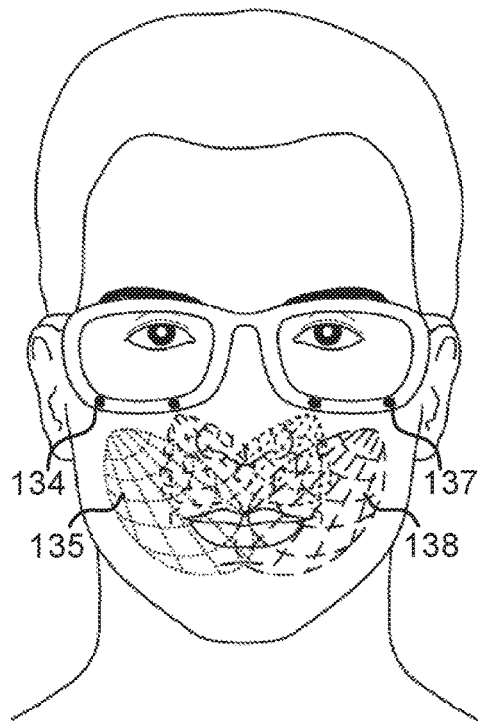

FIG. 10 to FIG. 13 illustrate various inward-facing head-mounted cameras having multi-pixel sensors (FPA sensors), configured to measure various ROIs relevant to some of the embodiments describes herein. FIG. 10 illustrates head-mounted cameras 120 and 122 that measure regions 121 and 123 on the forehead, respectively, and mounts head-mounted camera 124 that measure region 125 on the nose. FIG. 11 illustrates head-mounted cameras 126 and 128 that measure regions 127 and 129 on the upper lip, respectively, in addition to the head-mounted cameras already described in FIG. 10. FIG. 12 illustrates head-mounted cameras 130 and 132 that measure larger regions 131 and 133 on the upper lip and the sides of the nose, respectively. And FIG. 13 illustrates head-mounted cameras 134 and 137 that measure regions 135 and 138 on the right and left cheeks and right and left sides of the mouth, respectively, in addition to the head-mounted cameras already described in FIG. 12.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 14b, FIG. 15b, and FIG. 18), or alternatively, most of the clip-on device may be located behind the frame, as illustrated in FIG. 16b and FIG. 17b.

Figure 14A:
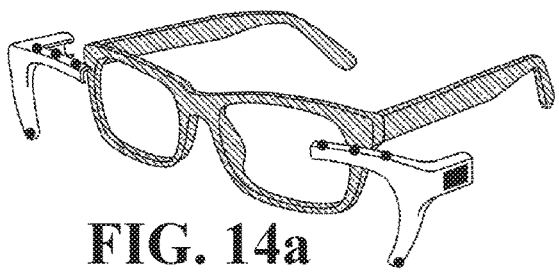
FIG. 14a, FIG. 14b, and FIG. 14c illustrate embodiments of two right and left clip-on devices that are configured to attached/detached from an eyeglasses frame.
Figure 14C:
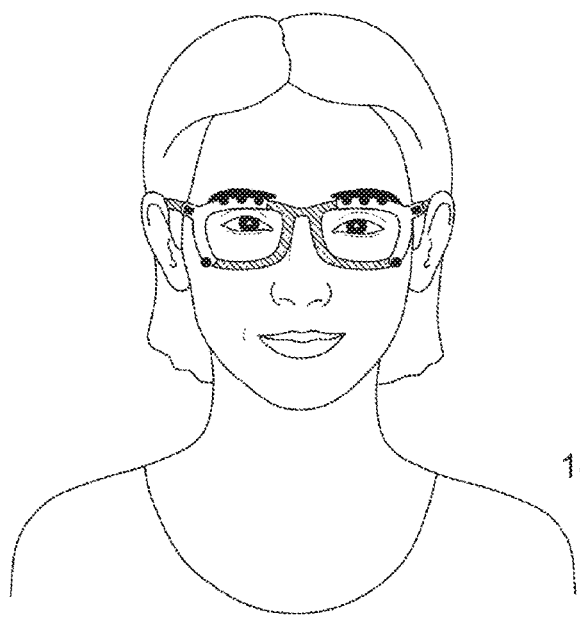
Figure 14B:
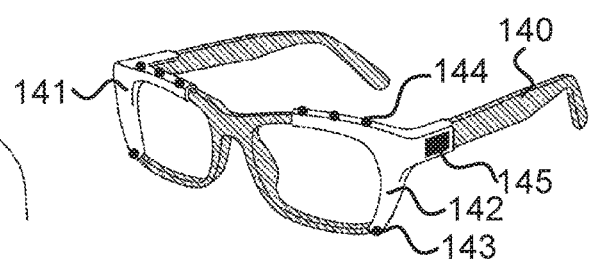

FIG. 14a. FIG. 14b, and FIG. 14c illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

Figure 15A:
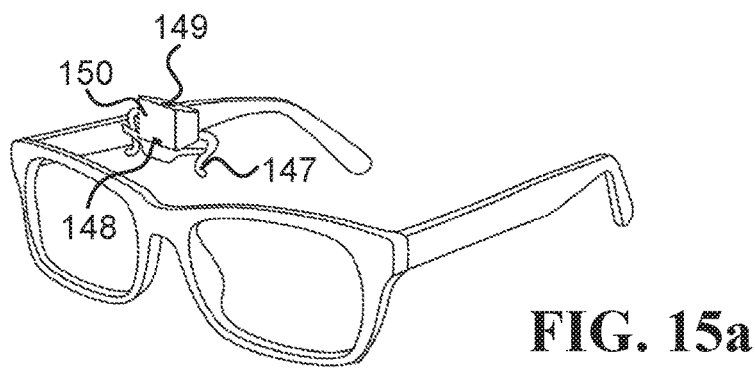
FIG. 15a and FIG. 15b illustrate an embodiment of a clip-on device that includes inward-facing head-mounted cameras pointed at the lower part of the face and the forehead.
Figure 15B:
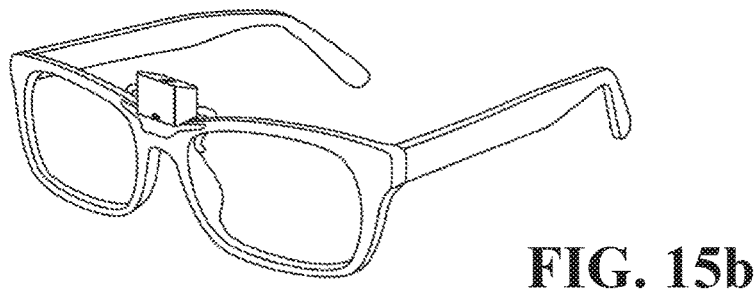

FIG. 15a and FIG. 15b illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

FIG. 16a and FIG. 16b illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or check), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

FIG. 17a and FIG. 17b illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 18 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a thermal camera is physically coupled, or by placing a LED instead of the sensor (while maintaining the same field of view) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a CAM having just one pixel or a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

Various embodiments described herein involve detections of physiological responses based on user measurements. Some examples of physiological responses include stress, an allergic reaction, an asthma attack, a stroke, dehydration, intoxication or a headache (which includes a migraine). Other examples of physiological responses include manifestations of fear, startle, sexual arousal, anxiety, joy, pain or guilt. Still other examples of physiological responses include physiological signals such as a heart rate or a value of a respiratory parameter of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing thermal measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of thermal measurements taken during multiple of the above-described windows, such as measurements taken during different days. In some embodiments, a computer may receive a stream of thermal measurements, taken while the user wears an HMS with coupled thermal cameras during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with thermal cameras, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken of a long period (e.g., measurements taken on "different days") may have an advantage, in some embodiments, of contributing to the generalizability of a trained model. Measurements taken over the long period likely include measurements taken in different environments and/or measurements taken while the measured user was in various physiological and/or mental states (e.g., before/after meals and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing thermal measurements to a threshold (when the threshold is reached that may be indicative of an occurrence of the physiological response), comparing thermal measurements to a reference time series, and/or by performing calculations that involve a model trained using machine learning methods. Optionally, the thermal measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minute, one hour, four hours, one day, or one week. In another example, the window may be longer than one or more of the aforementioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline thermal measurement values, most of which were taken when the user was not experiencing the physiological response. Optionally, detecting the physiological response may rely on observing a change to typical temperatures at one or more ROIs (the baseline), where different users might have different typical temperatures at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response. (iii) a categorical value indicative of the severity/extent of the physiological response, (iv) an expected change in thermal measurements of an ROI (denoted $TH_{ROI}$ or some variation thereof), and/or (v) rate of change in $TH_{ROI}$. Optionally, when the physiological response corresponds to a physiological signal (e.g., a heart rate, a breathing rate, and an extent of frontal lobe brain activity), the extent of the physiological response may be interpreted as the value of the physiological signal.

One approach for detecting a physiological response, which may be utilized in some embodiments, involves comparing thermal measurements of one or more ROIs to a threshold. In these embodiments, the computer may detect the physiological response by comparing the thermal measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to temperature, the certain change may be positive (increase in temperature) or negative (decrease in temperature). Different physiological responses described herein may involve different types of thresholds, which may be an upper threshold (where reaching the threshold means≥the threshold) or a lower threshold (where reaching the threshold means≤the threshold); for example, each physiological response may involve at least a certain degree of heating, or at least a certain degree cooling, at a certain ROI on the face.

Another approach for detecting a physiological response, which may be utilized in some embodiments, may be applicable when the thermal measurements of a user are treated as time series data. For example, the thermal measurements may include data indicative of temperatures at one or more ROIs at different points of time during a certain period. In some embodiments, the computer may compare thermal measurements (represented as a time series) to one or more reference time series that correspond to periods of time in which the physiological response occurred. Additionally or alternatively, the computer may compare the thermal measurements to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user had the physiological response. Optionally, if the similarity between the thermal measurements and a reference time series that does not correspond to a physiological response reaches another threshold, this is indicative of the fact that the thermal measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding. Hui, et al. "Querying and mining of time series data: experimental comparison of representations and distance measures." Proceedings of the VLDB Endowment 1.2 (2008): 1542-1552, and in Wang. Xiaoyue, et al. "Experimental comparison of representation methods and distance measures for time series data." Data Mining and Knowledge Discovery 26.2 (2013): 275-309.

Herein, "machine learning" methods refers to learning from examples using one or more approaches. Optionally, the approaches may be considered supervised, semi-supervised, and/or unsupervised methods. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

In some embodiments, which involve utilizing a machine learning-based model, a computer is configured to detect the physiological response by generating feature values based on the thermal measurements (and possibly other values), and/or based on values derived therefrom (e.g., statistics of the measurements). The computer then utilizes the machine learning-based model to calculate, based on the feature values, a value that is indicative of whether, and/or to what extent, the user is experiencing (and/or is about to experience) the physiological response. Optionally, calculating said value is considered "detecting the physiological response". Optionally, the value calculated by the computer is indicative of the probability that the user has/had the physiological response.

Herein, feature values may be considered input to a computer that utilizes a model to perform the calculation of a value, such as the value indicative of the extent of the physiological response mentioned above. It is to be noted that the terms "feature" and "feature value" may be used interchangeably when the context of their use is clear. However, a "feature" typically refers to a certain type of value, and represents a property, while "feature value" is the value of the property with a certain instance (sample). For example, a feature may be temperature at a certain ROI, while the feature value corresponding to that feature may be 36.9° C. in one instance and 37.3° C. in another instance.

In some embodiments, a machine learning-based model used to detect a physiological response is trained based on data that includes samples. Each sample includes feature values and a label. The feature values may include various types of values. At least some of the feature values of a sample are generated based on measurements of a user taken during a certain period of time (e.g., thermal measurements taken during the certain period of time). Optionally, some of the feature values may be based on various other sources of information described herein. The label is indicative of a physiological response of the user corresponding to the certain period of time. Optionally, the label may be indicative of whether the physiological response occurred during the certain period and/or the extent of the physiological response during the certain period. Additionally or alternatively, the label may be indicative of how long the physiological response lasted. Labels of samples may be generated using various approaches, such as self-report by users, annotation by experts that analyze the training data, automatic annotation by a computer that analyzes the training data and/or analyzes additional data related to the training data, and/or utilizing additional sensors that provide data useful for generating the labels. It is to be noted that herein when it is stated that a model is trained based on certain measurements (e.g., "a model trained based on $TH_{ROI}$ taken on different days"), it means that the model was trained on samples comprising feature values generated based on the certain measurements and labels corresponding to the certain measurements. Optionally, a label corresponding to a measurement is indicative of the physiological response at the time the measurement was taken.

Various types of feature values may be generated based on thermal measurements. In one example, some feature values are indicative of temperatures at certain ROIs. In another example, other feature values may represent a temperature change at certain ROIs. The temperature changes may be with respect to a certain time and/or with respect to a different ROI. In order to better detect physiological responses that take some time to manifest, in some embodiments, some feature values may describe temperatures (or temperature changes) at a certain ROI at different points of time. Optionally, these feature values may include various functions and/or statistics of the thermal measurements such as minimum/maximum measurement values and/or average values during certain windows of time.

It is to be noted that when it is stated that feature values are generated based on data comprising multiple sources, it means that for each source, there is at least one feature value that is generated based on that source (and possibly other data). For example, stating that feature values are generated from thermal measurements of first and second ROIs ($TH_{ROI1}$ and $TH_{ROI2}$, respectively) means that the feature values may include a first feature value generated based on $TH_{ROI1}$ and a second feature value generated based on $TH_{ROI2}$. Optionally, a sample is considered generated based on measurements of a user (e.g., measurements comprising $TH_{ROI1}$ and $TH_{ROI2}$) when it includes feature values generated based on the measurements of the user.

In addition to feature values that are generated based on thermal measurements, in some embodiments, at least some feature values utilized by a computer (e.g., to detect a physiological response or train a mode) may be generated based on additional sources of data that may affect temperatures measured at various facial ROIs. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not thermal cameras, such as a visible-light camera, a photoplethysmogram (PPG) sensor, an electrocardiogram (ECG) sensor, an electroencephalography (EEG) sensor, a galvanic skin response (GSR) sensor, or a thermistor.

The machine learning-based model used to detect a physiological response may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may reduce the accuracy of the detection of the physiological response. Some examples of confounding factors include: (i) environmental phenomena such as direct sunlight, air conditioning, and/or wind: (ii) things that are on the user's face, which are not typically there and/or do not characterize the faces of most users (e.g., cosmetics, ointments, sweat, hair, facial hair, skin blemishes, acne, inflammation, piercings, body paint, and food leftovers); (iii) physical activity that may affect the user's heart rate, blood circulation, and/or blood distribution (e.g., walking, running, jumping, and/or bending over); (iv) consumption of substances to which the body has a physiological response that may involve changes to temperatures at various facial ROIs, such as various medications, alcohol, caffeine, tobacco, and/or certain types of food; and/or (v) disruptive facial movements (e.g., frowning, talking, eating, drinking, sneezing, and coughing).

Occurrences of confounding factors may not always be easily identified in thermal measurements. Thus, in some embodiments, systems may incorporate measures designed to accommodate for the confounding factors. In some embodiments, these measures may involve generating feature values that are based on additional sensors, other than the thermal cameras. In some embodiments, these measures may involve refraining from detecting the physiological response, which should be interpreted as refraining from providing an indication that the user has the physiological response. For example, if an occurrence of a certain confounding factor is identified, such as strong directional sunlight that heats one side of the face, the system may refrain from detecting that the user had a stroke. In this example, the user may not be alerted even though a temperature difference between symmetric ROIs on both sides of the face reaches a threshold that, under other circumstances, would warrant alerting the user.

Training data used to train a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user is in direct sunlight or touches the face) can lead to a model that is less susceptible to wrongfully detect the physiological response (which may be considered an occurrence of a false positive) in real world situations.

When a model is trained with training data comprising samples generated from measurements of multiple users, the model may be considered a general model. When a model is trained with training data comprising at least a certain proportion of samples generated from measurements of a certain user, and/or when the samples generated from the measurements of the certain user are associated with at least a certain proportion of weight in the training data, the model may be considered a personalized model for the certain user. Optionally, the personalized model for the certain user provides better results for the certain user, compared to a general model that was not personalized for the certain user. Optionally, personalized model may be trained based on measurements of the certain user, which were taken while the certain user was in different situations; for example, train the model based on measurements taken while the certain user had a headache/epilepsy/stress/anger attack, and while the certain user did not have said attack. Additionally or alternatively, the personalized model may be trained based on measurements of the certain user, which were taken over a duration long enough to span different situations; examples of such long enough durations may include: a week, a month, six months, a year, and three years.

Training a model that is personalized for a certain user may require collecting a sufficient number of training samples that are generated based on measurements of the certain user. Thus, initially detecting the physiological response with the certain user may be done utilizing a general model, which may be replaced by a personalized model for the certain user, as a sufficiently large number of samples are generated based on measurements of the certain user. Another approach involves gradually modifying a general model based on samples of the certain user in order to obtain the personalized model.

After a model is trained, the model may be provided for use by a system that detects the physiological response. Providing the model may involve performing different operations. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model, such as a database and/or cloud-based storage from which the system may retrieve the model. In still another embodiment, providing the model involves notifying the system regarding the existence of the model and/or regarding an update to the model. Optionally, this notification includes information needed in order for the system to obtain the model.

A model for detecting a physiological response may include different types of parameters. Following are some examples of various possibilities for the model and the type of calculations that may be accordingly performed by a computer in order to detect the physiological response: (a) the model comprises parameters of a decision tree. Optionally, the computer simulates a traversal along a path in the decision tree, determining which branches to take based on the feature values. A value indicative of the physiological response may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the physiological response; and/or (c) the model comprises parameters of a neural network. For example, the parameters may include values defining at least the following: (i) an interconnection pattern between different layers of neurons. (ii) weights of the interconnections, and (iii) activation functions that convert each neuron's weighted input to its output activation. Optionally, the computer provides the feature values as inputs to the neural network computes the values of the various activation functions and propagates values between layers, and obtains an output from the network, which is the value indicative of the physiological response.

A user interface (UI) may be utilized, in some embodiments, to notify the user and/or some other entity, such as a caregiver, about the physiological response and/or present an alert responsive to an indication that the extent of the physiological response reaches a threshold. The UI may include a screen to display the notification and/or alert, a speaker to play an audio notification, a tactile UI, and/or a vibrating UI. In some embodiments. "alerting" about a physiological response of a user refers to informing about one or more of the following: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or anger reaching a predetermined level).

FIG. 19 illustrates a scenario in which an alert regarding a possible stroke is issued. The figure illustrates a user wearing a frame with at least two CAMs (562 and 563) for measuring ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a VCAM provides additional data in the form of images that may help detecting the stroke.

The CAMs can take respiratory-related thermal measurements when their ROIs are on the user's upper lip, the user's mouth, the space where the exhale stream form the user's nose flows, and/or the space where the exhale stream from the user's mouth flows. In some embodiments, one or more of the following respiratory parameters may be calculated based on the respiratory-related thermal measurements taken during a certain period of time:

"Breathing rate" represents the number of breaths per minute the user took during the certain period. The breathing rate may also be formulated as the average time between successive inhales and/or the average between successive exhales.

"Respiration volume" represents the volume of air breathed over a certain duration (usually per minute), the volume of air breathed during a certain breath, tidal volume, and/or the ratio between two or more breaths. For example, the respiration volume may indicate that a first breath was deeper than a second breath, or that breaths during a first minute were shallower than breaths during a second minute.

"Mouth breathing vs nasal breathing" indicates whether during the certain period the user breathed mainly through the mouth (a state characterized as "mouth breathing") or mainly through the nose (a state characterized as "nose breathing" or "nasal breathing"). Optionally, this parameter may represent the ratio between nasal and mouth breathing, such as a proportion of the certain period during which the breathing was more mouth breathing, and/or the relative volume of air exhaled through the nose vs the mouth. In one example, breathing mainly through the mouth refers to inhaling more than 50% of the air through the mouth (and less than 50% of the air through the nose).

"Exhale duration/Inhale duration" represents the exhale (s) duration during the certain period, the inhale(s) duration during the certain period, and/or a ratio of the two aforementioned durations. Optionally, this respiratory parameter may represent one or more of the following: (i) the average duration of the exhales and/or inhales. (ii) a maximum and/or minimum duration of the exhales and/or inhales during the certain period, and (iii) a proportion of times in which the duration of exhaling and/or inhaling reached a certain threshold.

"Post-exhale breathing pause" represents the time that elapses between when the user finishes exhaling and starts inhaling again. "Post-inhale breathing pause" represents the time that elapses between when the user finishes inhaling and when the user starts exhaling after that. The post exhale/inhale breathing pauses may be formulated utilizing various statistics, such as an average post exhale/inhale breathing pause during a certain period, a maximum or minimum duration of post exhale/inhale breathing pause during the certain period, and/or a proportion of times in which the duration of post exhale/inhale breathing pause reached a certain threshold.

"Dominant nostril" is the nostril through which most of the air is exhaled (when exhaling through the nose). Normally the dominant nostril changes during the day, and the exhale is considered balanced when the amount of air exhaled through each nostril is similar. Optionally, the breathing may be considered balanced when the difference between the volumes of air exhaled through the right and left nostrils is below a predetermined threshold, such as 20% or 10%. Additionally or alternatively, the breathing may be considered balanced during a certain duration around the middle of the switching from right to left or left to right nostril dominance. For example, the certain duration of balanced breathing may be about 4 minutes at the middle of the switching between dominant nostrils.

"Temperature of the exhale stream" may be measured based on thermal measurements of the stream that flows from one or both nostrils, and/or the heat pattern generated on the upper lip by the exhale stream from the nose. In one example, it is not necessary to measure the exact temperature of the exhale stream as long as the system is able to differentiate between different temperatures of the exhale stream based on the differences between series of thermal measurements taken at different times. Optionally, the series of thermal measurements that are compared are temperature measurements received from the same pixel(s) of a head-mounted thermal camera.

"Shape of the exhale stream" (also referred to as "SHAPE") represents the three-dimensional (3D) shape of the exhale stream from at least one of the nostrils. The SHAPE changes during the day and may reflect the mental, physiological, and/or energetic state of a user. Usually the temperature of the exhale stream is different from the temperature of the air in the environment; this enables a thermal camera, which captures a portion of the volume through which the exhale stream flows, to take a measurement indicative of the SHAPE, and/or to differentiate between different shapes of the exhale stream (SHAPEs). Additionally, the temperature of the exhale stream is usually different from the temperature of the upper lip, and thus exhale streams having different shapes may generate different thermal patterns on the upper lip. Measuring these different thermal patterns on the upper lip may enable a computer to differentiate between different SHAPEs. In one embodiment, differences between values measured by adjacent thermal pixels of CAM, which measure the exhale stream and/or the upper lip over different time intervals, may correspond to different SHAPEs. In one example, it is not necessary to measure the exact SHAPE as long as it is possible to differentiate between different SHAPEs based on the differences between the values of the adjacent thermal pixels. In another embodiment, differences between average values, measured by the same thermal pixel over different time intervals, may correspond to different SHAPEs. In still another embodiment, the air that is within certain boundaries of a 3D shape that protrudes from the user's nose, which is warmer than the environment air, as measured by CAM, is considered to belong to the exhale stream.

In one embodiment, the SHAPE may be represented by one or more thermal images taken by one or more CAMs. In this embodiment, the shape may correspond to a certain pattern in the one or more images and/or a time series describing a changing pattern in multiple images. In another embodiment, the SHAPE may be represented by at least one of the following parameters: the angle from which the exhale stream blows from a nostril, the width of the exhale stream, the length of the exhale stream, and other parameters that are indicative of the 3D SHAPE. Optionally, the SHAPE may be defined by the shape of a geometric body that confines it, such as a cone or a cylinder, protruding from the user's nose. For example, the SHAPE may be represented by parameters such as the cone's height, the radius of the cone's base, and/or the angle between the cone's altitude axis and the nostril.

"Smoothness of the exhale stream" represents a level of smoothness of the exhale stream from the nose and/or the mouth. In one embodiment, the smoothness of the exhale stream is a value that can be determined based on observing the smoothness of a graph of the respiratory-related thermal measurements. Optionally, it is unnecessary for the system to measure the exact smoothness of the exhale stream as long as it is able to differentiate between smoothness levels of respiratory-related thermal measurements taken at different times. Optionally, the compared thermal measurements taken at different times may be measured by the same pixels and/or by different pixels. As a rule of thumb, the smoother the exhale stream, the lower the stress and the better the physical condition. For example, the exhale stream of a healthy young person is often smoother than the exhale stream of an elderly person, who may even experience short pauses in the act of exhaling.

There are well known mathematical methods to calculate the smoothness of a graph, such as Fourier transform analysis, polynomial fit differentiability classes, multivariate differentiability classes, parametric continuity, and/or geometric continuity. In one example, the smoothness of $TH_{ROI}$ indicative of the exhale stream is calculated based on a Fourier transform of a series of $TH_{ROI}$. In the case of Fourier transform, the smaller the power of the high-frequencies portion, the smoother the exhale is, and vice versa. Optionally, one or more predetermined thresholds differentiate between the high-frequency and low-frequency portions in the frequency domain. In another example, the smoothness of $TH_{ROI}$ indicative of the exhale stream is calculated using a polynomial fit (with a bounded degree) of a series of $TH_{ROI}$. Optionally, the degree of the polynomial used for the fit is proportional (e.g., linear) to the number of exhales in the time series. In the case of polynomial fit, the smoothness may be a measure of the goodness of fit between the series of $TH_{ROI}$ and the polynomial. For example, the lower the squared error, the smoother the graph is considered. In still another embodiment, the smoothness of $TH_{ROI}$ indicative of the exhale stream may be calculated using a machine learning-based model trained with training data comprising reference time series of $TH_{ROI}$ for which the extent of smoothness is known.

In an alternative embodiment, a microphone is used to measure the exhale sounds. The smoothness of the exhale stream may be a value that is proportional to the smoothness of the audio measurement time series taken by the microphone (e.g., as determined based on the power of the high-frequency portion obtained in a Fourier transform of the time series of the audio).

There are various approaches that may be employed in order to calculate values of one or more of the respiratory parameters mentioned above based on respiratory-related thermal measurements. Optionally, calculating the values of one or more of the respiratory parameters may be based on additional inputs, such as statistics about the user (e.g., age, gender, weight, height, and the like), indications about the user's activity level (e.g., input from a pedometer), and/or physiological signals of the user (e.g., heart rate and respiratory rate). Roughly speaking, some approaches may be considered analytical approaches, while other approaches may involve utilization of a machine learning-based model.

In some embodiments, one or more of the respiratory parameters mentioned above may be calculated based on the respiratory-related thermal measurements by observing differences in thermal measurements. In one embodiment, certain pixels that have alternating temperature changes may be identified as corresponding to exhale streams. In this embodiment, the breathing rate may be a calculated frequency of the alternating temperature changes at the certain pixels. In another embodiment, the relative difference in magnitude of temperature changes at different ROIs, such as the alternating temperature changes that correspond to breathing activity, may be used to characterize different types of breathing. For example, if temperature changes at ROI near the nostrils reach a first threshold, while temperature changes at an ROI related to the mouth do not reach a second threshold, then the breathing may be considered nasal breathing; while if the opposite occurs, the breathing may be considered mouth breathing. In another example, if temperature changes at an ROI near the left nostril and/or on the left side of the upper lip are higher than temperature changes at an ROI near the right nostril and/or on the right side of the upper lip, then the left nostril may be considered the dominant nostril at the time the measurements were taken. In still another example, the value of a respiratory parameter may be calculated as a function of one or more input values from among the respiratory-related thermal measurements.

In other embodiments, one or more of the respiratory parameters may be calculated by generating feature values based on the respiratory-related thermal measurements and utilizing a model to calculate, based on the feature values, the value of a certain respiratory parameter from among the parameters mentioned above. The model for the certain respiratory parameter is trained based on samples. Each sample comprises the feature values based on respiratory-related thermal measurements, taken during a certain period of time, and a label indicative of the value of the certain respiratory parameter during the certain period of time. For example, the feature values generated for a sample may include the values of pixels measured by the one or more cameras, statistics of the values of the pixels, and/or functions of differences of values of pixels at different times. Additionally or alternatively, some of the feature values may include various low-level image analysis features, such as feature derived using Gabor filters, local binary patterns and their derivatives, features derived using algorithms such as SIFT, SURF, and/or ORB, image keypoints, HOG descriptors and features derived using PCA or LDA. The labels of the samples may be obtained through various ways. Some examples of approaches for generating the labels include manual reporting (e.g., a user notes the type of his/her breathing), manual analysis of thermal images (e.g., an expert determines a shape of an exhale stream), and/or utilizing sensors (e.g., a chest strap that measures the breathing rate and volume).

Training the model for the certain respiratory parameter based on the samples may involve utilizing one or more machine learning-based training algorithms, such as a training algorithm for a decision tree, a regression model, or a neural network. Once the model is trained, it may be utilized to calculate the value of the certain respiratory parameter based on feature values generated based on respiratory-related thermal measurements taken during a certain period, for which the label (i.e., the value of the certain respiratory parameter) may not be known.

In one embodiment, a system configured to calculate a respiratory parameter includes an inward-facing head-mounted thermal camera (CAM) and a computer. CAM is worn on a user's head and takes thermal measurements of a region below the nostrils ($TH_{ROI}$), where $TH_{ROI}$ are indicative of the exhale stream. The "region below the nostrils", which is indicative of the exhale stream, refers to one or more regions on the upper lip, the mouth, and/or air volume (s) through which the exhale streams from the nose and/or mouth flow. The flowing of the typically warm air of the exhale stream can change the temperature at the one or more regions, and thus thermal measurements of these one or more regions can provide information about properties of the exhale stream. The computer (i) generates feature values based on $TH_{ROI}$, and (ii) utilizes a model to calculate the respiratory parameter based on the feature values. The respiratory parameter may be indicative of the user's breathing rate, and the model may be trained based on previous $TH_{ROI}$ of the user taken during different days. FIG. 34*b* illustrates one embodiment of a system for calculating a respiratory parameter. The system includes a computer 445 and CAM that is coupled to the eyeglasses frame worn by the user 420 and provides $TH_{ROI}$ 443.

The computer 445 generates feature values based on $TH_{ROI}$ 443, and possibly other sources of data. Then the computer utilizes a model 442 to calculate, based on the feature values, a value 447 of the respiratory parameter. The value 447 may be indicative of at least one of the following: breathing rate, respiration volume, whether the user is breathing mainly through the mouth or through the nose, exhale (inhale) duration, post-exhale (post-inhale) breathing pause, a dominant nostril a shape of the exhale stream, smoothness of the exhale stream, and/or temperature of the exhale stream. Optionally, the respiratory parameters calculated by the computer 445 may be indicative of the respiration volume. Optionally, the value 447 is stored (e.g., for life-logging purposes) and/or forwarded to a software agent operating on behalf of the user (e.g., in order for the software agent to make a decision regarding the user).

The feature values generated by the computer 445 may include any of the feature values described in this disclosure that are utilized to detect a physiological response. Optionally, the thermal measurements may undergo various forms of filtering and/or normalization. For example, the feature values generated based on $TH_{ROI}$ may include: time series data comprising values measured by CAM, average values of certain pixels of CAM, and/or values measured at certain times by the certain pixels. Additionally, the feature values may include values generated based on additional measurements of the user taken by one or more additional sensors (e.g., measurements of heart rate, heart rate variability, brainwave activity, galvanic skin response, muscle activity, and/or an extent of movement). Additionally or alternatively, at least some of the feature values may include measurements of the environment in which the user is in, and/or confounding factors that may interfere with the detection.

A user interface (UT) 448 may be utilized to present the value 447 of the respiratory parameter and/or present an alert (e.g., to the user 420 and/or to a caregiver). In one example, UI 448 may be used to alert responsive to an indication that the value 447 reaches a threshold (e.g., when the breathing rate exceeds a certain value and/or after the user 420 spent a certain duration mouth breathing instead of nasal breathing). In another example, UI 448 may be used to alert responsive to detecting that the probability of a respiratory-related attack reaches a threshold.

In one embodiment, the value 447 may be indicative of the smoothness of the exhale stream. Optionally, the value 447 may be presented to the user 420 to increase the user's awareness to the smoothness of his/her exhale stream. Optionally, responsive to detecting that the smoothness is below a predetermined threshold, the computer 445 may issue an alert for the user 420 (e.g., via the UI 448) in order to increase the user's awareness to the user's breathing.

The model 442 is trained on data that includes previous $TH_{ROI}$ of the user 420 and possibly other users. Optionally, the previous measurements were taken on different days and/or over a period longer than a week. Training the model 442 typically involves generating samples based on the previous $TH_{ROI}$ and corresponding labels indicative of values of the respiratory parameter. The labels may come from different sources. In one embodiment, one or more of the labels may be generated using a sensor that is not a thermal camera, which may or may not be physically coupled to a frame worn by the user. The sensor's measurements may be analyzed by a human expert and/or a software program in order to generate the labels. In one example, the sensor is part of a smart shirt and/or chest strap that measures various respiratory (and other) parameters, such as Hexoskin™ smart shirt. In another embodiment, one or more of the labels may come from an external source such as an entity that observes the user, which may be a human observer or a software program. In yet another embodiment, one or more of the labels may be provided by the user, for example by indicating whether he/she is breathing through the mouth or nose and/or which nostril is dominant.

The samples used to train the model 442 usually include samples corresponding to different values of the respiratory parameter. In some embodiments, the samples used to train the model 442 include samples generated based on $TH_{ROI}$ taken at different times of the day, while being at different locations, and/or while conducting different activities. In one example, the samples are generated based on $TH_{ROI}$ taken in the morning and $TH_{ROI}$ taken in the evening. In another example, the samples are generated based on $TH_{ROI}$ of a user taken while being indoors, and $TH_{ROI}$ of the user taken while being outdoors. In yet another example, the samples are generated based on $TH_{ROI}$ taken while a user was sitting down, and $TH_{ROI}$ taken while the user was walking, running, and/or engaging in physical exercise (e.g., dancing, biking, etc.).

Additionally or alternatively, the samples used to train the model 442 may be generated based on $TH_{ROI}$ taken while various environmental conditions persisted. For example, the samples include first and second samples generated based on $TH_{ROI}$ taken while the environment had first and second temperatures, with the first temperature being at least 10° C. warmer than the second temperature. In another example, the samples include samples generated based on measurements taken while there were different extents of direct sunlight and/or different extents of wind blowing.

Various computational approaches may be utilized to train the model 442 based on the samples described above. In one example, training the model 442 may involve selecting a threshold based on the samples. Optionally, if a certain feature value reaches the threshold then a certain respiratory condition is detected (e.g., unsmooth breathing). Optionally, the model 442 includes a value describing the threshold. In another example, a machine learning-based training algorithm may be utilized to train the model 442 based on the samples. Optionally, the model 442 includes parameters of at least one of the following types of models: a regression model, a neural network, a nearest neighbor model, a support vector machine, a support vector machine for regression, a naïve Bayes model, a Bayes network, and a decision tree.

In some embodiments, a deep learning algorithm may be used to train the model 442. In one example, the model 442 may include parameters describing multiple hidden layers of a neural network. In one embodiment, when $TH_{ROI}$ include measurements of multiple pixels, the model 442 may include a convolution neural network (CNN). In one example, the CNN may be utilized to identify certain patterns in the thermal images, such as patterns of temperatures in the region of the exhale stream that may be indicative of a respiratory parameter, which involve aspects such as the location, direction, size, and/or shape of an exhale stream from the nose and/or mouth. In another example, calculating a value of a respiratory parameter, such as the breathing rate, may be done based on multiple, possibly successive, thermal measurements. Optionally, calculating values of the respiratory parameter based on thermal measurements may involve retaining state information that is based on previous measurements. Optionally, the model 442 may include parameters that describe an architecture that supports such a capability. In one example, the model 442 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using bidirectional recurrent neural network architecture (BRNN).

The computer 445 may detect a respiratory-related attack (such as an asthma attack, an epileptic attack, an anxiety attack a panic attack, and a tantrum) based on feature values generated based on $TH_{ROI}$ 443. The computer 445 may further receive additional inputs (such as indications of consuming a substance, a situation of the user, and/or thermal measurements of the forehead), and detect the respiratory-related attack based on the additional inputs. For example, the computer 445 may generate one or more of the feature values used to calculate the value 447 based on the additional inputs.

In a first embodiment, the computer 445 utilizes an indication of consumption of a substance to detect a respiratory-related attack. Optionally, the model 442 is trained based on: a first set of $TH_{ROI}$ taken while the user experienced a respiratory-related attack after consuming the substance, and a second set of $TH_{ROI}$ taken while the user did not experience a respiratory-related attack after consuming the substance. The duration to which "after consuming" refers depends on the substance and may last from minutes to hours. Optionally, the consuming of the substance involves consuming a certain drug and/or consuming a certain food item, and the indication is indicative of the time and/or the amount consumed.

In a second embodiment, the computer 445 utilizes an indication of a situation of the user to detect a respiratory-related attack. Optionally, the model 442 is trained based on: a first set of $TH_{ROI}$ taken while the user was in the situation and experienced a respiratory-related attack, and a second set of $TH_{ROI}$ taken while the user was in the situation and did not experience a respiratory-related attack. Optionally, the situation involves (i) interacting with a certain person, (ii) a type of activity the user is conducting, selected from at least two different types of activities associated with different levels of stress, and/or (iii) a type of activity the user is about to conduct (e.g., within thirty minutes), selected from at least two different types of activities associated with different levels of stress.

In a third embodiment, the system includes another CAM that takes thermal measurements of a region on the forehead ($TH_F$) of the user, and the computer 445 detects a respiratory related attack based on $TH_{ROI}$ and $TH_F$. For example, $TH_{ROI}$ and $TH_F$ may be utilized to generate one or more of the feature values used to calculate the value indicative of the probability that the user is experiencing, or is about to experience, the respiratory-related attack. Optionally, the model 442 was trained based on a first set of $TH_{ROI}$ and $TH_F$ taken while the user experienced a respiratory-related attack, and a second set of $TH_{ROI}$ and $TH_F$ taken while the user did not experience a respiratory-related attack.

The system may optionally include a sensor 435 that takes measurements $m_{move}$ 450 that are indicative of movements of the user 420: the system further detects the physiological response based on $m_{move}$ 450. The sensor 435 may include one or more of the following sensors: a gyroscope and/or an accelerometer, an outward-facing visible-light camera (that feeds an image processing algorithm to detect movement from a series of images), a miniature radar (such as low-power radar operating in the range between 30 GHz and 3,000 GHz), a miniature active electro-optics distance measurement device (such as a miniature Lidar), and/or a triangulation wireless device (such as a GPS receiver). Optionally, the sensor 435 is physically coupled to the frame or belongs to a device carried by the user (e.g., a smartphone or a smartwatch).

In a first embodiment, the computer 445 may detect the respiratory-related attack if the value 447 of the respiratory parameter reaches a first threshold, while $m_{move}$ 450 do not reach a second threshold. In one example, reaching the first threshold indicates a high breathing rate, which may be considered too high for the user. Additionally, in this example, reaching the second threshold may mean that the user is conducting arduous physical activity. Thus, if the user is breathing too fast and this is not because of physical activity, then the computer 445 detects this as an occurrence of a respiratory-related attack (e.g., an asthma attack or a panic attack).

In a second embodiment, the computer 445 may generate feature values based on $m_{move}$ 450 in addition to $TH_{ROI}$ 443, and utilize an extended model to calculate, based on these feature values, a value indicative of the probability that the user is experiencing, or is about to experience, the respiratory related attack. In one example, the feature values used along with the extended model (which may be the model 442 or another model) include one or more of the following: (i) values comprised in $TH_{ROI}$ 443, (ii) values of a respiratory parameter of the user 420, which are generated based on $TH_{ROI}$ 443 (iii) values generated based on additional measurements of the user 420 (e.g., measurements of heart rate, heart rate variability, brainwave activity, galvanic skin response, muscle activity, and an extent of movement). (iv) measurements of the environment in which the user 420 was in while $TH_{ROI}$ 443 were taken. (v) indications of various occurrences which may be considered confounding factors (e.g., touching the face, thermal radiation directed at the face, or airflow directed at the face), and/or (vi) values indicative of movements of the user (which are based on $m_{move}$ 450).

The extended model is trained on samples generated from prior $m_{move}$ and $TH_{ROI}$, and corresponding labels indicating times of having the respiratory-related attack. The labels may come from various sources, such as measurements of the user (e.g., to detect respiratory distress), observations by a human and/or software, and/or the indications may be self-reported by the user. The samples used to train the extended model may be generated based on measurements taken over different days, and encompass measurements taken when the user was in different situations.

Usually the exhaled air warms up the skin below the nostrils, and during inhale the skin below the nostrils cools. This enables the system to identify the exhale based on measuring an increase in the temperature of the skin below the nostrils an inhale, and identify the inhale based on measuring a decrease in the temperature of the skin below the nostrils.

Synchronizing a physical effort with the breathing is highly recommended by therapists and sport instructors. For example, some elderly and/or unfit people can find it difficult to stand up and/or make other physical efforts because many of them do not exhale while making the effort, and/or do not synchronize the physical effort with their breathing. These people can benefit from a system that reminds them to exhale while making the effort, and/or helps them synchronize the physical effort with their breathing. As another example, in many kinds of physical activities it is highly recommended to exhale while making a physical effort and/or exhale during certain movements (such as exhale while bending down in Uttanasana).

In one embodiment, the computer 445 determines based on $m_{move}$ 450 and $TH_{ROI}$ 443 whether the user exhaled while making a physical effort above a predetermined threshold. Optionally, the computer receives a first indication that the user is making or is about to make the physical effort, commands a user interface (UI) to suggest the user to exhale while making the physical effort, and commands the UI to play a positive feedback in response to determining that the user managed to exhale while making the physical effort. Additionally, the computer may further command the UI to play an explanation why the user should try next time to exhale while making the physical effort in response to determining that the user did not exhale while making the physical effort.

FIG. 24a to FIG. 25c illustrate how the system described above may help train an elderly user to exhale during effort. In FIG. 24a the system identifies that the user inhaled rather than exhaled while getting up from a sitting position in a chair, the system alerts the user about this finding and suggests that next time the user should exhale while getting up. In FIG. 24b, the system identifies that the user exhaled at the correct time and commends the user on doing so. Examples of physical efforts include standing up, sitting down, manipulating with the hands an item that requires applying a significant force, defecating, dressing, leaning over, and/or lifting an item.

In FIG. 25a the system identifies that the user inhaled rather than exhaled while bending down to the dishwasher, and presents a thumbs-down signal (e.g., on the user's smartphone). In FIG. 25b the system identifies that the user exhaled while bending down to the dishwasher, and presents a thumbs-up signal. In FIG. 25c illustrates a smartphone app for counting the thumbs-up and thumbs-down signals identified during a day. The app may show various statistics, such as thumbs-up/thumbs-down during the past week, from start training with the app, according to locations the user is, while being with certain people, and/or organized according to types of exercises (such as a first counter for yoga, a second counter for housework, and a third counter for breathing during work time).

Figure 26A:
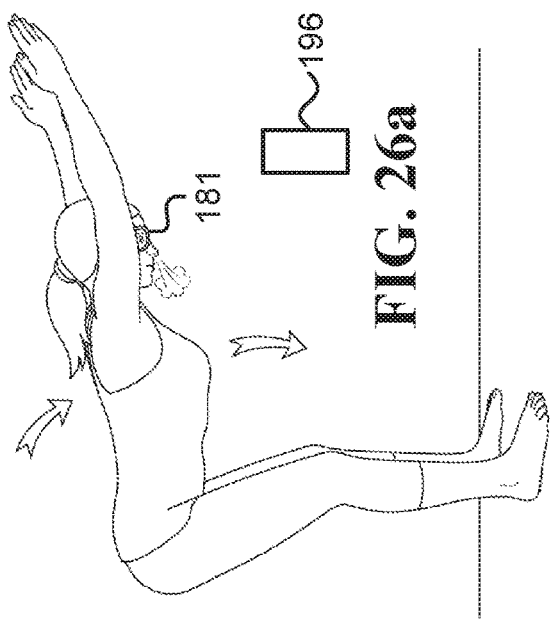
FIG. 26a and FIG. 26b illustrate a fitness app running on smartphone, which instructs the user to exhale while bending down and to inhale while straightening up.
Figure 26B:
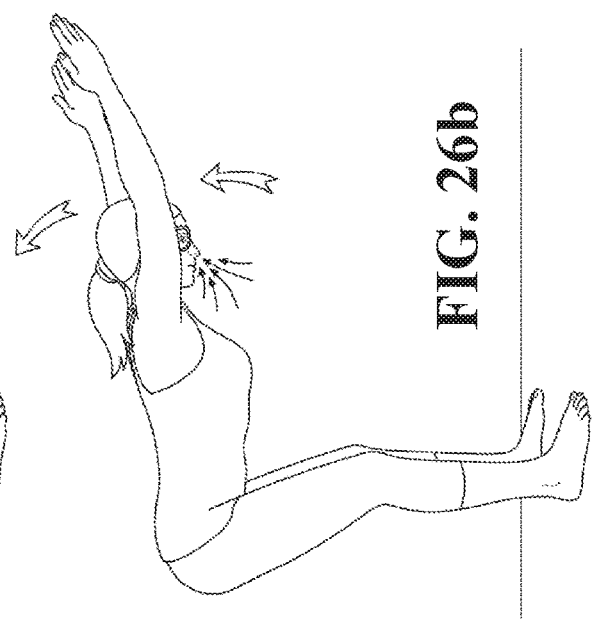

In one embodiment, the computer 445: (i) receives from a fitness app (also known as a personal trainer app) an indication that the user should exhale while making a movement, (ii) determines, based on $m_{move}$, when the user is making the movement, and (iii) determines, based on $TH_{ROI}$, whether the user exhaled while making the movement. Optionally, the computer commands the UI to (i) play a positive feedback in response to determining that the user managed to exhale while making the physical effort, and/or (ii) play an alert and/or an explanation why the user should try next time to exhale while making the physical effort in response to determining that the user did not exhale while making the physical effort. FIG. 26a illustrates a fitness app running on smartphone 196, which instructs the user to exhale while bending down. CAM coupled to eyeglasses frame 181 measures the user breathing and is utilized by the fitness app that helps the user to exhale correctly. FIG. 26b illustrates instructing the user to inhale while straightening up.

Figure 27:
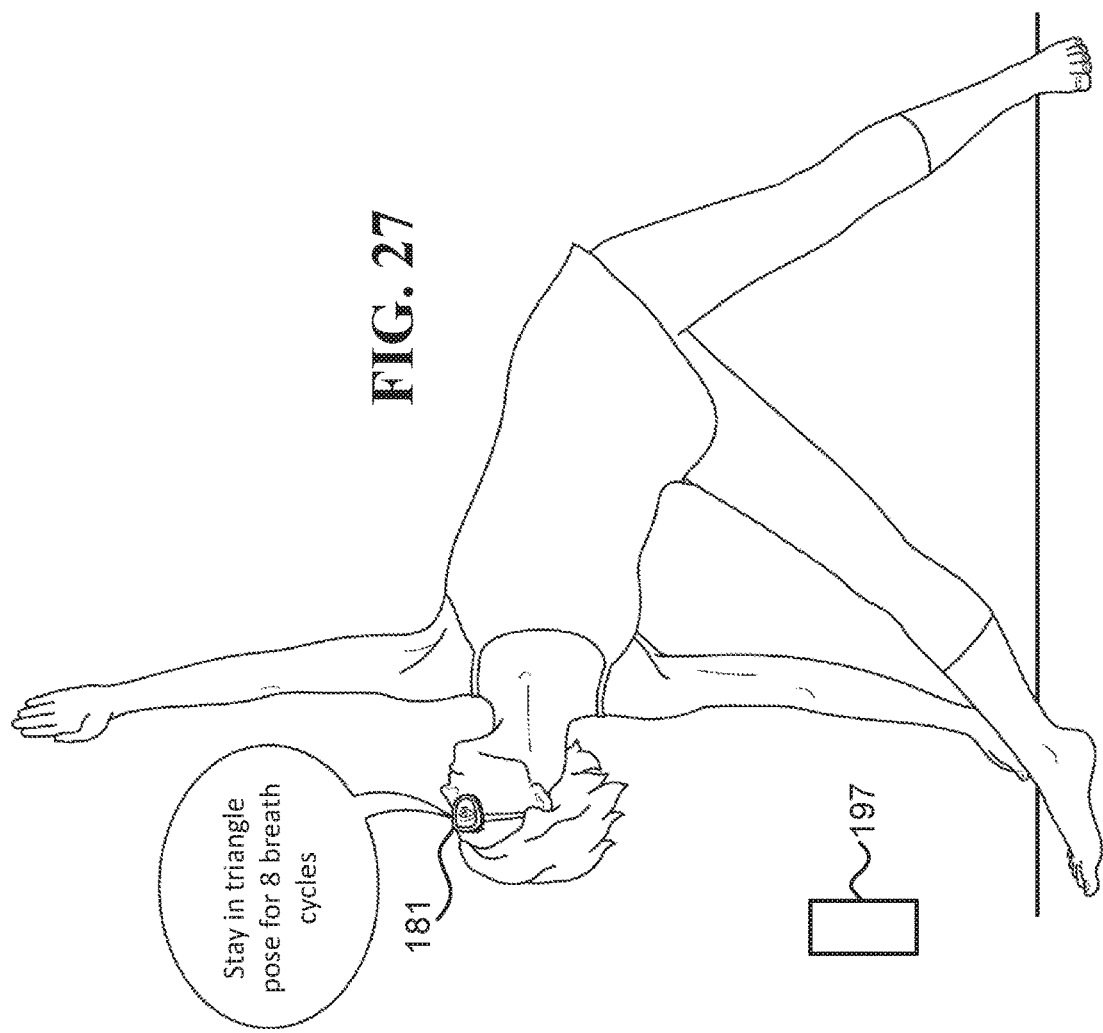
FIG. 27 illustrates a fitness app running on smartphone, which instructs the user to stay in a triangle pose for 8 breath cycles.

In another embodiment, the computer 445: (i) receives from a fitness app a certain number of breath cycles during which the user should perform a physical exercise, such as keeping a static yoga pose for a certain number of breath cycles, or riding a spin bike at a certain speed for a certain number of breath cycles. (ii) determines, based on $m_{move}$, when the user performs the physical exercise, and (iii) counts, based on $TH_{ROI}$, the number of breath cycles the user had while performing the physical exercise. Optionally, the computer commands the UI to play an instruction switch to another physical exercise responsive to detecting that the user performed the physical exercise for the certain number of breath cycles. Additionally or alternatively, the computer commands the UI to play a feedback that refers to the number of counted breath cycles responsive to detecting that the user performed the physical exercise for a number of breath cycles that is lower than the certain number of breath cycles. FIG. 27 illustrates a fitness app running on smartphone 197, which instructs the user to stay in a triangle pose for 8 breath cycles. CAM coupled to eyeglasses frame 181 measures the breathing and is utilized by the fitness app that calculates the breath cycles and counts the time to stay in the triangle pose according to the measured breath cycles.

The duration of exhaling and inhaling (denoted herein $t_{exhale}$ and $t_{inhale}$, respectively) can have various physiological effects. For example, for some users, breathing with prolonged inhales (relative to the exhales) can increase the possibility of suffering an asthma attack. In particular, keeping the duration of exhaling longer than the duration of inhaling (i.e., $t_{exhale}/t_{inhale} \geq 1$, and preferably $t_{exhale}/t_{inhale} \geq 2$) may provide many benefits, such as having a calming effect and relieving asthma symptoms. In one embodiment, a computer is further configured to calculate, based on $TH_{ROI}$, the ratio between exhale and inhale durations ($t_{exhale}/t_{inhale}$).

Many people are not aware of their breathing most of the time. These people can benefit from a system that is able to calculate $t_{exhale}/t_{inhale}$ and provide them with feedback when it is beneficial to increase the ratio. In one embodiment, a computer suggests the user, via the UI, to increase $t_{exhale}/t_{inhale}$ when it falls below a threshold. Optionally, the computer updates occasionally the calculation of $t_{exhale}/t_{inhale}$, and suggests to progressively increase $t_{exhale}/t_{inhale}$ at least until reaching a ratio of 1.5. Optionally, the computer stops suggesting to the user to increase $t_{exhale}/t_{inhale}$ responsive to identifying that $t_{exhale}/t_{inhale} \geq 2$. In another embodiment, the computer is configured to: (i) receive a first indication that the user's stress level reaches a first threshold, (ii) identify, based on $TH_{ROI}$ that the ratio between exhaling and inhaling durations ($t_{exhale}/t_{inhale}$) is below a second threshold that is below 1.5, and (iii) command the UT to suggest to the user to prolong the exhale until $t_{exhale}/t_{inhale}$ reaches a third threshold that is at least 1.5.

Figure 30:
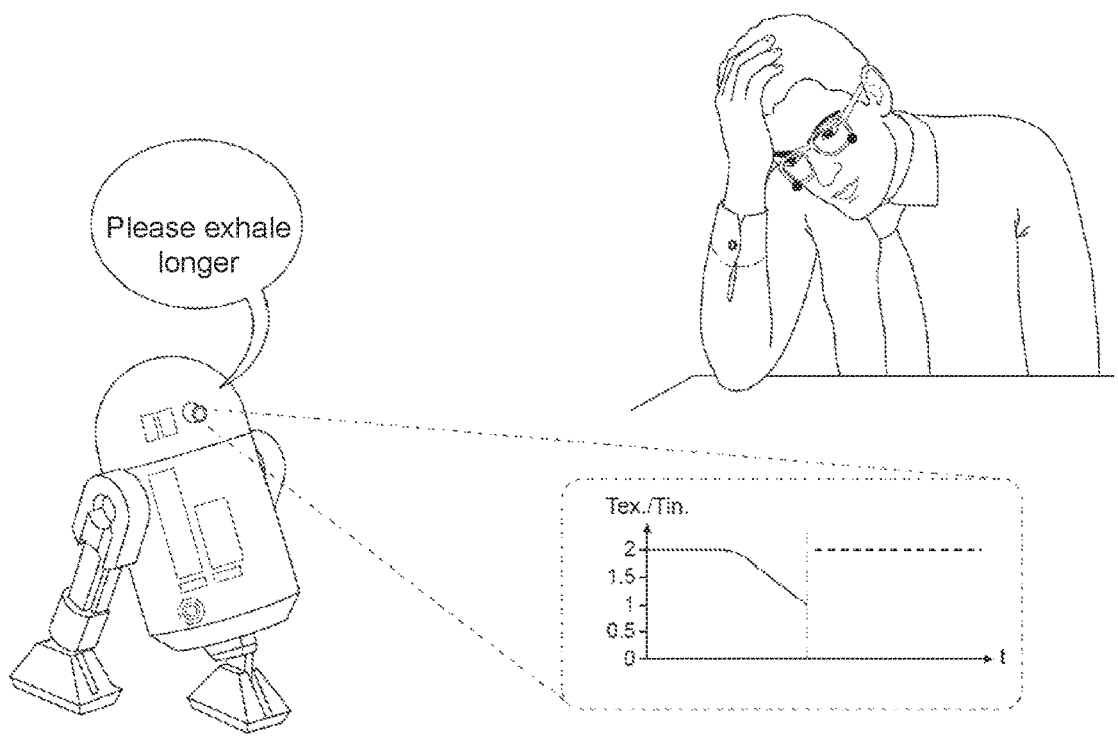
FIG. 30 illustrates a virtual robot that the user sees via augmented reality (AR), which urges the user to increase the ratio between the duration of the user's exhales and inhales.

FIG. 22 illustrates a situation in which an alert is issued to a user when it is detected that the ratio $t_{exhale}/t_{inhale}$ is too low. Another scenario in which such an alert may be issued to a user is illustrated in FIG. 30, which shows a virtual robot that the user sees via augmented reality (AR). The robot urges the user to increase the ratio between the duration of the user's exhales and inhales in order to alleviate the stress that builds up. Monitoring of respiratory parameters, and in particular, the ratio $t_{exhale}/t_{inhale}$ can help a user address a variety of respiratory-related symptoms, as described in the following examples.

Figure 31:
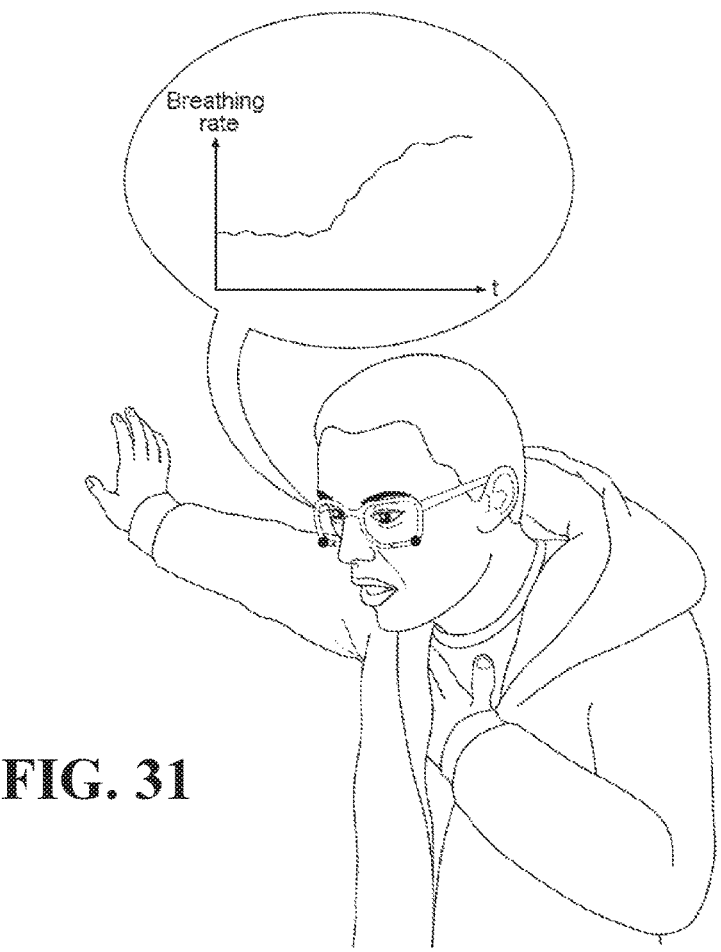
FIG. 31 illustrates an asthmatic patient who receives an alert that his breathing rate increased to an extent that often precedes an asthma attack.

Asthma attacks are related to a person's breathing. Identifying certain changes in respiratory parameters, such as breathing rate above a predetermined threshold, can help a computer to detect an asthma attack based on the thermal measurements. Optionally, the computer utilizes a model, which was trained on previous measurements of the user taken while the user had an asthma attack, to detect the asthma attack based on the thermal measurements. FIG. 31 illustrates an asthmatic patient who receives an alert (e.g., via an augmented reality display) that his breathing rate increased to an extent that often precedes an asthma attack. In addition to the breathing rate, the computer may base its determination that an asthma attack is imminent on additional factors, such as sounds and/or movement analysis as described below.

In a first embodiment, the computer may receive recordings of the user obtained with a microphone. Such recordings may include sounds that can indicate that an asthma attack is imminent, these sounds may include: asthmatic breathing sounds, asthma wheezing, and/or coughing. Optionally, the computer analyzes the recordings to identify occurrences of one or more of the above sounds. Optionally, taking into account the recordings of the user can affect how the computer issues alerts regarding an imminent asthma attack. For example, a first alert provided to the user in response to identifying the increase in the user's breathing rate above the predetermined threshold without identifying at least one of the body sounds may be less intense than a second alert provided to the user in response to identifying both the increase in the user's breathing rate above the predetermined threshold and at least one of the body sounds. Optionally, in the example above, the first alert may not be issued to the user at all.

In a second embodiment, the computer may receive measurements obtained from a movement sensor worn by the user and configured to measure user movements. Some movements that may be measured and may be related to an asthma attack include: spasms, shivering, and/or sagittal plane movements indicative of one or more of asthma wheezing, coughing, and/or chest tightness. Optionally, the computer analyzes the measurements of the movement sensor to identify occurrences of one or more of the above movements. Optionally, considering the measured movements can affect how the computer issues alerts regarding an imminent asthma attack. For example, a first alert provided to the user in response to identifying an increase in the user's breathing rate above a predetermined threshold, without measuring a movement related to an asthma attack, is less intense than a second alert provided to the user in response to identifying the increase in the user's breathing rate above the predetermined threshold while measuring a movement related to an asthma attack.

In some embodiments, a first alert may be considered less intense than a second alert if it is less likely to draw the user's attention. For example, the first alert may not involve a sound effect or involve a low-volume effect, while the second alert may involve a sound effect (which may be louder than the first's). In another example, the first alert may involve a weaker visual cue than the second alert (or no visual cue at all). Examples of visual cues include flashing lights on a device or images brought to the foreground on a display. In still another example, the first alert is not provided to the user and therefore does not draw the user's attention (while the second alert is provided to the user).

In one embodiment, responsive to a determination that an asthma attack is imminent, the UI suggests the user to take a precaution, such as increasing $t_{exhale}/t_{inhale}$, preforming various breathing exercises (e.g., exercises that involve holding the breath), and/or taking medication (e.g., medication administered using an inhaler), in order to decrease or prevent the severity of the imminent asthma attack. Optionally, detecting the signs of an imminent asthma attack includes identifying an increase in the breathing rate above a predetermined threshold.

Stress is also related to a person's breathing. In one embodiment, a computer receives a first indication that the user's stress level reaches a threshold and receives a second indication (i) that the ratio between exhaling and inhaling durations is below 1.5 ($t_{exhale}/t_{inhale}<1.5$), and/or (ii) that the user's breathing rate reached a predetermined threshold. Then the computer may command a UI to suggest the user to increase $t_{exhale}/t_{inhale}$ to at least 1.5. Optionally, the computer receives the first indication from a wearable device, calculates $t_{exhale}/t_{inhale}$ based on $TH_{ROI}$ (which is indicative of the exhale stream), and commands the UI to provide the user with an auditory and/or visual feedback indicative of the change in $t_{exhale}/t_{inhale}$ in response to the suggestion to increase the ratio. Optionally, the computer may command the UI to update the user about changes in the stress level in response to increasing $t_{exhale}/t_{inhale}$, and may provide positive reinforcement to help the user to maintain the required ratio at least until a certain improvement in the stress level is achieved.

FIG. 23 illustrates one embodiment of a system configured to collect thermal measurements related to respiration, in which four inward-facing head-mounted thermal cameras (CAMs) are coupled to the bottom of an eyeglasses frame 181. CAMs 182 and 185 are used to take thermal measurements of regions on the right and left sides of the upper lip (186 and 187, respectively), and CAMs 183 and 184 are used to take thermal measurements of a region on the user's mouth 188 and/or a volume protruding out of the user's mouth. At least some of the ROIs may overlap, which is illustrated as vertical lines in the overlapping areas. Optionally, one or more of the CAMs includes a microbolometer focal-plane array (FPA) sensor or a thermopile FPA sensor.

In one embodiment, a computer detects whether the user is breathing mainly through the mouth or through the nose based on measurements taken by CAMs 182, 183, 184 and 185. Optionally, the system helps the user to prefer breathing through the nose instead of breathing through the mouth by notifying the user when he/she is breathing through the mouth, and/or by notifying the user that the ratio between mouth breathing and nose breathing reaches a predetermined threshold. In one embodiment, the computer detects whether the user is breathing mainly through the right nostril or through the left nostril based on measurements taken by CAMs 182 and 185.

The system may further include an inward-facing head-mounted visible-light camera 189 to take images (IM) of a region on the nose and/or mouth, which are used to calculate a respiratory parameter (e.g., detect whether the user is breathing mainly through the mouth or through the nose, detect the inhale duration, and/or detect the post-inhale pause duration). In one embodiment, one or more feature values may be generated based on IM. The feature values may be generated using various image processing techniques and represent various low-level image properties. Some examples of such features may include features generated using Gabor filters, local binary patterns and their derivatives, features generated using algorithms such as SIFT. SURF, and/or ORB, and features generated using PCA or LDA. The one or more feature values may be utilized in the calculation of the respiratory parameter in addition to feature values generated based on the thermal measurements.

Figure 28:
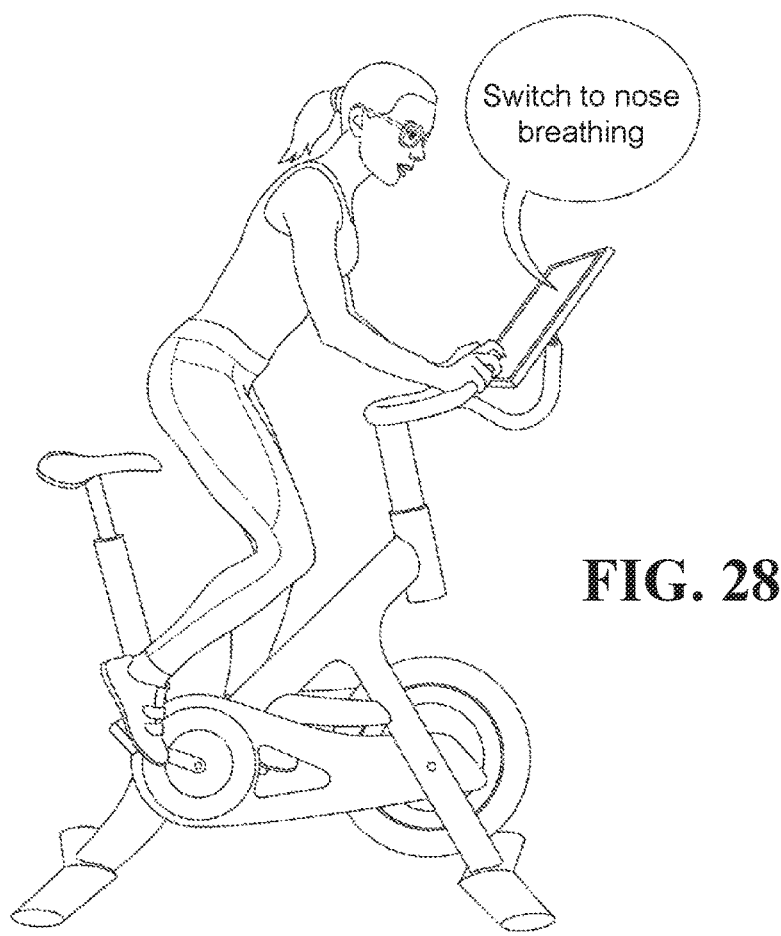
FIG. 28 illustrates notifying a user about mouth breathing and suggesting to breathe through the nose.
Figure 29:
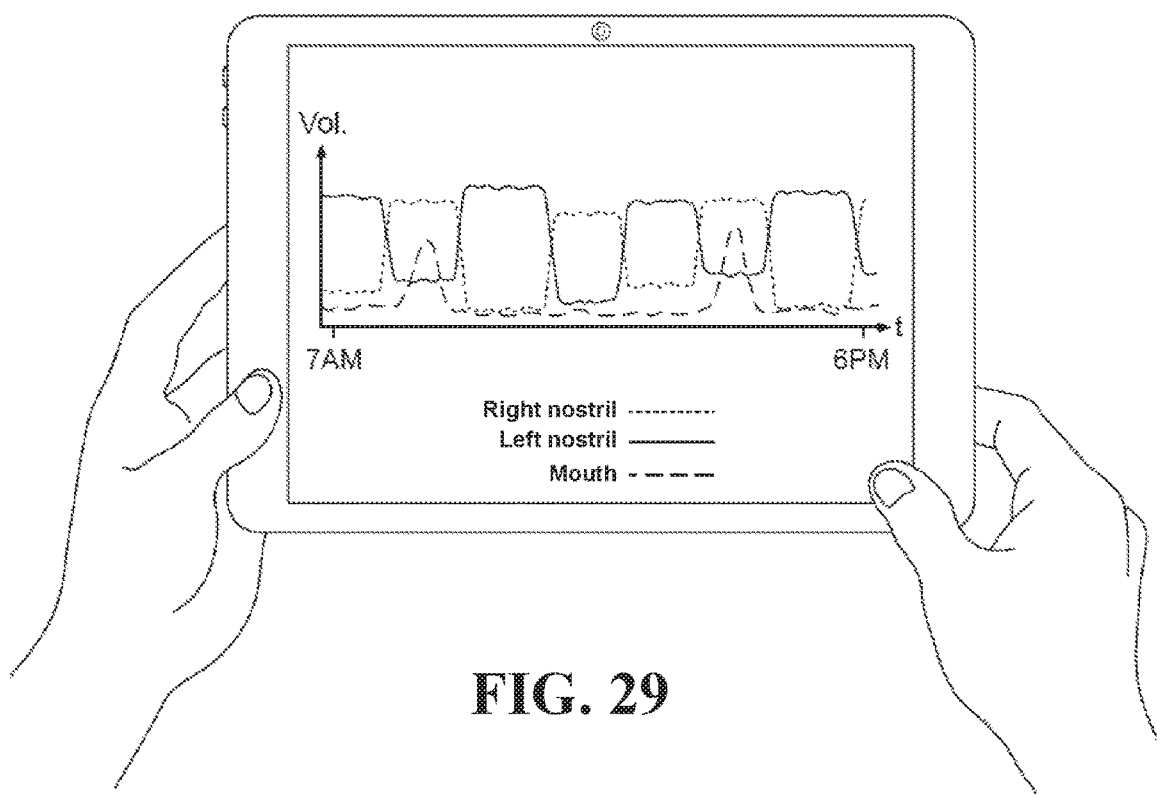
FIG. 29 illustrates an exemplary UI that shows statistics about the dominant nostril and mouth breathing during the day.

In one embodiment, the inward-facing head-mounted visible-light camera 189 takes images of a region on the user's mouth, and IM are indicative of whether the mouth is open or closed. A computer utilizes a model to detect, based on IM and $TH_{ROI}$ (such as the thermal measurements taken by at least one of CAMs 182-185), whether the user is breathing mainly through the mouth or through the nose. Optionally, the model was trained based on: a first set of $TH_{ROI}$ taken while IM was indicative that the mouth is open, and a second set of $TH_{ROI}$ taken while IM was indicative that the mouth is closed. Optionally, the system may help the user to prefer breathing through the nose instead of breathing through the mouth by notifying the user when he/she is breathing through the mouth, and/or by notifying the user that the ratio between mouth breathing and nose breathing reaches a predetermined threshold. FIG. 28 illustrates notifying the user that she breathes mainly through the mouth and should switch to breathing through the nose, while having a physical exercise such as spinning. FIG. 29 illustrates an exemplary UI that shows statistics about the dominant nostril and mouth breathing during the day.

In one embodiment, the inward-facing head-mounted visible-light camera 189 takes images of a region on the nose, and the computer identifies an inhale (and/or differentiates between an inhale and a breathing pause that follows the inhale) based on image processing of IM to detect movements of the nose, especially at the edges of the nostrils, which are indicative of inhaling.

FIG. 21 illustrates another embodiment of a system configured to collect thermal measurements related to respiration, in which four CAMs are coupled to a football helmet. CAMs 190 and 191 are used to take thermal measurements of regions on the right and left sides of the upper lip (appear as shaded regions on the users face), and CAMs 192 and 193 are used to take thermal measurements of a region on the user's mouth and/or a volume protruding out of the user's mouth. The illustrated CAMs are located outside of the exhale streams of the mouth and nostrils in order to maintain good measurement accuracy also when using thermal sensors such as thermopiles.

In some embodiments, the system further includes at least one in-the-ear earbud comprising a microphone to measure sounds inside the ear canal. A computer may identify an inhale based on analysis of the recordings from the earbud. Optionally, the inhale sounds measured by the earbud are stronger when the dominant nostril is the nostril closer to the ear in which the earbud is plugged in, compared to the inhale sounds measured by the earbud when the other nostril is the dominant nostril. Optionally, the computer detects whether the user is breathing mainly through the mouth or through the nose based on the thermal measurements and the sounds measured by the earbud. And then the system can help the user to prefer nasal breathing over mouth breathing by alerting the user when he/she breathes mainly through the mouth.

In some embodiments, the dominant nostril at a given time is the nostril through which most of the air is exhaled (with a closed mouth). Optionally, the dominant nostril is the nostril through which at least 70% of the air is exhaled. The different types of nostril dominance are illustrated in FIG. 32a to FIG. 32c. FIG. 32a is a schematic illustration of a left dominant nostril (note the significantly larger exhale stream from the left nostril). FIG. 32b is a schematic illustration of a right dominant nostril. And FIG. 32c is a schematic illustration of a balanced nasal breathing.

FIG. 33 is a schematic illustration of one embodiment of a system configured to identify the dominant nostril. The system includes at least one CAM 750, a computer 752, and an optional UI 754. CAM 750 may be similar to the CAMs in FIG. 23. CAM 750 takes thermal measurements of first and second ROIs below the right and left nostrils ($TH_{ROI1}$ and $TH_{ROI2}$, respectively) of the user. Optionally, each CAM does not occlude any of the user's mouth and nostrils. Optionally, each CAM is located less than 15 cm from the user's face and above the user's upper lip. Optionally, each CAM weighs below 10 g or below 2 g, aid utilizes microbolometer or thermopile sensors. Optionally, each CAM includes multiple sensing elements that are configured to take $TH_{ROI1}$ and/or $TH_{ROI2}$. In one example, each CAM includes at least 6 sensing elements, and each of $TH_{ROI1}$ and $TH_{ROI2}$ is based on measurements of at least 3 sensing elements. Optionally, the system includes a frame to which CAM is physically coupled.

In one embodiment, the at least one CAM includes at least first and second thermal cameras (CAM1 and CAM2, respectively) that take $TH_{ROI1}$ and $TH_{ROI2}$, respectively, located less than 15 cm from the user's face. CAM1 is physically coupled to the right half of the frame and captures the exhale stream from the right nostril better than it captures the exhale stream from the left nostril, and CAM2 is physically coupled to the left half of the frame and captures the exhale stream from the left nostril better than it captures the exhale stream from the right nostril.

The at least one CAM may be used to capture thermal measurements of various ROIs. In one embodiment, the first region of interest ($ROI_1$) includes a region on the right side of the user's upper lip, and the second region of interest ($ROI_2$) includes a region on the left side of the user's upper lip. In another embodiment, $ROI_1$ includes a portion of the volume of the air below the right nostril where the exhale stream from the right nostril flows and $ROI_2$ includes a portion of the volume of the air below the left nostril where the exhale stream from the left nostril flows. In yet another embodiment, the at least one CAM may take thermal measurements of a region on the mouth and/or a volume protruding out of the mouth ($TH_{ROI3}$) of the user, which is indicative of the exhale stream from the mouth, and the computer identifies the dominant nostril also based on $TH_{ROI3}$. Optionally, the computer may utilize $TH_{ROI3}$ similarly to how it utilizes $TH_{ROI1}$ and $TH_{ROI2}$ to identify the dominant nostril (e.g., the computer may generate feature values based on $TH_{ROI3}$, as discussed below).

The computer identifies the dominant nostril based on $TH_{ROI1}$ and $TH_{ROI2}$ (and possibly other data such as $TH_{ROI3}$), which were taken during a certain duration. Optionally, the certain duration is longer than at least one of the following durations: a duration of one exhale, a duration of one or more breathing cycles, a half a minute, a minute, and five minutes.

In one embodiment, the computer utilizes a model to identify the dominant nostril. Optionally, the model was trained based on previous $TH_{ROI1}$, $TH_{ROI2}$, and indications indicative of which of the nostrils was dominant while the previous $TH_{ROI1}$ and $TH_{ROI2}$ were taken. In one example, the computer generates feature values based on $TH_{ROI1}$ and $TH_{ROI2}$ (and optionally $TH_{ROI3}$), and utilizes the model to calculate, based on the feature values, a value indicative of which of the nostrils is dominant.

In one embodiment, the computer identifies whether the user's breathing may be considered balanced breathing. Optionally, breathing is considered balanced breathing when the streams through the right and the left nostrils are essentially equal, such as when the extent of air exhaled through the left nostril is 40% to 60% of the total of the air exhaled through the nose. Balanced breathing of a normal healthy human usually lasts 1-4 minutes during the time of switching between the dominant nostrils. Optionally, the computer notifies the user when the user's breathing is balanced. Optionally, the computer suggests to the user, via a UI, to meditate during the balanced breathing.

The total time the different nostrils remain dominant may be indicative of various medical conditions. In one embodiment, when there is a significant imbalance of the daily total time of left nostril dominance compared to total time of right nostril dominance, and especially if this condition continues for two or more days (and is significantly different from the user's average statistics), it may be an indication of an approaching health problem. For example, when the total time of left nostril dominance is greater than the total time of right nostril dominance, the approaching problem may be more mentally related than physically related; and when the total time of right nostril dominance is greater than the total time of left nostril dominance, the approaching problem may be more physically related than mentally related. In another embodiment, a greater extent of left nostril dominance is related to digestion problems, inner gas, diarrhea, and male impotence; and a greater extent of right nostril dominance may be related to high blood pressure, acid reflux, and ulcers.

In one embodiment, the computer monitors nostril dominance over a certain period, and issues an alert when at least one of the following occurs: (i) a ratio between the total times of the right and left nostril dominance during the certain period reaches a threshold (e.g., the threshold may be below 0.3 or above 0.7) (ii) an average time to switch from right to left nostril dominance reaches a threshold (e.g., a threshold longer than 3 hours), and (iii) an average time to switch from left to right nostril dominance reaches a threshold.

The following are some examples of various applications in which the computer may utilize information about the dominant nostril, which is identified based on $TH_{ROf1}$ and $TH_{ROf2}$, in order to assist the user in various ways.

For some people, a certain dominant nostril may be associated with a higher frequency of having certain health problems, such as an asthma attack or a headache. Making a person aware of which nostril is more associated with the health problem can help the user to alleviate the health problem by switching the dominant nostril. Two examples of ways to switch the dominant nostril include: (i) to plug the current dominant nostril and breathe through the other nostril; and (ii) to lay on the side of the current dominant nostril (i.e., lying on the left side to switch from left to right dominant nostril, and vice versa). In one embodiment, the computer detects that the user is having an asthma attack, notifies the user about the current dominant nostril (which is associated with a higher frequency of asthma attacks), and suggests to switch the dominant nostril (to alleviate the asthma attack). In another embodiment, the computer detects the user has a headache, notifies the user about the current dominant nostril (which is associated with a higher frequency of headaches), and suggests to switch the dominant nostril.

Achieving balanced breathing may be a desired goal at some times. Biofeedback training may help extend the duration and/or increase the frequency at which one has balanced breathing. In one embodiment, the computer provides, via the UT, biofeedback for the user to achieve balanced breathing by playing a feedback. The feedback may be generated according to any suitable known method, such as normally playing the feedback when the breathing becomes more balanced, and stopping, rewinding, and/or dithering the feedback when the breathing becomes less balanced. Examples of feedbacks that may be used include playing a movie, running a video game, and/or playing sounds.

In a similar manner, biofeedback training may help the user to achieve a required breathing pattern, such as making a certain nostril dominant, or learning how to change the nostril from which most of the air is exhaled using thought and optionally without touching the nostrils. In one embodiment, the computer provides, via the UI, biofeedback for the user to achieve the required breathing pattern by playing a feedback. The feedback may be generated according to any suitable known method, such as playing a first sound when the use exhales more air from the right nostril than the left nostril, playing a second sound when the use exhales more air from the left nostril than the right nostril, and playing a third sound when the use exhales essentially the same from the right and left nostrils.

In one embodiment, the length of the exhale stream is considered as the distance from the nose at which the exhale stream can still be detected. For each person, there is a threshold that may change during the day and responsive to different situations. When the length of the exhale stream is below the threshold, it may indicate that the person is calm; and when the length of the exhale stream is longer than the threshold, it may indicate excitement. In general, the shorter the length of the exhale stream the less energy is invested in the breathing process and the less stress the person experiences. An exception may be arduous physical activity (which can increase the length of the exhale stream due to larger volumes of air that are breathed). In one embodiment, $TH_{ROf1}$ and $TH_{ROf2}$ are indicative of the length of the exhale stream, and the computer calculates level of excitement of the user based on the length of the exhale stream. Optionally, the longer the length, the higher the excitement/stress, and vice versa. Additionally, the relationship between the length of the exhale stream and the level of excitement may be a function of parameters such as the time in day, the dominant nostril, the user's mental state, the user's physiological state, the environmental air quality, and/or the temperature of the environment. In one example, the at least one CAM uses multiple sensing elements to take thermal measurements of regions located at different lengths below the nostrils. In this example, the larger the number of the sensing elements that detect the exhale stream, the longer the length of the exhale stream. Optionally, the amplitude of the temperature changes measured by the sensing elements is also used to estimate the length, shape, and/or uniformity of the exhale stream.

Ancient yoga texts teach that learning to extend the duration of the time gaps between inhaling and exhaling, and/or between exhaling and inhaling, increases life span. In one embodiment, the computer assists the user to extend the duration of the time gap between inhaling and exhaling by performing at least one of the following: (i) calculating the average time gap between inhaling and exhaling over a predetermined duration, and providing the calculation to the user via a user interface (UI), (ii) calculating the average time gap between inhaling and exhaling over a first predetermined duration, and reminding the user via the UI to practice extending the duration when the average time gap is shorter than a first predetermined threshold, and (iii) calculating the average time gap between inhaling and exhaling over a second predetermined duration, and encouraging the user via the UI when the average time gap reaches a second predetermined threshold. It is to be noted that to stop breathing after exhaling is considered more beneficial but also more dangerous, therefore the system may enable the user to select different required durations for stopping the breathing after inhaling and for stopping breathing after exhaling.

Typically, the dominant nostril switches sides throughout the day, with the duration between each switch varying, depending on the individual and other factors. Disruption of the typical nasal switching cycle may be indicative of physiological imbalance, emotional imbalance, and/or sickness. For example, slower switching of the dominant nostril may be, in some cases, a precursor of some diseases. In one embodiment the computer learns the typical sequence of switching between dominant nostrils based on previous measurements of the user taken over more than a week, and issues an alert upon detecting an irregularity in the sequence of changes between the dominant nostrils. In one example, the irregularity involves a switching of the dominant nostril within a period of time that is shorter than a certain period typical for the user, such as shorter than forty minutes. In another example, the irregularity involves a lack of switching of the dominant nostril for a period that is greater than a certain period typical for the user, such as longer than three hours. In yet another example, the cycles of the dominant nostril may be described as a time series (e.g., stating for each minute a value indicative of the dominant nostril). In this example, the computer may have a record of previous time series of the user, acquired when the user was healthy, and the computer may compare the time series to one or more of the previous time series in order to determine whether a sufficiently similar match is found. A lack of such a similar match may be indicative of the irregularity.

The following is a discussion of the role of nostril dominance and other breathing aspects in Asian philosophy. According to Asian philosophy, and specifically the Vedas, all objects are made of the Five Great Elements, also known as the Classical elements, which include earth, water, fire, air, and space. The great elements represent types of energy, but they are related to the physical elements they are called after. During left or right nostril dominance, just one element is typically dominant in the body, and this is reflected in the form of the exhale stream (during balanced breath two elements may share dominance). When dominance in breathing is not forced, each of the five great elements in turn may become dominant and then cedes dominance to the next one. The normal order of dominance according to one text is: air, fire, earth, water, and space. The relative ratios of duration of dominance are: earth—5, water—4, fire—3, air—2, space—1. The dominant element affects breathing in two ways: the length of the exhale and the shape of the exhale stream (SHAPE). The average lengths and shapes of the outbreath are as follows according to one yoga textbook: earth—about 24 cm, straight out of the center of the nostril. Water—about 32 cm length, coming from the bottom of the nostril in a slight downward direction. Fire—8 cm, coming from the top of the nostril with an upward slant. Air—about 16 cm, coming from the external side of the nostril (left for the left nostril and right for the right nostril) with a slant outside. Space—very light and short breath from all parts of the nostril.

In one embodiment, the computer identifies, based on $TH_{RO_{I1}}$ and $TH_{RO_{I2}}$, the dominant element out of the five elements. Optionally, the computer monitors if relative durations and order of elements' dominance is regular. i.e. according to the order and duration ratios specified and optionally with approximate length as prescribed, or there is some irregularity. In one embodiment, irregularity may indicate a potential problem with the associated gland: for earth—ovaries or testes/prostate, water—adrenal, fire—intestines, air—none, space—thyroid and para-thyroid. In another embodiment, irregularity may indicate a potential mental and/or physiological problem(s).

If an element's dominance time (as evident from breathing characteristics) is too long, it may be balanced (reduced) by consuming appropriate food and/or drink. For example, air dominance can be reduced by consuming heavy oily food, fire dominance can be reduced by drinking water or by consuming water-absorbing food like buckwheat, and earth dominance can be reduced by eating light food with a lot of fiber.

If a dominant element is too weak (i.e., judging by breathing characteristics compared to the yardstick for that element, or comparing the SHAPE to a baseline SHAPE), it can be strengthened. For example, air dominance can be strengthened by active physical movement, fire dominance can be strengthened by breath-of-fire (from kundalini yoga), water dominance can be strengthened by drinking, earth can be strengthened by eating proteins and oily food, and space dominance can be strengthened by visualizing a picture that grows and shrinks in sire.

As discussed above, the shape of the exhale stream (SHAPE) from the nostrils changes over time. With the at least one CAM it is possible, in some embodiments, to obtain measurements indicative of at least some of the different typical SHAPEs. A non-limiting reason for the system's ability to measure the different SHAPEs is that the exhale stream has a higher temperature than both the typical temperature of the environment and the typical temperature of the upper lip. As a result the particles of the exhale stream emit at a higher power than both the environment and the upper lip, which enables CAM to measure the SHAPE over time.

As discussed above, different SHAPEs may be characterized by different 3D shape parameters (e.g., the angle from which the exhale stream blows from a nostril, the width of the exhale stream, the length of the exhale stream, and other parameters that are indicative of the 3D SHAPE). Additionally, different SHAPEs may be associated with different states of the user, such as different physiological and/or mental conditions the user may be in. In some embodiments, the computer calculates the SHAPE based on $TH_{RO_{I1}}$ and $TH_{RO_{I2}}$. Optionally, calculating the shape involves calculating values of one or more parameters that characterize the exhale stream's shape (e.g., parameters related to the 3D SHAPE). Optionally, calculating the SHAPE involves generating a reference pattern for the SHAPE. For example, the reference pattern may be a consensus image and/or heat map that is based on $TH_{RO_{I1}}$ and $TH_{RO_{I2}}$ taken over multiple breaths.

In other embodiments, the computer identifies a SHAPE based on $TH_{RO_{I1}}$ and $TH_{RO_{I2}}$. Optionally, the identified SHAPE belongs to a set that includes at least first and second SHAPEs, between which the computer differentiates. Optionally, the first and second SHAPEs are indicative of at least one of the following: two of the five great elements according to the Vedas, two different emotional states of the user, two different moods of the user, two different energetic levels of the user, and a healthy state of the user versus an unhealthy state of the user. In one example, the first SHAPE is indicative of a powerful alert energetic level, while the second SHAPE is indicative of a tired energetic level, and the computer uses this information to improve computerized interactions with the user.

The SHAPE may be related to the dominant nostril at the time. In one embodiment, the first SHAPE occurs more frequently when the right nostril is dominant, and the second SHAPE occurs more frequently when the left nostril is dominant. In another embodiment, both the first and the second SHAPEs occur more frequently when the right nostril is dominant.

In one example, differentiating between the first and second SHAPEs means that there are certain first $TH_{RO_{I1}}$ and $TH_{ROT2}$ that the computer identifies as corresponding to the first SHAPE and not as corresponding to the second SHAPE, and there are certain second $TH_{ROT1}$ and $TH_{ROT2}$ that the computer identifies as corresponding to the second SHAPR and as not corresponding to the first SHAPE. In another example, differentiating between first and second SHAPEs means that there are certain third $TH_{ROT1}$ and $TH_{ROT2}$ that the computer identifies as having a higher affinity to the first SHAPE compared to their affinity to the second SHAPE, and there are certain fourth $TH_{ROT1}$ and $TH_{ROT2}$ that the computer identifies as having a higher affinity to the second SHAPE compared to their affinity to the first SHAPE.

In some embodiments, the SHAPE is identified by the computer based on $TH_{ROT1}$, $TH_{ROT2}$, and optionally other sources of data. Since the SHAPE does not typically change between consecutive breaths, detecting the shape of the exhale may be done based on multiple measurements of multiple exhales. Using such multiple measurements can increase the accuracy of the identification of the shape. In one example, the first and second SHAPEs are identified based on first and second sets of $TH_{ROT1}$ and $TH_{ROT2}$ taken during multiple exhales over first and second non-overlapping respective durations, each longer than a minute.

The computer may utilize different approaches to identify the SHAPE. In one embodiment the computer may compare $TH_{ROT1}$ and $TH_{ROT2}$ to one or more reference patterns to determine whether $TH_{ROT1}$ and $TH_{ROT2}$ are similar to a reference pattern from among the one or more reference patterns. For example, if the similarity to a reference pattern reaches a threshold, the exhale stream measured with $TH_{ROT1}$ and $TH_{ROT2}$ may be identified as having the shape corresponding to the shape of the reference pattern. Determining whether $TH_{ROT1}$ and $TH_{ROT2}$ are similar to a reference pattern may be done using various image similarity functions, such as determining the distance between each pixel in the reference pattern and its counterpart in $TH_{ROT1}$ and $TH_{ROT2}$. One way this can be done is by converting $TH_{ROT1}$ and $TH_{ROT2}$ into a vector of pixel temperatures, and comparing it to a vector of the reference pattern (using some form of vector similarity metric like a dot product or the L2 norm).

The one or more reference patterns may be generated in different ways. In one embodiment, the one or more reference patterns are generated based on previous $TH_{ROT1}$ and $TH_{ROT2}$ of the user taken on different days. Optionally, the SHAPEs were known while previous $TH_{ROT1}$ and $TH_{ROT2}$ of the user taken. In one example, the SHAPE is associated with a state of the user at the time (e.g., relaxed vs. anxious). In another example, the SHAPE may be determined using an external thermal camera (which is not head-mounted). In yet another example, the SHAPE is determined by manual annotation. In one embodiment, the one or more reference patterns are generated based on previous $TH_{ROT1}$ and $TH_{ROT2}$ of one or more other users.

In some embodiments, the SHAPE may be discovered through clustering. Optionally, the computer may cluster sets of previous $TH_{ROT1}$ and $TH_{ROT2}$ of the user into clusters. Where sets of $TH_{ROT1}$ and $TH_{ROT2}$ in the same cluster are similar to each other and the exhale streams they measured are assumed to have the same shape. Thus, each of the clusters may be associated with a certain SHAPE to which it corresponds. In one example, the clusters include at least first and second clusters that correspond to the aforementioned first and second SHAPEs.

The computer may utilize a machine learning-based model to identify the SHAPE. In one embodiment, the computer generates feature values based on $TH_{ROT1}$ and $TH_{ROT2}$, and utilizes a model to classify $TH_{ROT1}$ and $TH_{ROT2}$ to a class corresponding to the SHAPE. Optionally, the class corresponds to the aforementioned first or second shapes. Optionally, the model is trained based on previous $TH_{ROT1}$ and $TH_{ROT2}$ of the user taken during different days.

In one embodiment, the computer receives an indication of the user's breathing rate, and uses this information along with the SHAPE at that time in order to suggest to the user to perform various activities and/or alert the user. Optionally, the indication of the user's breathing rate is calculated based on $TH_{ROT1}$ and $TH_{ROT2}$. In one example, the SHAPE is correlative with the state of the user, and different states combined with different breathing rates may have different meaning, which cause the computer to suggest different activities. The different activities may vary from different work/learning related activities to different physical activities to different treatments. In one example, the computer suggests to the user, via the UI, to perform a first activity in response to detecting that the breathing rate reached a threshold while identifying the first SHAPE. However, the computer suggest to the user to perform a second activity, which is different from the first activity, in response to detecting that the breathing rate reached the threshold while identifying the second SHAPE. In another example, the computer alerts the user, via the UI, in response to detecting that the breathing rate reached a threshold while identifying the first SHAPE, and the computer does not alert the user in response to detecting that the breathing rate reached the threshold while identifying the second SHAPE. In this example, the SHAPE may be correlated with the state of the user, and different states may be associated with different normal breathing rates. When the difference between the current breathing rate and the normal breathing rate (associated with the current SHAPE) reaches a threshold, the user may be in an abnormal state that warrants an alert.

In another embodiment, the computer configures a software agent that prioritizes activities for the user based on the identified SHAPE, such that a first activity is prioritized over a second activity responsive to identifying the first SHAPE, and the second activity is prioritized over the first activity responsive to identifying the second SHAPE. It is noted that the system may prioritize different activities for different SHAPEs also when the measured breathing rate and respiration volume are the same.

In still another embodiment, the computer learns a flow of typical changes between different SHAPEs based on previous measurements of the user, and issues an alert upon detecting an irregularity related to a flow of changes between the SHAPEs. For example, the irregularity may involve a new SHAPE, more frequent changes between SHAPEs, having certain SHAPEs for more or less time than usual, etc.

In yet another embodiment, the computer receives data about types of foods consumed by the user, stores the data in a memory, and finds correlations between the SHAPEs and the types of foods. These correlations may be used to make suggestions to the user. For example, the computer may suggest the user to eat a first type of food responsive to identifying the first SHAPE, and suggest the user to eat a second type of food responsive to identifying the second SHAPE. According to Ayurveda medicine, it is preferred to eat according to the three doshas and the five great elements. In times when the SHAPE is indicative of the dominant element (out of the five great elements), the computer may guide the user which types of food suit the identified dominant element, and/or may help the user to avoid inappropriate types of foods by identifying the types of food the user eats (and/or is about to eat), and alert the user when the identified food is inappropriate to the current dominant element (that was identified based on the SHAPE).

Data obtained from monitoring the dominant nostril can be utilized to make suggestions of activities for the user. FIG. 34a illustrates one embodiment of a system configured to suggest activities according to the dominant nostril. The system includes a sensor 451 for taking measurements 454 indicative of which of the user's nostrils is dominant at the time the measurements 454 were taken. Optionally, the sensor 451 is one or more thermal cameras, such as the thermal cameras illustrated in FIG. 23, however, as discussed below, other types of sensors may be utilized to take the measurements 454. The system also includes a computer 455 and optionally includes a UI 456.

The computer 455 predicts, based on the measurements 454, which of the user's nostrils will be the dominant nostril at a future time. Optionally, responsive to predicting that the right nostril will be dominant at the future time, the computer 455 suggests having at the future time a first activity, which is more suitable for a right dominant nostril than a second activity. Optionally, responsive to predicting that the left nostril will be dominant at the future time, the computer suggests having at the future time the second activity, which is more suitable for a left dominant nostril than the first activity. Optionally, the computer 455 suggests activities utilizing the UI 456. In one example, the first activity requires more verbal-analytical skills and less spatial skills compared to the second activity. In another example, the first activity requires more logic and/or locomotive skills compared to the second activity, and less empathy and/or imagination. In another example, the second activity requires more creativity and less physical effort compared to the first activity.

The suggestions of activities described above may be based on the premise that the dominant nostril is indicative of which of the user's brain hemispheres is more effective at performing activities that are associated with it. It is typically assumed that the left side of the user's brain is expected to be more effective at performing tasks when the right nostril is dominant (compared to when the left nostril is dominant). Conversely, the right side of the user's brain is expected to be more effective at performing tasks when the left nostril is dominant (compared to when the right nostril is dominant). The right hemisphere is usually believed to be better at expressive and creative tasks. Some of the abilities associated with the right hemisphere include recognizing faces, expressing emotions, music, reading emotions, color, images, intuition, and creativity. The left hemisphere is usually believed to be adept to tasks that involve logic, language, and analytical thinking. The left hemisphere is usually described as being better at language, logic, critical thinking, numbers, and reasoning. Thus, certain activities, which require certain skills that are associated with a certain hemisphere, may be more suitable to perform when one nostril is dominant compared to when the other nostril is dominant.

Additionally or alternatively, the suggestions of activities described above may be based on empirical data of the performances of the user and/or performances of other users. By analyzing the user's performances versus the dominant nostril (and optionally other parameters), and/or using big data analysis of the measured performances of many users versus their dominant nostril (and optionally other parameters), it is possible to identify a first set of activities that are statistically significantly more successfully achieved during right dominant nostril, a second set of activities that are statistically significantly more successfully achieved during left dominant nostril, and a third set of activities that are statistically significantly more successfully achieved during a balanced nasal breathing.

To predict the dominant nostril at the future time, the computer 455 relies on the measurements 454, which were taken prior to a current time, at which the prediction is made. Optionally, the future time may be at least five minutes after the current time, at least thirty minutes after the current time, at least one hour after the current time, at least three hours after the current time, or at least six hours after the current time.

In one embodiment, the computer 455 utilizes the measurements 454 to determine when the dominant nostril last switched (before the current time), and uses this information to predict when it will switch next (possibly multiple times). Thus, the computer can extrapolate, based on the measurements 454, a timeline until the future time, indicating which nostril is dominant at different times until (and including) the future time. Optionally, information useful for determining the time line (such as the time each nostril remains dominant) may be based on the measurements 454 and/or previous measurements of the user taken with the sensor 451 during different days.

In another embodiment, the computer 455 predicts the dominant nostril at the future by generating feature values and utilizing a machine learning-based model to estimate the dominant nostril at the future time (e.g., left nostril dominance, right nostril dominance, or balanced breathing). Optionally, the feature values comprise one or more feature values describing aspects of the future time such as the time to which it corresponds (e.g., how much time ahead the future time is), the location the user is expected to be at the future time, and/or an activity the user is expected to partake at the future time. Optionally, the feature values may include one or more features values corresponding to a state of the user at an earlier time that precedes the future time, such as the user's dominant nostril (e.g., as determine based on the measurements 454), manipulation of the dominant nostril performed by the user recently, previous measurements of the user taken after the user manipulated the dominant nostril and/or practiced pranavama and/or listened to brainwave entrainment, an activity the user had during the earlier time, and/or values of physiological signals of the user at the earlier time. In one embodiment, the machine learning-based model is trained based on samples that include measurements 454 taken at certain earlier times and their corresponding dominant nostrils following certain durations after the certain earlier times.

When a first activity is suggested for the future time (over the second activity), it typically means that the first activity is to be preferred over the second activity. Optionally, to suggest having the first activity at the future time means that the computer schedules the first activity at the future time and does not schedule the second activity at the future time. Additionally or alternatively, to suggest having the first activity at the future time means that the computer 455 ranks the first activity at the future time higher than it ranks the second activity at the future time. Optionally, when the first activity is ranked higher than the second activity it means that the first activity is given a stronger recommendation than the second activity. For example, a stronger recommendation may involve the first activity being suggested by displaying it first on a list of suggested activities. In another example, a stronger recommendation may involve suggesting the first activity with a larger image, a more prominent visual effect, and/or a more noticeable auditory signal than the one used to suggest the second activity.

The computer 455 may utilize a determination of which nostril is dominant at the current time and/or a prediction of which nostril will be dominant at the future in order to assist the user in performing activities at suitable times. In a first embodiment, the computer 455 assists the user to spend more time eating certain types of food when the right nostril is dominant. Additionally or alternatively, the computer 455 further assists the user to spend less time eating the certain types of food when the left nostril is dominant. In one example, the computer 455 may assist the user by identifying that the user starts looking for food during left nostril dominance, and reminding the user that eating while the left nostril is dominant is probably due to emotional reasons. In another example, the computer 455 may arrange the user's schedule such that at least 60% of the occurrences of lunch and/or dinner are planned to a time when the right nostril is dominant. Optionally, the computer 455 recommends to the user to have the main meal of the day while the right nostril is dominant. In a second embodiment, the computer 455 assists the user to increase the time spent at the toilet defecating while the right nostril is dominant. Optionally, the computer 455 recommends to the user to spend less time at the toilet defecating while the left nostril is dominant. For example, the computer 455 may recommend to go on a bathroom break when the right nostril is dominant. Optionally, the computer 455 may assist the user to decrease defecating during times of left nostril dominance by reminding the user that it is preferred to defecate during right nostril dominance, especially when suffering from constipation. In a third embodiment the activity involves creativity, such as creating art, and the computer 455 assists the user to spend more time on the creative activity when the left nostril is dominant.

It is recommended to perform some activities when the breathing through the nose is balanced. In one embodiment, the computer 455 identifies, based on the measurements 454, times in which the breathing through the nose is balanced, and suggests a third activity for those times. Optionally, the third activity is more suitable for balanced breathing compared to the first and second activities. Optionally, the third activity requires higher self-awareness compared to the first and second activities. For example, the third activity may include a spiritual practice (such as meditating or praying), while the first and second activities do not include spiritual practices.

Various hardware configurations may be utilized in different embodiments of the system configured to suggest activities according to the dominant nostril, in order to take the measurements 454 of the user.

In a first embodiment, the system includes a CAM that takes thermal measurements of a region below the user's nostrils (e.g., CAM 183 or CAM 184). In this embodiment, identifying the dominant nostril and/or whether the breathing is balanced may be done by the computer 455 based on signal processing of the thermal measurements taken by CAM.

In a second embodiment, the sensor 451 includes one or more implanted sensors located around the area of the nostrils. In this embodiment, identification of the dominant nostril and/or whether the breathing is balanced may be done based on signal processing of the measurements of the implanted sensors.

In a third embodiment, the sensor 451 includes right and left in-the-ear earbuds comprising microphones, configured to measure sounds inside the right and left ear canals; the computer 455 identifies the dominant nostril based on analysis of the recordings from the earbuds. For example, the computer 455 may identify the dominant nostril based on the assumption that the inhale sounds measured by the in-the-ear earbud in the dominant side are stronger than the inhale sounds measured by the in-the-ear earbud in the non-dominant side.

In a fourth embodiment, the system includes a frame configured to be worn on the user's head, and the sensor 451 comprises a visible-light camera; the visible-light camera is physically coupled to the frame, and takes images of a region on the user's nose. For example, the computer 455 may identify the dominant nostril based on analyzing the images of the nose by identifying movements of the nose, especially at the edges of the nostrils.

In a fifth embodiment, the sensor 451 includes thermistors that are in contact with the nostrils and/or the upper lip in order to take the measurements. Optionally, the dominant nostril may be identified based on signal processing of the thermistors' measurements.

In a sixth embodiment, the sensor 451 includes anemometers located inside the breathing streams of the nostrils in order to take the measurements. Optionally, the dominant nostril is identified based on signal processing of the anemometers' measurements.

In a seventh embodiment, the sensor 451 includes a non-wearable IR camera pointed to the area around the nostrils in order to take the measurements. Optionally, the dominant nostril is identified based on image processing of the measurements of the non-wearable IR camera.

The suggestions provided by the computer 455 may be done as part of various programs that may benefit the user. Optionally, the computer 455 provides functionality of at least one of the following programs: a virtual assistant (i.e., a software agent), a calendar management program, a priority management program, a project management program, a "to do" list program, a work schedule program, and a self-learning program.

Some embodiments of the system may involve notification of the user about which of the nostrils is dominant at a given time (e.g., via UI 456). Optionally, the notification involves providing a user with an indication (e.g., via sound and/or an image) when the dominant nostril changes and/or every certain period of time (e.g., every hour). Additionally or alternatively, notifying the user about which of the nostrils is dominant may involve utilizing different themes for UI 456. In one example, a first theme for UI 456 is utilized when the right nostril is the dominant nostril, and a second theme for UI 456 is utilized when the left nostril is the dominant nostril. Optionally, the first theme is more logical than the second theme (e.g., presenting data and/or suggestions involves providing more facts and/or detailed explanations), and the second theme is more emotional than the first theme (e.g., presenting data and/or suggestions includes more emotional phrases, abstract images, social-related data, and/or less factual information).

In one embodiment, the computer 455 is programmed to converse with the user according to at least first and second modes. The first mode is perceived by the user as more logical than the second mode, and the second mode is perceived by the user as more emotional than the first mode. The computer 455 uses, on average, the first mode more frequently than the second mode when the right nostril is the dominant nostril, and uses, on average, the second mode more frequently than the first mode when the left nostril is the dominant nostril. Examples of logical speech include sentences built around numbers and facts, while emotional speech includes sentences built around emotions and intuition.

The following is a description of steps involved in one embodiment of a method for suggesting activities according to the dominant nostril. The steps described below may be used by systems modeled according to FIG. 34a, and may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method.

In one embodiment, the method for alerting about stress includes at least the following steps: In Step 1, taking, utilizing a sensor, measurements of a user, which are indicative of the user's dominant nostril. In Step 2, predicting, based on the measurements, which of the user's nostrils will be the dominant nostril at a future time (that occurs after the measurements in Step 1 were taken). And In Step 3, responsive to predicting that the right nostril will be dominant at the future time, suggesting having at the future time a first activity, which is more suitable for a right dominant nostril than a second activity. Optionally, responsive to predicting that the left nostril will be dominant at the future time, this step involves suggesting having at the future time the second activity, which is more suitable for a left dominant nostril than the first activity. Optionally, the method further includes assisting the user to decrease eating certain types of food during left nostril dominance, and assisting the user to schedule the main meal of the day during right nostril dominance. Optionally, the method further includes learning the typical sequence of switching between dominant nostrils based on previous measurements of the user taken over more than a week, and alerting upon detecting an irregularity in the sequence of changes between the dominant nostrils.

In some embodiments, a system is configured to detect a physiological response based on respiratory parameters. Optionally, the physiological response is stress. Optionally, the respiratory parameters include the breathing rate and breathing rate variability (which is discussed further below).

The breathing rate variability (BRV) is a value that is indicative of the physiological phenomenon of variations between consecutive breathes, observed during a certain period of time (e.g., a minute). In a similar fashion to heart rate variability (HRV), which is the physiological phenomenon of variations between consecutive heartbeats, the extent of BRV can be indicative of various physiological phenomena, such as stress and/or physiological state.

In one embodiment, stress is detected based on thermal measurements of ROIs indicative of respiration performances, such as the mouth area, the upper lip area, and/or an air volume below the nostrils where the exhale from the nose flows. Optionally, $TH_{ROI}$ may be utilized to calculate various respiratory parameters, which include the breathing rate and/or the BRV.

The duration between successive breaths (such as the time between starting successive exhales) and/or breathing irregularity may be calculated using various methods, such as geometric methods, frequency-domain methods, and/or non-linear methods. The computer may calculate the BRV based on $TH_{ROI}$ taken during different periods of time, such as at least one minute long or at least 5 minutes long.

In one embodiment, the breathing rate variability (BRV) and the breathing rate (BR) are utilized by a computer in order to detect when the user is stressed. Optionally, elevated BRV in addition to elevated BR may serve as an indicator of stress. Optionally, elevated BRV, even when the BR is reduced, may serve as an indicator of stress. For example, the computer may calculate $BR_1$ and $BRV_1$ based on $TH_{ROI}$ taken during a first period, calculate $BR_2$ and $BRV_2$ based on $TH_{ROI}$ taken during a second following period, and determine that the user's stress level is higher at the second period relative to the first period because ($BRV_1 < BRV_2$), even though ($BR_1 > BR_2$).

In one embodiment, the computer calculates the stress level based on comparing BR and BRV to various thresholds that correspond to different stress levels. In one example, having a high BRV may lower the threshold on BR that is required in order to detect stress.

In another embodiment, the computer may utilize a machine learning-based model in order to detect the stress level. Optionally, the computer utilizes $TH_{ROI}$ to generate feature values indicative of the BR and/or the BRV, and the model was trained based on samples that each include feature values based on $TH_{ROI}$ and labels indicative of the user's stress level.

Figure 35A:
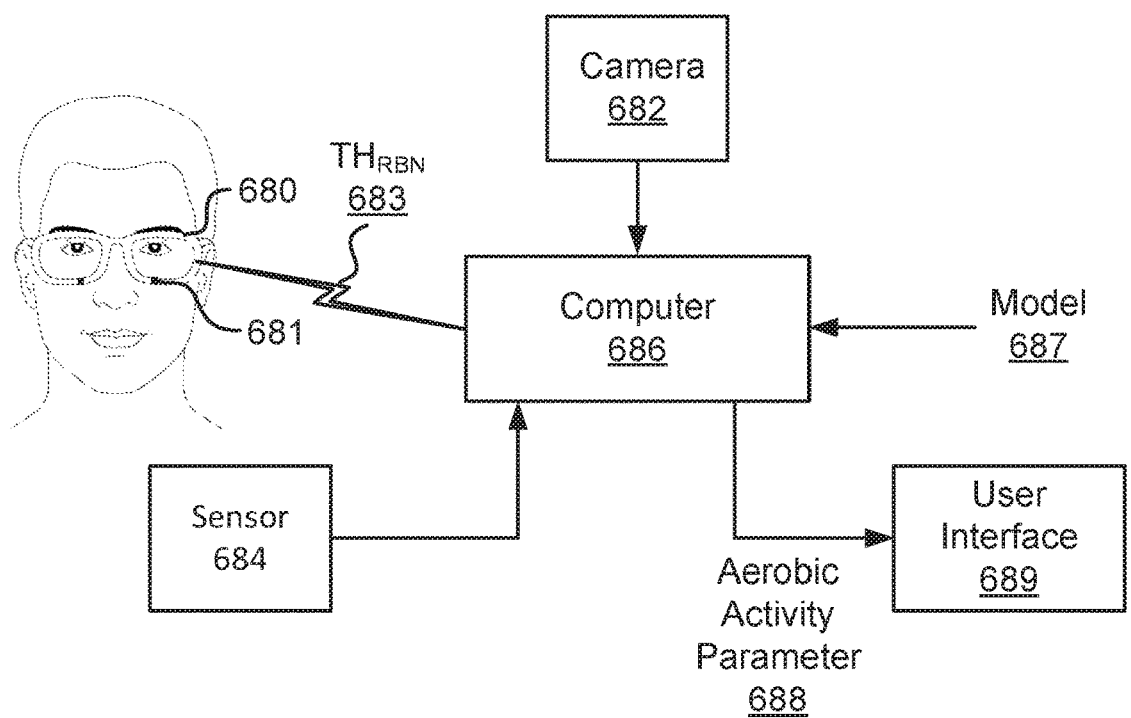
FIG. 35a illustrates an embodiment of a system for estimating an aerobic activity parameter.
Figure 35B:
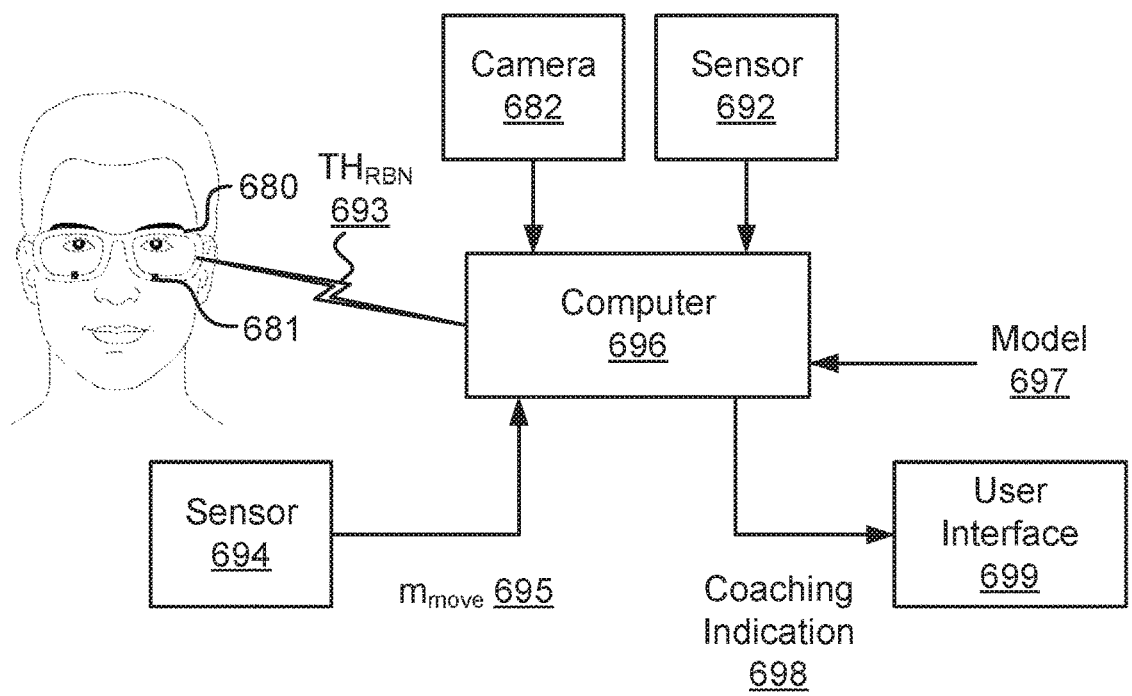
FIG. 35b illustrates an embodiment of an athletic coaching system.

Some embodiments described herein involve utilization of at least one inward-facing head-mounted thermal cameras (such a camera is denoted below CAM) to take thermal measurements of a region below the nostrils (these measurements are denoted below $TH_{RBN}$). $TH_{RBN}$ are indicative of an exhale stream of the user, such as air exhaled from a nostril and/or the mouth of the user. Since exhaled air usually has a different temperature than the environment and/or the human skin, $TH_{RBN}$ can provide indications regarding the user's respiratory activity, such as the breathing rate, whether exhaling is done through the mouth or nose, the respiration volume, and other respiratory parameters described herein. Additionally or alternatively. $TH_{RBN}$ may be used to calculate an aerobic activity parameter (as illustrated in FIG. 35a) and/or a coaching indication (as illustrated in FIG. 35b). The following is a description of embodiments of such systems that utilize $TH_{RBN}$ for such respiratory-related applications. The systems illustrated in FIG. 35a and FIG. 35b include at least one CAM and a computer.

The at least one CAM may include various combinations of one or more CAMs, as described in the various examples given in this disclosure of embodiments that include a single inward-facing head-mounted thermal camera that measures $TH_{RBN}$ (e.g., a single CAM coupled to the bottom of one of the sides of a frame worn by the user) or multiple CAMs (e.g., multiple CAMs coupled to different locations on a frame worn by the user). In one example, the at least one CAM includes CAM 681 illustrated in FIG. 35a. In other examples, the at least one CAM may include one or more of the CAMs described in various figures in this disclosure. For example, FIG. 23 illustrates one embodiment of an HMS that may be used to measure $TH_{RBN}$, in which at least one CAM (four CAMs in this case), is coupled to the bottom of an eyeglasses frame 181. CAMs 182 and 185 are used to take thermal measurements of regions on the right and left sides of the upper lip (186 and 187, respectively), and CAMs 183 and 184 are used to take thermal measurements of a region on the user's mouth 188 and/or a volume protruding out of the user's mouth. At least some of the ROIs may overlap, which is illustrated as vertical lines in the overlapping areas. Optionally, a CAM from among the one or more of the CAMs includes at least one of the following sensors: a thermopile sensor, and a microbolometer sensor. Optionally, a CAM from among the one or more of the CAMs includes a microbolometer focal-plane array (FPA) sensor or a thermopile FPA sensor. Additional examples of systems that include at least one CAM that may be used to take $TH_{RBN}$ are illustrated in FIG. 7 to FIG. 9 as well as FIG. 1b (one or more of the cameras 22, 24, and 28).

In some embodiments, each CAM, from among the at least one CAM, is physically coupled to frame worn on the head of a user (whose measurements are being taken), such as frames of eyeglasses, an augmented reality HMS, a virtual reality HMS, or a mixed reality HMS. In one example, each CAM, from among the at least one CAM, is physically coupled to frame 680. Optionally, each CAM, from among the at least one CAM, is located less than 15 cm from the user's face and weighs less than 10 g. Optionally, the frame holds each CAM, from among the at least one CAM, such that the CAM does not protrude beyond the tip of the user's nose.

In one embodiment, each CAM, from among the at least one CAM, is located above the user's upper lip and less than 15 cm from the user's face, and does not occlude any of the user's mouth and nostrils. Optionally. $TH_{RBN}$ include thermal measurements of at least one of first and second regions below right and left nostrils ($TH_{RBN1}$ and $TH_{RBN2}$, respectively) of the user, which are indicative of exhale streams from the right and left nostrils, respectively. Additionally or alternatively, $TH_{RBN}$ may include thermal measurements of at least one of a region on the mouth and a volume protruding out of the mouth ($TH_{RBN3}$) of the user, indicative of exhale stream from the mouth.

The following is a description of one possible utilization of $TH_{RBN}$, which involves calculation of an aerobic activity parameter of a user. FIG. 35a illustrates an embodiment of a system configured to estimate an aerobic activity parameter 688. The system includes at least one CAM (as described above) that is used to measure $TH_{RBN}$ 683 and a computer 686. Some embodiments of the system may optionally include additional elements, such as the frame 680, a head-mounted inward-facing video camera 682, a sensor 684, and a user interface 689.

The computer 686 is configured, in one embodiment, to calculate, based on $TH_{RBN}$ (taken by the at least one CAM), the aerobic activity parameter 688. Optionally, the aerobic activity parameter 688 is indicative of one or more of the following values: oxygen consumption ($VO_2$), maximal oxygen consumption ($VO_2$ max), and energy expenditure (EE). Optionally, the computer 686 may utilize additional inputs to calculate the aerobic activity parameter such as measurements of the heart rate (HR) of the user, values of the activity level of the user, and/or various statistics about the user (e.g., age, weight, height, gender, etc.).

Herein. $VO_2$ refers to a value indicative of the rate of oxygen consumption. This value typically rises as physical activity becomes more strenuous and the body has a larger demand for oxygen for various metabolic processes. In one example, VO2 is a value expressed in units of mL/(kg min), or some other units proportional to mL/(kg-min). VO2 max refers to a value indicative of the maximal rate of oxygen consumption; typically, the higher VO2 max, the higher the person's cardiorespiratory fitness and endurance capacity during prolonged exercises. EE may refer to a value indicative of the rate of energy expenditure, and may be expressed in various units such as kcal/h, or some other unit proportional to kcal/h. When the rate of energy expenditure is integrated over a period time, then EE may refer to a value indicative of the total energy expenditure over the period of time, and may be a value expressed in calories or some other unit proportional to calories.

Since direct measurements of aerobic activity parameters such as $VO_2$, $VO_2$ max, and EE are typically cumbersome uncomfortable procedures that need to be performed in controlled settings (e.g., running on a treadmill while wearing a mask that is used to collect and analyze exhaled breath), these values are often estimated based on various values that are correlated to some extent with the aerobic activity parameters. For example, various formulas and/or models were developed to estimate values of aerobic activity parameters from values such as heart rate (and changes from resting heart rate), activity level, and various statistics e.g., age, weight, height, gender, etc.)

Embodiments described herein utilize values indicative of the respiratory activity, such as $TH_{RBN}$ 683 and/or values derived from $TH_{RBN}$ 683 (e.g., respiration rate and/or respiration volume) in order to enhance the accuracy of the estimation of aerobic activity parameters. Respiration parameters such as the respiration rate and/or respiration volume are tightly related to parameters such as $VO_2$ and EE and thus provide additional information about these parameters. Additionally, respiration values can help reduce inaccuracies in estimation of aerobic activity parameters due to various artifacts. For example, during changes in body positions (e.g., postural hypotension), there are usually only minor changes in $VO_2$ and respiration but major changes in HR. In another example, a value such as the respiration rate can distinguish between non-metabolic (e.g. mental and non-exercise related physical stress) and metabolic (physical activity induced) increases in HR Thus, for example, using respiration data in addition to other values (e.g., HR) may provide better estimations of the values of the aerobic activity parameters, compared to estimations that do not involve respiration data.

The computer 686 may utilize various approaches in order to estimate aerobic activity parameters based on data that includes $TH_{RBN}$ 683 and/or values derived from $TH_{RBN}$. In one embodiment, the computer 686 generates feature values based on data comprising $TH_{RBN}$, and utilizes a model 687 to calculate the aerobic activity parameter 688 based on the feature values. Optionally, the model 687 is trained based on data indicative of aerobic activity of multiple users (e.g., data that includes physiological signals such as respiratory rate, heart rate, etc., of the multiple users). Additionally or alternatively, the model 687 is trained based on data that includes previous $TH_{RBN}$ of the multiple users and values of the aerobic activity parameter of the multiple users corresponding to when the previous $TH_{RBN}$ were taken. For example, the training data includes samples, each sample comprising: (i) feature values were generated from certain pervious $TH_{RBN}$ of a certain user taken during certain period of time, and (ii) a label generated based on a measurement of the value of the aerobic activity parameter of the certain user during the certain period of time (i.e., the value of $VO_2$, $VO_2$ max, or EE, as measured during the certain period of time).

The computer 686 may generate various types of feature values that are used to estimate the value of the aerobic activity parameter 688. Optionally, the computer 686 generates one or more feature values, based on $TH_{RBN}$ 683, which may be any of the feature values described in this disclosure that are used to detect a physiological response, and in particular, the one or more feature values may be any of the feature values described in this disclosure as being pertinent to calculation of a respiratory parameter. Additionally or alternatively, feature values generated by the computer 686 may include: time series data comprising values measured by a CAM, average values of certain pixels of a CAM, and/or values measured at certain times by the certain pixels. Additionally or alternatively, at least some of the feature values generated by the computer 686 may include measurements of the environment in which the user is in and/or indications of confounding factors (e.g., indications of use of medication).

In some embodiments, feature values generated by the computer 686 may include values of one or more respiratory parameters calculated based on $TH_{RBN}$ 683. In one example, the feature values generated by the computer 686 include a feature value indicative of a ratio between an extent to which the user breathed via the mouth and an extent to which the user breathed via the nose. In another example, the feature values generated by the computer 686 include a feature value indicative of a ratio between durations of exhales of the user and duration of inhales of the user.

In some embodiment, the feature values generated by the computer 686 may include a feature value indicative of heart rate (HR) of the user while $TH_{RBN}$ 683 were taken. Additionally or alternatively, the feature values generated by the computer 686 include another feature value indicative of cardiac activity such as heart rate variability (HRV). For example, measurements indicative of HR and/or HRV may be obtained by a different sensor, which is not a CAM, such as a photoplethysmogram (PPG) sensor that is head-mounted (e.g., coupled to the temple of eyeglasses worn by the user), coupled to a wearable device such as a smartwatch, or embedded in a garment worn by the user, such as a smart shirt.

In addition to data describing physiological signals mentioned above, in some embodiments, data used to generate at least some of the feature values by the computer 686 may include various values describing the user, such as one or more of the following: age, gender, height, weight, type of body build, and body fat percentage. Additionally or alternatively, data used to generate at least some of the feature values by the computer 686 may include various values describing an activity of the user while $TH_{RBN}$ 683 of the user were taken. Optionally, data describing the activity is obtained by sensor 684. In one example, the sensor 684 comprises at least one of an accelerometer and a gyroscope, and the data describing the activity is indicative of at least one of the following: cadence, stride length, and/or type of movement (e.g., walking, running, rowing, cycling, etc.) In another example, the sensor 684 comprises a GPS receiver and/or some other sensor that may be used to determine the user's location. In this example, the data describing the activity may be indicative of one or more of the following: the speed of the user's movement, the distance of the user's movement, and/or changes in the user's elevation.

A person's baseline physiological signals, such as resting HR, respiration rate, or blood pressure may be indicative of the aerobic fitness of the person, and may provide useful information for calculation of an aerobic activity parameter. Thus, in some embodiments, the computer 686 may generate one or more feature values that are indicative of a baseline physiological signal of the user.

How a person's physiological signals change due to physical activity are indicative of the aerobic fitness of the person. Typically, the more fit an individual, the less dramatic the changes in the physiological signals for a certain type of activity. For example, a fit person's respiration rate will typically increase to a lesser extent after a few minutes of jogging compared to the increase in respiration that occurs to a less fit individual after performing the activity. To capture such aspects that may reflect on fitness, in some embodiments, the feature values generated by the computer 686 may include one or more feature values that reflect a change in the values of a physiological signal, before and after a certain extent of activity. For example, a feature value may be indicative of the change in the respiratory rate, change to the respiration volume, or respiration volume after conducting a certain activity (e.g., five minutes of moderate cycling). In another example, a feature value may be indicative of the change to the heart rate after running at a pace of 12 km/h for five minutes.

In other embodiments, the feature values generated by the computer 686 may include one or more feature values that are indicative of athletic performance of the user. For example, a feature value may be indicative of the time it took the user to complete a certain exercise such as running a mile as fast as the user is capable.

The model 687 is trained on data that includes previous $TH_{RBN}$ of the user and/or other users. Training the model 687 typically involves generating samples based on the previous $TH_{RBN}$ and corresponding labels indicative of values of the aerobic activity parameter when the previous $TH_{RBN}$ were taken. For example, each sample may comprise feature values generated based on at least some of the previous $TH_{RBN}$, and the sample's label represents the value of the aerobic activity parameter corresponding to when the at least some of the previous $TH_{RBN}$ were taken.

In some embodiments, the samples used to train the model 687 include data pertaining to a diverse set of users comprising users of different genders, ages, body builds, and athletic abilities. Optionally, the samples used to train the model 687 include samples generated based on $TH_{RBN}$ taken at different times of the day, while being at different locations, and/or while conducting different activities. In one example, at least some of the samples are generated based on $TH_{RBN}$ taken in the morning and $TH_{RBN}$ taken in the evening. In another example, at least some of the samples are generated based on $TH_{RBN}$ of a user taken while being indoors, and $TH_{RBN}$ of the user taken while being outdoors. In yet another example, at least some of the samples are generated based on $TH_{RBN}$ taken while a user was sitting down, and $TH_{RBN}$ taken while the user was walking, running, and/or engaging in physical exercise (e.g., dancing, biking, etc.). Additionally or alternatively, the samples used to train the model 687 may be generated based on $TH_{RBN}$ taken while various environmental conditions persisted. For example, the samples include first and second samples generated based on $TH_{RBN}$ taken while the environment had first and second temperatures, with the first temperature being at least 10° C. warmer than the second temperature. In another example, the samples include samples generated based on measurements taken while there were different extents of direct sunlight and/or different extents of wind blowing.

Various computational approaches may be utilized to train the model 687 based on the samples described above. In one example, a machine learning-based training algorithm may be utilized to train the model 687 based on the samples. Optionally, the model 687 includes parameters of at least one of the following types of models: a regression model, a neural network, a nearest neighbor model, a support vector machine, a support vector machine for regression, a naïve Bayes model, a Bayes network, and a decision tree.

In some embodiments, a deep learning algorithm may be used to train the model 687. In one example, the model 687 may include parameters describing multiple hidden layers of a neural network. In one embodiment, when $TH_{RBN}$ include measurements of multiple pixels, the model 687 may include a convolution neural network (CNN). In one example, the CNN may be utilized to identify certain patterns in the thermal images, such as patterns of temperatures in the region of the exhale stream that may be indicative of respiratory activity, which involve aspects such as the location, direction, size, and/or shape of an exhale stream from the nose and/or mouth. In another example, calculating a value of an aerobic activity parameter may be done based on multiple, possibly successive, thermal measurements. Optionally, calculating values of the aerobic activity parameter based on thermal measurements may involve retaining state information that is based on previous measurements. Optionally, the model 687 may include parameters that describe an architecture that supports such a capability. In one example, the model 687 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using bidirectional recurrent neural network architecture (BRNN).

Monitoring a user over time can produce many observations indicative of the user's fitness. For example, the extent of increase in the user's respiration rate, change to respiration volume, and/or change in heart rate after moderate running of a few minutes, is indicative of the user's fitness, and can be measured multiple times. These multiple observations can be used to estimate the value of an aerobic activity parameter of the user such as $VO_2$ max (which is also indicative of the user's fitness) as follows. In one embodiment, the computer 686 calculates, based on $TH_{RBN}$ 683, $n \geq 1$ values $x_1 \ldots x_n$, of observations of a parameter related to respiration such as the respiration rate, change to respiration rate, respiration volume, change to respiration volume, and the like. For example, $x_i$ may be the increase to the respiration rate observed after moderate running for a period (e.g., five minutes). In another example, $x_i$ may be the change to respiration volume and/or average respiration volume during a half hour of cycling.

The computer 686 may calculate an estimation of a value of the aerobic activity parameter (denoted $\theta^*$) utilizing one or more probability functions of the form $P(X=x|\theta)$, which is a conditional probability of a value of the parameter related to respiration given a value of the aerobic activity parameter is equal to $\theta$. Optionally, the computer 686 performs at least one of the following in order to calculate $\theta^*$ (the estimation value of the aerobic activity parameter): a maximum likelihood (ML) estimation, and a maximum a posteriori probability (MAP) estimation.

The one or more probability functions of the form $P(X=x|\theta)$ may be calculated based on data pertaining to a diverse set users comprising users of different genders, ages, body builds, and athletic abilities. Optionally, the data includes observations of a parameter related to respiration calculated based on $TH_{RBN}$ of the users. In one embodiment, a probability function of the form $P(X=x|\theta)$ may be a table describing the probability of observing different values of x given a certain value of $\theta$. For example, the table may describe an empirically observed probabilities for various increases in respiration (e.g., increases of 2, 4, 6, . . . , 40 breaths per minute) given different values of 0, such as $VO_2$ max=10, 15, 20, . . . , 75, 80 mL/(kg·min). In another embodiment, a probability function of the form $P(X=x|\theta)$ may be described by a model that includes parameters of the distribution, where the parameters may be set using various approaches such as regression and/or maximum entropy approaches. Optionally, the parameters of the probability function describe a continuous exponential distribution.

A user interface 689 may be utilized to present the aerobic activity parameter 688 and/or present an alert related to the aerobic activity parameter 688. In one example, user interface 689 may be used to alert the user responsive to an indication that the aerobic activity parameter has fallen below a threshold (e.g., when the rate of energy expenditure falls below a threshold) or when the aerobic activity parameter reaches a certain threshold (e.g., when the total energy expenditure during a session reaches a certain caloric goal). Optionally, the user interface 689 includes a display, such as the display of a smart phone, a smartwatch, or a head-mounted augmented reality display. Optionally, the user interface 689 includes a speaker, such as a speaker of a smart phone, a smartwatch, or a head-mounted augmented reality display, or a speaker of a pair of headphones or an earbud.

As discussed herein, thermal measurements indicative of an exhale stream may be used by a computer to calculate various respiratory parameters, aerobic activity parameters, and coaching indications. In order to produce a better signal regarding the user's respiratory activity, in some embodiments, the computer 686 (or the computer 696 discussed below) may utilize additional input sources (besides thermal cameras).

In some embodiment, the additional input sources may include one or more visible-light cameras that capture images indicative of respiratory activity. In one example, the additional input sources include at least one inward-facing head-mounted visible-light camera (e.g., the camera 682), which is configured to take images of a region on the mouth ($IM_M$) of the user. In this example, $IM_M$ are indicative of whether the mouth is open or closed. In another example, the additional input sources include at least one inward-facing head-mounted visible-light camera configured to take images of a region on the nose ($IM_N$) of the user, in this example, $IM_N$ are indicative of movement of the nose while the user inhales (in this example, the camera 682 may be configured to take images of the nose in addition to, or instead of, the images of the mouth). Optionally, calculating various values (e.g., breathing rate, an aerobic activity parameters, or a coaching indication) based on $IM_M$ and/or $IM_N$ involves generating feature values based on $IM_M$ and/or $IM_N$ and using them in the calculation of said values (e.g., in addition to feature values generated based on $TH_{RBN}$). For example, feature values generated based on $IM_M$ and/or $IM_N$ involve using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. Optionally, $IM_M$ and/or $IM_N$ may be used to identify different states of the user (e.g., open vs, closed mouth or movement of the nostrils), and the information regarding the different states may be used as input (e.g., feature values) when calculating parameters such as the breathing rate.

In other embodiments, the additional input sources may include one or more microphones configured to record sounds made by the user's respiration. For example, the one or more sensors may include microphones in right and/or left in-the-ear earbuds, and feature values may be generated based on audio signal analysis of the recordings from the earbuds and utilized to calculating parameters such as the breathing rate, to detect inhaling/exhaling events, etc. Optionally, such in-ear measurements are used to calculate the user's breathing rate while the user was walking or running in an environment having ambient noise level above 50 dBA.

Other examples or sensors that may be used as additional input sources include sensors physically that are coupled to a garment worn over the user's torso and comprises at least one of the following: a pressure sensor, a stretch sensor, an electromechanical sensor, and a radio receiver. Optionally, these sensors are configured to measure movements of the chest due to respiration activity of the user, and these measurements are utilized to calculate various parameters such as the breathing rate.

The additional input sources described above may serve, in some embodiments, as complementary data that enhance accuracy of respiratory signals detected based on $TH_{RBN}$. For example, in some embodiments, exhaling air produces a stronger thermal signal than inhaling air. In these embodiments, detection of inhalation events can be assisted by images of the nostrils (which often show distinct movement when inhaling). In another example, there may be conditions in which exhaling may produce a relatively weak thermal signal, e.g., when exercising in warm environments in which the temperature of the exhaled air is close to the temperature in the environment. In such cases, additional data, such as data from sensors embedded in a garment or microphones in earbuds, may help and provide better indications of breathing.

The following is a description of another possible utilization of $TH_{RBN}$, which involves virtual coaching based on respiration data. FIG. 35b illustrates an embodiment of an athletic coaching system. The system includes at least one CAM (as described above) that is used to measure $TH_{RBN}$ 693 and a computer 696. Some embodiments of the system may optionally include additional elements, such as the frame 680, a head-mounted inward-facing video camera 692, a sensor 694, and a user interface 699.

The computer 696 is configured, in some embodiments to: receive measurements of movements ($M_{move}$ 695) involving the user, generate, based on $TH_{RBN}$ 693 and $M_{move}$ 695, a coaching indication 698; and present, via a user interface 699, the coaching indication 698 to the user. Various virtual coaching applications may be realized by analyzing $TH_{RBN}$ 693 and $M_{move}$ 695, and providing the user with insights and/or instructions based on the analysis. These insights and/or instructions may assist to improve the user's athletic performance in various ways.

One type of coaching application built on the system illustrated in FIG. 35b provides insights and/or instructions to a user performing an athletic activity that involves an aerobic exercise with repetitive motions such as running, rowing, or cycling. In one embodiment, the computer 696 generates the coaching indication 698, which is indicative of a change the user should make to one or more of the following: cadence of movements, stride length (if the user is running), breathing rate, breathing type (mouth or nasal), and duration of exhales. Optionally, responsive to a determination that the change is needed, the computer 696 provides, via the user interface 699, an indication to the user of this fact. For example, the user interface 699 may include a speaker (e.g., in earbuds) and the computer 696 generates an audio indication (e.g., a certain sound effect such as beeping at a certain frequency and/or speech conveying the coaching indication 698). In another example, the user interface may include a display and the coaching indication may be provided via visual cues (e.g., text, an image, or a light flashing at a certain frequency). The following are various examples of computations that may be performed by the computer 696 in order to generate the coaching indication 698.

In one embodiment, the computer 696 calculates the breathing rate of the user based on $TH_{RBN}$ 693 and then checks if it is in a desired range. Responsive to the breathing rate being below a first threshold, the computer 696 includes in the coaching indication 698, an instruction to increase the breathing rate. Additionally or alternatively, responsive to the breathing rate being above a second threshold (which is higher than the first threshold), the computer includes in the coaching indication 698 an instruction to decrease the breathing rate. Optionally, the first and/or second thresholds are calculated based on $M_{move}$ 695. For example, the first threshold (minimal desired breathing rate) and/or the second threshold (maximal desired breathing rate) are set according to the level of activity of the user. Optionally. "level of activity" may refer to one or more of the following: the speed of the user (e.g., when running or cycling), the cadence of the user's movement, a value of an aerobic activity parameter of the user (e.g., $VO_2$ or EE).

In another embodiment, the computer 696 calculates a value indicative of the cadence of the user based on $M_{move}$ 695. For example, the computer 696 may identify cyclic signals indicating movement such as pedaling, rowing, or strides. Optionally, the computer 696 utilizes a machine learning model to calculate the cadence based on $M_{move}$ 695, where the model is trained based on $M_{move}$ of other users. Optionally, responsive to the cadence being below a first threshold, the computer 696 includes in the coaching indication 698 an instruction to increase the cadence. Additionally or alternatively, responsive to the cadence being above a second threshold, the computer 696 includes in the coaching indication 698 an instruction to decrease the cadence. Optionally, the first and/or second thresholds are calculated according to $TH_{RBN}$ 693. For example, the first and/or second thresholds may correspond to a desired cadence that is appropriate for the breathing rate of the user, as determined based on $TH_{RBN}$ 693.

In yet another example, the computer 696 calculates a value indicative of exhale durations of the user based on $TH_{RBN}$ 693. Optionally, the computer 696 includes in the coaching indication 698 an instruction to increase the exhale durations responsive to determining that the exhale durations are below a threshold. Optionally, the threshold is calculated based on at least one of $M_{move}$ 695 and $TH_{RBN}$ 693. For example, the threshold may be set according to a predetermined function that assigns a minimal desired duration of exhales based on the cadence or speed of the user (e.g., as determined based on $M_{move}$ 695) and/or based on the breathing rate of the user (e.g., as determined based on $TH_{RBN}$ 693).

In still another embodiment, the computer 696 detects, based on $TH_{RBN}$ 693, whether the user is breathing through the mouth. Responsive to detecting that the user is breathing through the mouth, the computer 696 includes in the coaching indication 698 an instruction to the user to breathe through the nose.

The computer 696 may utilize a machine learning model 697 to generate the coaching indication 698. In some embodiments, the computer generates feature values based on $TH_{RBN}$ 693 and/or $M_{move}$ 695. For example, the feature values may include one or more of the feature values described above which are generated based on $TH_{RBN}$ 683 and/or measurements of the sensor 684 and are used to estimate the aerobic activity parameter 688. Optionally, the computer 696 utilizes the model 697 to calculate, based on the feature values generated based on $TH_{RBN}$ 693 and/or $M_{move}$ 695, a value indicative of whether the change is needed and/or what change in the user's activity should be indicated in the coaching indication 698.

The model 697 may be generated based on data comprising previously taken $TH_{RBN}$ and $M_{move}$ of the user and/or other users and indications of appropriate coaching instructions (and whether coaching instructions are needed) corresponding to the time previously taken $TH_{RBN}$ and $M_{move}$ were taken. For example, the previously taken $TH_{RBN}$ and $M_{move}$ may be used to generate samples; each sample comprising feature values generated based on $TH_{RBN}$ and $M_{move}$ taken during a certain period (the same type of feature values generate by the computer 696, as described above). The indications on appropriate coaching instructions may be used to create labels for the samples. In one example, the coaching instructions are provided by a human annotator (e.g., a human coach) that reviews the data and determines whether changes could be made to improve the athletic performance. In another example, the coaching instructions are provided by an expert system (e.g., a rule based system such as a decision tree), which is designed for this purpose.

In some embodiments, $M_{move}$ 695 are generated by a sensor 694, which may represent herein one or more of various types of sensors. In one embodiment, the sensor 694 is an accelerometer and/or gyroscope in a device carried or worn by the user. For example, the sensor 694 may be a movement sensor in a smartwatch or smart glasses worn by the user or a movement sensor in a smartphone carried by the user. Optionally, analysis of measurements of the sensor 694 provides information about one or more of the following: the types of movements the user is making (e.g., running, cycling, or rowing), the cadence of the user (e.g., number of steps per minute, number of revolutions per minute in cycling, or the number of strokes per minute), and/or the speed of the user. In another embodiment, the sensor 694 is a location identifying sensor, such as a GPS receiver. Optionally, analysis of measurements of the sensor 694 provides information on the speed of the user, the elevation and/or distance traveled, etc. In some embodiments, $M_{move}$ 695 may include information obtained from multiple movement sensors. In one example, information about the speed and/or distance traveled by the user, coupled with information about the cadence, is used in order to determine the length of the user's strides.

Another type of coaching application that may utilize $TH_{RBN}$ 693 and $M_{move}$ 695 provides the user with breathing cues (e.g., a breathing pacer application) in order to assist the user to breathe at a desired pace while conducting athletic activity. In one embodiment, the computer 696 calculates a target breathing rate based on data comprising at least one of $TH_{RBN}$ 693 and $M_{move}$ 695, and includes in the coaching indication breathing cues that correspond to the target breathing rate. Optionally, the computer 696 receives a value indicative of the heart rate (HR) of the user and uses HR to calculate the target breathing rate (in addition to utilizing at least one of $TH_{RBN}$ 693 and $M_{move}$ 695). In one example, $M_{move}$ 695 is utilized to calculate a value indicative of the speed of the user and/or the cadence of the user, and the computer 696 utilizes a predetermined function to select for the user the target breathing rate, based on the speed and/or the cadence. In another example, a current breathing rate of the user, which is calculated based on $TH_{RBN}$ 693, is used to select a target breathing rate that will match the cadence of the user (e.g., which is determined based on $M_{move}$ 695). In still another example, $TH_{RBN}$ 693 and $M_{move}$ 695 are used as input to a function that calculates the target breathing rate. For example, the computer 696 may generate feature values (e.g., as discussed above with respect to the coaching indication regarding an instruction to change an aspect of the user's activity) and utilize a certain model to calculate, based on these feature values, the target breathing rate. Optionally, the certain model is generated based on data comprising previously taken $TH_{RBN}$ and $M_{move}$ of the user and/or other users and indications of the appropriate breathing rate as determined by an expert (e.g., a human or an expert system). The various computational approaches described herein with respect to detecting a physiological response may be employed in order to calculate the target breathing rate (e.g., comparison to threshold, reference time series, and/or machine learning approaches described herein).

In one embodiment, the computer 696 calculates a current breathing rate based on $TH_{RBN}$ 693 and compares the current breathing rate to first and second thresholds, where the first threshold is below the target breathing rate and second threshold is above the target breathing rate. Responsive to the current breathing rate being below the first threshold or above the second threshold, the computer 696 instructs the user interface 699 to start providing the breathing cues or to increase intensity of provided breathing cues. Optionally, responsive to the current breathing rate being above the first threshold and below the second threshold, for at least a certain duration, the computer 696 instructs the user interface 699 to cease from providing the breathing cues or to provide weaker breathing cues.

Figure 35C:
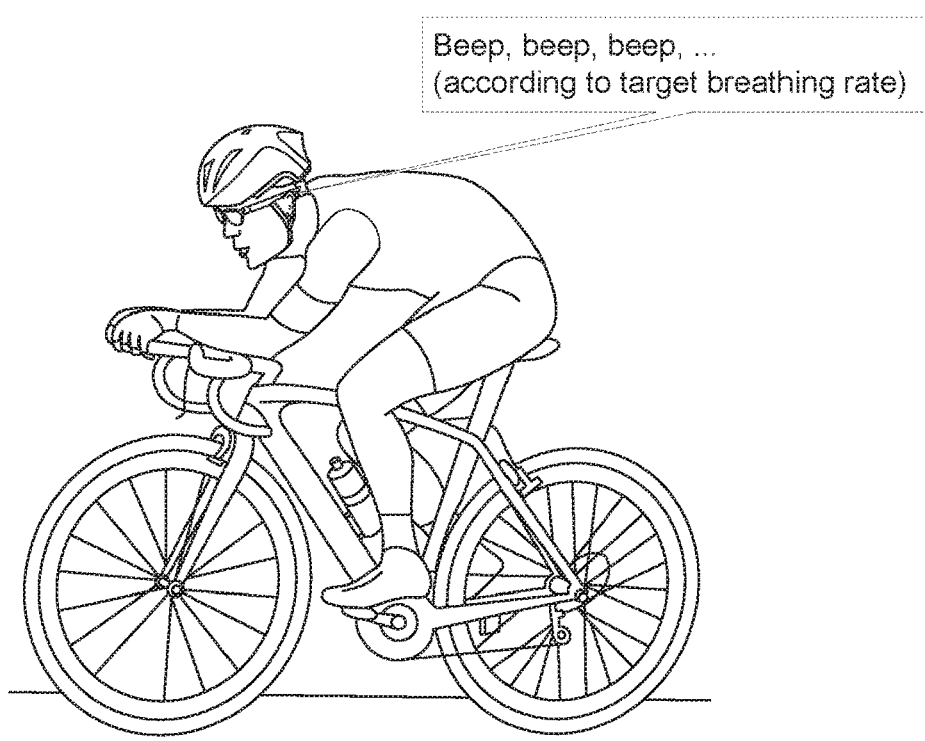
FIG. 35c illustrates a cycler who receives breathing cues via an earbud.

The breathing cues may be provided in various ways. In one example, the user interface 699 includes a speaker (e.g., in an earbud) and the breathing cues comprise auditory cues that have a frequency that corresponds to the target breathing rate (e.g., a beeping sound at the frequency or a music that has an underlying beat at the frequency). FIG. 35c illustrates a cycler who receives breathing cues via an earbud, which correspond to the target breathing rate. In another example, the user interface 699 includes a display (e.g., a display of augmented reality smart glasses, and the breathing cues comprise visual cues that have a frequency that corresponds to the target breathing rate (e.g., a flashing light or icon that changes its size at a frequency that corresponds to the target breathing rate).

Yet another type of coaching application that may utilize $TH_{RBN}$ 693 and $M_{move}$ 695 a coaching indication indicative synchronization of a breathing pattern of the user with a sequence of movements of the user. Optionally, the coaching indication 698 may be indicative of whether the breathing is synchronized with a sequence of movements (i.e., indicate to the user whether the user is breathing correctly when performing the sequence of movements). Additionally or alternatively, the coaching indication 698 may provide cues of the correct breathing pattern corresponding to the sequence of movements (i.e., provide cues that indicate to the user a synchronized breathing pattern). In one embodiment, the computer 696 provides the user, via the user interface 699, an indication indicative of whether the user's breathing is synchronized with the sequence of movements. Additionally or alternatively, the computer 696 determine whether the user did not breathe in an appropriate pattern while performing a sequences of movements. Responsive to determining that the user did not breathe in the appropriate pattern, the computer 696 notifies the user of this fact via a user interface 699.

A "correct" breathing pattern refers to a breathing pattern that is considered appropriate for the sequence of movements, and thus may be considered synchronized with the sequence of movements. Optionally, determining a breathing pattern that is correct for a sequence of movements may be done based on expert knowledge (e.g., coaches, experts in athletics and physiology, etc.) Additionally or alternatively, correct breathing patterns for a sequence of movements may be learned from observations. For example, performance of one or more users may be monitored while they breathe in various patterns while performing a certain sequence of movements, and the optimal breathing pattern (i.e., the breathing pattern that is synchronized with the certain sequence) may be determined based on detecting a breathing pattern for which the performance is maximized (e.g., farthest/most accurate driver hit).

The sequence of movements performed by the user may be, in some embodiments, sequences involved in performing a specific operation, such as swinging a bat, a racket or a golf club, lifting weights, performing a move in yoga, etc. In such cases, various sensors may be utilized in order to obtain $M_{move}$ 695, which provide indications of the type of movements the user is performing and/or how the user is manipulates objects (such as a bat, a racket, a golf club, a barbell, etc.). In some embodiments, the sensor 694 is a camera that takes images of the user, the user's limbs, and/or objects held by the user. In one example, the sensor 694 is an outward-facing head-mounted camera (e.g., a camera pointed outwards that is coupled to a frame worn on the user's head). In another example, the sensor 694 is an external camera, such as a camera in a laptop, smart TV, or a webcam. Optionally, the computer 696 performs image analysis of $M_{move}$ 695 that includes images taken by the sensor 694 in order to identify various movements of the user.

In some embodiments, the sensor 694 may include at least one of LiDAR system and a RADAR system. Optionally, the computer 696 analyzes $M_{move}$ 695 in order to identify movements of the user's limbs, changes to the user's pose, and/or the location of an object held by the user (e.g., a barbell, racket, golf club, etc.)

The following are examples of various sequences of movements and coaching indications that may be generated for them based on $TH_{RBN}$ 693 and $M_{move}$ 695.

In one embodiment, a sequence of movements of the user corresponds to a pressing motion of weights or a barbell, and the coaching indication 698 indicates to inhale in the concentric phase of the press and exhale in the eccentric phase of the press. In one example, the sensor 694 is a movement sensor (e.g., an accelerometer embedded in a garment worn by the user) and the computer 696 analyzes $M_{move}$ 695 to identify different movements involved in the pressing motion. In another example, the sensor 694 is an outward-facing head-mounted camera or a camera external to the user, and $M_{move}$ 695 include images of the user and/or of the weights or barbell. In this example, the computer 696 may utilize image analysis of $M_{move}$ 695 in order to identify different movements involved in the pressing motion. Optionally, the coaching indication 698 is provided to the user while the user performs the sequence of movements, such that when the computer 696 recognizes that the user is about push the weights or barbell, or starts to push (initiating the concentric phase), the user is instructed, in the coaching indication 698, to exhale.

In another embodiment, a sequence of movements of the user corresponds to swinging a racket in order to hit a ball with the racket (e.g., while playing tennis), and the coaching indication 698 indicates to exhale while hitting the ball. In one example, the sensor 694 is a movement sensor (e.g., an accelerometer) on the user's body, and the computer 696 analyzes $M_{move}$ 695 to identify movements that characterize a swinging motion. In another example, the sensor 694 comprises at least one of a LiDAR system and a RADAR system, and the computer 696 analyzes $M_{move}$ 695 to determine the location of the arms and/or the racket relative to the user's body in order to identify the swinging motion. Optionally, the coaching indication 698 is provided to the user while the user performs the sequence of movements, such that when the computer 696 recognizes that the user is about swing the racket, or starts to starts to swing the racket, the user is instructed, in the coaching indication 698, to exhale.

Figure 35D:
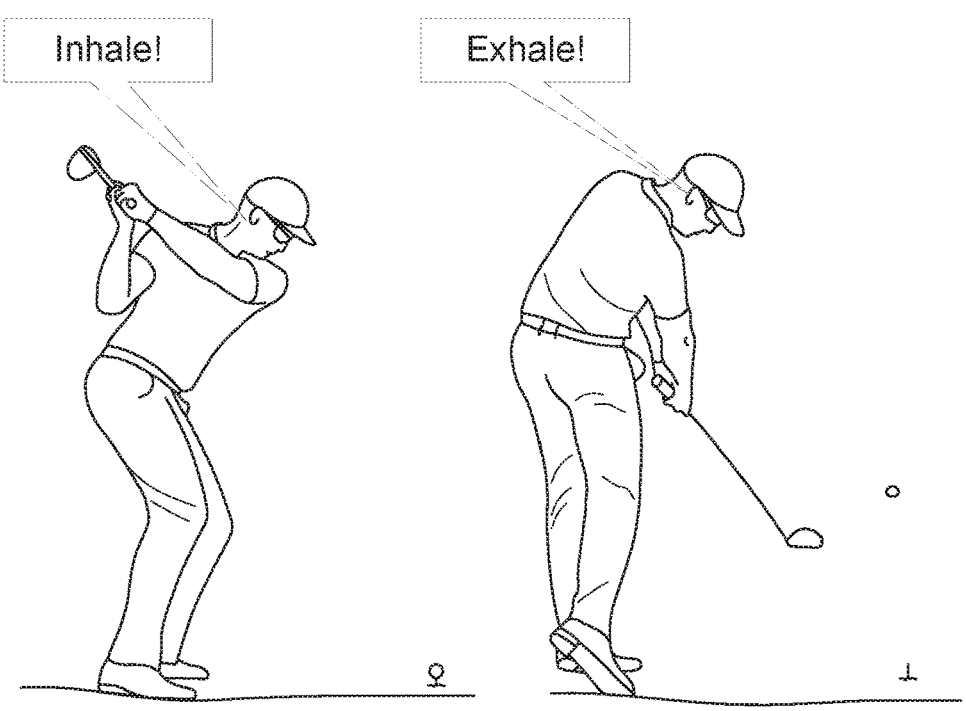
FIG. 35d illustrates a user receiving coaching instructions while hitting a driver in golf.

In yet another embodiment, a sequence of movements of the user corresponds to making a drive shot in golf, and the coaching indication 698 indicates to inhale during the backswing and exhale again on the downswing. Optionally, the coaching indication 698 also indicates to exhale at address. Optionally, the coaching indication 698 is provided to the user while the user performs the sequence of movements, such that when the computer 696 recognizes that the user is about to drive the shot (e.g., based on characteristic movements in the address), or starts the drive shot (e.g., by starting the backswing), the user is instructed, in the coaching indication 698, to exhale. FIG. 35*d* illustrates a user receiving coaching instructions while hitting a driver in golf; the figure illustrates the user receiving instructions (e.g., via an earbud) to inhale on the backswing and exhale of the downswing.

In still another embodiment, the computer 696: (i) receives from a fitness app (also known as a personal trainer app) an indication that the user should exhale while making a movement, (ii) determines, based on $m_{move}$ 695, when the user is making the movement, and (iii) determines, based on $TH_{RBN}$ 693, whether the user exhaled while making the movement. Optionally, the computer 696 commands the user interface 699 to (i) play a positive feedback in response to determining that the user managed to exhale while making the physical effort, and/or (ii) play an alert and/or an explanation why the user should try next time to exhale while making the physical effort in response to determining that the user did not exhale while making the physical effort. FIG. 26*a* illustrates a fitness app running on smartphone 196, which instructs the user to exhale while bending down. CAM coupled to eyeglasses frame 181 measures the user breathing and is utilized by the fitness app that helps the user to exhale correctly. FIG. 26*b* illustrates inhaling while straightening up.

There are various ways in which the computer 696 may generate a coaching indication that is indicative of synchronization of a breathing pattern of the user with a sequence of movements of the user. In some embodiments, generating the coaching indication 698 involves identifying a breathing pattern based on $TH_N$ 693 and/or the sequence of movements based on $M_{move}$ 695. Additionally or alternatively, a machine learning model may be used to calculate, based on $TH_{RBN}$ 693 and $M_{move}$ 695, a value indicative of an extent to which the breathing pattern of the user is synchronized with the sequence of movements.

In some embodiments, a breathing pattern may refer to a description of characteristics of the user's breathes during a certain period of time. Optionally, the breathing pattern is determined by identifying, based on $TH_{RBN}$ 693, times at which the user inhaled or exhaled and/or by calculating, based on $TH_{RBN}$ 693, one or more of the various respiratory parameters described herein. Optionally, a breathing pattern may describe one or more of the following values: times at which the user inhaled, times at which the user exhaled, durations of inhales, durations of exhales, respiration volume (or changes to the respiration volume), indications of whether the user exhaled and/or inhaled from the mouth, and indications of whether the user exhaled and/or inhaled from the nose. Optionally, the values comprised in a breathing pattern include corresponding temporal values. For example, a breathing pattern may include the following: at time t=0 inhaling, at time t=1.5 exhaling, at time t=3 inhaling, . . . , etc. Additionally or alternatively, a breathing pattern may include qualitative descriptors of respiration (determined based on $TH_{RBN}$ 693). For example, a breathing pattern may include the following descriptors: a regular inhaling followed by a short bursty exhaling (e.g., when hitting a ball).

In some embodiments, a sequence of movements of the user may refer to values describing movement of the user's body (changing location in the 3D space) and/or changes to pose and/or orientation of limbs. Optionally, the sequence of movements may be represented using descriptors that represent specific movements that are identified based on $M_{move}$ 695. For example, the sequence of movements describing a drive shot in golf may include descriptors such as: getting into position (address), a backswing, and a downswing. Optionally, the descriptors of movements in a sequence of movements may have associated temporal values describing properties such as when each of the movements started and/or how long each of the movements lasted.

In one embodiment, identifying a certain movement, from among the sequence of movements, is done using a machine learning-based model. $M_{move}$ 695 (or a portion thereof, e.g., a segment lasting a second) are converted into feature values representing values of $M_{move}$ (e.g., values of an accelerometer, low-level image features, etc.), using approaches described herein and/or approaches known in the art. A model is utilized to calculate, based on the feature values, a value indicative of whether the user performed the certain movement. Optionally, the model is trained on samples of one or more users, each comprising feature values generated based on $M_{move}$ of a user taken while said user performed the certain movement. Optionally, the model is trained on samples of one or more users, each comprising feature values generated based on $M_{move}$ of a user taken while said user did not perform the certain movement.

In one embodiment, identifying a certain movement, from among the sequence of movements, is done using similarity to reference $M_{move}$ taken while a certain user performed the certain movement. $M_{move}$ 695 (or a portion thereof, e.g., a segment lasting a second), is compared to the reference $M_{move}$ and if the similarity reaches a threshold, the user is considered to have performed the certain movement while $M_{move}$ 695 (or the portion thereof) were taken. In one example, the segments of $M_{move}$ being compared are treated as time series data, and one or more of the methods referenced herein with respect to determining similarity of time series are used to determine the similarity. In another example, the segments of $M_{move}$ being compared may be represented as points in a high dimensional space, and a distance function such as the Euclidian distance or some other distance function is used find the distance between the points. The threshold, to which the similarity is compared, may be determined experimentally and selected in order to achieve a desirable balance between specificity and sensitivity of identifications of the certain movement.

In order to determine to what extent the sequence of movements (determined based on $M_{move}$ 695) is synchronized with the breathing pattern (determined based on $TH_{RBN}$ 693) the computer 696 may align the sequence of movements and breathing pattern (e.g., by using temporal information associated with both). This alignment may be done in different ways. In one example, the alignment determines which respiratory actions were performed when different movements of the sequence of movements were performed. In this example, the computer 696 may utilized the alignment to determine whether the respiratory actions correspond to one or more predetermined breathing patterns appropriate for the certain movement sequence.

In another embodiment, feature values are generated based on the sequence of movements and the breathing pattern. For example, some of the feature values may describe which movements were performed, their relative order, and timing. Additionally some feature values may describe which respiratory activities were performed, their order/timing/duration, and other related properties described above. A model is used to calculate, based on the feature values, a value indicative of the extent to the breathing pattern is synchronized with the sequence of movements. Optionally, the model is trained based samples generated from $M_{move}$ and $TH_{RBN}$ of one or more users, which include samples generated based on $M_{move}$ and $TH_{RBN}$ taken while the sequence of movements was performed and a user was breathing in a breathing pattern that was synchronized with the sequence of movements. Additionally, the samples used to train the model may include samples generated based on $M_{move}$ and $TH_{RBN}$ taken while the sequence of movements was performed and a user was not breathing in a breathing pattern that was synchronized with the sequence of movements. Optionally, a breathing pattern is considered not to be synchronized with a sequence of movements if the extent of the synchronization between the two is below a predetermined threshold (and considered synchronized otherwise).

In yet another embodiment, a unified sequence is created from the breathing pattern and the sequence of movements, which describes both movements and respiration activities. For example, the sequence of movements and the breathing pattern may be merged to a single sequence using temporal data. This unified sequence may then be evaluated to determine whether it corresponds to a breathing pattern that is synchronized to a sequence of movements based on similarity to a reference unified sequence and/or a machine learning-based model trained on samples generated based on unified sequences that are generated based on $M_{move}$ and $TH_{RBN}$ taken while the sequence of movements was performed and a user was breathing in a breathing pattern that was synchronized with the sequence of movements.

In some embodiments, determining whether a breathing pattern is synchronized with a sequence of movements of the user is done using a machine learning-based model. The computer 696 generates feature values based on $TH_{RBN}$ 693 (e.g., one or more feature values of types described herein which are used to calculate a respiratory parameter) and/or based on Mm. 695 (e.g., feature values described above which are used to identify certain movements). The computer 696 utilizes the machine learning-based model to calculate, based on the feature values, a value indicative of whether the breathing pattern was synchronized with the sequence of movements. Optionally, the model was trained based on data comprising: a first set of previous $TH_{RBN}$ and $M_{move}$ of one or more users, taken while performing the sequence of movements and breathing in a pattern that is synchronized with the sequence of movements, and a second set of previous $TH_{RBN}$ and $M_{move}$ of the one or more users taken while performing the sequence of movements and breathing in a pattern that is not synchronized with the sequence of movements.

One application for which thermal measurements of the face may be useful is to detect an allergic reaction. In one embodiment, a system configured to detect an allergic reaction of a user includes at least a CAM that takes thermal measurements of a region on the nose ($TH_N$) of the user, and a computer that detects an allergic reaction of the user based on $TH_N$. Optionally, an allergen may be any substance that causes the user to experience an allergic reaction due to the exposure of the user to the allergen (e.g., by consuming, inhaling, and/or coming into physical contact with the allergen). For example, an allergic reaction may be a reaction to a drug, peanuts, eggs, wheat, dairy products, seafood, pollen, dust, and/or perfume.

In one embodiment. CAM is physically coupled to a frame worn on the user's head (e.g., a frame of glasses or an augmented reality display). Optionally, CAM is located less than 15 cm from the user's face. Optionally. CAM weighs less than 10 g, 5 g or 1 g. Optionally, CAM uses a thermopile, a pyroelectric sensor, or a microbolometer sensor, which may be a focal-plane array sensor. For example, CAM may be the thermal cameras 48 and/or 49, which are illustrated in FIG. 1*b*, or the thermal camera 540 illustrated in FIG. 40.

Optionally, multiple CAMs may be utilized to obtain measurements of various ROIs such as different regions/sides of the nose, mouth and/or cheeks. For example, allergic reaction may cause red eyes, itchy eyes, tearing eyes, swollen eyelids, and/or burning eyes/eyelids. In some cases, a thermal camera that captures a region on the periorbital ($TH_{peri}$) around at least one of the eyes may detect an eye allergy symptom before the user is aware of the allergic reaction and/or used to assess the extent of the allergic reaction. As another example, allergic reaction may cause hives (urticaria) around the mouth and/or other parts of the face. In some cases, a thermal camera that captures the area around the mouth ($TH_{lips}$) may detect the hives around the mouth before the user is aware of the allergic reaction and/or used to assess the extent of the allergic reaction. In still some cases, thermal measurements of regions on the right and/or left cheeks ($TH_{ch}$) may help detecting the allergic reaction.

The computer is configured, in one embodiment, to detect the allergic reaction based on $TH_N$ and optionally other data, such as $TH_{CH}$, $TH_{peri}$, and/or $TH_{lips}$ mentioned above and/or other sources of information mentioned below. In one embodiment, detecting the allergic reaction may involve one or more of the following: determining whether the user is experiencing an allergic reaction, and/or determining the extent of the allergic reaction. Optionally, the extent of the allergic reaction may be indicative of the severity of the allergic reaction, and/or the duration of the allergic reaction (e.g., total time of the allergic reaction and/or the time remaining until the allergic reaction subsides).

In some cases, changes to temperatures at regions of the face (e.g., in the nasal area) occur quickly at the initial stages of an allergic reaction. Thus, the computer may detect the allergic reaction at its initial stages even before the user is aware of the allergic reaction. Thus, in some embodiments, detecting the allergic reaction involves detecting an onset of the allergic reaction, which may involve determining the time until the reaction reaches its peak severity (e.g., a rash, coughing, respiratory distress, sneezing) and/or determining the expected degree of severity (extent) of the allergic reaction.

In some cases, at the time the allergic reaction is identified, a user having the allergic reaction may not be aware of the allergic reaction, e.g., because the symptoms are not strong enough at the time. Thus, being notified about an allergic reaction before its full manifestation may have an advantage, in some embodiments, of allowing the user to take early action to alleviate and/or decrease the symptoms (e.g., take antihistamines) or seek medical attention.

In some allergic reactions, the nasal temperature can rise rapidly within minutes, before other more noticeable symptoms may manifest themselves (e.g., sneezing, itching, and/or respiratory problems). Thus, rising nasal temperatures may serve as an indication of an allergic reaction. For example, a fast increase due to an allergic reaction may correspond to an increase of more than 0.8° C. within a period of less than 10 minutes, or even less than 5 minutes.

Figure 39A:
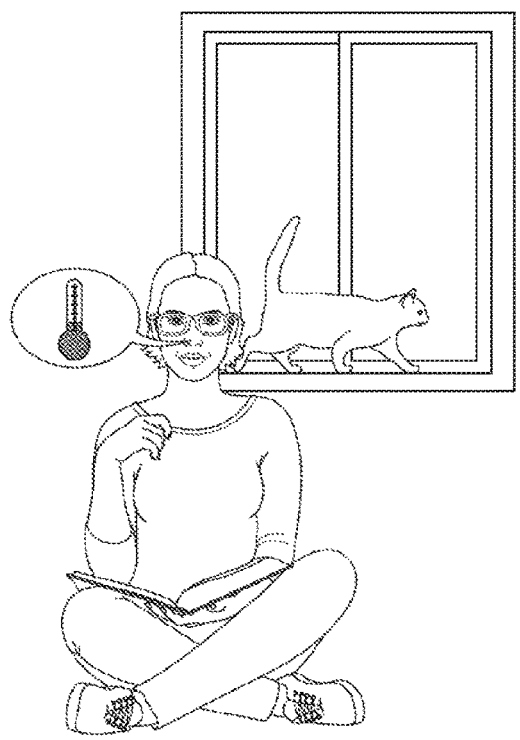
FIG. 39a and FIG. 39b illustrate a scenario in which a user is alerted about an expected allergic reaction.
Figure 39B:
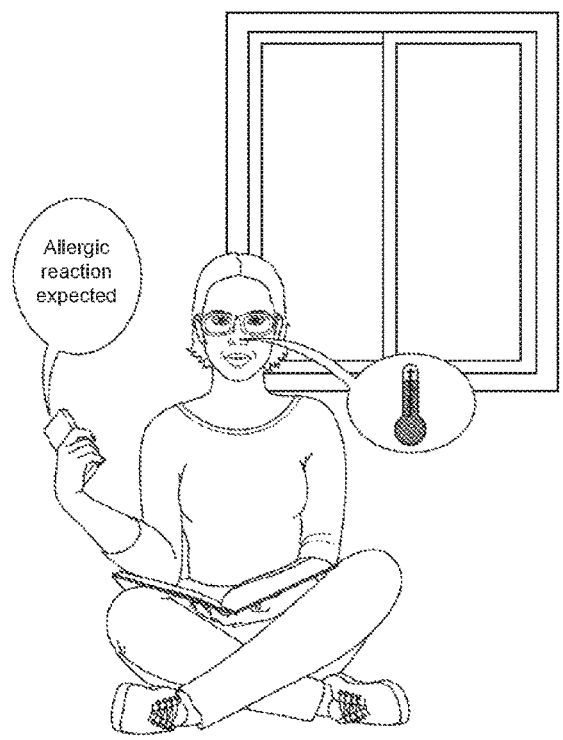

FIG. 39*a* and FIG. 39*b* illustrate a scenario in which a user is alerted about an expected allergic reaction. In FIG. 39*a*, the user's nasal temperature is normal. At that time, a cat, to which the user is allergic, walks past the user. FIG. 39*b* illustrates the situation shortly after. The user's nasal temperature has increased, and based on thermal measurements of the nasal region a computer issues an alert to the user about the expected allergic reaction. Note that at the time the alert is issued, the user may not be aware of any symptoms of the allergic reaction. Receiving an early warning in this case may enable the user to take measures to alleviate the effects of the allergic reaction, such as taking an antihistamine medicine.

In one embodiment, a system configured to alert about an allergic reaction includes at least CAM (which is discussed above) and a user interface (UI), such as UI 373. CAM is worn on a user's head and takes thermal measurements of a region on the user's nose ($TH_N$). Optionally. CAM weighs below 10 g, is physically coupled to a frame worn on the user's head, and is located less than 15 cm from the user's face. Optionally, the system includes a transmitter that may be used to transmit $TH_N$ to a computer that detects the allergic reaction based on $TH_N$. In one example, the computer may belong to a device of the user, such as a computer of an HMS of which CAM is part, or a computer belonging to a smartphone or a smartwatch carried by the user. In another example, the computer may be remote of the user, such as cloud-based server. Various approaches that may be utilized by the computer to detect the allergic reaction are discussed below. Optionally, responsive to detecting the allergic reaction (e.g., by calculating that an extent of the allergic reaction reaches a threshold), the computer commands the UI to provide the alert. For example, the computer may send a signal to a smartphone app, and/or to a software agent that has control of the UI, to provide the alert. In another example, the computer may send an instruction to the UI to provide the alert. Optionally, the alert is provided as text, image, sound, and/or haptic feedback.

There are various ways the computer may utilize $TH_N$ and possibly other thermal measurements such as $TH_{CH}$, $TH_{peri}$, and/or $TH_{lips}$ in order to detect the allergic reaction. In one embodiment, the computer may compare values derived from $TH_N$ (and/or from $TH_{CH}$, $TH_{peri}$, and/or $TH_{lips}$) to a certain threshold, and determine whether the threshold is reached (which is indicative of an occurrence of the allergic reaction). Optionally, the threshold is determined based on previous thermal measurements of the user. Optionally, the threshold is determined based on previous thermal measurements of other users. In another embodiment, the computer may determine a similarity between a reference time series corresponding to the allergic reaction and $TH_N$ and optionally the other thermal measurements (or a time series derived therefrom). Optionally, when a sufficiently high similarity is detected, the computer may interpret that as an indication of an occurrence of the allergic reaction. The reference time series may be generated based on previous thermal measurements of the user and/or of other users.

In yet another embodiment, the computer may generate feature values based on thermal measurements comprising $TH_N$ and optionally $TH_{CH}$, $TH_{peri}$, and/or $TH_{lips}$, and utilize a machine learning-based model to calculate, based on the feature values, a value indicative of whether the allergic reaction occurred and/or indicative of an extent of the allergic reaction (calculating the value be considered herein as "detecting the allergic reaction"). Optionally, the model was trained based on previous thermal measurements of the user. For example, the previous thermal measurements may include a first set of thermal measurements taken while the user had an allergic reaction, and a second set of thermal measurements taken while the user did not have an allergic reaction. In this example, the model may be considered a personalized model for the user. Additionally or alternatively, the model may be trained on thermal measurements of other users (e.g., a general model). Optionally, different models may be created to detect different types of allergic reactions, to detect allergic reactions to different allergens, and/or to detect different extents of an allergic reaction.

In one example, detection of the allergic reaction may involve the computer performing the following: (i) generating feature values based on thermal measurements comprising $TH_N$ and optionally $TH_{CH}$, $TH_{peri}$, and/or $TH_{lips}$; and (ii) utilizing a model to detect the allergic reaction based on the feature values. Optionally, the model was trained based on previous thermal measurements of the user comprising $TH_N$ and optionally $TH_{CH}$, $TH_{peri}$, and/or $TH_{lips}$, which were taken while the user had an allergic reaction. Alternatively, the model was trained based on a first set of previous thermal measurements of the user comprising $TH_N$ and optionally $TH_{CH}$, $TH_{peri}$, and/or $TH_{lips}$, which were taken while the user had an allergic reaction and a second set of previous thermal measurements of the user comprising $TH_N$ and optionally $TH_{CH}$, $TH_{peri}$, and/or $TH_{lips}$, which were taken while the user did not have an allergic reaction.

In some embodiments, detecting the allergic reaction may involve utilizing baseline $TH_N$, most of which were taken when the user did not have an allergic reaction. Thus, detecting the allergic reaction may rely on observing a change relative to typical temperatures at the ROIs. In one example, the computer detects the allergic reaction based a difference between $TH_N$ and a baseline value determined based on a set of previous $TH_N$ taken with CAM. In this example, most of $TH_N$ belonging to the set were taken while the user had an allergic reaction, or within thirty minutes before or after the user had an allergic reaction.

Confounding factors such as extensive physical activity, touching the nose, and/or direct sunlight aimed at the nose may lead, in some embodiments, to less accurate detections of an allergic reaction (e.g., by increasing the frequency of false detections of the allergic reaction). In some embodiments, the system may include a sensor that takes additional measurements ($m_{conf}$) of the user, and/or of the environment in which the user was in while $TH_N$ were taken. Optionally, $m_{conf}$ are indicative of an extent to which a confounding factor occurred while $TH_N$ were taken. Another approach that may be utilized by the computer is to generate feature values based on $m_{conf}$ and to utilize these feature values in the detection of the allergic reaction.

Receiving early notice regarding an allergic reaction may be useful in some embodiments, since it may enable a user to take action in order to reduce the severity of the allergic reaction. For example, the user may attempt to reduce exposure to an allergen (e.g., leave an area that has a high concentration of pollen), take certain medication (e.g., antihistamines) to reduce the effects of the allergic reaction, and/or promptly seek medical attention (in anticipation of a more severe allergic reaction that is to come). However, providing such early indications may involve relaxing the conditions under which an allergic reaction is detected (e.g., lowering thresholds for $TH_N$). This can come at a cost of having more false positives in the detection of allergic reactions. Thus, in order to avoid excessive false positives the system may need to be judicious about when it employs more relaxed conditions for detecting an allergic reaction.

One way in which false positive allergic reaction detections may be reduced is to utilize knowledge of conditions and/or times in which it is more likely that the user may experience an allergic reaction. For example, if it is known with high probability that the user was exposed to an allergen to which the user is known, or suspected, to be allergic, then more relaxed conditions for detecting the allergic reaction may be employed. Optionally, if there is no reason to believe that the user was exposed to an allergen, then the more strict conditions may be employed for detecting the allergic reaction.

In some embodiments, the computer receives an indication of whether the user was exposed to an allergen and utilizes the indication in the process of detecting the allergic reactions. This indication may be utilized in various ways, which may depend on how the computer detects allergic reactions, as the following embodiments demonstrate.

In one embodiment, the computer compares $TH_N$ (or certain values computed based on $TH_N$) to a threshold, such that if $TH_N$ reach the threshold, this is indicative of a likely occurrence of the allergic reaction. In this embodiment, the threshold may be selected based on the indication that indicates exposure, or possible exposure, to the allergen. For example, responsive to receiving a first indication indicating that the user was exposed to the allergen the computer selects a first threshold, and responsive to receiving a second indication indicating that the user was not exposed to the allergen, the computer selects a second threshold that is higher than the first threshold. Thus, the second threshold requires a greater change in $TH_N$ in order to detect the allergic reaction.

In another embodiment, the computer calculates a similarity between $TH_N$ and a reference time series comprising data indicative of temperatures at different points in time during an allergic reaction (e.g., time series of the user having the allergic reaction). When the similarity reaches a certain threshold, this is indicative of an occurrence of the allergic reaction. In this embodiment, the certain threshold may be selected based on the indication that indicates exposure, or possible exposure, to the allergen. For example, responsive to receiving a first indication indicating that the user was exposed to the allergen, the computer selects a first certain threshold, and responsive to receiving a second indication indicating that the user was not exposed to the allergen, the computer selects a second certain threshold that corresponds to a higher extent of similarity than the first certain threshold. Thus, the second certain threshold requires greater similarity to the reference time series in order to detect the allergic reaction.

In yet another embodiment, the computer utilizes $TH_N$ to generate feature values, and to utilize a model to calculate, based on the feature values, an extent of the allergic reaction. In this embodiment, the model is a machine learning-based model that is generated based on previous thermal measurements of regions on the noses of one or more users (which may include the user and/or other users). At least some of the feature values are generated based on the indication, and may describe various properties of the exposure to an allergen, such as the type of allergen, the duration of exposure, the extent of exposure (e.g., dosage), and/or the time that has elapsed since the exposure. Thus, the above factors may be taken into account by the model, which may increase the chances of detecting an allergic reaction when the features indicate sufficient exposure to certain allergens.

The indication that is indicative of exposure to the allergen may be received from various sources. In one embodiment, the indication may be self-reported by the user. For example, the user may provide information about the exposure through interaction with a device such as a smartphone or speaking with a software agent via a microphone. In another embodiment, various camera-based systems may be utilized to take images comprising the allergen or an object associated with the allergen, analyze the images, and generate the indication about the exposure based on the analysis. Such systems that monitor the environment the user is in and/or substances the user consumes are discussed in more detail below. In yet another embodiment, an external source may provide indication based on determining the location of the user. For example, the user's location may be determined based on GPS, cellphone transmissions, and/or Wi-Fi transmissions. Additionally, an external database that includes real-time data about the presence of various allergens (e.g., dust or pollen) may be queried in order to determine whether the user is likely exposed to a potential allergen substance.

Figure 37:
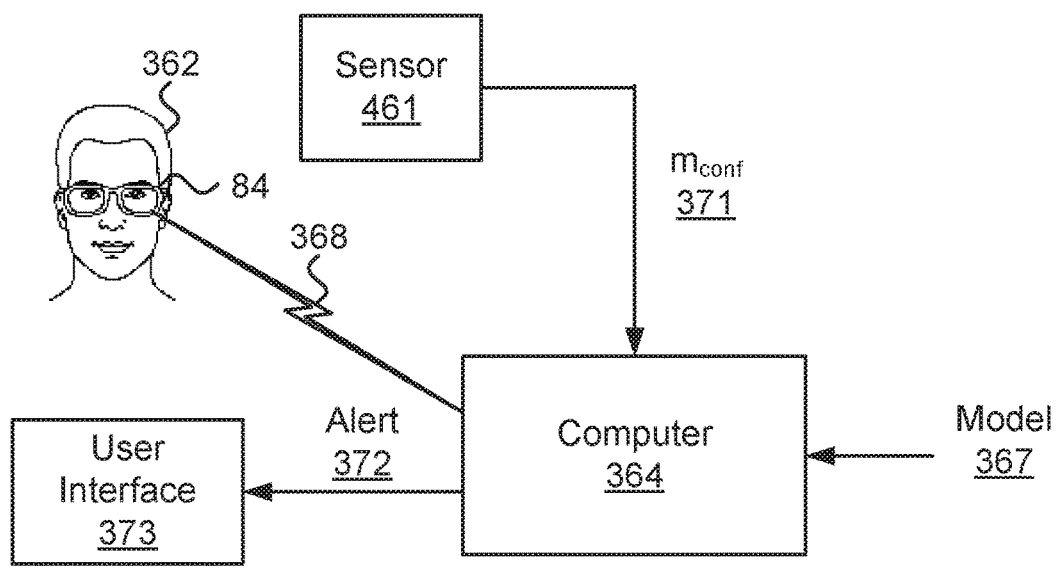
FIG. 37 illustrates an embodiment of a system configured to detect an allergic reaction.

The following method for detecting an allergic reaction of a user may be used, in some embodiments, by systems modeled according to FIG. 37. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of a region on the nose ($TH_N$) of the user using an inward-facing head-mounted thermal camera.

In Step 2, training a model based on previous $TH_N$ taken during different days.

And in Step 3, detecting the allergic reaction based on $TH_N$ and the model. Optionally, the system detects and alerts about the allergic reaction before the user is aware of the symptom of the allergic reaction. Optionally, the alert is provided as text, image, sound, and/or haptic feedback. Optionally, detecting the allergic reaction involves generating feature values based on a subset of $TH_N$ comprising $TH_N$ taken during a window of a certain length, and utilizing a model to calculate, based on the feature values, a value indicative of the extent of allergic reaction. Optionally, the model may be personalized for the user. For example, the model was trained based on previous $TH_N$ of the user, taken during different days, which include: a first set of measurements taken while the user had an allergic reaction, and a second set of measurements taken while the user did not have an allergic reaction. Optionally, the model may be based on measurements of multiple users, taken during different days, which include: a first set of measurements taken while the users had an allergic reaction, and a second set of measurements taken while the users did not have an allergic reaction. The step of generating feature values and utilizing the model may be performed multiple times throughout the period of different days during which $TH_N$ were taken, each time utilizing a subset of $TH_N$ taken during a different window of a certain length: the alerting is done at a certain time for which an allergic reaction of at least a certain extent is detected (which warrants an alert).

Some of the embodiments described herein may be utilized to identify potential causes for the change (e.g., rise) of the temperature at an ROI. These causes may include inhaled allergens, food, drugs, and/or various chemicals which the user might have been exposed to (e.g., via ingestion, inhalation, and/or physical contact). In one embodiment, the computer may identify a potential allergen substance by estimating a time of exposure to the allergen from data indicative of a deviation over time of mean nasal temperature from a baseline and identifying the substances consumed by the user, and/or to which the user was exposed, around that time. For example, by identifying based on $TH_N$ when the nasal temperature started to rise, and taking into account the time required for the allergic reaction to be manifested via a temperature rise, a window of time can be determined during which the user was likely exposed to the allergen. Examining which substances the user was exposed to during the window can yield a list of one or more potential allergen substances. Optionally, the system alerts the user about the one or more potential allergen substances. Optionally, the system stores in a database potential allergen substances identified based on data indicative of a deviation over time of mean nasal temperature from baseline (such as allergens identified based on deviation over time of mean nasal temperature from baseline). In some embodiments, the system includes a camera that captures images of substances consumed by the user. Optionally, the camera is mounted to a frame worn on the user's head. Optionally, the system displays to the user an image of a substance associated with the potential allergen substance.

There are various known systems that may be utilized to monitor what substances a user was exposed to and/or what substances a user consumed. For example, systems that may be utilized to determine what the user ate or drank are described in US patent application 20110318717 (Personalized Food Identification and Nutrition Guidance System), in U.S. Pat. No. 9,053,483 (Personal audio/visual system providing allergy awareness), and in U.S. Pat. No. 9,189,021 (Wearable food nutrition feedback system). Additionally, obtaining indications of possible allergens to which the user was exposed is described in U.S. Pat. No. 9,000,933 (Automated allergy alerts). In one embodiment, upon identifying an increase in nasal temperature, the system can identify the potential cause to be one of the substances to which the user was exposed during a predetermined preceding duration, such as the preceding 20 min. 10 min, or 5 min.

Figure 40:
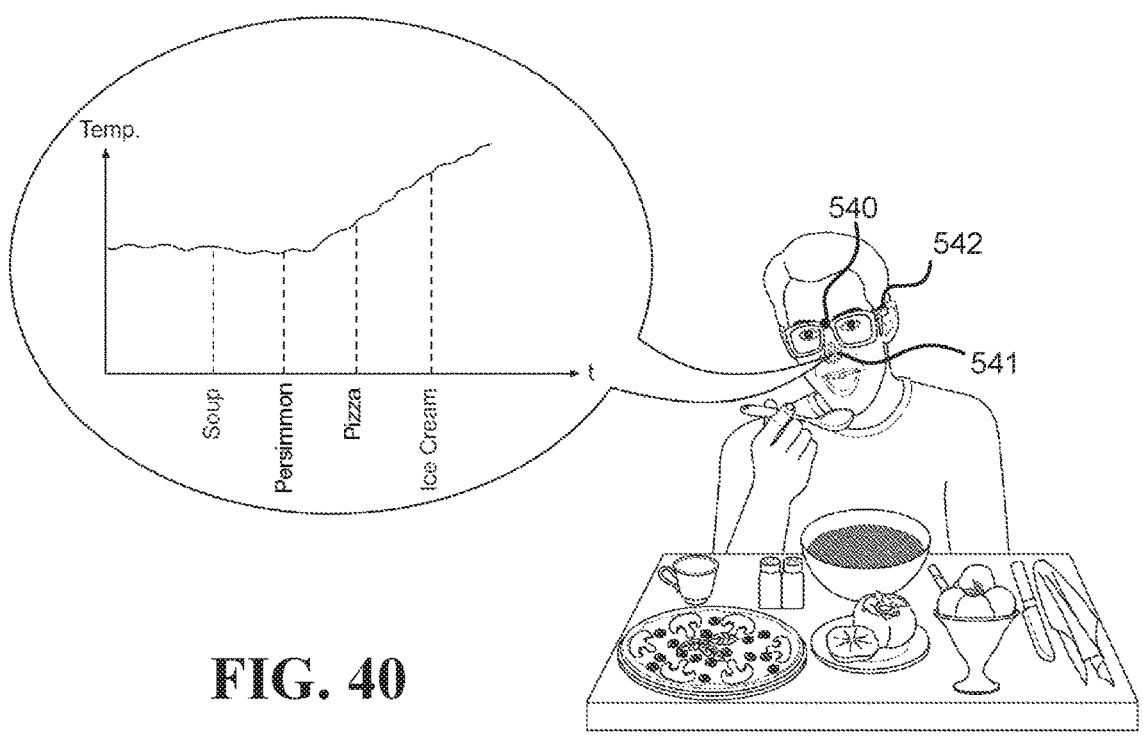
FIG. 40 illustrates how the system may be utilized to identify a trigger of an allergic reaction.

FIG. 40 illustrates how the system may be utilized to identify a trigger of an allergic reaction. CAM 540 is coupled to a frame of eyeglasses worn by the user and takes thermal measurements of a region on the user's nose 541, while the user eats different types of food. The dotted lines on the graph indicate when the user started eating each type of food. The nasal temperature increases shortly after starting eating the persimmon; however, it may reach a threshold indicating an allergic reaction only after some time, during which the user eats the pizza or the ice cream. Thus, in this case, the allergic reaction should likely be attributed to the persimmon or the soup, and not attributed to the pizza or the ice cream. Optionally, outward-facing head-mounted visible-light camera 542 takes images of the food the user eats, and the computer uses image processing to detect the types of food.

Another approach for identifying a cause of an allergic reaction (a "trigger" of an allergic reaction), involves analysis of potential triggers and the user's detected response when affected by the potential triggers. In one embodiment, the computer is further configured to: receive indications of times during which the user was exposed to potential triggers of the allergic reaction, and select a trigger, from among the potential triggers, based on the indications and extents of the allergic reaction detected based on $TH_N$. Optionally, during most of the time the user was affected by the trigger, an effect of the trigger, as manifested via changes to $TH_N$, was higher than effects of most of the potential triggers. Optionally, a camera is utilized to take images of the surroundings of the user, and the computer generates at least some of the indications based on analysis of the images. In one example, the exposure to the potential triggers involves consuming a certain drug and/or a certain food item. In another example, the exposure to the potential triggers involves being exposed to pollen, dust and/or a certain cosmetics product. In still another example, the exposure to the potential triggers involves the user being at a certain location, and/or the user being in contact with a certain animal.

In some embodiments, determination of the extent of the allergic reaction may be utilized in the context of allergen challenge tests. For example, the system may receive an indication of when a non-invasive intranasal histamine and/or an allergen challenge is performed, and estimate effects of the histamine and/or allergen challenge in the tissues, based on an increase of nasal temperature as observed in $TH_N$. In one example, this involves utilizing a change in $TH_N$, induced by the histamine provocation (of the non-invasive intranasal histamine), as a marker of an intensity of the activity of the histamine in the nose. In another example, this may involve utilizing a change in $TH_N$, induced by the allergen challenge, as a marker of an intensity of the activity of the allergen in the nose.

Figure 36:
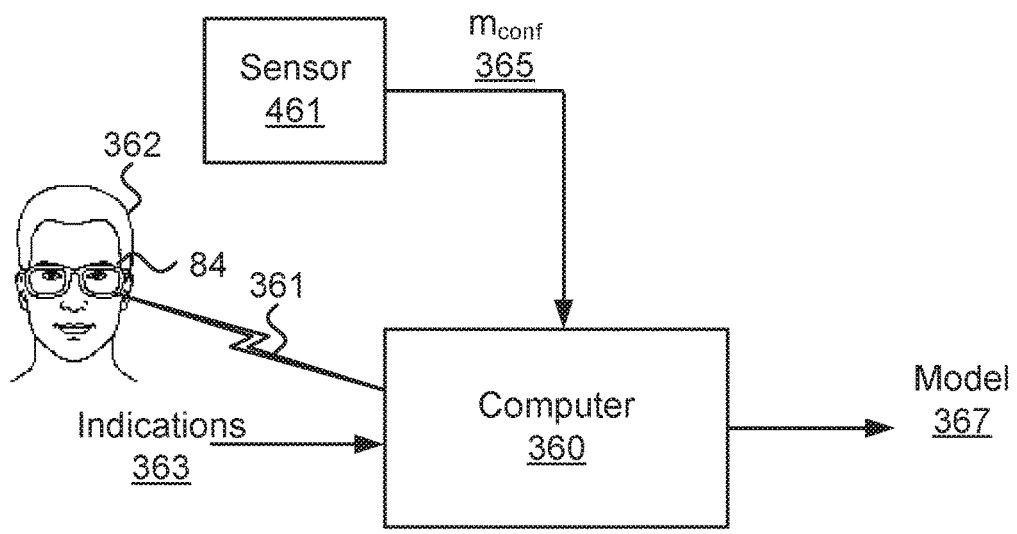
FIG. 36 illustrates an embodiment of a system that generates a model used to detect an allergic reaction.

FIG. 36 illustrates one embodiment of a system that generates a model to detect an allergic reaction. The system includes a CAM and a computer 360. Optionally. CAM is physically coupled to a frame worn on the head of a user 362. CAM takes measurements of a region on the nose ($TH_N$) 361 of the user. Optionally, CAM weighs below 10 g and is located less than 15 cm from the user's face.

In one embodiment, the computer 360 generates samples based on data comprising: (i) $TH_N$ 361, and (ii) indications 363, which correspond to different times, which are indicative of whether the user 362 experienced an allergic reaction at the different times. Optionally, each sample comprises: (i) feature values based on $TH_N$ taken during a certain period (which are from among $TH_N$ 361), and (ii) a label based on an indication from among the indications 363, which is indicative of whether the user 362 had an allergic reaction and/or to what extent the user 362 had the allergic reaction. Optionally, the label is indicative of the extent of the allergic reaction of the user 362 during the certain period and/or up to a certain time after the certain period (e.g., up to 30 minutes after the certain period). Optionally, at least some of the feature values in the sample may be generated based on other sources of information, as explained below. The computer 360 trains a model 367 based on the samples. Optionally, the computer 360 also provides the model 367 to be used by a system that detects an allergic reaction based on $TH_N$, such as the system illustrated in FIG. 37.

The indications 363 may be generated in different ways. In one embodiment, some of the indications 363 are generated by an entity that observes the user 362, such as a human observer or a software program (e.g., a software agent operating on behalf of the user). In another embodiment, some of the indications 363 are provided by the user 362. For example, the user may provide an indication via a smartphone app by pressing a certain button on a screen of a smartphone, and/or by speech that is interpreted by a software agent and/or a program with speech analysis capabilities. In yet another embodiment, some of the indications are determined based on analysis of the user's behavior. For example, monitoring the user using a camera and/or a microphone may indicate that the user is suffering from an allergic reaction by detecting coughing and/or sneezing. And in still another embodiment, some of the indications are determined based on physiological signals of the user, which are not thermal measurements of ROIs on the face, such as measurements of the user's heart rate and/or brainwave activity.

The following are some examples of feature values that may be generated for the samples used to train the model 367. The samples include feature values based on $TH_N$ of the user 362 (from among $TH_N$ 361), which were taken during a certain period, and possibly other information sources mentioned below. Additionally, the samples may include feature values generated based on $m_{conf}$ taken during the certain period (as discussed below).

In one embodiment, the computer 360 receives additional measurements of the user 362 taken during the certain period, and generates feature values based on the additional measurements. Optionally, the additional measurements are indicative of: a heart rate, heart rate variability, brainwave activity, galvanic skin response, muscle activity, and/or an extent of movement. In another embodiment, the computer 360 receives measurements of the environment in which the user 362 was in during the certain period and generates feature values based on the measurements of the environment. Optionally, each measurement of the environment is indicative of: a temperature of the environment, a humidity level of the environment, a noise level of the environment, air quality in the environment, a wind speed in the environment, an extent of precipitation in the environment, and/or an infrared radiation level in the environment.

In another embodiment, the computer 360 generates feature values based on values indicative of exposure of the user 362 to allergens during the certain period. Optionally, the values are indicative of: consumption of a certain drug, consumption of a certain food item, exposure to at least a certain concentration of pollen, exposure to at least a certain concentration of dust, exposure to a certain cosmetics product, and/or exposure to a certain aerosol.

In yet another embodiment, the computer 360 receives measurements (denoted $m_{conf}$ 365), which are indicative of at least one of the following confounding factors: a skin inflammation on the user's face, touching the user's face, a magnitude of thermal radiation directed at the user's face, and a magnitude of direct airflow on the user's face. Optionally, $m_{conf}$ 365 are measured utilizing the sensor 461. Optionally, the computer 360 generates feature values based on $m_{conf}$ from among $m_{conf}$ 365, which were taken during the certain period.

The sensor 461 may involve different types of sensors in embodiments described herein. In one example, the sensor 461 is physically coupled to a frame worn on the head of the user 362. In another example, the sensor 461 is coupled to a device carried by the user 362, such as a smartphone, a smartwatch, and/or smart clothing (e.g., clothing embedded with sensors that can measure the user and/or the environment). In yet another example, the sensor 461 may be an external sensor that is not carried by the user 362. The following are some examples of specific types of sensors that the sensor 461 may include. In one example, the sensor 461 is a visible-light camera physically coupled to the frame, and configured to take images of a region on the user's face that includes at least 25% of the nose. Optionally, in this example, the confounding factor includes inflammation of the skin, skin blemishes, and/or touching the face. In another example, the sensor 461 includes a movement sensor that measures a movement of the user 362 and the confounding factor involves the user walking, running, exercising, bending over, and/or getting up from a sitting or lying position. And in yet another example, the sensor 461 measures at least one of the following environmental parameters: a temperature of the environment, a humidity level of the environment a noise level of the environment, air quality in the environment, a wind speed in the environment, an extent of precipitation in the environment, and an infrared radiation level in the environment.

In one embodiment, the model 367 is trained on samples that were generated based on $TH_N$ taken while the user 362 had an allergic reaction, and samples that were generated based on $TH_N$ taken while the user 362 did not have an allergic reaction.

The samples utilized to train the model 367 may be generated based on feature values taken while user 362 was in different environments during first and second periods, optionally with different environmental conditions, such as (i) the environment temperature was at least 10° C. higher during the first period than during the second period; (ii) the humidity level in the environment during the first period was at least 30% higher than the humidity level during the second period; and (iii) the user was exposed to rain, hail, and/or snow during the first period, while the user was not exposed to any of rain, hail, and snow during the second period.

Additionally or alternatively, the samples utilized to train the model 367 may be generated based on feature values taken while the user 362 was in various situations during first and second periods, such as (i) the user 362 was sedentary during the first period, while the user 362 was walking, running, or biking during the second period; and/or (ii) the user 362 was indoors during the first period, while the user 362 was outdoors during the second period.

Additionally or alternatively, the samples utilized to train the model 367 may be based on $TH_N$ taken over a long period of time, such as more than a day, more than a week, more than a month, or more than a year.

Training the model 367 may involve various computational approaches. In one example, training the model 367 may involve selecting, based on the samples, a threshold; if a certain feature value reaches the threshold then an allergic reaction is detected. In another example, the computer 360 utilizes a machine learning-based training algorithm to train the model 367 based on the samples. Optionally, the model includes parameters of at least one of the following models: a regression model, a model utilized by a neural network, a nearest neighbor model, a model for a support vector machine for regression, and a model of a decision tree.

In some embodiments, the computer 360 may utilize deep learning algorithms to train the model 367. In one example, the model 367 may include parameters describing multiple hidden layers of a neural network. In one embodiment, when $TH_N$ include measurements of multiple pixels, such as when CAM includes a FPA, the model 367 may include parameters of a convolution neural network (CNN). In another embodiment, detecting the allergic reaction may be done based on multiple, possibly successive, measurements. For example, the allergic reaction may involve a progression of a state of the user (e.g., a gradual warming of the nose). In such cases, detecting the allergic reaction may involve retaining state information that is based on previous measurements. Optionally, the model 367 may include parameters that describe an architecture that supports such a capability. In one example, the model 367 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

FIG. 37 illustrates one embodiment of a system configured to detect an allergic reaction. The system includes a CAM and a computer 364. CAM takes measurements of a region on the nose ($TH_N$) 368 of the user 362. Optionally. CAM weighs below 10 g and is located less than 15 cm from the user's face.

The computer 364 generates feature values and utilize the model 367 to detect an allergic reaction of the user 362 based on the feature values. Some feature values are generated based on $TH_N$ 368, and some feature values may be generated based on other data (as described below). Optionally, the model 367 was trained based on previous $TH_N$ of the user 362 (e.g., $TH_N$ 361). Optionally, the previous $TH_N$ of the user 362 were taken during different days and/or over more than a week. Optionally, the previous $TH_N$ include: a first set of $TH_N$ taken while the user had an allergic reaction, and a second set of $TH_N$ taken while the user did not have an allergic reaction.

The feature values generated by the computer 364 are similar in their nature to the feature values generated by the computer 360, which were discussed in more detail above. Optionally, the same modules and/or procedures are used by the computer 364 and the computer 360 to generate feature values based on $TH_N$ (and possibly other data). Some examples of feature values that may be generated by the computer 364 based on $TH_N$ 368 and possibly other data include: (i) values comprised in $TH_N$ 368 (optionally these values may undergo various forms of filtering and/or normalization). (ii) values of one or more respiratory parameters calculated based on $TH_N$ 368, (iii) values generated based on additional measurements of the user 362 (e.g., measurements of heart rate, heart rate variability, brainwave activity, galvanic skin response, muscle activity, and an extent of movement), and/or (iv) measurements of the environment in which the user 362 was in while $TH_N$ 368 were taken.

In one embodiment, the computer 364 may receive indications indicative of exposure of the user 362 to an allergen while $TH_N$ 368 were taken, or up to a predetermined duration before $TH_N$ 368 were taken (e.g., up to twelve hours before), and generate feature values based on the indications. Optionally, the indications are indicative of consumption of a certain drug, consumption of a certain food item, exposure to at least a certain concentration of pollen, exposure to at least a certain concentration of dust, exposure to a certain cosmetics product, and/or exposure to a certain aerosol. Optionally, determining exposure of the user 362 to the allergen may be done by analyzing images received from a camera that captures substances consumed by the user 362.

In another embodiment, the computer 364 may receive measurements ($m_{conf}$ 371), which are indicative of at least one of the following confounding factors: a skin inflammation on the user's face, touching the user's face, a magnitude of thermal radiation directed at the user's face, and/or a magnitude of direct airflow on the user's face. Optionally, $m_{conf}$ 371 are measured utilizing the sensor 461. In one embodiment, the computer 364 generates at least some of feature values based on $m_{conf}$ 371 and utilizes the at least some feature values to detect the allergic reaction.

In one embodiment, the computer 364 utilizes the model 367 to calculate, based on the feature values, a value indicative of the extent of an allergic reaction of the user 362. Optionally, the extent is presented to the user 362 via UI 373. Optionally, responsive to the extent reaching a threshold, the computer 364 generates an alert 372 that is presented to the user 362 via the UI 373.

In one embodiment, the extent of the allergic reaction may be indicative of whether there is an allergic reaction, the severity of the allergic reaction (e.g., a level of manifestation of symptoms on a scale of 1 to 10), and/or the duration of the allergic reaction (e.g., total time of the allergic reaction and/or time remaining until the allergic reaction subsides). Optionally, the extent may be indicative of the time until the allergic reaction reaches its peak severity (e.g., a rash, coughing, respiratory distress, sneezing), and/or the expected degree of severity of the allergic reaction.

In one embodiment, the computer 364 detects an early rise in nasal temperature of the user 362, which is detectable before the user 362 is aware of a manifestation of a symptom of the allergic reaction. Optionally, the UI 373 may present the user 362 with the alert 372 that is indicative of a possible allergic reaction, before the user 362 is aware of the symptom. In one example, an early rise in nasal temperature may involve a rise of at least 0.5° C. within less than 10 minutes and/or a rise of at least 0.75° C. within less than 20 minutes.

The system may optionally include additional CAMs, and thermal measurements of the additional CAMs may be used to generate feature values similarly to how $TH_N$ 368 are utilized. Optionally, the additional CAMs are physically coupled to a frame worn on the head of the user 362. For example, the system may include a second CAM, or second and third CAMs (CAM2 and CAM3, respectively), each of which weighs below 10 g and is located less than 15 cm from the user's face. CAM2 and CAM3 are located to the right and to the left of the vertical symmetry axis that divides the face of the user 362, respectively, and take thermal measurements of regions on the right and left cheeks ($TH_{ROI1}$ and $TH_{ROI2}$, respectively), respectively. Optionally, the computer 364 generates additional feature values based on $TH_{ROI1}$ and $TH_{ROI2}$, and utilizes the additional features values to detect the allergic reaction. In another example, the system includes a second CAM, or second and third CAMs (CAM2 and CAM3), each of which weighs below 10 g and is located less than 15 cm from the user's face. CAM2 and CAM3 are located to the right and to the left of the vertical symmetry axis, respectively, and take thermal measurements of regions on the right and left periorbital areas ($TH_{ROI1}$ and $TH_{ROI2}$, respectively). Optionally, the computer 364 generates additional feature values based on $TH_{ROI1}$ and $TH_{ROI2}$, and utilizes the additional feature values to detect the allergic reaction.

Analysis of detections of allergic reactions combined with information regarding potential triggers that affected the user at different times can reveal what are likely triggers of the allergic reaction. Some examples of potential triggers that may be considered triggers for certain users include ingested substances such as food (e.g., eggs, dairy, or peanuts) or certain drugs and chemicals and/or compounds to which the user may be exposed (e.g., pollen dust, a certain cosmetics product, and a certain aerosol). Additionally, a trigger may be an indirect potential trigger that is correlated with allergic reactions of the user, such as being at a certain location, being in contact with a certain animal, conducting in a certain activity, and being in contact with a certain object.

Figure 38:
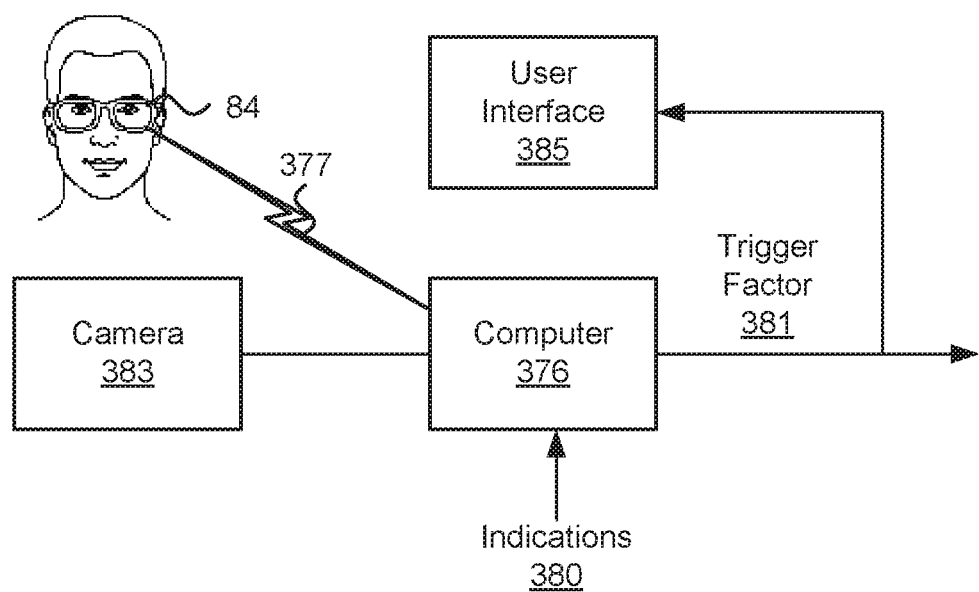
FIG. 38 illustrates an embodiment of a system configured to select a trigger of an allergic reaction of a user.

FIG. 38 illustrates one embodiment of a system configured to select a trigger of an allergic reaction of a user. The system includes a CAM and a computer 376. The system may optionally include a frame 84, a camera 383, and/or a UT 385. CAM takes thermal measurements of a region on the nose ($TH_N$, 377) of the user.

In one embodiment, the thermal camera used to take $TH_N$ 377 is a head-mounted thermal camera. In another embodiment, the thermal camera used to take $TH_N$ 377 is not a head-mounted thermal camera. Examples of non-head-mounted thermal cameras include (i) thermal cameras embedded in a device such as a smartphone or a smartwatch, (ii) a thermal camera embedded in a device such as a laptop computer, a tablet, a television, or a gaming console, and/or (iii) a standalone thermal camera.

In some embodiments, multiple thermal cameras may be utilized to measure $TH_N$ 377. Additionally or alternatively. $TH_N$ 377 may include thermal measurements of multiple ROIs on the user's nose and/or thermal measurements of additional ROIs on other regions of the user's face (besides the nose).

$TH_N$ 377 are provided, in one embodiment, to the computer 376, which detects, based on $TH_N$ 377, extents of the allergic reaction of the user at different times. Optionally, the computer 376 employs a similar approach for detecting the extents of the allergic reaction to the approach described above involving the computer 364.

In some embodiments, detecting the extents of the allergic reaction of the user at different times may involve utilizing thermal measurements of other regions on the face, in addition to $TH_N$ 377.

In one example, the system includes second and third CAMs located to the right and to the left of the vertical symmetry axis that divides the user's face, which take thermal measurements of regions on the right and left cheeks ($TH_R$ and $TH_L$, respectively). Optionally, the computer 376 detects the extents of the allergic reaction also utilizing $TH_R$ and $TH_L$ (in addition to $TH_N$ 377).

In another example, the system includes second and third CAMs located to the right and left of a vertical symmetry axis that divides the user's face, respectively, which take thermal measurements of regions on the right and left periorbital areas ($TH_R$ and $TH_L$, respectively). Optionally, the computer 376 detects the extents of the allergic reaction also utilizing $TH_R$ and $TH_L$ (in addition to $TH_N$ 377).

The computer 376 is configured, in one embodiment, to receive indications 380 of potential triggers that affected the user at various times. Optionally, each of the indications 380 is indicative of a time during which the user was exposed to a certain potential trigger. Additionally or alternatively, each of the indications 380 may be indicative of a time during which the user was affected by a certain potential trigger. In some embodiments, at any given time, the user may be exposed to more than one of the potential triggers. Optionally, at least some of $TH_N$ 377, and optionally all of $TH_N$ 377, were taken while the user was exposed to two or more of the potential triggers.

The computer 376 selects a trigger 381, from among the potential triggers, based on the indications 380 and the extents of the allergic reaction. Optionally, an effect of a potential trigger is indicative how much the potential trigger influences the extent of the user's allergic reaction, which can range from no influence to a profound influence. Optionally, during most of the time the user is affected by the trigger 381, the effect of the trigger 381 on the extent of the allergic reaction of the user is higher than the effect of most of the other potential triggers on the allergic reaction of the user.

In one embodiment, the indications 380 include a list of periods of time during which various potential triggers affected the user. Optionally, the indications 380 are provided via a data structure and/or a queryable system that provides information for different points in time about which of the potential triggers affected the user at the points in time. Following are three examples of types of potential triggers that may be analyzed.

In a first example, some of the potential triggers relate to allergens in various foods, beverages, and/or other substances that may be consumed and digested by the user and may lead to an allergic reaction. For instance, the indications 380 may comprise a certain indication of a potential trigger that is indicative of the user consuming a certain drug and/or a certain food item.

In a second example, some of the potential triggers relate to allergens to which the user may be exposed in the environment. Optionally, an allergic reaction may occur after such an allergen is inhaled by the user and/or comes in contact with the user's skin. For instance, the indications 380 may comprise a certain indication of a potential trigger that is indicative of the user being exposed to pollen, dust, a certain cosmetics product, and/or a certain aerosol (e.g., a certain perfume fragrance).

In a third example, some of the potential triggers indirectly relate to the allergic reaction (e.g., they may be correlated with allergic reactions of the user). For instance, the indications 380 may include a certain indication of a potential trigger that is indicative of the user being at a certain location, the user being in contact with a certain animal, the user conducting in a certain activity, and/or the user being in contact with a certain object.

The extent of an allergic reaction may depend on quantitative aspects of the potential triggers. For example, a person who is allergic to dairy products may not have a noticeable allergic reaction following digestion of a small amount of dairy (e.g., adding milk to a cup of coffee), but may have a noticeable allergic reaction following a consumption of a larger amount of a dairy product (e.g., drinking a large milkshake). Thus, in some embodiments, the indications 380 include values that quantify how much at least some of the potential triggers affected the user. For example, these values may corresponds to amounts of substances consumed by the user, time spent by the user in certain environments, and/or values of environmental parameters (e.g., a concentration of pollen in the air).

The trigger 381 may be correlated with the occurrence of an allergic reaction of the user. Additionally, in some embodiments, the trigger 381 may be considered a direct cause of the allergic reaction (e.g., when the trigger 381 is a substance to which the user's immune system has an excessive reaction). Optionally, during most of the time the user was affected by the trigger 381, an effect of the trigger 381, as manifested via changes to $TH_N$, was higher than effects of most of the potential triggers. Optionally, the trigger 381 has a maximal effect (i.e., there is no other potential triggers that have a higher effect). Optionally, the trigger 381 has an effect that reaches a threshold, while the effect of most of the potential triggers does not reach the threshold.

In some embodiments, the effect of the trigger 381 is higher than the effect observed when the trigger 381 does not affect the user. For example, based on the values indicative of the extents of the allergic reaction and indications 380, an average extent of the allergic reaction of the user at a time $t+\Delta$ when the user was affected by the trigger 381 at some time during $[t, t+\Delta]$, is greater than an average extent of the allergic reaction of the user at a time $t+\Delta$ when the user was not affected by the trigger 381 at any time during $[t, t+\Delta]$. Here $\Delta$ may be some predetermined period of time that is greater than five minutes, fifteen minutes, one hour, four hours, or twelve hours.

There are various ways in which the computer 376 may select, based on the indications 380 and the extents of the allergic reaction, the trigger 381 from among the multiple potential triggers being considered.

In some embodiments, the computer 376 performs a direct analysis of the effect of each of the potential triggers in order to identify which have a large effect (meaning they are likely to cause an allergic reaction with the user). Optionally, the effect of each potential trigger is calculated by determining, based on the indications 380, times at which the user was affected by each potential trigger, and observing the extent of the allergic reaction of the user at one or more times that are up to a certain period $\Delta$ later (where $\Delta$ may be for example a period of time up to 12 hours long or shorter, depending on the type of allergic reaction). In one example, an observed extent of the allergic reaction following being affected by a potential trigger is the maximum extent of the allergic reaction that is observed from the time t the user was affected by the potential trigger until the time $t+\Delta$. In another example, the observed extent of the allergic reaction following being affected by a potential trigger is the extent of the allergic reaction that is observed at the time $t+\Delta$ (when the user was affected by the potential trigger at time t). Optionally, the observed extent of allergic reaction may be normalized based on a quantitative value representing how much the user was affected by the potential trigger (e.g., the observed extent may be normalized based on a dosage of a drug taken or the amount of time spent outdoors). Optionally, the effect of each potential trigger is calculated based on the observed extents of the allergic reactions following being affected by the potential trigger, as described above. In one example, the effect may be an average of the observed extents. In another example, the effect may be a value indicative of the proportion of the observed extents that reach a threshold. Following a calculation of the effects of the potential triggers, in one embodiment, the computer 376 selects the trigger 381 from among the potential triggers based on the effects.

In one embodiment, in order to increase confidence in the selection of the trigger 381, the trigger 381 is selected based on at least a certain number of times in which the user was affected by the trigger 381. For example, the certain number may be at least 3, 5, or 10 different times. Thus, in this embodiment, potential triggers that did not affect the user at least the certain number of times are not selected.

In some embodiments, the computer 376 generates a machine learning-based model based on the indications 380 and the extents of the allergic reaction, and selects the trigger 381 based on an analysis of the model. Optionally, the computer 376 generates samples used to train the model. In one embodiment, the samples may correspond to different times, with each sample corresponding to a time t+Δ including feature values and a label (target value) indicative of the extent of the allergic reaction of the user at the time t+Δ (where depending on the embodiment Δ may have a value between several minutes to 12 or even 24 hours). Optionally, Δ is at least one minute. Optionally, the label of each sample is determined based on values indicative of the extent of the allergic reaction at the time t+Δ or thereabouts (e.g., up to an hour before or after the time t+Δ). Optionally, the feature values are based on indications, from among the indications 380, which are indicative of the degree various potential trigger affected the user during a period [t, t+Δ]. Optionally, some of the feature values are indicative of how long before t+Δ some of the potential triggers affected the user and/or magnitudes of some of the potential triggers (e.g., amounts of food items consumed, dosages of drugs taken, etc.)

Each of the samples described above may be considered to represent a snapshot of potential triggers that affected the user during a certain period and a label that is indicative of the extent of the allergic reaction of the user following being affected by those potential triggers. Given multiple such samples, a machine learning training algorithm can be utilized to train a model for a predictor module that can predict the extent of the user's allergic reaction at a certain time based on feature values that describe the potential triggers that affected the user during a certain period of time leading up to the certain time. For example, if the model is a regression model the predictor module may perform a dot product multiplication between a vector of regression coefficients (from the model) and a vector of the feature values in order to calculate a value corresponding to the predicted extent of the allergic reaction of the user at the certain time.

When such a predictor module is capable of predicting extents of the allergic reaction of the user based on the feature values described above, this may mean that the model captures, at least to some extent, the effects of at least some of the potential triggers on the extent of the allergic reaction of the user.

Training the model based on the samples described above may involve utilizing various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model to name a few possibilities. There are various training algorithms known in the art for generating these models and other models with similar properties.

In some embodiments, the predictor module may be provided multiple inputs representing the potential triggers that affected the user at different points of time. For example, the predictor module may be provided with a series of vectors of feature values, each representing the potential triggers that affect the user during a period (e.g., during one minute, five minutes, thirty minutes, an hour, or six hours). In these embodiments, the predictor module may have a capability to store state information of previous inputs corresponding to earlier times when it comes to predict the extent of the allergic reaction of the user at a certain time. One example of a predictor module with such a capability is a predictor module that is based on a recurrent neural network.

Once the model is trained, it may be analyzed by the computer 376 to determine the effects of one or more of the potential triggers on the extent of the allergic reaction. Depending on the type of model that was trained, this analysis may be performed in different ways.

In one embodiment, the computer 376 performs the analysis of the model by evaluating parameters of the model that correspond to the potential triggers. Optionally, the computer 376 selects as the trigger 381 a certain potential trigger that has a corresponding parameter that is indicative of an effect that reaches a threshold while effects indicated in parameters corresponding to most of the potential triggers do not reach the threshold. In one example, the model may be a linear regression model in which each potential trigger corresponds to a regression variable. In this example, a magnitude of a value of a regression coefficient may be indicative of the magnitude of the effect of its corresponding potential trigger. In another example, the model may be a naïve Bayes model in which various classes correspond to extents of an allergic reaction (e.g., a binary classification model that is used to classify a vector of feature values to classes corresponding to allergic reaction vs, no allergic reaction). In this example, each feature value may correspond to a potential trigger, and the class conditional probabilities in the model are indicative of the magnitude of the effect of each of the potential triggers on the user.

In another embodiment, the computer 376 performs an analysis of the model, which may be characterized as "black box" analysis. In this approach, the predictor module is provided with various inputs that correspond to different potential triggers that affect the user, and calculates, based on the inputs and the model various predicted extents of an allergic reaction of the user. The various inputs can be used to independently and individually increase the degree to which each of the potential triggers affects the user. This type of the model probing can help identify certain potential triggers that display an increase in the predicted extent of the allergic reaction, which corresponds to an increase in the degree to which the potential triggers affect the user (according to the model). Optionally, with the trigger 381 there is a positive correlation observed between increasing the degree to which the trigger 381 affects that user, and the predicted extent of the allergic reaction of the user. Optionally, the trigger 381 is selected from among the potential triggers, responsive to identifying that that: (i) based on a first subset of the various predicted extents of an allergic reaction of the user, an effect of the trigger 381 reaches a threshold, and (ii) based on a second subset of the various predicted extents of an allergic reaction of the user, effects of most of the potential triggers do not reach the threshold.

The indications 380 may be received from various sources. In one embodiment, the user may provide at least some of the indications 380 (e.g., by inputting data via an app and/or providing vocal annotations that are interpreted by a speech analysis software). In other embodiments, some indications 380 are provided by analysis of data sources. Optionally, the computer 376 generates some indications 380 based on the analysis of data obtained from the data sources. The following are some examples of data sources that may be utilized to identify potential triggers that affected the user at different times.

In a first example, a camera 383 captures images of the surroundings of the user. The camera 383 may be head-mounted or belong to a device of the user (e.g., a smartphone or a webcam). In one example, the camera 383 may belong to a camera-based systems such as OrCam (http://www.orcam.com/), which is utilized to identify various objects, products, faces, and/or recognize text. In another example, images captured by the camera 383 may be utilized to determine the nutritional composition of food a user consumes. Such an approach in which images of meals are utilized to generate estimates of food intake and meal composition, is described in Noronha, et al., "Platemate: crowdsourcing nutritional analysis from food photographs". Proceedings of the 24th annual ACM symposium on User interface software and technology, ACM, 2011.

In a second example, other sensors such as microphones, accelerometers, thermometers, pressure sensors, and/or barometers may be used to identify potential triggers that affect the user, by identifying what the user is doing (e.g., by analyzing movement patterns) and/or under what conditions (e.g., by analyzing ambient noise, temperature, and/or pressure).

In a third example, measurements of the environment that user is in are another source of information for determining potential stressor. The measurements may be received from a third party (e.g., a website that provides environmental information for various locations), and may indicate temperature, pressure, humidity, and/or particle counts for various types of chemicals or compounds (e.g., pollutants and/or allergens).

In a fourth example, Internet of Things (IoT) devices provide information when they are moved and/or utilized. Additionally or alternatively, communications of the user (e.g., email, text messages, voice conversations, and/or video conversations) may also be analyzed to provide context and/or to identify some potential stressors. Similarly, the user's calendar and/or schedule, as well as billing information, may provide information that may be used in some embodiments to identify potential stressors.

There are various approaches known in the art for identifying, indexing, and/or searching for potential triggers that may affect the user, which may be utilized in embodiments described herein. In one example, identifying potential triggers that may be done according to the teachings described in U.S. Pat. No. 9,087,058 titled "Method and apparatus for enabling a searchable history of real-world user experiences", which describes a searchable history of real-world user experiences of a user utilizing data captured by a mobile computing device. In another example, identifying potential triggers may be done according to the teachings described in U.S. Pat. No. 8,762,102 titled "Methods and systems for generation and rendering interactive events having combined activity and location information", which describes identification of events based on sensor data of mobile devices.

Knowledge of the trigger 381 may be utilized for various purposes. In one embodiment, the trigger 381 is utilized by a software agent operating on behalf of the user in order to better serve the user. For example, the software agent may ensure that food items that are ordered for the user do not include components that are known to trigger an allergic reaction (e.g., if the trigger 381 is a type of food). In another example, the software agent may plan routes for the user that do not include environments in which the trigger 381 may be present (e.g., if the trigger 381 is bloom).

In some embodiments, information about the trigger 381 is provided to the user via a UT 385. UI 385 may be utilized on a day-to-day basis to warn the user when the trigger 381 is detected. Optionally, a database may be consulted to determine whether the identified food items contain the trigger 381. If the trigger 381 is detected, the UI 385 may indicate that to the user.

Due to the mostly symmetric nature of the human body, when the face undergoes temperature changes, e.g., due to external factors such as the temperature in the environment or internal factors such as an activity-related rise in body temperature, the changes to the face are generally symmetric. That is, the temperature changes at a region of interest (ROI) on the left side of the face (e.g., the left side of the forehead) are similar to the temperature changes at the symmetric ROI on the right side of the face (e.g., the right side of the forehead). However, when the temperature on the face changes in an asymmetric way, this can be indicative of various physiological responses and/or undesirable phenomena. Some examples of phenomena that may be identified by detecting asymmetric thermal patterns ("thermal asymmetry") on a user's face include a headache, sinusitis, nerve damage, some types of strokes, orofacial pain, and Bell's palsy. Additionally, some forms of disorders such as Attention Deficit Hyperactivity Disorder (ADHD), stress, anxiety, and/or depression can also be identified based on thermal asymmetry of the forehead, and in some cases of other regions of the face.

In other cases, and sometime depending on personal characteristics of the user, certain physiological responses may manifest differently on different sides of the face. In particular, the temperatures at different positions on the right side of the face may not be a mirror image of the temperatures at the corresponding positions on the left side of the face. Thus, having two or more thermal cameras pointed at different areas of the face can in some embodiments, help make more accurate detections of a physiological response. For example, stress may be manifested with some people by the cooling of an area on one side of the nose more than the symmetric area on the other side. Similarly, with some people, an allergic reaction may manifest by the nose heating to different extents on each of its sides. Thus, having, in this example, two or more thermal cameras pointed at different sides of the nose, may enable a more accurate detection of the physiological response.

Measuring and utilizing the asymmetric data also improves the robustness of the system against interferences that may cause an asymmetric thermal effect, such as an external heat source located to the user's side, a cooling air-conditioner that blows air from the top, touching and/or wiping one side of the face, and for some people also eating and/or conducting a physical activity. Therefore, utilizing thermal cameras pointed at symmetric ROIs may improve the system's ability to detect a physiological response compared to the case in which just one thermal camera is used.

In one embodiment, a system configured to collect thermal measurements indicative of thermal asymmetry on a user's face includes first and second inward-facing head-mounted thermal cameras (CAM1 and CAM2). Optionally. CAM1 and CAM2 are physically coupled to a frame worn on the user's head, and are located less than 15 cm, 5 cm, or 2 cm from the user's face. Optionally, CAM1 and CAM2 are located at least 0.5 cm to the right and to the left of the vertical symmetry axis that divides the face, respectively. Optionally, each of CAM1 and CAM2 weighs below 10 g, 5 g, or 1 g.

CAM1 and CAM2 take thermal measurements of regions on the right and left sides of the face ($TH_{ROI1}$ and $TH_{ROI2}$, respectively) of the user, and optionally do not occlude $ROI_1$ and $ROI_2$. Optionally, CAM1 and CAM2 are based on thermopile, microbolometer, or pyroelectric sensors, which may be focal-plane array sensors. Optionally, $ROI_1$ and $ROI_2$ have symmetric overlapping above 60%. In one example, CAM1 and CAM2 may be thermal cameras 120 and 122 in FIG. 10. In another example, CAM1 and CAM2 are thermal cameras 126 and 128 in FIG. 11.

The symmetric overlapping is considered with respect to the vertical symmetry axis that divides the face to the right and left portions. The symmetric overlapping between $ROI_1$ and $ROI_2$ may be observed by comparing the overlap between $ROI_1$ and a mirror image of $ROI_2$, where the mirror image is with respect to a mirror that is perpendicular to the front of the face and whose intersection with the face is along the vertical symmetry axis (which goes through the middle of the forehead and the middle of the nose). Depending on the application for which the thermal measurements are utilized, the ROIs may have different degrees of symmetric overlapping. In one example, the symmetric overlapping between $ROI_1$ and $ROI_2$ is above 80% of the smallest area from among the areas of $ROI_1$, and $ROI_2$. In another example, the overlap between $ROI_1$ and $ROI_2$ is above 25% and below 80% of the smallest area from among the areas of $ROI_1$ and $ROI_2$.

Depending on the locations of $ROI_1$ and $ROI_2$, in different embodiments, CAM1 and CAM2 may be located in specific locations on the frame and/or with respect to the face. In one example, $ROI_1$ and $ROI_2$ are on the nose and/or a region on the mouth, and CAM1 and CAM2 are located outside the exhale streams of the mouth and/or nostrils.

In one embodiment, each of CAM1 and CAM2 is located less than 10 cm from the face and there are angles greater than 200 between the Frankfort horizontal plane and the optical axes of CAM1 and CAM2.

Due to the angle between the optical axis of CAM1 and CAM2 and the Frankfort horizontal plane, in some embodiments, the Scheimpflug principle, may be employed in order to capture sharper images. For example, when the user wears the frame, CAM1 and/or CAM2 may have a certain tilt greater than 20 between their sensor and lens planes, in order to produce the sharper images.

In one embodiment, CAM1 and CAM2 utilize focal-plane array (FPA) sensors. Optionally, each FPA includes at least 6 or at least 12 sensing elements (pixels). Optionally, there are angles greater than 200 between the Frankfort horizontal plane and the optical axes of CAM1 and CAM2. Optionally, CAM1 is located to the right of the vertical symmetry axis and takes thermal measurements of a first region of interest ($TH_{ROI1}$), where $ROI_1$ covers more of the right side of the face than of the left side of the face; CAM2 is located to the left of the vertical symmetry axis and takes thermal measurements of a second region of interest ($TH_{ROI2}$), where $ROI_2$ covers more of the left side of the face than of the right side of the face. Optionally, the cameras do not occlude $ROI_1$ and $ROI_2$. Alternatively, the cameras occlude at least part of $ROI_1$ and $ROI_2$.

In some embodiments, the system for collecting thermal measurements indicative of thermal asymmetry on a user's face includes a computer. Optionally, the computer detects a physiological response based on the thermal measurements.

In one embodiment, the detection of the physiological response utilizes a personalized model of the user. Optionally, the computer (i) generates feature values based on $TH_{ROI1}$ and $TH_{ROI2}$, and (ii) utilizes a model to detect the physiological response based on the feature values. Optionally, at least some feature values used to detect the physiological response may be generated based on additional sources of information (other than CAM1 and CAM2), such as additional thermal cameras, additional sensors that measure physiological signals of the user (e.g., heart rate or galvanic skin response), and/or additional sensors that measure the environment. Optionally, the model is trained based on previous $TH_{ROI1}$ and $TH_{ROI2}$ taken while the user had the physiological response. Optionally, the physiological response involves the user experiencing stress, mental workload, fear, sexual arousal, anxiety, pain, a headache, dehydration, intoxication, and/or a stroke. Optionally, the physiological response is associated with facial thermal asymmetry, and the model was trained based on previous feature values taken during different days. Optionally, the previous feature values include: a first set of feature values generated based on $TH_{ROI1}$ and $TH_{ROI2}$ taken while the user had the physiological response, and a second set of feature values generated based on $TH_{ROI1}$ and $TH_{ROI2}$ taken while the user did not have the physiological response.

In different embodiments, the difference between $TH_{ROI1}$ and $TH_{ROI2}$ may be interpreted in different ways. In one embodiment, an extent of a physiological response may be proportional to the difference between $TH_{ROI1}$ and $TH_{ROI2}$ when the value of the difference is in a certain range. Optionally, when the value of the difference is outside of the range, this may be indicative of the occurrence of other phenomena (which are not the physiological response). In another embodiment, when the value of the difference between $TH_{ROI1}$ and $TH_{ROI2}$ reaches a threshold, that is indicative of an occurrence of the physiological response. In yet another embodiment, at least one feature value utilized by a predictor that predicts occurrences of the physiological response is based on the value of the difference between $TH_{ROI1}$ and $TH_{ROI2}$.

Often a change in the thermal asymmetry may be indicative of a physiological response. Optionally, the computer detects a change to thermal asymmetry on the face based on a change between thermal measurements taken at different times. The computer may further calculate the extent of the physiological response based on the change. This calculation can be performed in different ways, as described below.

In one embodiment, the computer calculates the change between the thermal measurements as follows: calculate a temperature difference between $ROI_1$ and $ROI_2$ at time x ($\Delta T_x$) based on [$TH_{ROI1}$, $TH_{ROI2}$] taken at time x, calculate a temperature difference between $ROI_1$ and $ROI_2$ at time y ($\Delta T_y$) based on [$TH_{ROI1}$, $TH_{ROI2}$] taken at time y, and calculate the output indicative of the change in the thermal asymmetry on the face based on a difference between $\Delta T_x$ and $\Delta T_y$.

The embodiment described above may optionally be implemented using a differential amplifier that receives $TH_{ROI1}$ and $TH_{ROI2}$ as inputs, and output the temperature difference between $ROI_1$ and $ROI_2$. Optionally. CAM1 and CAM2 are based on thermopile sensors. Alternatively, CAM1 and CAM2 are based on pyroelectric sensors. In one example, pairs of thermal sensor elements are wired as opposite inputs to a differential amplifier in order for the thermal measurements to cancel each other and thereby remove the average temperature of the field of view from the electrical signal. This allows CAM1 and CAM2 to be less prone to provide false indications of temperature changes in the event of being exposed to brief flashes of radiation or field-wide illumination. This embodiment may also minimize common-mode interference, and as a result improve the accuracy of the thermal cameras.

In another embodiment, the computer calculates the change between the thermal measurements as follows: calculate a temperature change between $TH_{ROI1}$ taken at times $t_1$ and $t_2$ ($\Delta TH_{ROI1}$), calculate a temperature change between $TH_{ROI2}$ taken at times $t_1$ and $t_2$ ($\Delta TH_{ROI2}$), and then calculate the output indicative of the thermal asymmetry on the face based on a difference between $\Delta TH_{ROI1}$ and $\Delta TH_{ROI2}$.

It is noted that sentences such as "calculate a difference between X and Y" or "detect a difference between X and Y" may be achieved by any function that is proportional to the difference between X and Y.

The computer may utilize the change in thermal asymmetry in order to detect a physiological response in various ways. For example, the change may be compared to a threshold, which if reached, is indicative of the occurrence of the physiological response. Optionally, the threshold needs to be reached a certain number of times and/or for a certain amount time, before it is assumed that the user experienced the physiological response. In another example, time series data that include changes to thermal asymmetry of the face may be compared to reference time series comprising changes in thermal asymmetry observed with the physiological response. In still another example, changes in thermal asymmetry may be utilized to generate feature values that are used along with a machine learning-based model to detect an occurrence of a physiological response (as discussed above).

Additional CAMs may be utilized to take thermal measurements used for detecting the physiological response. FIG. 9 illustrates one embodiment of a system that collects thermal measurements indicative of thermal asymmetry on a user's face, which involves additional CAMs. The system includes a frame 90, which has six CAMs coupled to it (some embedded in protruding arms). CAMs 91 and 92 are located on arms on the right and left sides of the top of the frame 90, respectively, and take thermal measurements of regions on the right and left sides of the forehead (97 and 98, respectively). CAMs 93 and 94 are located on the right and left sides of the frame 90 near the nose, respectively, and take thermal measurements of regions on the right and left periorbital areas (99 and 100), respectively. CAMs 95 and 96 are located on arms connected to the bottom of right and left rims, respectively, and take thermal measurements of right and left lower regions of the face (101 and 102, respectively). Optionally, some (or all) of the cameras contain multiple sensing elements.

In one embodiment, the system for collecting thermal measurements indicative of thermal asymmetry on a user's face further includes third and fourth CAMs (in addition to CAM1 and CAM2), each of which: weighs below 10 g, is physically coupled to the frame, and is located less than 15 cm from the face. The third and fourth CAMs take thermal measurements of regions on the right and left sides of the upper lip ($TH_{ROI3}$ and $TH_{ROI4}$, respectively) of the user, without occluding the upper lip. Optionally, the symmetric overlapping between the regions on the right and left sides of the upper lip is above 60%. Optionally, the system includes a computer that (i) generates feature values based on $TH_{ROI1}$, $TH_{ROI2}$, $TH_{ROI3}$, and $TH_{ROI4}$, and (ii) utilizes a model to detect a physiological response based on the feature values. Optionally, the model was trained based on previous $TH_{ROI1}$, $TH_{ROI2}$, $TH_{ROI3}$, and $TH_{ROI4}$ taken while the user had a physiological response associated with at least one of the following: stress, mental workload, fear, sexual arousal, anxiety, pain, a headache, dehydration, intoxication, and a stroke.

In another embodiment, $ROI_1$ and $ROI_2$ are on the right and left sides of the forehead, respectively, and the system further includes at least third and fourth CAMs, located less than 10 cm from the face, which take thermal measurements of regions on the right and left periorbital areas ($TH_{ROI3}$ and $TH_{ROI4}$, respectively). Optionally, the system includes a computer that utilizes a model to detect an emotional state and/or stress level based on $TH_{ROI1}$, $TH_{ROI2}$, $TH_{ROI3}$, and $TH_{ROI4}$. Optionally, the model was trained based on previous $TH_{ROI1}$, $TH_{ROI2}$, $TH_{ROI3}$, and $TH_{ROI4}$ taken during different days. Optionally, the system includes additional fifth and sixth CAMs, located less than 10 cm from the face, which take thermal measurements of regions on the right and left cheeks ($TH_{ROI5}$ and $TH_{ROI6}$, respectively). Optionally, the computer detects the physiological response also based on $TH_{ROI5}$ and $TH_{ROI6}$ (e.g., by generating based on $TH_{ROI5}$ and $TH_{ROI6}$ at least some of the feature values used to detect the physiological response).

In yet another embodiment, the system further includes third and fourth CAMs for taking thermal measurements of the environment to the right and to the left of the face ($TH_{ENV1}$ and $TH_{ENV2}$, respectively). The computer utilizes $TH_{ENV1}$ and $TH_{ENV2}$ to identify asymmetry resulting from the environment rather than from a physiological response. For example, the computer may generate feature values based on $TH_{ENV1}$ and $TH_{ENV2}$, and utilize these feature values, in addition to feature values generated based on thermal measurements of the ROIs on the face, in order to detect the physiological response. Optionally, the third and fourth CAMs are based on at least one of the following sensor types: a thermopile, a pyroelectric sensor, and a microbolometer. Optionally, the environmental cause of the asymmetry involves at least one of the following: sunlight, air blowing from an air-conditioner, radiation from a heater, and radiation from an oven.

The following examples of physiological responses may be identified utilizing embodiments of the system for collecting thermal measurements indicative of thermal asymmetry on a user's face.

There are various forms of sinusitis that may be detected utilizing different embodiments of the system. In one embodiment, $ROI_1$ and $ROI_2$ are on the right and left anterior sinuses, respectively. Optionally, the computer utilizes a model to detect sinusitis based on $TH_{ROI1}$ and $TH_{ROI2}$ (as described above). Optionally, the data used to train the model includes $TH_{ROI1}$ and $TH_{ROI2}$ taken from other users who suffer from maxillary sinusitis, frontal sinusitis, unilateral frontal sinusitis, and/or unilateral maxillary sinusitis. In a first example, $ROI_1$ and $ROI_2$ are on the right and left anterior sinus group, respectively. Optionally, the right/left anterior sinus group includes the right/left frontal sinus, the right/left maxillary sinus, and the right/left anterior ethmoid sinus. In a second example, $ROI_1$ and $ROI_2$ are on the user's right and left frontal sinuses, respectively, and the computer detects an occurrence of a unilateral frontal sinusitis. In a third example, $ROI_1$ and $ROI_2$ are on the user's right and left maxillary sinuses, respectively, and the computer detects an occurrence of a unilateral maxillary sinusitis.

Some forms of strokes may be detected using embodiments of the system. In a first example, $ROI_1$ and $ROI_2$ are on the right and left superficial temporal arteries. In a second example, each of $ROI_1$ and $ROI_2$ cover above 20%, or above 40%, of the right and left sides of the face that include exposed facial skin between the mouth level and the eyebrow level, respectively (e.g., the right and left cheeks and/or the right and left sides of the upper lip). Herein. "exposed facial skin" refers to facial skin that does not have excessive hair growth, such as a beard that usually damages the ability of CAM to measure the skin under the beard. In these two examples, a computer may detect whether the user has a stroke based on changes observed by comparing $TH_{ROI1}$ and $TH_{ROI2}$ taken from the user during different days. Optionally, if the probability that the user has a stroke reaches a certain threshold, such as at least 5%, 25%, or 50%, then the user and/or a third party are alerted about this finding so the user can receive immediate medical attention.

FIG. 19 illustrates a scenario in which an alert regarding a possible stroke is issued. The figure illustrates a user wearing a frame with at least two CAMs (562 and 563) for measuring ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a VCAM provides additional data in the form of images that may help detecting the stroke.

Various forms of nerve damage often cause detectable thermal differences on the face. At times, the thermal differences may manifest prior to changes to the appearance of the face. Thus, thermal measurements may be utilized for early detection of nerve damage, which may improve the outcome of a treatment. For example, in one embodiment, $ROI_1$ and $ROI_2$ may each be on the periorbital area around the eyes, the nose, and/or the mouth. Optionally, the computer may identify nerve damage based on changes observed by comparing $TH_{ROI1}$ and $TH_{ROI2}$ taken from the user during different days, and/or by using a model trained based on measurements of other users taken while they had nerve damages.

Headaches (which also include migraines), symptomatic behavior of Attention Deficit Hyperactivity Disorder (ADHD), and/or anger attacks are physiological responses that may also be detected by embodiments described herein. In one embodiment, detecting these physiological responses is done with a system in which $ROI_1$ and $ROI_2$ are on the right and left sides of the user's forehead. Alternatively, $ROI_1$ and $ROI_2$ may cover right and left regions on the periorbital areas, the nose, and/or the mouth. Optionally, the computer detects headaches utilizing a model that was trained based on previous $TH_{ROI1}$ and $TH_{ROI2}$ taken during different days, optionally including samples taken while the user had a headache and while the user did not have a headache.

Additionally, in some embodiments, a relationship between the stress the user feels and headache the user has may be studied. Optionally, the computer receive training data comprising physiological measurements indicative of levels of stress of the user, values indicative of durations during which the user felt stressed, and values indicative of durations during which the user had a headache. The computer utilizes a machine learning-based training algorithm to train the model based on the training data. The model may be used to detect a headache based on $TH_{ROI1}$ and $TH_{ROI2}$ and optionally, additional values indicative of stress the user felt.

Orofacial pain often results from dental causes (e.g., toothache caused by pulpitis or a dental abscess). Such pain may also be detected utilizing some embodiments of the system. In one embodiment. $ROI_1$ and $ROI_2$ are on the right and left sides of at least one of the jaws. Optionally, the computer detects orofacial pain based on $TH_{ROI1}$ and $TH_{ROI2}$ utilizing a model that was trained based on previous $TH_{ROI1}$ and $TH_{ROI2}$ taken during different days.

Bell's palsy is another medical disorder that may be identified based on thermal measurements. In one embodiment the system includes a computer that detects Bell's palsy based on comparing $TH_{ROI1}$ and $TH_{ROI2}$ taken from the user during different days. Optionally, the system further includes a VCAM for taking photos of the face, and the computer analyzes the photos for asymmetry in order to improve the probability of identifying Bell's palsy. For example, the detection of Bell's palsy may be done based on feature values that include feature values generated based on the thermal measurements (e.g., corresponding to differences in values of thermal measurements at the same locations during different times), and feature values generated based on images taken by VCAM (e.g., corresponding to differences in facial features at the same locations during different times). Optionally, the system suggests the user to take a medical examination when the facial thermal asymmetry reaches a threshold for more than a predetermined duration (such as 1 minute, 5 minutes, or more than 30 minutes).

In one embodiment, a method for detecting a physiological response that causes a thermal asymmetry on a user's face includes the following steps: In step 1, taking, using first and second CAMs (CAM1 and CAM2), thermal measurements of regions on the right and left sides of the face ($TH_{ROI1}$ and $TH_{ROI2}$, respectively). The regions on the right and left sides of the face have a symmetric overlapping above 60%. CAM1 and CAM2 are less than 10 cm away from the face, and the angles between the Frankfort horizontal plane and the optical axes of CAM1 and CAM2 are greater than 200. And in Step 2, detecting the physiological response based on $TH_{ROI1}$ and $TH_{ROI2}$.

In one embodiment, the method further includes the steps of (i) generating feature values based on $TH_{ROI1}$ and $TH_{ROI2}$, and (ii) utilizing a model to detect the physiological response based on the feature values. Optionally, the model was trained based on previous $TH_{ROI1}$ and $TH_{ROI2}$ taken while the user had a physiological response associated with stress, mental workload, fear, sexual arousal, anxiety, pain, a headache, dehydration, intoxication, and/or a stroke. Optionally, the previous $TH_{ROI1}$ and $TH_{ROI2}$ were taken on different days. Optionally, the method further alerts about the physiological response that causes the thermal asymmetry.

Some of the disclosed embodiments may be utilized to detect a stress level of a user based on thermal measurements of the user's face, such as the periorbital areas (i.e., areas around the eyes). In one embodiment, a system configured to detect a stress level includes a CAM and a computer. CAM takes thermal measurements of a region on a periorbital area ($TH_{ROI1}$) of the user, and is located less than 10 cm from the user's head. The computer detects the stress level based on $TH_{ROI1}$.

In one embodiment, in which the region is on the periorbital area of the right eye, the system further includes a second inward-facing head-mounted thermal camera (CAM2), which is located less than 10 cm from the user's head and takes thermal measurements of a region on the periorbital area of the left eye ($TH_{ROI2}$). Optionally, the computer detects the stress level based on both $TH_{ROI1}$ and $TH_{ROI2}$. Optionally. CAM and CAM2 are located at least 0.5 cm to the right and to the left of the vertical symmetry axis (which goes through the middle of the forehead and the middle of the nose), respectively. Optionally, each of CAM and CAM2 weighs below 10 g and is based on a thermopile, a microbolometer, or a pyroelectric sensor, which may be a focal-plane array sensor.

It is to be noted that while various embodiments may utilize a single CAM, due to asymmetrical placement of blood vessels in the face, thermal emissions of faces of many people are asymmetric to a certain extent. That is, the pattern of thermal emission from the left side of the face may be different (possibly even noticeably different) from the pattern of thermal emission from the right side of the face. Thus, for example, the temperature changes at the periorbital areas, in response to experiencing at least a certain level of stress, may be asymmetric for some users. The fact that various embodiments described below may include two (or more) CAMs that take measurements of ROIs covering different sides of the face (referred to as $TH_{ROI1}$ and $TH_{ROI2}$)

can enable the computer to account for the thermal asymmetry when detecting the stress level.

In some cases, interferences (such as an external heat source, touching one of the eyes, or an irritated eye) cause an asymmetric effect on the right and left periorbital areas. As a result, utilizing right and left CAMs, which are located in different angles relative to the interfering source, provides the computer additional data that can improve its performances. The following are some examples of various ways in which the computer may account for the asymmetry when detecting the stress level based on $TH_{ROI1}$ and $TH_{ROI2}$, which include measurements of the of regions on the periorbital areas of the right and left eyes of the user, respectively.

In one embodiment, when comparing $TH_{ROI1}$ and $TH_{ROI2}$, to thresholds, the computer may utilize different thresholds for $TH_{ROI1}$ and $TH_{ROI2}$, in order to determine whether the user experienced a certain level of stress. Optionally, the different thresholds may be learned based on previous $TH_{ROI1}$ and $TH_{ROI2}$, which were measured when the user experienced the certain level of stress and/or suffered from certain interferences.

In another embodiment, the computer may utilize different reference time series to which $TH_{ROI1}$ and $TH_{ROI2}$ are compared in order to determine whether the user experienced the certain level of stress. Optionally, accounting for the asymmetric manifestation of the stress is reflected in the fact that a reference time series to which $TH_{ROI1}$ is compared is different from a reference time series to which $TH_{ROI2}$ is compared.

In yet another embodiment, when the computer utilizes a model to calculate a stress level based on feature values generated based on $TH_{ROI1}$ and/or $TH_{ROI2}$. Optionally, the feature values include: (i) at least first and second feature values generated based on $TH_{ROI1}$ and $TH_{ROI2}$, respectively; and/or (ii) a third feature value indicative of the magnitude of a difference between $TH_{ROI1}$ and $TH_{ROI2}$. In this embodiment, the computer may provide different results for first and second events that involve the same average change in $TH_{ROI1}$ and $TH_{ROI2}$, but with different extents of asymmetry between $TH_{ROI1}$ and $TH_{ROI2}$, and/or different magnitudes of interferences on the right and left eyes.

In still another embodiment, the computer may utilize the fact that asymmetric temperature changes occur when the user experiences stress in order to distinguish between stress and other causes of temperature changes in the periorbital areas. For example, drinking a hot beverage or having a physical exercise may cause in some people a more symmetric warming pattern to the periorbital areas than stress. Thus, if such a more symmetric warming pattern is observed, the computer may refrain from identifying the temperature changes as being stress-related. However, if the warming pattern is asymmetric and corresponds to temperature changes in the periorbital areas of the user when the user experiences stress, then the computer may identify the changes in the temperatures being stress-related.

The computer may employ different approaches when detecting the stress level based on $TH_{ROI1}$ (and possibly other sources of data such as $TH_{ROI2}$). In one embodiment, the computer may compare $TH_{ROI1}$ (and possibly other data) to a threshold(s), which when reached would indicate a certain stress level. In another embodiment, the computer may generate feature values based on $TH_{ROI1}$ and $TH_{ROI2}$, and utilize a model (also referred to as a "machine learning-based model") to calculate a value indicative of the stress level based on the feature values (calculating the value indicative of the stress level may be considered herein as "detecting the stress level"). At least some of the feature values are generated based on $TH_{ROI1}$. Optionally, at least some of the feature values may be generated based on other sources of data, such as $TH_{ROI2}$ and/or $TH_{ROI3}$ (described below). Optionally, the model was trained based on samples comprising feature values generated based on previous $TH_{ROI1}$ (and possibly other data, as explained below), and corresponding labels indicative of a stress level of the user. Optionally, the data used to train the model includes previous $TH_{ROI1}$ taken while the user as under elevated stress, and other previous $TH_{ROI1}$ taken while the user was not under elevated stress. Optionally, "elevated stress" refers to a stress level that reaches a certain threshold, where the value of the threshold is set according to a predetermined stress scale (examples of stress scales are given further below). Optionally, "elevated stress" refers to a physiological state defined by certain threshold values of physiological signals (e.g., pulse, breathing rate, and/or concentration of cortisol in the blood).

In a first embodiment, when the stress level exceeds a certain value. $TH_{ROI1}$ reach a threshold, and when the stress level does not exceed the certain value. $TH_{ROI1}$ do not reach the threshold. Optionally, the stress level is proportional to the values of $TH_{ROI1}$ (which are thermal measurements of the region on the periorbital area), such that the higher $TH_{ROI}$ and/or the higher the change to $TH_{ROI1}$ (e.g., with reference to a baseline), the higher the stress level.

In a second embodiment, the computer detects the stress level based on a difference between $TH_{ROI1}$ and a baseline value determined based on a set of previous measurements taken by CAM. Optionally, most of the measurements belonging to the set were taken while the user was not under elevated stress.

In a third embodiment, the stress level is detected using a model and feature values generated based on additional measurements ($m_{conf}$) of the user and/or of the environment in which the user was in while $TH_{ROI1}$ were taken, $m_{conf}$ may be taken by sensor 461. Optionally, $m_{conf}$ are indicative of an extent to which a confounding factor occurred while $TH_{ROI1}$ were taken. The following are some examples of sources of information for $m_{conf}$ which may be used to detect the stress level.

In a first example, $m_{conf}$ are physiological signals such as a heart rate, heart rate variability, galvanic skin response, a respiratory rate, and respiratory rate variability, which are taken using sensors such as PPG, ECG, EEG, GSR and/or a thermistor.

In a second example, $m_{conf}$ represent an environmental condition and/or a situation of the user that may be considered a confounding factor, such as an indication of whether the user touched at least one of the eyes, an indication of whether the user is engaged in physical activity (and possibly the type and/or extent of the physical activity), temperature, humidity. IR radiation level, and a noise level. Optionally, the one or more values are obtained based on using an accelerometer, a pedometer, a humidity sensor, a miniature radar (such as low-power radar operating in the range between 30 GHz and 3,000 GHz), a miniature active electro-optics distance measurement device (such as a miniature Lidar), an anemometer, an acoustic sensor, and/or a light meter.

In a third example, $m_{conf}$ represent properties describing the user, such as the user's age, gender, marital status, occupation, education level, health conditions, and/or mental health issues that the user may have.

Stress may be thought of as the body's method of reacting to a challenge. Optionally, stress may be considered a physiological reaction to a stressor. Some examples of stressors include mental stressors that may include, but are not limited to, disturbing thoughts, discontent with something, events, situations, individuals, comments, or anything a user may interpret as negative or threatening. Other examples of stressors include physical stressors that may put strain on the body (e.g., very cold/hot temperatures, injury, chronic illness, or pain). In one example, a (high) workload may be considered a stressor. The extent to which a user feels stressed is referred to herein as a "stress level" and being under a certain level of stress may be referred to herein as "experiencing a certain stress level". Depending on the embodiment, a stress level may be expressed via various types of values, such as a binary value (the user is "stressed" or "not stressed", or the user is under "elevated stress" or "not under elevated stress"), a categorical value (e.g., no stress/low stress/medium stress/high stress), and/or a numerical value (e.g., a value on a scale of 0 to 10). In some embodiments, a "stress level" may refer to a "fight or flight" reaction level.

Evaluation of stress typically involves determining an amount of stress a person may be feeling according to some standard scale. There are various approaches known in the literature that may be used for this task. One approach involves identifying various situations the person may be in, which are associated with certain predefined extents of stress (which are empirically derived based on observations). Example of popular approaches include the Holmes and Rahe stress scale, the Perceived Stress Scale, and the Standard Stress Scale (SSS). A common trait of many the various stress scales is that they require a manual evaluation of situations a user undergoes, and do not measure the actual physiological effects of stress.

In some embodiments, the computer may receive an indication of a type of stressor, and utilize the indication to detect the stress level. Optionally, the indication is indicative of a period and/or duration during which the user was affected by the stressor. In one example, the indication is utilized to select a certain threshold value, which is appropriate for the type of stressor, and to which $TH_{ROI1}$ may be compared in order to determine whether the user is experiencing a certain stress level. Optionally, the certain threshold is determined based on thermal measurements of the user when the user reacted to a stressor of the indicated type. In another example, the indication is utilized to select a certain reference time series, which corresponds to the type of stressor, and to which $TH_{ROI1}$ may be compared in order to determine whether the user is experiencing a certain stress level. Optionally, the certain time series is based on thermal measurements of the user taken when the user reacted to a stressor of the indicated type. In yet another example, the computer generates one or more feature values based on the indication, and the one or more feature values are utilized to detect the stress level using a model (in addition to feature values generated based on $TH_{ROI1}$). In still another example, the computer may select a window of time based on the indication, which corresponds to the expected duration of stress induced by the type of stressor indicated in the indication. In this example, in order to detect the stress level of the user, the computer evaluates thermal measurements from among $TH_{ROI1}$ that were taken at a time that falls in the window.

Additional CAMs may be utilized to detect the stress level. The thermal measurements of the additional CAMs, typically denoted $TH_{ROI2}$ below, may be utilized to generate one or more feature values that are used along with the machine learning-based model to detect the stress level.

In one embodiment, the system includes a second inward-facing head-mounted thermal camera (CAM2) that takes thermal measurements of an additional ROI on the face ($TH_{ROI2}$), such as the forehead, the nose, and/or a region below the nostrils. The region below the nostrils refer to one or more regions on the upper lip, the mouth, and/or air volume through which the exhale streams from the nose and/or mouth flow, and it's thermal measurements are indicative of the user's breathing.

Given $TH_{ROI2}$, the computer may generate feature values based on $TH_{ROI1}$ and $TH_{ROI2}$ (and possibly other sources of data) and utilizes a model to detect the stress level based on the feature values. Optionally, the model was trained based on previous $TH_{ROI1}$ and $TH_{ROI2}$ taken while the user had at least two different stress levels according to a predetermined stress scale. For example, a first set of previous $TH_{ROI1}$ and $TH_{ROI2}$ taken while the user was under elevated stress, and a second set of previous $TH_{ROI1}$ and $TH_{ROI2}$ taken while the user was not under elevated stress.

In another embodiment, the system further includes second and third CAMs that take thermal measurements of regions on the right and left cheeks, respectively. Optionally, the computer detects the stress level also based on the thermal measurements of the cheeks.

Figure 41:
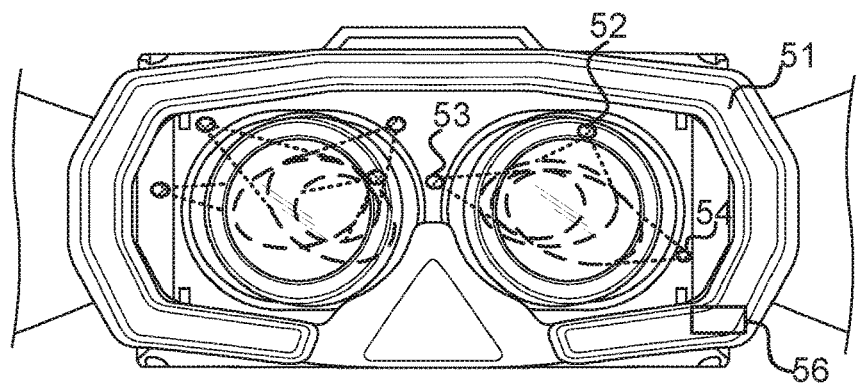
FIG. 41 illustrates an embodiment of an HMS able to measure stress level.

FIG. 41 illustrates one embodiment of an HMS able to measure stress level. The system includes a frame 51, CAMs (52, 53, 54), and a computer 56. CAMs are physically coupled to the frame and take thermal measurements of ROIs on the periorbital areas. Because CAMs are located close to their respective ROIs, they can be small, lightweight, and may be placed in many potential locations having line of sight to their respective ROIs. The computer 56, which may by located on the HMS, worn by the user, and/or remote such as in the cloud, detects the stress level based on changes to temperature of the periorbital areas received from the CAMs.

Due to the asymmetry of blood vessels in human faces and different shapes of human faces, having CAMs pointed at the right and left periorbital areas may enable a more accurate detection of physiological phenomena such as stress, and/or may enable detection of stress that is harder to detect based on measuring only a single periorbital area.

Figure 42:
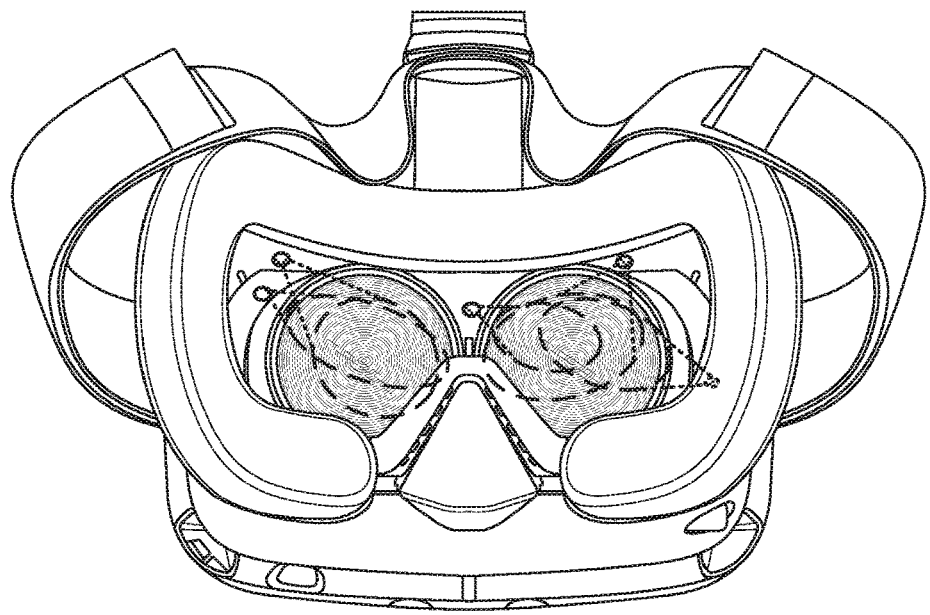
FIG. 42 illustrates examples of asymmetric locations of inward-facing head-mounted thermal cameras (CAMs) that measure the periorbital areas.
Figure 43:
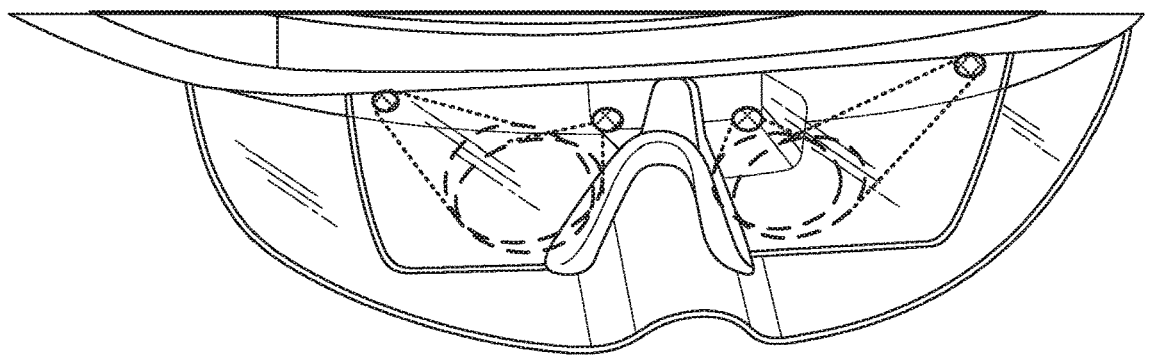
FIG. 43 illustrates an example of symmetric locations of the CAMs that measure the periorbital areas.

While FIG. 41 and FIG. 42 illustrate examples of asymmetric locations of CAMs that measure the right periorbital area relative to the locations of CAMs that measure the left periorbital area, FIG. 43 illustrates an example of symmetric locations of the CAMs that measure the right periorbital area relative to the locations of the CAMs that measure the left periorbital area. In some embodiments, using thermal measurements from both symmetric and asymmetric located CAMs may improve the system's adaptability to different faces having different proportions.

Figure 45A:
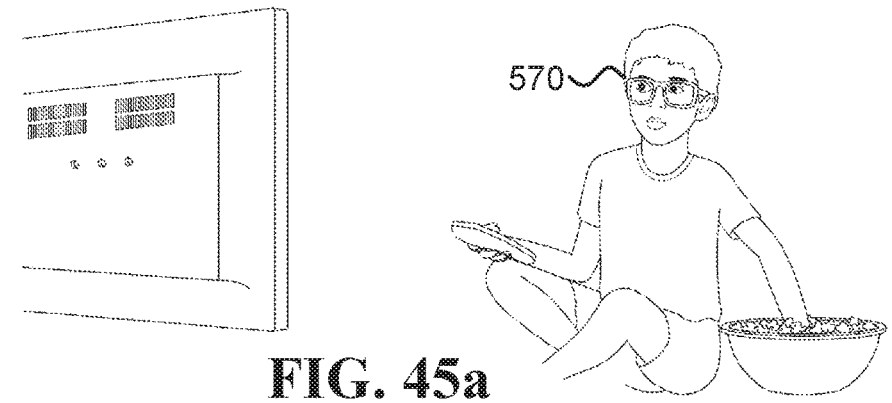
FIG. 45a illustrates a child watching a movie while wearing an eyeglasses frame with at least five CAMs.
Figure 45B:
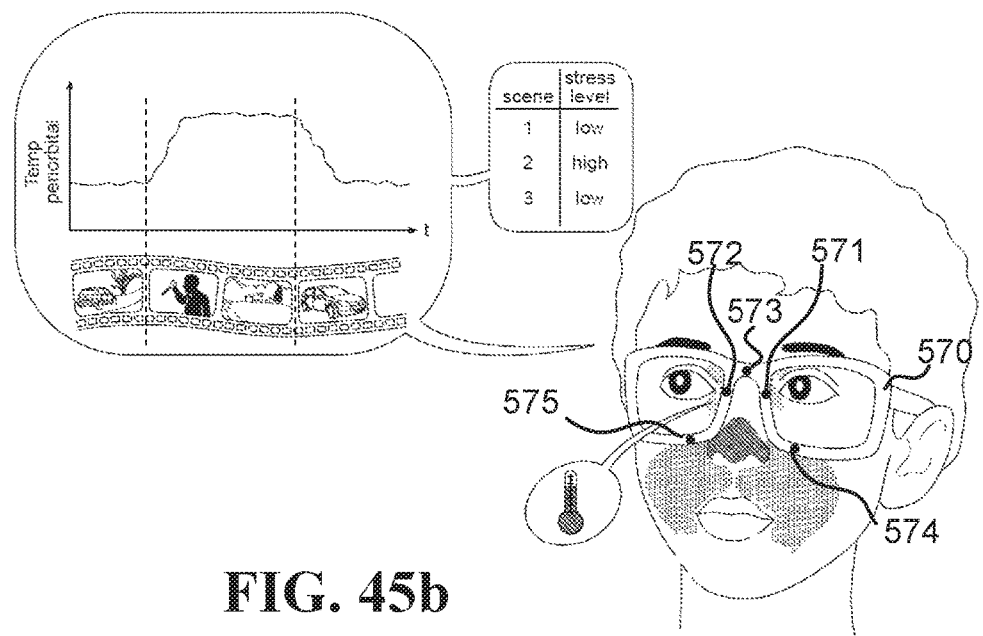
FIG. 45b illustrates generation of a graph of the stress level of the child detected at different times while different movie scenes were viewed.

FIG. 45a and FIG. 45b illustrate one scenario of detecting a user's stress level. FIG. 45a illustrates a child watching a movie while wearing an eyeglasses frame 570 with at least five CAMs. FIG. 45b illustrates the at least five CAMs 571, 572, 573, 574, and 575, which measure the right and left periorbital areas, the nose, and the right and left cheeks, respectively (the different ROIs are designated by different patterns). The figure further illustrates how the system produces a graph of the stress level detected at different times while different movie scenes were viewed.

In one embodiment, the system may include a head-mounted display (HMD) that presents digital content to the user and does not prevent CAM from measuring the ROI. In another embodiment, the system may include an eye tracker to track the user's gaze, and an optical see through HMD that operates in cooperation with the following components: a visible-light camera that captures images of objects the user is looking at, and a computer that matches the objects the user is looking at with the detected stress levels. Optionally, the eye tracker is coupled to a frame worn by the user. In yet another embodiment, the system may include a HMD that presents video comprising objects, and an eye tracker. The computer utilizes data generated by the eye tracker to match the objects the user is looking at with the detected stress levels. It is to be noted that there may be a delay between being affected by a stressor and a manifestation of stress as a reaction, and this delay may be taken into account when determining what objects caused the user stress.

Figure 47:
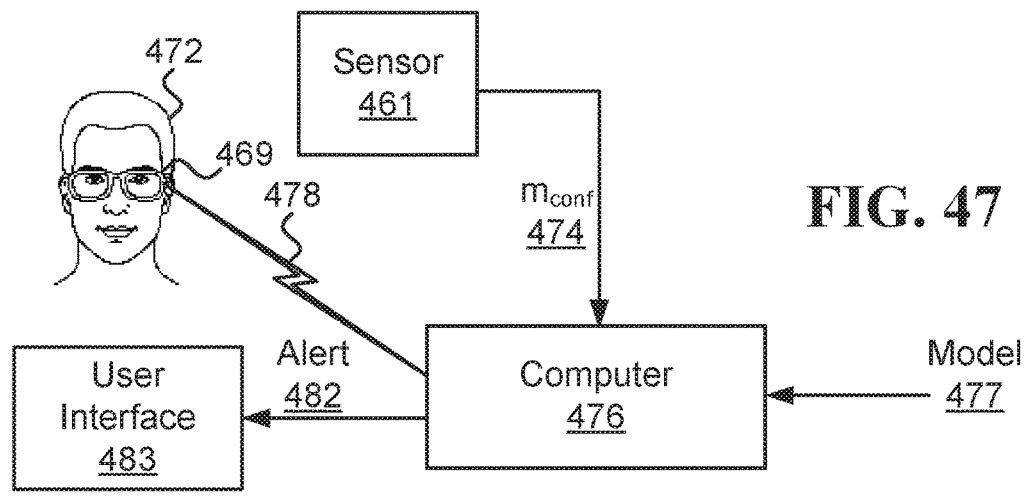
FIG. 47 illustrates an embodiment of a system that includes a user interface, which notifies a user when the stress level of the user reaches a predetermined threshold.

In one embodiment, the system further includes a user interface (UT), such as user interface 483 illustrated in FIG. 47, which notifies the user when the stress level reaches a predetermined threshold. Optionally, the UT notifies the user by an audio indication, a visual indication, and/or a haptic notification. Optionally, the greater the change to the temperature of the periorbital areas, the higher the detected stress level, and the indication is proportional to the stress level. Optionally, the UI also provides the user with encouragement not to engage in certain behavior that causes stress, such as displaying anger, screaming, denigrating others, lying, and/or cheating. In one example, the encouragement may include evidence based on detected stress levels of the user, which indicates that conducting in the certain behavior increases stress. In another example, the encouragement may include reminding the user that the certain behavior is against the user's beliefs and/or the certain behavior is contrary to the user's goals, interests, and/or resolutions.

In one embodiment, a system configured to alert about stress includes at least CAM1 and CAM2 located at least 0.5 cm to the right and to the left of the vertical symmetry axis that divides the user's face, respectively. CAM1 and CAM2 take thermal measurements of regions on the periorbital areas of the right and left eyes ($TH_{ROI1}$ and $TH_{ROI2}$, respectively) of the user. UI 483 provides an alert about a stress level reaching a threshold. Optionally, the system includes a frame that is worn on the user's head, CAM1 and CAM2 are physically coupled to the frame, weighs below 10 g each, and located less than 15 cm from the user's face. Optionally, the system includes a transmitter that may be used to transmit $TH_{ROI1}$ and $TH_{ROI2}$ to a computer that detects the stress level based on $TH_{ROI1}$ and $TH_{ROI2}$. Optionally, responsive to detecting a stress level that reaches a threshold, the computer commands the user interface to provide the alert. For example, the computer may send a signal to a smartphone app, and/or to a software agent that has control of the user interface, to provide the alert.

One embodiment of a method for alerting about stress includes at least the following steps: In Step 1, taking thermal measurements of regions on the periorbital areas of the right and left eyes ($TH_{ROI1}$ and $TH_{ROI2}$, respectively) of a user utilizing first and second CAMs worn on the user's head and located at least 0.5 cm to the right and to the left of the vertical symmetry axis that divides the user's face, respectively. And in Step 2, alerting about a stress level that is detected based on $TH_{ROI1}$ and $TH_{ROI2}$. Optionally, the alert about the allergic reaction is provided as text, image, sound, and/or haptic feedback.

Optionally, the method further includes generating feature values based on $TH_{ROI1}$ and $TH_{ROI2}$, and using a model for detecting the stress level based on the feature values. The model was trained based on previous $TH_{ROI1}$ and $TH_{ROI2}$ of the user, taken during different days, which include: a first set of measurements taken while the user had a first stress level according to a predetermined stress scale, and a second set of measurements taken while the user had a second stress level according to the predetermined stress scale.

Optionally, the method further includes generating feature values based on $TH_{ROI1}$ and $TH_{ROI2}$, and using a model for detecting the stress level based on the feature values. The model was trained based on previous $TH_{ROI1}$ and $TH_{ROI2}$ of one or more users, taken during different days, which comprise: a first set of measurements taken while the one or more users had a first stress level according to a predetermined stress scale, and a second set of measurements taken while the one or more users had a second stress level according to the predetermined stress scale.

The above steps of generating the feature values and utilizing the model may be performed multiple times throughout the period of the different days during which $TH_{ROI1}$ and $TH_{ROI2}$ were taken, each time utilizing a subset of $TH_{ROI1}$ and $TH_{ROI2}$ taken during a different window of a certain length. In these embodiments, the alerting in Step 2 may be done at a certain time for which a certain stress level is detected (which warrants an alert).

Figure 44:
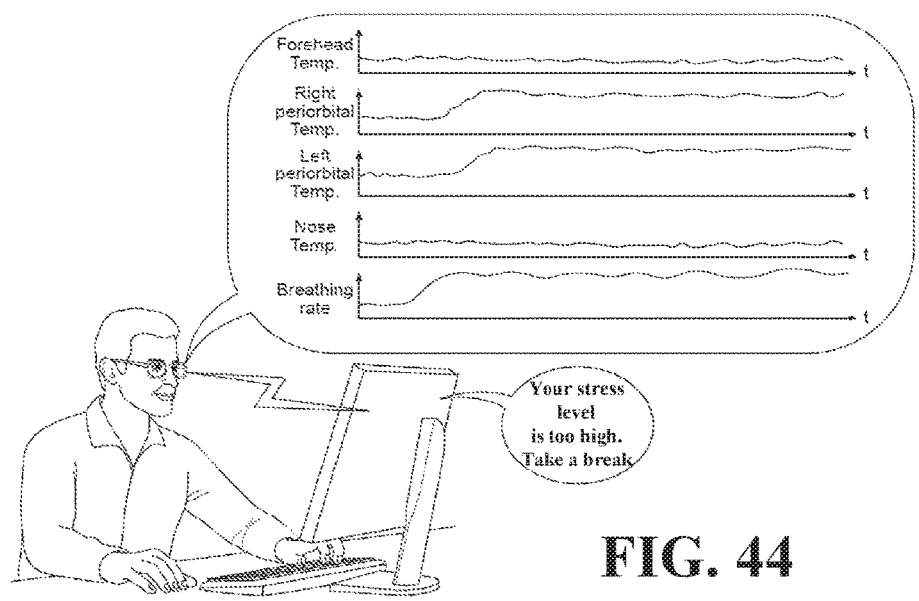
FIG. 44 illustrates a scenario in which a system suggests to the user to take a break in order to reduce the stress level.

FIG. 44 illustrates a scenario in which a system (which measures the forehead, right and left periorbital areas, nose, and below the nostrils) suggests to the user to take a break in order to reduce the stress level of the user. The system may suggest the user to partake in at least one of the following activities when the stress level reaches a first threshold: practice pranayama, physical exercise, listen to brainwave entrainment, and listen to positive loving statements. Optionally, the computer suggests to the user to stop the activity when the stress level gets below a second threshold. Optionally, the system shows the user video comprising objects, and the detected stress level associated with the objects.

Figure 46:
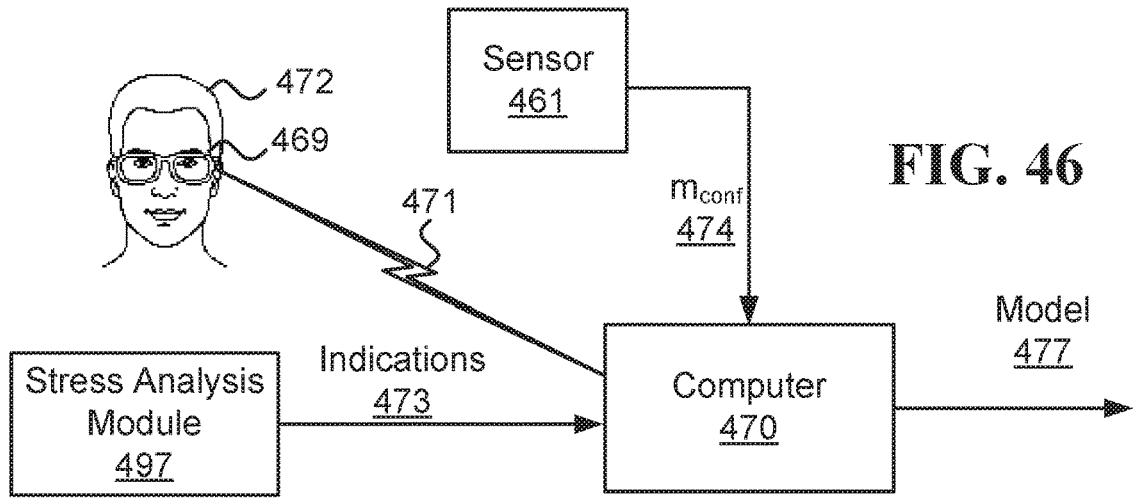
FIG. 46 illustrates an embodiment of a system that generates a personalized model for detecting stress based on thermal measurements of the face.

FIG. 46 illustrates one embodiment of a system configured to generate a personalized model for detecting stress based on thermal measurements of the face. The system includes a frame, first and second CAMs, and a computer 470. The first and second CAMs take thermal measurements 471 of regions on the periorbital areas of the right and left eyes ($TH_{ROI1}$ and $TH_{ROI2}$, respectively) of the user 472.

The computer 470 generates samples based on data comprising: (i) $TH_{ROI1}$ and $TH_{ROI2}$ 471, and (ii) indications 473 corresponding to different times, which are indicative of stress levels of the user at the different times. Optionally, each sample comprises: (i) feature values generated values based on $TH_{ROI1}$ and $TH_{ROI2}$ taken during a certain period, and (ii) a label indicative of a stress level of the user during the certain period. Optionally, at least one of the feature values in a sample may be generated based on other sources of information such as physiological measurements of the user 472 and/or measurements of the environment in which the user 472 was in when while $TH_{ROI1}$ and $TH_{ROI2}$ 471 were taken. Optionally, the stress levels indicated in the indications 473 correspond to levels of a known stress level scale. The computer 470 trains a model 477 based on the samples. Optionally, the computer 470 also provides the model 477 to be used by a system that detects stress based on $TH_{ROI1}$ and $TH_{ROI2}$.

The indications 473 may be generated in different ways, in different embodiments. One or more of the indications 473 may be (i) generated by an entity that observes the user 472, such as a human observer or a software program (e.g., a software agent operating on behalf of the user 472), (ii) provided by the user 472, such as via a smartphone app by pressing a certain button on a screen of a smartphone, and/or by speech that is interpreted by a software agent and/or a program with speech analysis capabilities, (iii) determined based on analysis of behavior of the user 472, such as by analyzing measurements of a camera and/or a microphone that indicate that the user 472 is experiencing a certain stress level, and (iv) determined based on physiological signals of the user 472 that are not thermal measurements of one or more ROIs on the face, such as measurements of the user's heart rate and/or brainwave activity.

Optional stress analysis module 497 receives descriptions of events corresponding to when at least some of $TH_{ROI1}$ and $TH_{ROI2}$ 471 were taken, and generates one or more of the indications 473 based on analyzing the descriptions. The stress analysis module 497 is implemented by the computer 470 or another computer. Optionally, all of the indications 473 are generated by the stress analysis module 497. Optionally, the stress analysis module 497 may be a module of a software agent operating on behalf of the user 472. The descriptions received by the stress analysis module 497 may include various forms of information. In one example, the descriptions include content of a communication of the user 472, and the stress analysis module 497 utilizes semantic analysis in order to determine whether the communication is indicative a stressful event for the user 472 (e.g., the communication is indicative of something going wrong at work). Optionally, the stress analysis module 497 utilizes a machine learning-based model to calculate based on features derived from the communication, a predicted stress level for the user 472. In another example, the stress analysis module 497 receives images of an event, such as images taken by an outward-facing head-mounted visible-light camera, utilizes image analysis to determine whether the event corresponds to a stressful event, and utilizes a machine learning-based model to calculate the predicted stress based on features derived from the images.

The model is trained on samples comprising feature values based on $TH_{ROI1}$ and $TH_{ROI2}$, and additional feature values described in the following examples:

In a first example, the additional feature values include additional thermal measurements, taken with another CAM, of an ROI that includes the nasal and/or mouth regions.

In a second example, the additional feature values are indicative of one or more of the following signals of the user 472: a heart rate, heart rate variability, brainwave activity, galvanic skin response, muscle activity, and an extent of movement.

In a third example, the additional feature values are measurements ($m_{conf}$ 474) of the user 472 and/or of the environment in which the user 472 as in while $TH_{ROI1}$ and $TH_{ROI2}$ 471 were taken. Optionally, $m_{conf}$ 474 are taken by a sensor 461, which may be physically coupled to the frame. In another example, the sensor 461 is coupled to a device carried by the user, such as a smartphone, a smartwatch, and/or smart clothing (e.g., clothing embedded with sensors that can measure the user and/or the environment). In yet another example, the sensor 461 may be an external sensor that is not carried by the user. Optionally, the computer 470 is generates, based on $m_{conf}$ 474, one or more feature values of at least some of the samples. $m_{conf}$ 474 are indicative of an extent to which one or more confounding factors occurred while $TH_{ROI1}$ and $TH_{ROI2}$ 471 were taken.

In one embodiment, the sensor 461 is a visible-light camera physically coupled to the frame, which takes images of a region on the face of the user 472, which includes at least 25% of the $ROI_1$ and/or $ROI_2$. Optionally, the confounding factor in this embodiment involves inflammation of the skin, skin blemishes, food residues on the face, talking, eating, drinking, and/or touching the face. In another embodiment, the sensor 461 includes a movement sensor that measures a movement of the user 472. Optionally, the confounding factor in this embodiment involves the user 472 walking, running, exercising, bending over, and/or getting up from a sitting or lying position. In yet another embodiment, the sensor 461 measures at least one of the following environmental parameters: a temperature of the environment, a humidity level of the environment, a noise level of the environment, air quality in the environment a wind speed in the environment, an extent of precipitation in the environment, and an infrared radiation level in the environment.

In some embodiments, the samples used to train the model 477 include samples that were generated based on $TH_{ROI1}$ and $TH_{ROI2}$ of the user 472 taken while the user 472 had different stress levels. In one embodiment, one or more samples that were generated based on $TH_{ROI1}$ and $TH_{ROI2}$ of the user 472 taken while a stress level of the user 472 reached a threshold. Optionally, the stress level is evaluated using one or more known stress level scales. Optionally, a user whose stress level reaches the threshold is considered "stressed". Additionally, in this embodiment, the samples include one or more samples that were generated based $TH_{ROI1}$ and $TH_{ROI2}$ of the user 472, which were taken while a stress level of the user 472 did not reach the threshold. Optionally, a user whose stress level does not reach the threshold is not considered "stressed". Thus, the samples may be utilized to train a model that can help distinguish between cases in which $TH_{ROI1}$ and $TH_{ROI2}$ of the user 472 are taken while the user 472 is stressed (and/or the user 472 has a certain stress level), and cases in which $TH_{ROI1}$ and $TH_{ROI2}$ of the user 472 are taken while the user 472 is not stressed (and/or the user 472 does not have a certain stress level).

The samples used to train the model 477 may include samples generated based on measurements taken while user 472 was in different environments. In one example, the samples comprise first and second samples that are based on $TH_{ROI1}$ and $TH_{ROI2}$ of the user 472 taken during first and second periods, respectively. Optionally, different environmental conditions prevailed during the first and second periods, which involved one or more of the following differences: (i) the temperature of the environment in which the user 472 was during the first period was at least 10° C. higher than the temperature of the environment in which the user 472 was during the second period; (ii) the humidity level in the environment in which the user 472 was during the first period was at least 30% higher than the humidity level in the environment in which the user 472 was during the second period; and (iii) the user 472 was exposed to rain, hail, and/or snow during the first period and the user was not exposed to any of rain, hail, and snow during the second period.

Additionally or alternatively, the samples utilized to train the model 477 may include samples generated based on measurements taken while the user 472 was in various situations. In one example, the samples comprise first and second samples that are based on $TH_{ROI1}$ and $TH_{ROI2}$ of the user 472 taken during first and second periods, respectively. Optionally, the user 472 was in different situations during the first and second periods, which involved one or more of the following differences: (i) the user 472 was sedentary during the first period, while the user 472 was walking, running, and/or biking during the second period; and (ii) the user 472 was indoors during the first period, while the user 472 was outdoors during the second.

Additionally or alternatively, the samples utilized to train the model 477 may be based on $TH_{ROI1}$ and $TH_{ROI2}$ taken during different days and/or over a long period, such as more than a week, more than a month, or more than a year.

Training the model 477 may involve one or more of the various computational approaches mentioned in this disclosure for training a model used to detect a physiological response. In one example, training the model 477 may involve selecting, based on the samples, a threshold: if a certain feature value reaches the threshold then a certain level of stress of the user is detected. In another example, the computer 470 utilizes a machine learning-based training algorithm to train the model 477 based on the samples. Optionally, the model comprises parameters of at least one of the following models: a regression model, a model utilized by a neural network, a nearest neighbor model, a model for a support vector machine for regression, and a model of a decision tree.

In some embodiments, the computer 470 may utilize deep learning algorithms to train the model 477. In one example, the model 477 may include parameters describing multiple hidden layers of a neural network. In one embodiment, when $TH_{ROI1}$ and $TH_{ROI2}$ include measurements of multiple pixels, such as when CAM includes a FPA, the model 477 may include parameters of a convolution neural network (CNN). In one example, a CNN may be utilized to identify certain patterns in the thermal images, such as patterns of temperatures on the forehead that may be indicative of a certain physiological response (e.g., a headache, stress, or anger). In another embodiment, detecting the stress level may be done based on multiple, possibly successive, measurements. For example, stress may involve a progression of a state of the user (e.g., a gradual warming of certain areas of the forehead). In such cases, detecting the stress level may involve retaining state information that is based on previous measurements. Optionally, the model 477 may include parameters that describe an architecture that supports such a capability. In one example, the model 477 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In one embodiment, training the model 477 involves altering parameters of another model, which is generated based on $TH_{ROI1}$ and $TH_{ROI2}$ of one or more other users. For example, the computer 470 may utilize the other model as an initial model. As the samples are acquired from measurements of the user 472, the computer 470 may update parameters of the initial model based on the samples. Thus, this process may be considered personalizing a general model according to measurements of the user 472.

Once the model 477 is generated, it may be utilized to detect stress of the user 472 based on other $TH_{ROI1}$ and $TH_{ROI2}$ of the user 472, which are not among $TH_{ROI1}$ and $TH_{ROI2}$ 471 that were used for training the model 477. Such utilization of the model 477 is illustrated in FIG. 47, which illustrates one embodiment of a system configured to perform personalized detection of stress based on thermal measurements of the periorbital area. One embodiment of the illustrated system includes a frame 469, first and second CAMs, and a computer 476.

The computer 476 is configured to: generate feature values based on $TH_{ROI1}$ and $TH_{ROI2}$ 478 and utilize the model 477 to detect the stress level of the user 472 based on the feature values. Optionally, the model 477 was trained based on previous $TH_{ROI1}$ and $TH_{ROI2}$ of the user 472 (e.g., $TH_{ROI1}$ and $TH_{ROI2}$ 471), which were taken during different days. The feature values generated based on $TH_{ROI1}$ and $TH_{ROI2}$ 478 are similar in their nature to the feature values generated based on $TH_{ROI1}$ and $TH_{ROI2}$ 471, which were discussed in more detail above. Optionally, the computer 476 and the computer 470 may utilize the same modules and/or procedures to generate feature values based on $TH_{ROI1}$ and $TH_{ROI2}$ (and possibly other data). Optionally, the computer 476 receives measurements $m_{conf}$ 474 indicative of an extent to which a confounding factor occurred while $TH_{ROI1}$ and $TH_{ROI2}$ 478 were taken, as discussed above.

Since the model 477 is personalized for the user 472, when such a model is trained for different users, it may lead to different detections of stress, even when provided with similar $TH_{ROI}$ and $TH_{ROI2}$ of the users. In one example, first and second models are generated based on previous $TH_{ROI1}$ and $TH_{ROI2}$ of first and second different users, respectively. Responsive to utilizing the first model, a first value is detected based on first feature values generated based on $TH_{ROI1}$ and $TH_{ROI2}$ of the first user, which is indicative of a first stress level. Responsive to utilizing the second model, a second value is detected based on second feature values generated based on $TH_{ROI1}$ and $TH_{ROI1}$ of the second user, which is indicative of a second stress level. In this example, $TH_{ROI1}$ and $TH_{ROI2}$ of the first user indicate a greater temperature change at the periorbital areas of the first user compared to the change at the periorbital areas of the second user indicated by $TH_{ROI1}$ and $TH_{ROI2}$ of the second user. However, in this example, the first stress level is lower than the second stress level.

Some aspects of this disclosure involve monitoring a user over time with CAM that takes thermal measurements of a region on a periorbital area ($TH_{ROI1}$) of the user. One application for which $TH_{ROI1}$ may be useful is to detect the stress level of the user. Analysis of these detections combined with information regarding factors that affected the user at different times, which may be considered potential stressors, can reveal which of the factors may be stressor that increase the stress level of the user.

Some examples of factors that may be considered potential stressors for certain users include being in certain locations, interacting with certain entities, partaking in certain activities, or being exposed to certain content. Having knowledge of which potential stressor are likely to actually be stressors for a certain user can help that user avoid the stressors and/or take early measures to alleviate the effects of the stress they cause.

Figure 48:
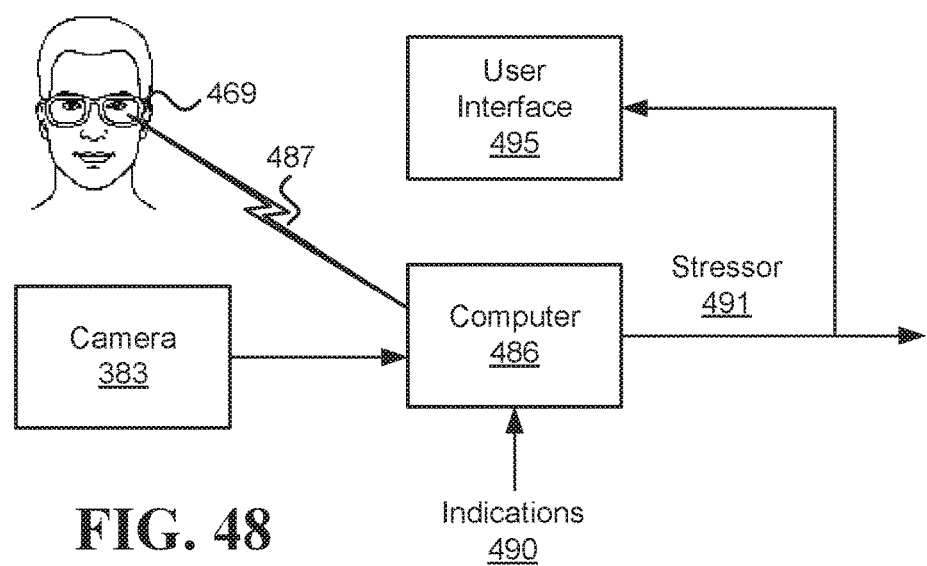
FIG. 48 illustrates an embodiment of a system that selects a stressor.

FIG. 48 illustrates one embodiment of a system configured to select a stressor. The system includes at least a computer 486 and CAM. The system may optionally include a frame 469, a camera 383, and/or a UI 495. In one example, CAM takes thermal measurements of the periorbital area of the right eye, and an additional CAM (CAM2) takes thermal measurements of a region on the periorbital area of the left eye ($TH_{ROI2}$) of the user.

In one embodiment, computer 486 calculates, based on the thermal measurements 487 (e.g., $TH_{ROI}$ and $TH_{ROI2}$), values that are indicative of stress levels of the user at different times (i.e., detect the stress levels of the user at the different times). Optionally, $TH_{ROI1}$ and $TH_{ROI2}$ include thermal measurements taken while the user had at least two different stress levels according to a predetermined stress scale. Optionally, the thermal measurements 487 comprise thermal measurements taken during different days.

In some embodiments, the system that selects a stressor may include additional CAMs that take thermal measurements of one or more regions on the user's forehead, nose, and/or below the nostrils. Optionally, thermal measurements taken by the additional CAMs are utilized by the computer 486 when calculating the user's stress level.

Furthermore, the computer 486 may receive indications 490 of factors that affected the user at various times, which may be considered potential stressors. The computer 486 also selects a stressor 491, from among the potential stressors, based on the indications 490 and the values that are indicative of stress levels of the user at different times. Optionally, each of the indications 490 is indicative of a time during which the user was exposed to a potential stressor. Additionally or alternatively, each of the indications 490 may be indicative of a time during which the user was affected by a potential stressor. In some embodiments, at any given time, the user may be exposed to more than one of the potential stressors. Thus, in some embodiments, at least some of the thermal measurements 487, and optionally all of the thermal measurements 487, were taken while the user was exposed to two or more potential stressors.

In one embodiment, the indications 490 include a list of periods of time during which various potential stressors affected the user. Optionally, the indications 490 are provided via a data structure and/or a queryable system that provides information for different points in time about which of the potential stressors affected the user at the points in time. There are various types of potential stressors that may be indicated by the indications 490.

In one embodiment, one or more of the potential stressors may relate to various locations the user was at (e.g., work, school, doctor's office, in-laws house, etc.) and/or to various activities the user partakes in (e.g., driving, public speaking, operating machinery, caring for children, choosing clothes to wear, etc.)

In another embodiment, one or more of the potential stressors may relate to entities with which the user interacts. For example, an entity may be a certain person, a person with a certain role (e.g., a teacher, a police officer, a doctor, etc.), a certain software agent, and/or an avatar (representing a person or a software agent).

In yet another embodiment, one or more of the potential stressors may relate to situations in which the user is in, which can increase stress. For example, a situation may be being unemployed, having financial difficulties, being separated after being in a relationship with another person, being alone, or awaiting an important event (e.g., an exam, a job interview, or results of an important medical test). In another example, a situation may relate to a physical condition of the user, such as being sick or suffering from a certain chronic disease. Optionally, when the situations described above are applicable to another person who the user cares about (e.g., a spouse, child, parent, or close friend), then those situations, which relate to the other person, may be considered potential stressors that can lead to stress in the user.

In still another embodiment, one or more of the potential stressors may relate to the user's behavior. For example, behaving in a way that is argumentative, manipulative, deceptive, and/or untruthful may increase the stress level.

When a user is affected by one or more potential stressors, in some embodiments, the stress level of the user may depend on quantitative aspects of the potential stressors. In some examples, the degree to which a potential stressor affects the user's stress level may depend on the amount of time the potential stressor affected the user (e.g., the duration the user spent at a certain location) and/or the magnitude of the potential stressor (e.g., the extent to which an argument was heated—which may be expressed by the level of noise in peoples shouting). In some embodiments, the indications 490 include values that quantify how much at least some of the potential stressors affected the user.

The stressor 491 is a potential stressor that is correlated with an increase in the stress level of the user. Additionally, in some embodiments, the stressor 491 may be a potential stressor that may be considered a direct cause of the increase in the stress level of the user. When considering how being affected by the potential stressors relates to the stress level of the user, an effect of the stressor 491 is higher than effects of most of the potential stressors.

The effect of a potential stressor may be considered a measure of how much the potential stressor influences the stress level the user. This can range from no influence to a profound influence. More specifically, in one embodiment, the effect of a potential stressor is a value indicative of the average extent of change to the stress level of the user at a time t+Δ after being affected by the potential stressor at time t. Here, Δ corresponds to the typical time it may take the stress to manifest itself in the user after being affected by the potential stressor. This time may range from a short period e.g., several seconds or minutes, to hours.

There are various ways in which the computer 486 may select, based on the indications 490 and the thermal measurements 487, the stressor 491 from among the potential stressors being considered.

In some embodiments, the computer 486 performs a direct analysis of the effect of each of the potential stressors in order to identify which ones have a large effect on the user. Optionally, the effect of each potential stressor is indicative of the extent to which it increases the stress level of the user. Optionally, the effect of each potential stressor is calculated by determining, based on the indications 490, times at which the user was affected by the potential stressor, and observing the stress level of the user at one or more times that are up to a certain period Δ later (where Δ depends on the user and the type of stressor). In one example, Δ is ten seconds, thirty seconds, or one minute. In another example, Δ is one minute, ten minutes, or one hour.

In one embodiment, a stress level (or change to the stress level) following being affected by a potential stressor is the maximum stress level that is detected from the time t the user was affected by the potential stressor until the time t+Δ. In another example, the stress level (or change to the stress level) following being affected by the potential stressor is the extent of the stress level and/or change to the stress level that is detected at a time t+Δ (when the user was affected by the potential stressor at time t). Optionally, the extent may be normalized based on a quantitative value representing how much the user was affected by the potential stressor. Optionally, the stress level may be normalized with respect to a stress level detected prior to being affected by the potential stressor.

Following a calculation of the effects of the potential stressors, in one embodiment, the computer 486 selects the stressor 491 from among the potential stressors. Optionally, the stressor 491 is a potential stressor that has a maximal effect (i.e., there is no other potential stressor that has a higher effect). Optionally, the stressor 491 is a potential stressor that has an effect that reaches a threshold, while the effects of most of the potential stressors do not reach the threshold.

In one embodiment, in order to increase confidence in the selection of the stressor, the stressor 491 is selected based on at least a certain number of times in which the user was affected by the stressor 491. For example, the certain number may be at least 3 or 10 different times. Thus, in this embodiment, potential stressors that did not affect the user at least the certain number of times are not selected.

In some embodiments, the computer 486 generates a machine learning-based model based on the indications 490 and the values indicative of the stress levels of the user, and selects the stressor 491 based on an analysis of the model. Optionally, the computer 486 generates samples used to train the model. The samples used to train the model may correspond to different times, with each sample corresponding to a time $t+\Delta$ including feature values and a label indicative of the stress level of the user at the time $t+\Delta$. Each sample may be considered to represent a snapshot of potential stressors that affected the user during a certain period, and a label that is indicative of the stress level of the user following being affected by those potential stressors. Given multiple such samples, a machine learning training algorithm can be utilized to train a model for a predictor module that can predict the stress level at a certain time based on feature values that describe potential stressors that affected the user during a certain period of time leading up to the certain time. For example, if the model is a regression model, the predictor module may perform a dot product multiplication between a vector of regression coefficients (from the model) and a vector of the feature values in order to calculate a value corresponding to the predicted stress level of the user at the certain time.

When such a predictor module is capable of predicting stress level of the user based on the feature values described above, this may mean that the model captures, at least to some extent, the effects of at least some of the potential stressors on the stress level of the user.

Training the model based on the samples described above may involve utilizing one or more of various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model, to name a few possibilities. There are various training algorithms known in the art for generating these models and other models with similar properties.

The predictor module may be provided multiple inputs representing the potential stressors that affected the user at different points of time, and have a capability to store state information of previous inputs corresponding to earlier times when it comes to predict the stress level of the user at a certain time. For example, the predictor module may be based on a recurrent neural network.

Once the model is trained, in some embodiments, it is analyzed by the computer 486 in order to determine the effects of one or more of the stressors on the stress level of the user. Depending on the type of model that was trained, this analysis may be performed in different ways.

In one embodiment, the computer 486 performs the analysis of the model by evaluating parameters of the model that correspond to the potential stressors. Optionally, the computer 486 selects as the stressor 491 a certain potential stressor that has a corresponding parameter that is indicative of an effect that reaches a threshold while effects indicated in parameters corresponding to most of the stressors do not reach the threshold. In one example, the model may be a linear regression model in which each potential stressor corresponds to a regression variable. In this example, a magnitude of a value of a regression coefficient may be indicative of the extent of the effect of its corresponding potential stressor. In another example, the model may be a naïve Bayes model in which various classes correspond to stress levels (e.g., a binary classification model that is used to classify a vector of feature values to classes corresponding to "stressed" vs. "not stressed"). In this example, each feature value may correspond to a potential stressor, and the class conditional probabilities in the model are indicative of the effect of each of the potential stressors on the user.

In another embodiment, the computer 486 performs an analysis of the model, which may be characterized as "black box" analysis. In this approach, the predictor module is provided with various inputs that correspond to different potential stressors that affect the user, and calculates, based on the inputs and the model, various predicted stress levels of the user. The various inputs can be used to independently and/or individually increase the extent to which each of the potential stressors affects the user. This type of the model probing can help identify certain potential stressors that display an increase in the predicted stress level, which corresponds to an increase in the extent to which the potential stressors affect the user (according to the model). Optionally, the stressor 491 is a potential stressor for which a positive correlation is observed between increasing the extent to which the potential stressor affects that user, and the predicted stress level of the user. Optionally, the stressor 491 is selected from among the potential stressors, responsive to identifying that: (i) based on a first subset of the various predicted stress levels of the user, an effect of the stressor 491 reaches a threshold, and (ii) based on a second subset of the various predicted stress levels of the user, effects of most of the potential stressors do not reach the threshold.

The indications 490 may be received from various sources. In one embodiment, the user may provide at least some of the indications 490 (e.g., by inputting data via an app and/or providing vocal annotations that are interpreted by a speech analysis software). In other embodiments, at least some of the indications 490 are provided by analysis of one or more sources of data Optionally, the computer 486 generates one or more of the indications 490 based on an analysis of data obtained from the one or more sources. The following four examples, discussed herein in relation to allergy, are also relevant as examples of sources of data that may be utilized to identify potential stressors that affected the user at different times: (i) a camera 383 captures images of the surroundings of the user, (ii) sensors such as microphones, accelerometers, thermometers, pressure sensors, and/or barometers may be used to identify potential stressors by identifying what the user is doing and/or under what conditions, (iii) measurements of the environment that user is in, and (iv) IoT devices, communications of the user, calendar, and/or billing information may provide information that may be used in some embodiments to identify potential stressors.

Knowledge of the stressor 491 may be utilized for various purposes. Optionally, the knowledge of the stressor 491 is utilized by a software agent operating on behalf of the user in order to better serve the user. In some embodiments, information about the stressor 491 is provided to the user via a UI 495, such as a smartphone. HMD, and/or an earphone).

UI 495 may be utilized on a day-to-day basis to warn the user when the stressor 491 is detected. For example, the computer 486 may provide real-time indications of potential stressors. Upon detecting that those potential stressors include the stressor 491, the UI notifies the user about the stressor in order for the user to take action, such as reducing exposure to the stressor (e.g., by leaving a certain location or ceasing a certain activity) and/or performing actions aimed at reducing stress (e.g., a breathing exercises).

In one embodiment, a software agent identifies that the user is going to be affected by the stressor 491 (e.g., by analyzing the user's calendar schedule and/or communications), and suggests the user, via UI 495, to perform various exercises (e.g., breathing exercises) and/or prepare himself for the stressor 491 in order to reduce its effect.

With little modifications, the system illustrated in FIG. 48 may be utilized to detect a calming factor that reduces the user's stress, rather than one that increases it. In particular, instead of selecting a stressor that has a large effect (or maximal effect) on the user, a factor that has a large negative effect on the stress level may be selected. Optionally, in the event that a high stress level of the user is detected, the calming factor may be suggested to the user (to reduce the user's stress level).

The following is a description of steps involved in one embodiment of a method for selecting a stressor. The steps described below may be used by systems modeled according to FIG. 48, and may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method for alerting about stress includes at least the following steps:

In Step 1, taking, utilizing a CAM, thermal measurements of a region on a periorbital area ($TH_{ROI1}$) of a user who wears CAM. Optionally, the region on the periorbital area is a region of the periorbital area of the right eye, and this step also involves taking, utilizing a second inward-facing head-mounted thermal camera (CAM2), thermal measurements of a region on the periorbital area of the left eye ($TH_{ROI2}$).

In Step 2, detecting extents of stress based on $TH_{ROI1}$. Optionally, detecting the extents may be done utilizing the computer, as discussed above. Optionally, the extents are also detected based on $TH_{ROI2}$ (and/or other thermal measurements mentioned below).

In Step 3, receiving indications of times during which the user was exposed to potential stressors.

And in Step 4, selecting the stressor, from among the potential stressors, based on the indications and the extents. Optionally, during most of the time the user was affected by the stressor, an effect of the stressor, as manifested via changes to $TH_{ROI1}$, was higher than effects of most of the potential stressors.

In one embodiment, the method may optionally include a step of taking images of the surroundings of the user and generating at least some of the indications based on analysis of the images. Optionally, the images are taken with the camera 383, as discussed above.

In one embodiment, selecting the stressor is done by generating a machine learning-based model based on the indications and extents, and selecting the stressor based on an analysis of the model. In one example, performing the analysis of the model involves evaluating parameters of the model that correspond to the potential stressors. In this example, a certain potential stressor is selected as a stress. The certain potential stressor has a corresponding parameter in the model that is indicative of an effect that reaches a threshold, while effects indicated in parameters corresponding to most of the other potential stressors do not reach the threshold. In another example, performing the analysis of the model involves: (i) providing a predictor module with various inputs that correspond to different potential stressors that affect the user, (ii) calculating, based on the inputs and the model, various predicted stress levels; (iii) determining, based on the various predicted stress levels, effects of the potential stressors; and (iv) selecting the stressor based on the effects. In this example, the effect of the stressor reaches a threshold, while effects of most of the other potential stressors do not reach the threshold.

In one embodiment, a system configured to detect an irregular physiological response of a user while the user is exposed to sensitive data includes at least a head-mounted display (HMD), a CAM, and a computer. Optionally. CAM is coupled to the HMD (e.g., they are both components of an HMS). The HMD exposes sensitive data to a user who wears the HMD. For example, the HMD may display text, images, and/or video. Optionally, the HMD may be a virtual reality display or an augmented reality display. Optionally, the HMD is designed such that only the user who wears the HMD can view the sensitive data displayed on the HMD. CAM takes thermal measurements of an ROI ($TH_{ROI}$) on the user's face while the user is exposed to the sensitive data, and is optionally located less than 15 cm from the face. In some embodiments, the system may include additional CAMs that take thermal measurements of additional ROIs on the user's face. In some embodiments. CAM may weigh below 5 g and/or CAM may be located less than 5 cm from the user's face.

The computer detects, based on certain $TH_{ROI}$ taken while the user is exposed to certain sensitive data, whether the user experienced the irregular physiological response while being exposed to the certain sensitive data.

In one embodiment, the certain $TH_{ROI}$ are taken during a certain window of time that depends on the type of the irregular physiological response (e.g., a certain stress level and/or a certain emotional response). Optionally, the window is at least five seconds long, at least thirty seconds long, at least two minutes long, at least five minutes long, at least fifteen minutes long, at least one hour long, or is some other window that is longer than one second. Optionally, during the time the user is exposed to sensitive data. $TH_{ROI}$ from multiple windows may be evaluated (e.g., using a sliding window approach), which include a window that contains a period during which the certain $TH_{ROI}$ were taken.

In some embodiments, detecting the irregular physiological response is done based on additional inputs such as thermal measurements taken by additional CAMs (which may cover additional ROIs), and/or values of physiological signals and/or behavioral cues of the user such as heart rate, breathing rate, galvanic skin response, movements, facial expressions, and/or brainwave activity. Optionally, the values of physiological signals and/or behavioral cues are obtained utilizing sensors other than CAMs.

What corresponds to an "irregular physiological response" may vary between different embodiments. The following are some examples of criteria and/or ways of determining whether a physiological response is considered an "irregular physiological response". In one example, the irregular physiological response involves the user experiencing stress that reaches a certain threshold. Optionally, for most of the time the user wears the HMD, the stress level detected for the user does not reach the certain threshold. In another example, the irregular physiological response involves the user experiencing at least a certain level of one or more of the following emotions: anxiety, fear, and anger. Optionally, for most of the time the user wears the HMD, the extent to which the user experiences the one or more emotions does not reach the certain level. In yet another example, an irregular physiological response corresponds to atypical measurement values. For example, if a probability density function is generated based on previously taken $TH_{ROI}$ of the user, values with a low probability, such as a probability value that is lower than the probability of 97% of the previously taken $TH_{ROI}$, may be considered atypical.

In order to detect the irregular physiological response, the computer may utilize $TH_{ROI}$ in various ways, as described below. Optionally, detection of the irregular physiological response is done while taking into account various factors that may influence the user's measured physiological responses, such as the user's emotional state (e.g., whether the user is anxious, distraught, or calm), the environmental conditions (e.g., the temperature, humidity level, and/or level of oxygen in the air), and/or the type of sensitive data that the user accesses.

In one embodiment, the computer compares one or more values derived from the certain $TH_{ROI}$ to a certain threshold, and determines whether the threshold is reached (which is indicative of an occurrence of the irregular physiological response). Optionally, the threshold is determined based on previously taken $TH_{ROI}$ of the user (e.g., taken when the user had an irregular physiological response). Optionally, the threshold is determined based on baseline thermal measurements of the user, and the threshold represents a difference of a certain magnitude relative to the baseline measurements. Optionally, different thresholds may be utilized to detect different types of irregular physiological responses, to detect irregular physiological responses to different types of sensitive data, and/or to detect irregular physiological responses when the user is in certain emotional states and/or under certain environmental conditions.

In another embodiment, the computer generates feature values and utilizes a machine learning-based model to detect, based on the feature values, whether the user had an irregular physiological response. One or more of the feature values are generated based on the certain $TH_{ROI}$. Optionally, at least one of the feature values is generated based on the sensitive data, e.g., the at least one of the feature values may describe properties of the sensitive data. In one example, the model may be generated based on previous $TH_{ROI}$ of the user. In another example, the model may be generated based on previous $TH_{ROI}$ of other users.

The emotional state of the user, while accessing the certain sensitive data, may influence the user's physiological response, and thus may play a role in determining whether the user had an irregular physiological response. Similarly, the environmental conditions that prevail when the user accesses the certain sensitive data, and also the type of sensitive data being accessed, may influence the user's physiological response and thus may have a bearing on whether the user's physiological response should be considered irregular or not. Addressing these factors may be done in different ways.

In one embodiment, multiple machine learning-based models may be generated utilizing different training sets of data. For example, different models may be created to detect different types of irregular physiological responses, to detect irregular physiological responses to different types of sensitive data, and/or to detect irregular physiological responses when the user is in a certain emotional state and/or under certain environmental conditions.

In another embodiment, the feature values generated by the computer may include feature values that describe one or more of the following factors: an emotional state of the user while accessing the certain sensitive data, a condition of the environment in which the user accessed the certain sensitive data, and the type of the certain sensitive data. Thus, the factors mentioned above may be considered when the determination is made regarding whether the user experienced an irregular physiological response. In one example, the computer receives values indicative of the user's emotional state while being exposed to the certain sensitive data, and utilizes a machine learning-based model to detect whether the user experienced the irregular physiological response based on the certain $TH_{ROI}$. Optionally, in this example, the machine learning-based model was trained based on previous $TH_{ROI}$ taken while the user was in a similar emotional state. In another example, the computer is receives values indicative of the environment the user was in while being exposed to the certain sensitive data (e.g., temperature and/or humidity level), and utilizes a machine learning-based model to detect whether the user experienced the irregular physiological response based on the certain $TH_{ROI}$. Optionally, in this example, the machine learning-based model was trained based on previous $TH_{ROI}$ taken while the user was in a similar environment.

Determining what constitutes a certain type of sensitive data may be done according to various criteria. In one example, different types of sensitive data involve data with different classes of content (e.g., intelligence reports vs, billing statements). In another example, different types of sensitive data involve data with different levels of sensitivity (e.g., involve different levels of security clearance). In yet another example, different types of sensitive data come from different sources. In another example, different types of sensitive data involve different types of media (e.g., text information vs, video). In still another example, different types of sensitive data may correspond to the relationship of the sensitive data to the user (e.g., data that involves someone close to the user vs, data that involves a stranger).

The following describes how the system may utilize information about the type of sensitive data the user is exposed to in order to improve the detection of an irregular physiological response during exposure to that data. In one example, certain sensitive data is associated with a first type of sensitive data, and the computer detects the irregular physiological response when the certain $TH_{ROI}$ reach a first threshold. Optionally, the first threshold is calculated based on other $TH_{ROI}$ taken while the user was exposed to sensitive data associated with the first type of sensitive data. Additionally, the user is exposed to second certain sensitive data, which is associated with a second type of sensitive data. In this case, the computer detects the irregular physiological response when second certain $TH_{ROI}$ reach a second threshold. The second certain $TH_{ROI}$ are taken while the user is exposed to the second certain sensitive data, the second threshold is calculated based on other $TH_{ROI}$ taken while the user was exposed to sensitive data associated with the second type of sensitive data. In this example, the second threshold is different from the first threshold.

In one embodiment, the sensitive data is associated with a type of data that belongs to a set that includes at least first and second types of sensitive data. The computer utilizes $TH_{ROI}$ to generate feature values, and utilizes a model to calculate, based on the feature values, an extent of the irregular physiological response. Optionally, at least one of the feature values indicates the type of sensitive data to which the user was exposed. Optionally, the model was trained based on previous $TH_{ROI}$ of one or more users and indications of the type of sensitive data to which each of the one or more users was exposed. Optionally, the previous $TH_{ROI}$ comprise at least some measurements taken while the one or more users were exposed to the first type of sensitive data and at least some measurements taken while the one or more users were exposed to the second type of sensitive data.

Detecting the irregular physiological response may involve utilization of one or more baselines. Optionally, a baseline may be indicative of typical values for the user, such as typical thermal measurements when exposed to sensitive data, the extent to which a user is typically stressed when exposed to sensitive data, and/or the extent the user typically expresses one or more of the following emotions when exposed to sensitive data: anxiety, fear, and anger. Optionally, a baseline may correspond to the user, i.e., it may represent expected values of the user. Additionally or alternatively, a baseline may correspond to multiple users, and represent expected values of other users (e.g., a general response).

In some embodiments, a baseline may be determined based on previous thermal measurements. In one example, the previous thermal measurements comprise thermal measurements of the user. In another example, the previous thermal measurements comprise thermal measurements of other users. Optionally, the previous thermal measurements are taken while being exposed to baseline sensitive data. Optionally, the baseline sensitive data may be of the same type as the certain sensitive data. Optionally, the previous thermal measurements are taken with essentially the same system as the certain $TH_{ROI}$ (e.g., the same headset or a headset with a similar positioning of CAM).

In some embodiments, multiple baselines may be generated, corresponding to different types of sensitive data, different environmental conditions, and/or different emotional states of the user. Optionally, the multiple baselines are each generated based on corresponding thermal measurements, such as thermal measurements taken while the person being measured (e.g., the user or some other user) was exposed to a certain type of sensitive data, in a certain type of environment, and/or while in a certain emotional state.

In some cases, it may be useful to generate a baseline based on measurements taken in temporal proximity to when the user is exposed to the certain sensitive data. Comparing close events may be beneficial because the shorter the time between being exposed to baseline sensitive data and being exposed to the certain sensitive data, the smaller the effect of environmental changes and/or normal physiological changes may be. In one example, the user is exposed to the certain sensitive data immediately before and/or after being exposed to the baseline sensitive data. In another example, the user is exposed to the certain sensitive data within less than 5 minutes before and/or after being exposed to the baseline sensitive data. In still another example, the user exposed to the certain sensitive data within less than 15 minutes before or after being exposed to the baseline sensitive data.

In some embodiments, a baseline may be calculated utilizing a predictor, which receives input comprising feature values describing various values such as characteristics of user (e.g., age, gender, weight, occupation), the sensitive data, the environment in which the user is in, and/or the emotional state of the user. The predictor utilizes a machine learning-based model to calculate, based on the feature values, the baseline which may be, for example, a value of thermal measurements, a stress level, or an extent of expressing a certain emotion. Optionally, the model was trained based on measurements of the user. Optionally, the model was trained based on measurements of other users.

Baseline values may be utilized by the computer in various ways. For example, thermal measurements may be normalized with respect to a baseline in order to help identify when the thermal measurements deviate from the expected values (which may be indicative of the irregular physiological response). In another example, a threshold to which the computer compares the certain $TH_{ROI}$ may be a value that is defined relative to the baseline. In yet another example, a reference time series may be selected based on a corresponding baseline (i.e., a reference time series may correspond to an irregular physiological response that occurs when the user is in a certain baseline state). In still another example, one or more feature values utilized to detect a physiological response may be generated based on a baseline value (i.e., the baseline may be one of the inputs for detecting the physiological response).

In one embodiment. $TH_{ROI}$ express temperature at the ROI, and the baseline expresses ordinary temperature at the ROI while the user is exposed to sensitive data. In another embodiment. $TH_{ROI}$ express temperature change at the ROI, and the baseline expresses ordinary temperature changes at the ROI around the time of switching from being exposed to non-sensitive data to being exposed to sensitive data. In still another embodiment. $TH_{ROI}$ express temperature change at the ROI, and the baseline expresses ordinary temperature changes at the ROI around the time of switching from being exposed to sensitive data to being exposed to non-sensitive data.

It is noted that when the user is exposed to data over a period of time, in some embodiments, each segment of data (e.g., data watched during a certain span of a few minutes) may serve both as a baseline sensitive data and/or as the certain sensitive data.

In one embodiment, the certain sensitive data is associated with a first type of sensitive data, and the computer detects the irregular physiological response when a difference between the certain $TH_{ROI}$ and a first baseline reaches a first threshold. Optionally, the first baseline is calculated based on other $TH_{ROI}$ taken while the user was exposed to sensitive data associated with the first type of sensitive data. Additionally, the user is exposed to a second certain sensitive data that is associated with a second type of sensitive data, and the computer detects the irregular physiological response while being exposed to the second certain sensitive data when a difference between second certain $TH_{ROI}$ and a second baseline reaches a second threshold. Here, the second certain $TH_{ROI}$ are taken while the user is exposed to the second certain sensitive data, the second baseline is calculated based on other $TH_{ROI}$ taken while the user was exposed to sensitive data associated with the second type of sensitive data. In this embodiment, the second threshold is different from the first threshold. Optionally, the system estimates job burnout; the greater the differences between $TH_{ROI}$ and their associated baselines, the worse is the job burnout.

In different embodiments of the system configured to detect an irregular physiological response of a user while the user is exposed to sensitive data, the ROI may comprise different regions of the face and/or the system may involve various hardware configurations (e.g., certain types of CAMs and/or additional CAMs). Optionally, measurements taken by an additional CAM are utilized to generate one or more of the feature values utilized by the computer to detect the irregular physiological response.

In one embodiment, the ROI is on periorbital area of the user and CAM includes an uncooled thermal sensor. Optionally, the ROI is on the periorbital area of the right eye, and the system includes a second CAM that takes thermal measurements of a region on the periorbital area of the left eye. Optionally, the computer detects the irregular physiological response based on the measurements of the periorbital areas of the right and left eyes.

In another embodiment, the ROI is on the user's nose and CAM includes an uncooled thermal sensor. Optionally, the ROI is on the right side of the user's nose and the system includes a second CAM that takes thermal measurements of a region on the left side of the nose. Optionally, the computer detects the irregular physiological response based on the measurements of the regions on the left and right sides of the nose.

In yet another embodiment, the ROI is on the user's forehead. Optionally, the ROI is on the right side of the user's forehead, and the system includes a second CAM that takes thermal measurements of the left side of the user's forehead. Optionally, the computer detects the irregular physiological response based on the measurements of the regions on the left and right sides of the forehead.

Figure 49:
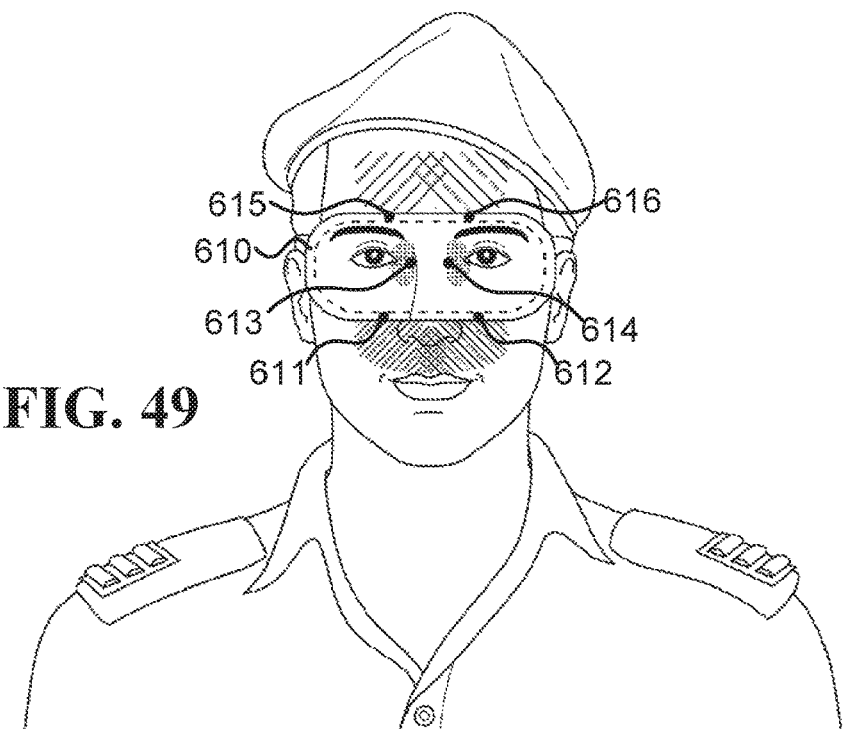
FIG. 49 illustrates an embodiment of a system that detects an irregular physiological response of a user while the user is exposed to sensitive data.

FIG. 49 illustrates one embodiment of a system configured to detect an irregular physiological response of a user while the user is exposed to sensitive data. The system includes head-mounted system HMS 610, which includes a head-mounted display (HMD) for exposing the user to sensitive data (not depicted in the figure) and six CAMs coupled to the frame of the HMS 610, which are 611 and 612 on the bottom of the frame to measure the upper lip and nose, 613 and 614 inside the HMS to measure the periorbital areas, and 615 and 616 on the top of the frame to measure the forehead (the measured regions on the face are illustrated as shaded areas). It is to be noted that though the user's eyes are visible in the figure, the front of the HMS may be opaque as is common with virtual reality headsets.

Figure 50:
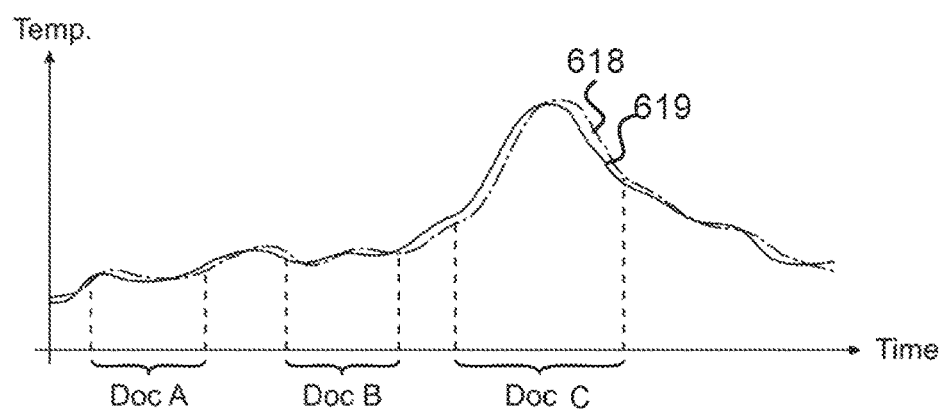
FIG. 50 illustrates detection of an irregular physiological response.

FIG. 50 illustrates detection of an irregular physiological response. The figure depicts a graph displaying temperatures at the right and left periorbital areas (lines 618 and 619 in the figure). The user is exposed to three documents via a HMD. "doc A", "doc B", and "doc C". With the first two documents ("doc A" and "doc B"), the temperatures remain low, but when the user is exposed to "doc C" the temperature rises dramatically, which in this exemplary figure may constitute an irregular physiological response.

Figure 52:
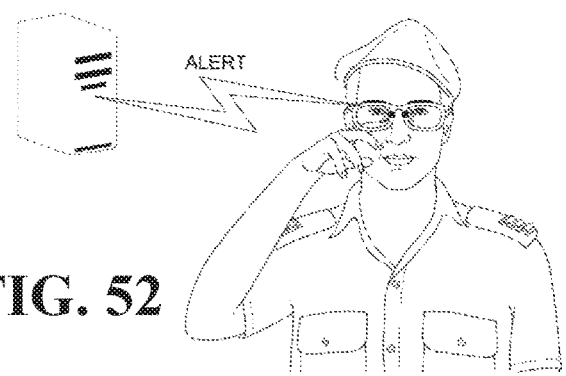
FIG. 52 illustrates triggering an alert when the user moves the HMD and touches the CAM.

In order to avoid detection of an irregular physiological response, a user exposed to sensitive data via the HMD may attempt to take evasive measures such as touching the face, moving the HMD, and/or occluding the sensors (e.g., in order to disrupt sensor measurements). An example of such behavior is illustrated in FIG. 52 in which the user moves the HMD a bit and touches a CAM, which triggers an alert.

In one embodiment, the system may detect whether the user moves the HMD relative to the face while being exposed to the certain sensitive data, based on measurements of an additional sensor (e.g., a sensor that measures a confounding factor). Optionally, the computer takes one or more security-related measures responsive to detecting that the user moved the HMD relative to the face while being exposed to the certain sensitive data. Optionally, the system identifies moving the HMD relative to the face based on one or more of the following: (i) analysis of images taken by an optical sensor physically coupled to the HMD, such as a CAM, an active near-IR camera physically coupled to the HMD, and/or a visible-light camera physically coupled to the HMD, (ii) analysis of images taken by an optical sensor that captures the user's face without being physically coupled to the HMD, such as a 2D or a 3D camera located in a position that faces the user or located on a smartwatch or a smart-shirt, and/or (iii) analysis of measurements of a non-optical sensor physically coupled to the HMD, such as a movement sensor, a miniature radar operating in the Extremely High Frequency (EHF) band, an acoustic sensor, an electroencephalogram sensor, an electromyogram sensor, a piezoelectric sensor, and/or strain gauges, as mentioned for example in the reference Li, Hao, t al. "Facial performance sensing head-mounted display" ACM Transactions on Graphics 2015, and (iv) analysis of measurements of a non-optical sensor physically coupled to the user's body, such as a movement sensor embedded in a wrist band or embedded in a smart-shirt.

It is noted that sentences such as "while being exposed to the certain sensitive data" does not include removing the HMD off the face, because after removing the HMD off the face the user is not exposed to the certain sensitive data. In one example, moving the HMD relative to the face refers to a relative movement above a minimum threshold (e.g., moving the frame to a distance that is greater than 1 cm). In another example, making facial expressions does not cause the system to detect that the user is moving the HMD relative to the face.

Some non-limiting examples of the security-related measures that the system may take include performing one or more of the following: storing in a database an indication that the user made a suspicious action (like moving the HMD relative to the face while being exposed to the certain sensitive data at a certain point in time), ceasing from exposing the user to the certain sensitive data, not allowing the user to perform a certain transaction related to the certain sensitive data, blocking the user's access to the certain sensitive data, issuing an alert, marking as suspicious the relationship between the user and the certain sensitive data, tightening the security restrictions for the user for accessing sensitive data on the system, providing the user a canary trap, and providing the user a barium meal test.

A "canary trap" refers to a practice of providing the user with a version of the sensitive data that contains certain indicators (e.g., small variations) that are unique to the version provided to the user. Thus, if the sensitive data is leaked, the user may be identified as the source based on detecting the small variations in the leaked data. A "barium meal test" refers to a practice of including in the sensitive data certain information; when the certain information reaches an entity it causes the entity to take a certain action (e.g., visit a certain website it would not ordinarily visit). Thus, detecting the certain action is indicative of the sensitive data (to which the user was exposed) being passed on to the entity.

In another embodiment, the system includes a sensor that provides measurements indicative of times at which the user touches the ROI. Optionally, touching the ROI is expected to influence $TH_{ROI}$ and/or disrupt the ability to detect the irregular physiological response. The user may touch the ROI using a finger, the palm, a tissue or a towel held by the user, a makeup-related item held by the user, a material that is expected to cool the ROI (such as a metal that is colder than the skin), and/or a material that is transparent in the visible spectrum (such as a transparent glass that is colder than the skin). Optionally, responsive to detecting that the user touched the ROI while being exposed to the certain sensitive data, the computer stores in a database an indication thereof, and/or the system may perform at least one of the aforementioned security-related measures.

In yet another embodiment, the system detects occlusion of CAM based on identifying a sudden change of more than 2° C. in $TH_{ROI}$ and/or utilizing a sensor that generates a signal indicative of whether a solid object is located between CAM and the ROI. Optionally, responsive to detecting that the user occluded CAM while being exposed to the certain sensitive data, the computer stores in a database an indication thereof and/or the system may perform at least one of the aforementioned security-related measures.

In one embodiment, the computer tightens security restrictions for the user responsive to detecting multiple occurrences possibly evasive measures such as touching the ROI, moving the HMD, and/or occluding the ROI. Optionally, the multiple occurrences are detected while the user is exposed to sensitive data that is of the same type as the certain sensitive data. Optionally, tightening security restrictions for the user involves restricting the user from performing a certain transaction related to the sensitive data. In one example, the certain transaction comprises copying, reading, and/or modifying the certain sensitive data. In another example, the certain sensitive data relates to money, and the certain transaction comprises an electronic funds transfer from one person or entity to another person or entity.

In some embodiments, responsive to a detection of the irregular physiological response, the system initiates a process to detect an illegal activity. Optionally, the process is initiated within less than two minutes after detecting the irregular physiological response. Optionally, the sensitive data belongs to an organization, the user is an employee of the organization, and the system helps in preventing illegal activities of employees related to sensitive data.

Some embodiments of the system configured to detect an irregular physiological response while being exposed to sensitive data include added security measures such as encryption of the sensitive data. Optionally, the system receives the certain sensitive data in an encrypted form, and the computer decrypts the certain sensitive data before presentation via the HMD. The decryption may involve hardware-based decryption, requesting a password from the user, and/or measuring the user with a sensor (e.g., an iris scan), and/or multi-factor authentication.

Another security measure that may be included in some embodiments of the system involves biometric identification of the user. In these embodiments, the system may include a biometric identification device, which is physically coupled to the HMD, and identifies the user while the user wears the HMD. Optionally, the computer exposes the user to the sensitive data responsive to receiving an indication that confirms the user's identity. Optionally, the biometric identification device performs one or more of the following operations: an iris scan, detection of brainwave patterns, detection of a cardiac activity pattern, and detection of thermal patterns on the user's face. Optionally, the biometric identification device performs a fingerprint-based identification of the user.

Figure 51:
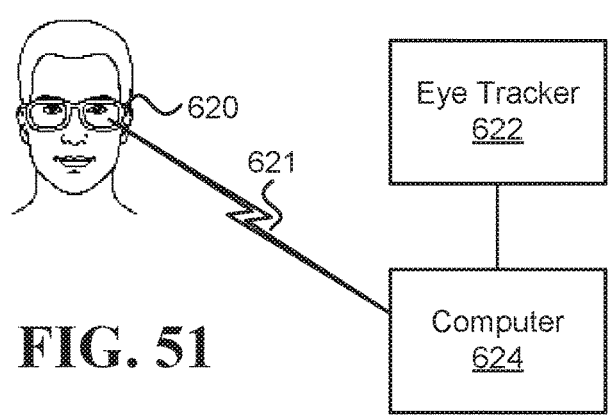
FIG. 51 is a schematic illustration of a system that includes a frame, CAM, a computer, and an eye tracker.

In one embodiment, a system that identifies whether a visual content (such as a video) includes an item that agitates a user includes an eye tracker, CAM, and a computer. The system may optionally include other components, such as a frame that is worn on the user's head (to which CAM, the eye tracker, and/or other components may be physically coupled). Additionally, the system may optionally include one or more additional CAMs and one or more sensors (which are not CAMs). The system may also include a head-mounted display (HMD) to display video to the user. FIG. 51 is a schematic illustration of such a system that includes frame 620 with CAM coupled to it, a computer 624, and an eye tracker 622.

CAM takes thermal measurements of an ROI ($TH_{ROI}$) on the user's face. Optionally. CAM is located less than 15 cm from the user's face. Optionally, CAM weighs less than 10 g. The ROI exhibits a change in temperature when the user experiences stress, such as the periorbital areas around the eyes, the nose, and/or the forehead.

In one embodiment. $TH_{ROI}$ are taken during a window of time that lasts between a second to a few minutes during which the user views a visual content that depicts items. Optionally, the window is at least five seconds long, at least thirty seconds long, at least two minutes long, at least five minutes long, at least fifteen minutes long, at least one hour long, or is some other window that is longer than one second. Optionally, during the time the user is exposed to the visual content, $TH_{ROI}$ from multiple windows may be evaluated (e.g., using a sliding window approach).

The eye tracker tracks the user's gaze while watching the video that depicts items. Optionally, the user's gaze is indicative of attention the user paid to the items. Optionally, data generated by the eye tracker is indicative of attention the user paid to each of the items. The eye tracker may be head-mounted or non-head-mounted.

The data generated by the eye tracker describes the gaze of the user. For example, the data may be indicative of the coordinates, on a display displaying the visual content (e.g., video), on which the user focused during various times while watching the video. Optionally, the coordinates represent certain pixels and/or sets of pixels. This information may be analyzed along with information that describes the boundaries (e.g., coordinates) of the items in the video at different times during its presentation in order to determine when the user focuses on each item. Optionally, determining which items were presented in the video may involve utilizing various image processing algorithms, which can identify items (e.g., objects and/or people) in the video and/or define the boundaries of the items in the video at various times. Thus, using the data generated by the eye tracker, attention levels of the user in at least some of the items can be determined (e.g., by the computer). In one example, an attention level of the user in an item is indicative of the amount of time the user spent focusing on the item (e.g., before moving to another item). In another example, the attention level of the user in an item is indicative of the number of times the user's sight was focused on the item during certain duration. In still another example, the attention level of the user is a relative value, which indicates whether the user paid more attention or less attention to the item compared to the other items in the video.

The computer is configured, in some embodiments, to detect, based on $TH_{ROI}$ taken while the user views the video, a stress level of the user. Additionally, the computer is configured to calculate an extent of discordance between the attention the user paid to the items and expected attention levels in the items. These two values (the stress level and extent of discordance) are utilized by the computer to determine whether at least one of the items agitated the user. In one embodiment, if the stress level reaches a first threshold and the extent of discordance reaches a second threshold, the computer makes a determination that at least one of the items in the video agitated the user. In another embodiment, the computer calculates, based on the stress level and the extent of discordance, a value indicative of a probability that the items include an item that agitates the user. Optionally, if the value indicates a probability above a third threshold, the computer makes a determination that at least one of the items in the video agitated the user.

The value indicative of the probability that the items include an item that agitates the user is, in some embodiments, proportional to a product of the stress level and the extent of the discordance. That is, in most scenarios, the larger one or both of these values (the stress level and the extent of the discordance), the larger probability that the items include an item that agitates the user. In one example, the value is indicative of negative feelings related to an item and/or a situation presented in the video (the larger the value the likelier it is that the user harbors such negative feelings). In another example, the value is indicative of an extent to which it is likely that the user is concealing something related to the content of the video.

In one embodiment, the computer may utilize the stress levels and the information of the user's gaze to select the item, from among the items depicted in the video, which agitates the user. Optionally, agitation due to the item may be manifested by an increase of at least a certain level in the stress of the user and/or by the user having an atypical gaze pattern in which the user pays significantly less attention or significantly more attention to the item than expected. In one example, "significantly more attention" refers to staring at the item at least double the expected time, and "significantly less attention" refers to staring at the item less than half the expected time.

The expected attention levels in the items may be based, in some embodiments, on tracking gazes during previous viewings of the video and/or previous viewings of similar videos in order to determine attention in the items. In one embodiment, the attention levels in the items are based on attention levels detected when the same video was viewed by other people. For example, the attention levels may represent the average attention paid by the other users to each item. In another embodiment, the attention levels in the items are based on attention levels of the user to items in similar videos. For example, if the video depicts a scene (e.g., a person filling out a loan application), then a similar video may include the same scene, possibly with slightly different items (e.g., a different person filling out a loan application).

In some embodiments, determining the expected attention levels in the items may involve utilizing a model. Optionally, the model is trained based on previous tracking of the user's gaze when observing other videos. Additionally or alternatively, the model is trained based on tracking of other users' gaze when observing other videos. Optionally, the model may be generated using one or more of the various attention modelling algorithms known in the art (such algorithms may also be referred to as saliency mapping algorithms). Some of the many algorithms that may be utilized are surveyed in A. Borji, L. Itti, "State-of-the-Art in Visual Attention Modeling", IEEE Transactions on Pattern Analysis & Machine Intelligence vol. 35(1), p. 185-207, 2013.

In one embodiment, a model for attention in visual items may be generated by creating a training set of samples. Where each sample corresponds to an item in a video and includes features values and a label describing the extent of attention in the item. Various feature values may be included in each sample. For example, some feature values may be generated using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. In another example, at least some feature values may include higher-level description of the items (e.g., after identification of the items and/or actions depicted in the video). In yet another example, some feature values may describe the user viewing the video (e.g., demographic information about the user and/or data related to the user's physiological state). A collection of samples, such as the ones described above, may be provided to a machine learning-based training algorithm in order to train the model. Some examples of the types of models that may be generated include support vector machines (SVMs) and neural networks.

Obtaining the expected attention levels may be done in various ways. In one embodiment, values of the attention levels are determined based on tracking the gaze of the user (and/or other users) in previous viewing the video and/or similar videos: the attention levels determined in this tracking may be used as the expected attention levels in the items displayed in the video while $TH_{ROI}$ are taken. In another embodiment, feature values are generated based on the video and/or a description of the user, and the expected attention values are calculated based on the feature values utilizing a model for attention in visual items, as described above.

In one embodiment, the expected attention levels comprise values of attention in two or more of the items. Additionally, the attention the user paid to the two or more items is determined based on the gaze of the user. These two sets of values may be compared in order to calculate the extent of the discordance between the attention the user paid to the items and expected attention levels in the items. In one example, a divergence metric, such as the Kullback-Leibler divergence may be used to calculate the discordance between the two sets of values. In another example, a distance metric, such as a vector dot product may be used to calculate the discordance between the two sets of values.

In another embodiment, the expected attention levels comprise an indication of a subset comprising one or more of the items to which the user is expected to pay at least a certain amount of attention or one or more of the items to which the user is expected to pay at most a certain amount of attention. Additionally, a subset of the items to which the user paid at least the certain amount of attention (or at most the certain amount of attention), is determined based on the gaze of the user. In this embodiment, a comparison between the subset of items selected based on expected attention levels and the subset selected based on the gaze of the user may be done in order to calculate the extent of the discordance between the attention the user paid to the items and expected attention levels in the items. In one example, the extent of the discordance is proportional to the size of the symmetric difference between the two subsets.

In one embodiment, the stress level is calculated by comparing one or more values derived from $TH_{ROI}$ to a certain threshold, and determining whether the threshold is reached (which is indicative of an occurrence of at least a certain amount of stress). Optionally, the certain threshold is determined based on previous thermal measurements of the user taken with CAM. Optionally, most of the previous measurements were taken while the user was not under elevated stress. Alternatively, most of the previous measurements were taken while the user was under elevated stress. Optionally, the certain threshold is determined based on baseline thermal measurements of the user, and the certain threshold represents a difference of a certain magnitude relative to the baseline measurements. Optionally, different thresholds may be utilized to detect the stress level when the user is in a certain emotional state and/or is in an environment characterized by certain environmental conditions.

In another embodiment, the stress level is calculated by generating feature values based on $TH_{ROI}$ and utilizing a machine learning-based model to calculate, based on the feature values, a stress level experienced by the user. Optionally, at least some of the feature values are generated based on the video, e.g., the at least some of the feature values describe properties of the items depicted in the video. In one example, the model is trained based on previous $TH_{ROI}$ taken while the user had at least two different stress levels according to a predetermined stress scale. In another example, the model is trained based on thermal measurements of other users (e.g., the model is a general model). Optionally, at least some of the feature values describe the emotional state of the user and/or environmental conditions corresponding to when $TH_{ROI}$ were taken. Optionally, at least some of the feature values are generated based on previous $TH_{ROI}$ taken before the user viewed the video (e.g., up to 15 minutes before); thus, when determining the extent of stress the user experienced, the computer can account for the user's baseline stress level.

In some embodiments, at least some feature values utilized to calculate the stress level may be based on thermal measurements obtained with other thermal cameras. In one embodiment, the ROI is on a periorbital area, and the system includes second and third CAMs configured to take thermal measurements of a region on the forehead ($TH_{ROI2}$) of the user and thermal measurements of a region on the nose ($TH_{ROI3}$) of the user, respectively. Optionally, the computer detects the stress level also based on $TH_{ROI2}$ and/or $TH_{ROI3}$. In one example, the computer generates feature values based on $TH_{ROI}$ and on $TH_{ROI2}$ and/or $TH_{ROI3}$, and utilizes a certain model to calculate, based on the feature values, the stress level of the user. In this example, the certain model is trained based on previous $TH_{ROI}$ and $TH_{ROI2}$ and/or $TH_{ROI3}$ taken while the user had at least two different stress levels according to a predetermined stress scale.

There are various ways in which the computer may calculate, based on the stress level and the extent of discordance, a value indicative of a probability that the items include an item that agitates the user.

In one embodiment, the value indicative of the probability is calculated by comparing the stress level and the extent of discordance to corresponding thresholds. For example, when the stress level reaches at least a certain level and the discordance is at least a certain extent, that is indicative that there is at least a certain probability that that the items include an item that agitates the user. Optionally, calculating the probability involves utilizing a table that includes probability values for different combinations of thresholds (i.e., for different combinations of minimal stress levels and extents of discordance). Optionally, the table is generated based on observations of events in which the extent of stress of users was measured along with the extent of discordance based on their gaze, along with indications of whether the events involved a video that includes an item that agitated the viewer.

In another embodiment, the computer generates feature values based on the stress level and the extent of discordance and utilizes a machine learning-based model to calculate, based on the feature values, the probability that the items include an item that agitates the user. It is to be noted that this machine learning-based model is a different model than the one used in the embodiment described further above to detect the stress level. Optionally, the feature values include at least some features values indicative of the value of the stress level and/or the extent of discordance. Optionally, the feature values include at least one feature value indicative of a difference between the stress level and a baseline stress level of the user. Optionally, the feature values include at least one feature value that describes the video. For example, the at least one feature values may be indicative of what types of items are presented in the video. Optionally, the feature values include at least one feature value describing the user (e.g., the at least one feature value may be indicative of values such as the user's, the user's gender, the user's occupation, etc.) Optionally, the machine learning-based model is trained based on samples generated from previous events in which the extent of stress of users was measured along with the extent of discordance based on their gaze, along with indications of whether the events involved a video that includes an item that agitated the viewer.

When utilizing feature values along with a machine learning-based model, such as the model used to detect the stress level or the model used to calculate the value indicative of the probability that the items in the video include an item that agitates the user, in some embodiments, the feature values may include values based on additional inputs. In one example, the computer (i) receives one or more values indicative of at least one of the following parameters of the user: heart rate, heart rate variability, galvanic skin response, respiratory rate, and respiratory rate variability, and (ii) generates one or more of the feature values based on the one or more values. In another example, the computer (i) receives one or more values measured by at least one of the following sensors coupled to the user: a photoplethysmogram (PPG) sensor, an electrocardiogram (ECG) sensor, an electroencephalography (EEG) sensor, a galvanic skin response (GSR) sensor, and a thermistor, and (ii) generates one or more of the feature values based on the one or more values. In yet another example, the computer (i) receives one or more values indicative of whether the user touched at least one of the eyes, whether the user is engaged in physical activity, and/or an environmental parameter, and (ii) generates one or more of the feature values based on the one or more values. In still another example, the computer (i) receives one or more values measured by an accelerometer, a pedometer, a humidity sensor, a miniature radar, a miniature active electro-optics distance measurement device, an anemometer, an acoustic sensor, and/or a light meter, and (ii) generates one or more of the feature values based on the one or more values. And in another example, the computer (i) receives values indicative of at least one of the following properties describing the user age, gender, weight, height, health problems, mental health problems, occupation, education level, marital status, and (ii) generates one or more of the feature values based on the one or more values.

Figure 53:
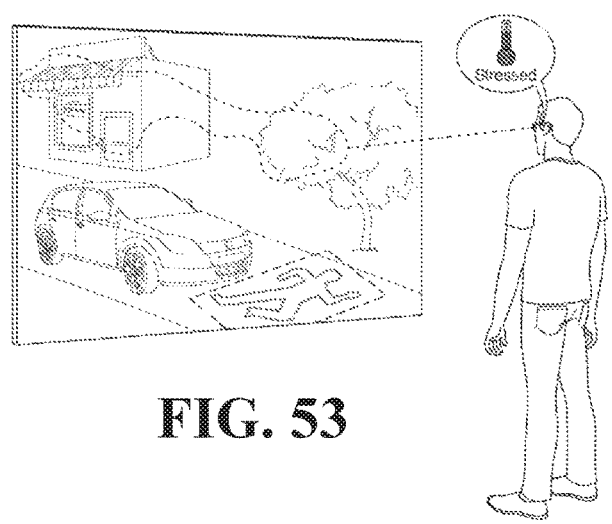
FIG. 53 illustrates a scenario that identifies that a user is agitated from viewing a video.

FIG. 53 illustrates a scenario in which an embodiment of a system described above is utilized to identify that a user is agitated (stressed) from viewing a video. In this scenario, a user is measured with CAMs coupled to a frame worn on the user's head while viewing an image of an accident scene. Eye tracking reveals that the user is avoiding a region that corresponds to the accident and the thermal measurements indicate an elevated stress level. Thus, the system may indicate that there is a high probability that the scene includes something that particularly agitates the user.

In one embodiment, a system configured to identify whether a visual content includes an item that agitates a user, includes: an eye tracker configured to track the user's gaze while watching a visual content depicting items; where the user's gaze is indicative of attention the user paid to the items; an inward-facing head-mounted thermal camera (CAM) configured to take thermal measurements of a region of interest on the face ($TH_{ROI}$) of the user, and a computer configured to: calculate stress levels based on $TH_{ROI}$, calculate an extent of discordance between the attention the user paid to the items and expected attention levels in the items, and determine, based on the stress level and the extent of discordance, whether at least one of the items agitated the user.

The following is a description of steps involved in one embodiment of a method for identifying when video includes an item that agitates a user. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method includes at least the following steps:

In Step 1, tracking the user's gaze while the user watches a video depicting items. Optionally, the user's gaze is indicative of attention the user paid to the items. Optionally, tracking the user's gaze is performed by an eye tracker.

In Step 2, taking thermal measurements of a region of interest on the face ($TH_{ROI}$) of the user, while the user watches the video, with an inward-facing head-mounted thermal camera.

In Step 3, calculating stress levels based on $TH_{ROI}$.

In Step 4, calculating an extent of discordance between the attention the user paid to the items and expected attention levels in the items.

And in Step 5, calculating, based on the stress level and the extent of discordance, a value indicative of a probability that the items include an item that agitates the user.

In one embodiment, the method may optionally include a step involving calculating the expected attention levels in the items utilizing a model of the user. Optionally, the model used in this step was trained based on previous tracking of the user's gaze when observing other videos. Additionally or alternatively, calculating the expected attention levels in the items using a saliency mapping algorithm.

In another embodiment the method may optionally include a step involving calculating, based on $TH_{ROI}$, stress levels corresponding to different times, and utilizing tracking of the user's gaze to assign stress levels to different items.

In yet another embodiment, the method may optionally include a step involving identifying that an item from among the items is a suspicious item based on the stress level reaching a first threshold and a difference between the attention the user paid to the item and the expected attention to the item reaching a second threshold.

Some aspects of this disclosure involve monitoring a user while performing his or her job in order to create a model of the user's typical behavior. This monitoring may involve determining the typical stress levels of the user and gaze patterns (e.g., what the user typically pays attention too when performing the usual activities on the job). When the user exhibits atypical behavior while performing a job, it may be an indication that something illicit and/or illegal is being performed. For example, a bank loan officer knowingly approving a faulty loan may exhibit higher stress levels while evaluating the loan forms and may also have a significantly different gaze pattern compared to when working on a usual loan application. In another example, a doctor examining a patient in order to assist in a faulty insurance claim may also be more stressed and/or have a different gaze pattern. In yet another example, a customs official "looking the other way" when an accomplice smuggles contraband is also expected to have elevated stress levels and a different gaze pattern than ordinarily observed on the job. When atypical behavior is detected, it can be noted in order to have the event to which it corresponds inspected more thoroughly by other parties (e.g., a supervisor).

Figures 54A, 54B:
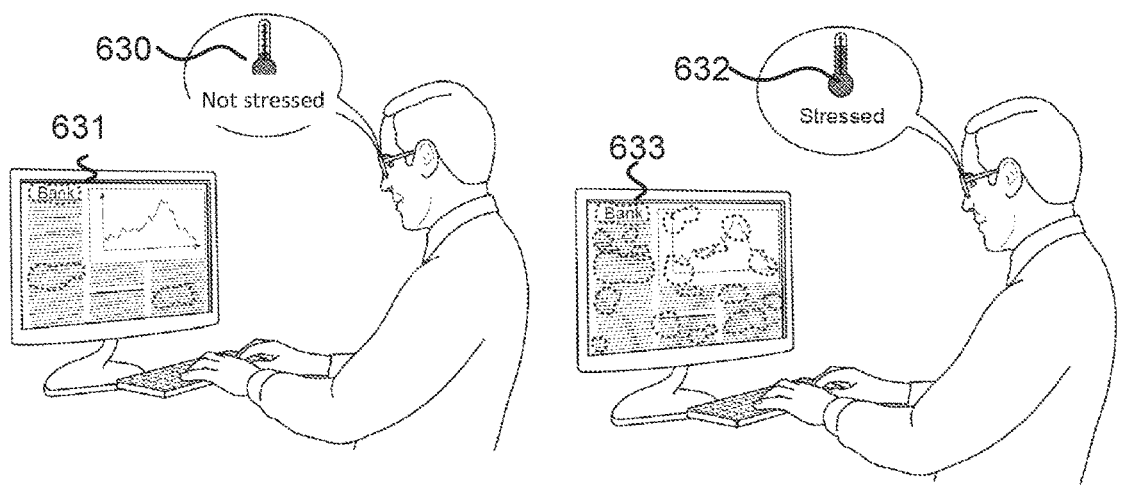
FIG. 54a and FIG. 54b illustrate scenarios in which stress levels and gaze patterns are utilized do detect atypical user behavior.

FIG. 54a and FIG. 54b illustrate a scenario in which stress levels and gaze patterns may be utilized do detect atypical user behavior. FIG. 54a illustrates a typical gaze pattern of the user shown as dashed-line closed-shapes on screen 631 (obtained using eye tracking), while the user performs his job at a computer terminal. Thermal measurements of the user 630 indicate that the user is not stressed. FIG. 54b illustrates an instance in which the user has an atypical gaze pattern shown as dashed-line closed-shapes on screen 633, and in addition, the thermal measurements of the user 632 indicate that the user is stressed. Embodiments of the system described below can identify the atypical gaze pattern and the user elevated stress level and generate an indication that the user is behaving atypically.

In one embodiment, a system configured to identify atypical behavior of a user includes an eye tracker, a CAM, and a computer. CAM takes thermal measurements of a region of interest ($TH_{ROI}$) on the user's face. Optionally, CAM is located less than 15 cm from the face. Optionally, the ROI is on a periorbital area. Optionally, the system also includes a head-mounted display (HMD), which displays video to the user. The system may optionally include a frame which is worn on the user's head, and one or more of the following components are physically coupled to the frame: the HMD, CAM, the eye tracker, and the computer.

The eye tracker tracks the user's gaze while viewing items. Optionally, the user's gaze is indicative of attention of the user in the items. Optionally, the user's gaze is indicative of attention the user paid to each of the items. In one embodiment, the user's gaze is tracked while the user performs some work related task, such as performing office work (e.g., if the user is a clerk) or examining a patient (e.g., if the user is a doctor). Optionally, the user's gaze is tracked while the user views video related to the task the user is performing. In one example, the video is presented via the HMD, which may be a virtual reality display or an augmented reality display.

In some embodiments, the computer generates features values and utilizes a model to identify, based on the feature values, whether the user's behavior while viewing the items was atypical. Optionally, the feature values include feature values generated based on $TH_{ROI}$ taken while the user viewed the items and a set of feature values generated based on tracking the user's gaze. Optionally, the feature values generated based on the eye tracking are indicative of the attention of the user in the items. Optionally, the feature values may include at least some feature values indicative of expected attention levels in the items.

In one embodiment, the system configured to identify atypical behavior includes a second inward-facing head-mounted thermal camera that takes measurements of a second region on the face ($TH_{ROI2}$). Optionally, the computer generates one or more of the feature values used to detect the atypical behavior based on $TH_{ROI2}$. In one example, the second region is on the forehead. In another example, the second region is on the nose.

In another embodiment, the computer generates one or more of the feature values based on a difference between $TH_{ROI}$ and a baseline value determined based on a set of previous measurements taken by CAM. Optionally, most of the measurements belonging to the set were taken while the behavior of the user was not considered atypical according to the model.

In one embodiment, the model used to identify whether the user's behavior was atypical is generated based on previous tracking of the user's gaze while viewing other items and previous $TH_{ROI}$ taken during the viewing of the other items. Optionally, the user's behavior during most of the viewing of the other items was typical (i.e., it was not considered atypical). Optionally, the viewing of the previous items was done while the user was performing a similar activity to one performed by the user while $TH_{ROI}$ were taken. Optionally, the previous $TH_{ROI}$ were taken on different days. Optionally, the previous $TH_{ROI}$ were taken in different situations that include first $TH_{ROI}$ taken at most one hour before having a meal and second $TH_{ROI}$ taken at most one hour after having a meal. Optionally, the model is trained based on training samples, with each training sample corresponding to an event in which the user was monitored with the eye tracker and CAM, and each training sample comprising feature values generated based on a tracking of the user's gaze and $TH_{ROI}$ taken during the event.

In one embodiment, the model is indicative of a probability density function (pdf) of values derived from $TH_{ROI}$ and/or values derived from tracking the gaze of the user. For example, the model may be a regression model (e.g., a maximum entropy model) generated based on the training samples described above. Optionally, if the value calculated by the computer represents a probability that is below a threshold, the behavior of the user is considered atypical.

In another embodiment, the model describes one or more thresholds derived from $TH_{ROI}$ and/or values derived from tracking the gaze of the user. For example, the model may include typical ranges for $TH_{ROI}$, which are indicative of typical stress levels, and/or typical gaze patterns of the user, which are indicative of how much attention the user pays to different items. Optionally, if the user exhibits behavior that does not correspond to values in the ranges that appear in the model, that is indicative that the user's behavior while viewing the items was atypical.

The computer may calculate, based on $TH_{ROI}$ a value describing a stress level of the user. Additionally or alternatively, the computer may calculate an extent of discordance between the attention the user paid to the items and expected attention levels in the items. Optionally, the stress level and/or the extent of discordance are utilized by the computer to identify whether the user's behavior while viewing the items was atypical. For example, one or more of the feature values may be generated based on the stress level and/or one or more of the feature values may be generated based on the extent of the discordance.

In some embodiments, when the user's behavior while viewing the items was atypical, a stress level of the user during the viewing, which is calculated based on $TH_{ROI}$, reaches a threshold. The stress levels of the user during most of the time spent viewing the other items, as calculated based on the previous $TH_{ROI}$, do not reach the threshold. As discussed in more detail further above, there are various ways in which the computer may detect the stress level based on $TH_{ROI}$. In one embodiment, the stress level is calculated by comparing one or more values derived from $TH_{ROI}$ to a certain threshold, and determining whether the threshold is reached (which is indicative of an occurrence of at least a certain amount of stress). Optionally, the certain threshold is determined based on thermal measurements of the user (e.g., thermal measurements taken when the user was stressed). In another embodiment, the stress level is calculated by generating certain feature values based on $TH_{ROI}$ and utilizing a certain machine learning-based model to calculate, based on the certain feature values, the stress level experienced by the user.

In some embodiments, when the user's behavior while viewing the items was atypical, a divergence between the attention of the user in the items and expected attention of the user in the items is above a certain value. During most of the time spent viewing of the other items, divergences between the attention of the user in the other items and expected attention of the user in the other items were below the threshold. As discussed in more detail above, expected attention levels may be obtained in various ways. In one example, the expected attention levels in the other items are calculated utilizing a certain model of the user, which is trained based on previous tracking of the user's gaze. In another example, the expected attention levels in the other items are calculated utilizing a certain model that is trained based on tracking of other users' gaze. In yet another example, the expected attention levels in the other items are calculated using a saliency mapping algorithm.

When utilizing feature values along with a model, such as the certain model used to detect the stress level and/or the model used to identify whether the user's behavior was atypical, in some embodiments, the feature values may include values based on additional inputs (beyond $TH_{ROI}$), which are also utilized to detect the stress level. In one example, the computer (i) receives one or more values indicative of at least one of the following parameters of the user: heart rate, heart rate variability, galvanic skin response, respiratory rate, and respiratory rate variability, and (ii) generates one or more of the feature values based on the one or more values. In another example, the computer (i) receives one or more values measured by at least one of the following sensors coupled to the user a photoplethysmogram (PPG) sensor, an electrocardiogram (ECG) sensor, an electroencephalography (EEG) sensor, a galvanic skin response (GSR) sensor, and a thermistor, and (ii) generates one or more of the feature values based on the one or more values. In yet another example, the computer (i) receives one or more values indicative of whether the user touched at least one of the eyes, whether the user is engaged in physical activity, and/or an environmental parameter, and (ii) generates one or more of the feature values based on the one or more values. In still another example, the computer (i) receives one or more values measured by an accelerometer, a pedometer, a humidity sensor, a miniature radar, a miniature active electro-optics distance measurement device, an anemometer, an acoustic sensor, and/or a light meter, and (ii) generates one or more of the feature values based on the one or more values. And in another example, the computer (i) receives values indicative of at least one of the following properties describing the user: age, gender, weight, height, health problems, mental health problems, occupation, education level, marital status, and (ii) generates one or more of the feature values based on the one or more values.

The following is a description of steps involved in one embodiment of a method for identifying atypical behavior. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method includes at least the following steps:

In Step 1, tracking the user's gaze while the user views items. Optionally, the user's gaze is indicative of attention the user paid to the items. Optionally, tracking the user's gaze is performed by the eye tracker described above.

In Step 2, taking thermal measurements of a region of interest ($TH_{ROI}$) on the user's face, while the user views the items, with an inward-facing head-mounted thermal camera.

In Step 3, generating feature values. Optionally, the generated feature values include feature values generated based on $TH_{ROI}$ and feature values based on the tracking in Step 1.

And in Step 4, utilizing a model to identify, based on the feature values generated in Step 3, whether the user's behavior, while viewing the items, was atypical. Optionally, the model was trained based on previous tracking of the user's gaze while viewing other items and previous $TH_{ROI}$ taken during the viewing of the other items.

In one embodiment, the method may optionally involve a step of calculating expected attention of the user in the items and generating at least some of the feature values based on the expected attention of the user in the items. Optionally, the user's gaze is indicative of attention of the user in the items, and when the user's behavior while viewing the items is atypical, a divergence between the attention of the user in the items and the expected attention of the user in the items is above a certain value.

In one embodiment, the method may optionally include steps that involve: taking, using a second inward-facing head-mounted thermal camera, additional thermal measurements of a region on the forehead, and generating one or more of the feature values used in Step 4, based on the additional thermal measurements.

In another embodiment, the method may optionally include steps that involve: taking, using a second inward-facing head-mounted thermal camera, additional thermal measurements of a region on the nose, and generating one or more of the feature values used in Step 4, based on the additional thermal measurements.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

FIG. 20a is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 20b is a schematic illustration of a camera that is able to change the relative tilt between its lens and sensor planes according to the Scheimpflug principle. Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, an HMS device includes a frame configured to be worn on a user's head, and an inward-facing camera physically coupled to the frame. The inward-facing camera may assume one of two configurations: (i) the inward-facing camera is oriented such that the optical axis of the camera is above the Frankfort horizontal plane and pointed upward to capture an image of a region of interest (ROI) above the user's eyes, or (ii) the inward-facing camera is oriented such that the optical axis is below the Frankfort horizontal plane and pointed downward to capture an image of an ROI below the user's eyes. The inward-facing camera includes a sensor and a lens. The sensor plane is tilted by more than 2° relative to the lens plane according to the Scheimpflug principle in order to capture a sharper image.

In another embodiment, an HMS includes an inward-facing head-mounted camera that captures an image of an ROI on a user's face, when worn on the user's head. The ROI is on the user's forehead, nose, upper lip, cheek, and/or lips. The camera includes a sensor and a lens. And the sensor plane is tilted by more than 2° relative to the lens plane according to the Scheimpflug principle in order to capture a sharper image.

Because the face is not planar and the inward-facing head-mounted camera is located close to the face, an image captured by a camera having a wide field of view (FOV) and a low f-number may not be perfectly sharp, even after applying the Scheimpflug principle. Therefore, in some embodiments, the tilt between the lens plane and the sensor plane is selected such as to adjust the sharpness of the various areas covered in the ROI according to their importance for detecting the user's physiological response (which may be the user's emotional response in some cases). In one embodiment, the ROI covers first and second areas, where the first area includes finer details and/or is more important for detecting the physiological response than the second area. Therefore, the tilt between the lens and sensor planes is adjusted such that the image of the first area is shaper than the image of the second area.

In another embodiment, the ROI covers both a first area on the upper lip and a second area on a cheek, and the tilt is adjusted such that the image of the first area is shaper than the image of the second area, possibly because the upper lip usually provides more information and has more details relative to the cheek.

In still another embodiment, the ROI covers both a first area on the upper lip and a second area on the nose, and the tilt is adjusted such that the image of the first area is shaper than the image of the second area, possibly because the upper lip usually provides more information relative to the nose.

In still another embodiment, the ROI covers a first area on the cheek straight above the upper lip, a second area on the cheek from the edge of the upper lip towards the ear, and a third area on the nose. And the tilt between the lens plane and the sensor plane is adjusted such that the image of the first area is shaper than both the images of the second and third areas.

In still another embodiment, the ROI covers both a first area on the lips and a second area on the chin, and the tilt is adjusted such that the image of the first area is shaper than the image of the second area, possibly because the lips usually provides more information than the chin.

In still another embodiment, the camera is a visible-light camera, and the ROI covers both a first area on the lower forehead (including an eyebrow) and a second area on the upper forehead, and the tilt is adjusted such that the image of the first area is shaper than the image of the second area, possibly because the eyebrow provides more information about the user's emotional response than the upper forehead.

In still another embodiment, the camera is a thermal camera, and the ROI covers an area on the forehead, and the tilt is adjusted such that the image of a portion of the middle and upper part of the forehead (below the hair line) is shaper than the image of a portion of the lower part of the forehead, possibly because the middle and upper parts of the forehead are more indicative of prefrontal cortex activity than the lower part of the forehead, and movements of the eyebrows disturb the thermal measurements of the lower part of the forehead.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt between the lens and sensor planes according to the Scheimpflug principle based on the orientation between the camera and the ROI when the frame is worn by the user. The tilt may be achieved using at least one motor, such as a brushless DC motor, a stepper motor (without a feedback sensor), a brushed DC electric motor, a piezoelectric motor, and/or a micro-motion motor.

The adjustable electromechanical tilting mechanism configured to change the tilt between the lens and sensor planes may include one or more of the following mechanisms: (i) a mirror that changes its angle: (ii) a device that changes the angle of the lens relative to the sensor, and/or (iii) a device that changes the angle of the sensor relative to the lens. In one embodiment, the camera, including the adjustable electromechanical tilting mechanism, weighs less than 10 g, and the adjustable electromechanical tilting mechanism is able to change the tilt in a limited range below 30° between the two utmost orientations between the lens and sensor planes. Optionally, the adjustable electromechanical tilting mechanism is able to change the tilt in a limited range below 20° between the two utmost orientations between the lens and sensor planes. In another embodiment, the adjustable electromechanical tilting mechanism is able to change the tilt in a limited range below 10°. In some embodiments, being able to change the tilt in a limited range reduces at least one of the weight, cost, and size of the camera, which is advantageous for a wearable device. In one example, the camera is manufactured with a fixed predetermined tilt between the lens and sensor planes, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt between the lens and sensor planes for the specific user who wears the frame and has facial dimensions that are different from the average user.

Various types of cameras may be utilized in different embodiments described herein. In one embodiment, the camera is a thermal camera that takes thermal measurements of the ROI with a focal plane array thermal sensor having an angle above 2° between the lens and sensor planes. Optionally, the thermal camera weighs below 10 g, is located less than 10 cm from the user's face, and the tilt of the lens plane relative to the sensor plane is fixed. The fixed tilt is selected according to an expected orientation between the camera and the ROI when the user wears the frame. Optionally, the system includes a computer to detect a physiological response based on the thermal measurements. Optionally, the computer processes time series measurements of each sensing element individually to detect the physiological response.

In another embodiment, the camera is a visible-light camera that takes visible-light images of the ROI, and a computer generates an avatar for the user based on the visible-light images. Some of the various approaches that may be utilized to generate the avatar based on the visible-light images are described in co-pending US patent publication 2016/0360970. Additionally or alternatively, the computer may detect an emotional response of the user based on (i) facial expressions in the visible-light images utilizing image processing, and/or (ii) facial skin color changes (FSCC), which result from concentration changes of hemoglobin and/or oxygenation.

It is to be noted that there are various approaches known in the art for identifying facial expressions from images. While many of these approaches were originally designed for full-face frontal images, those skilled in the art will recognize that algorithms designed for full-face frontal images may be easily adapted to be used with images obtained using the inward-facing head-mounted visible-light cameras disclosed herein. For example, the various machine learning techniques described in prior art references may be applied to feature values extracted from images that include portions of the face from orientations that are not directly in front of the user. Furthermore, due to the closeness of the visible-light cameras to the face, facial features are typically larger in images obtained by the systems described herein. Moreover, challenges such as image registration and face tracking are vastly simplified and possibly non-existent when using inward-facing head-mounted cameras. The reference Zeng, Zhihong, et al. "A survey of affect recognition methods: Audio, visual, and spontaneous expressions." IEEE transactions on pattern analysis and machine intelligence 31.1 (2009): 39-58, describes some of the algorithmic approaches that may be used for this task. The following references discuss detection of emotional responses based on FSCC: (i) Ramirez, Geovany A., et al. "Color analysis of facial skin: Detection of emotional state" in Proceedings of the IEEE Conference on Computer Vision and Pattern Recognition Workshops, 2014; and (ii) Wang. Su-Jing, et al. "Micro-expression recognition using color spaces", in IEEE Transactions on Image Processing 24.12 (2015): 6034-6047.

In still another embodiment, the camera is a light field camera that implements a predetermined blurring at a certain Scheimpflug angle, and decodes the predetermined blurring as function of the certain Scheimpflug angle. The light field camera may include an autofocusing of the image obtained using the tilting mechanism based on the principle that scene points that are not in focus are blurred while scene points in focus are sharp. The autofocusing may study a small region around a given pixel; the region is expected to get sharper as the Scheimpflug adjustment gets better, and vice versa. Additionally or alternatively, the autofocusing may use the variance of the neighborhood around each pixel as a measure of sharpness, where a proper Scheimpflug adjustment should increase the variance.

Figure 55A:
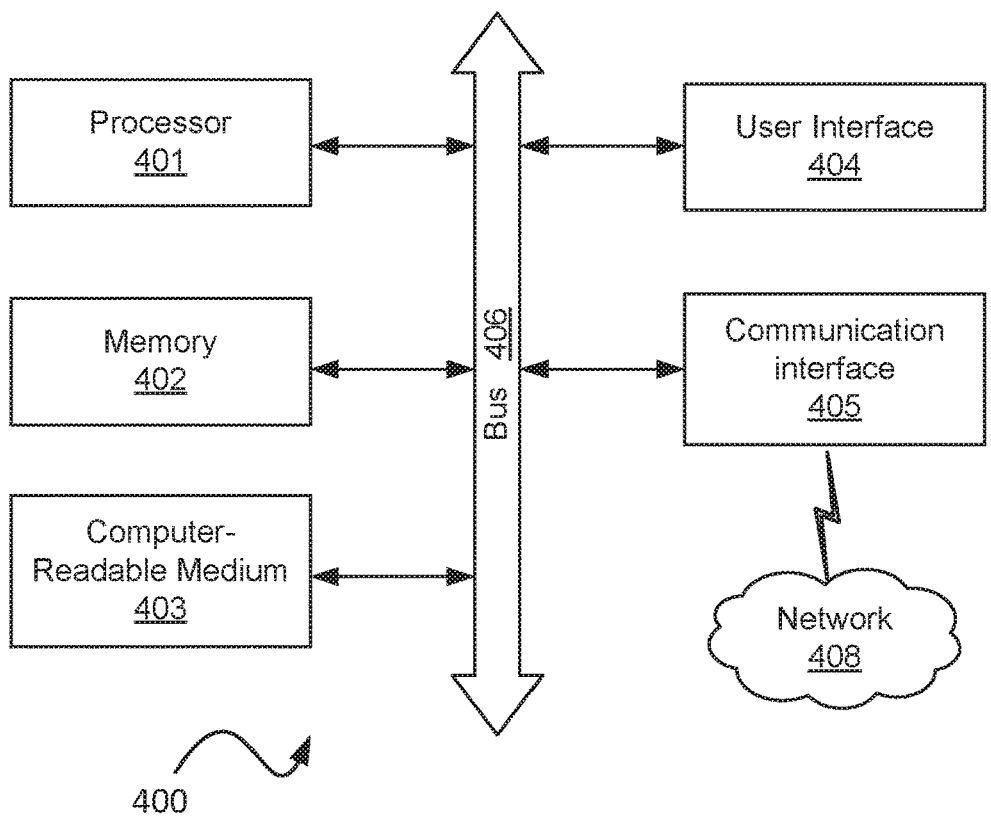
FIG. 55a and FIG. 55b are schematic illustrations of possible embodiments for computers.
Figure 55B:
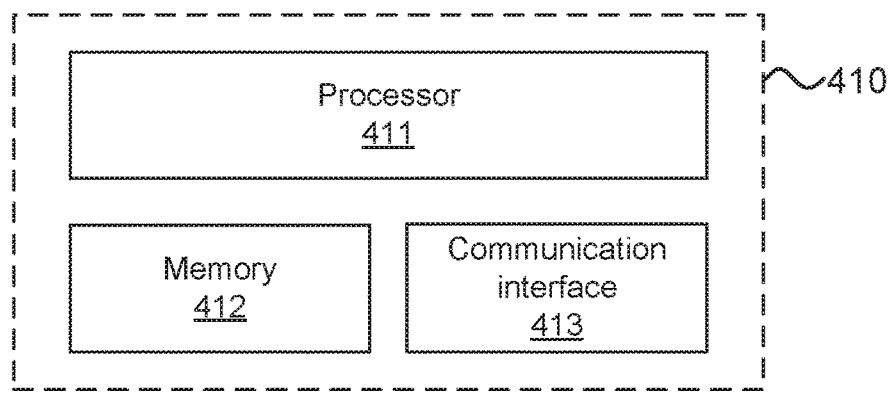

FIG. 55a and FIG. 55b are schematic illustrations of possible embodiments for computers (400, 410) that are able to realize one or more of the embodiments discussed herein that include a "computer". The computer (400, 410) may be implemented in various ways, such as, but not limited to, a server, a client, a personal computer, a network device, a handheld device (e.g., a smartphone), an HMS (such as smart glasses, an augmented reality system, and/or a virtual reality system), a computing device embedded in a wearable device (e.g., a smartwatch or a computer embedded in clothing), a computing device implanted in the human body, and/or any other computer form capable of executing a set of computer instructions. Herein, an augmented reality system refers also to a mixed reality system. Further, references to a computer or processor include any collection of one or more computers and/or processors (which may be at different locations) that individually or jointly execute one or more sets of computer instructions. For example, a first computer may be embedded in the HMS that communicates with a second computer embedded in the user's smartphone that communicates over the Internet with a cloud computer.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Thermal measurements that are forwarded to a processor/computer may include "raw" values that are essentially the same as the values measured by thermal cameras, and/or processed values that are the result of applying some form of preprocessing and/or analysis to the raw values. Examples of methods that may be used to process the raw values include analog signal processing, digital signal processing, and various forms of normalization, noise cancellation, and/or feature extraction.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

Herein, a direction of the optical axis of a VCAM or a CAM that has focusing optics is determined by the focusing optics, while the direction of the optical axis of a CAM without focusing optics (such as a single pixel thermopile) is determined by the angle of maximum responsivity of its sensor. When optics are utilized to take measurements with a CAM, then the term CAM includes the optics (e.g., one or more lenses). In some embodiments, the optics of a CAM may include one or more lenses made of a material suitable for the required wavelength, such as one or more of the following materials: Calcium Fluoride. Gallium Arsenide, Germanium, Potassium Bromide. Sapphire, Silicon. Sodium Chloride, and Zinc Sulfide. In other embodiments, the CAM optics may include one or more diffractive optical elements, and/or or a combination of one or more diffractive optical elements and one or more refractive optical elements.

When CAM includes an optical limiter/field limiter/FOV limiter (such as a thermopile sensor inside a standard TO-39 package with a window, or a thermopile sensor with a polished metal field limiter), then the term CAM may also refer to the optical limiter. Depending on the context, the term CAM may also refer to a readout circuit adjacent to CAM, and/or to the housing that holds CAM.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence in the form of "calculating based on $TH_{ROI}$" may be interpreted as "calculating based on the values of $TH_{ROI}$", and a sentence in the form of "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (usually denoted $TH_{ROI}$ or using a similar notation) may have various forms, such as time series, measurements taken according to a varying sampling frequency, and/or measurements taken at irregular intervals. In some embodiments, thermal measurements may include various statistics of the temperature measurements (T) and/or the changes to temperature measurements ($\Delta T$), such as minimum, maximum, and/or average values. Thermal measurements may be raw and/or processed values. When a thermal camera has multiple sensing elements (pixels), the thermal measurements may include values corresponding to each of the pixels, and/or include values representing processing of the values of the pixels. The thermal measurements may be normalized, such as normalized with respect to a baseline (which is based on earlier thermal measurements), time of day, day in the month, type of activity being conducted by the user, and/or various environmental parameters (e.g., the environment's temperature, humidity, radiation level, etc.).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.10% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

Sentences in the form of "angle greater than 20°" refer to absolute values (which may be +20° or −20° in this example), unless specifically indicated, such as in a phrase having the form of "the optical axis of CAM is 200 above/below the Frankfort horizontal plane" where it is clearly indicated that the CAM is pointed upwards/downwards. The Frankfort horizontal plane is created by two lines from the superior aspects of the right/left external auditory canal to the most inferior point of the right/left orbital rims.

The terms "comprises." "comprising," "includes." "including," "has," "having", or any other variation thereof, indicate an open-ended claim language that does not exclude additional limitations. The "a" or "an" is employed to describe one or more, and the singular also includes the plural unless it is obvious that it is meant otherwise; for example, sentences in the form of "a CAM configured to take thermal measurements of a region ($TH_{ROI}$)" refers to one or more CAMs that take thermal measurements of one or more regions, including one CAM that takes thermal measurements of multiple regions; as another example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first". "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. An athletic coaching system, comprising:
at least one inward-facing head-mounted thermal camera (CAM) configured to take thermal measurements of a region below the nostrils ($TH_{RBN}$) of a user; wherein $TH_{RBN}$ are indicative of an exhale stream of the user; and
a computer configured to:
receive measurements of movements ($M_{move}$) involving the user;
generate, based on $TH_{RBN}$ and $M_{move}$ a coaching indication; and
present, via a user interface, the coaching indication to the user.

2. The athletic coaching system of claim 1, further comprising a frame configured to be worn on the user's head; wherein each CAM, from among the at least one CAM, is physically coupled to the frame and weighs below 10 g; and wherein the frame is further configured to hold each CAM, from among the at least one CAM, less than 15 cm from the user's face and above the user's upper lip.

3. The athletic coaching system of claim 1, further comprising a frame configured to be worn on the user's head; wherein the at least one CAM comprises at least first and second inward-facing head-mounted thermal cameras (CAM1 and CAM2, respectively) that are physically coupled to the right and left sides of the frame, respectively, at a distance that is less than 15 cm from the user's face.

4. The athletic coaching system of claim 1, further comprising an in-the-ear earbud comprising a microphone configured to measure sounds inside an ear canal ($M_{ear}$) of the user; wherein the computer is further configured to generate the coaching indication also based on $M_{ear}$ (in addition to $TH_{RBN}$ and $M_{move}$).

5. The athletic coaching system of claim 1, wherein the coaching indication is indicative of a change the user should make to one or more of the following: cadence of movements, stride length, breathing rate, breathing type (mouth or nasal), and duration of exhales.

6. The athletic coaching system of claim 5, wherein the computer is further configured to calculate the breathing rate of the user based on $TH_{RBN}$, and to perform at least one of the following: (i) responsive to the breathing rate being below a first threshold, to include in the coaching indication an instruction to increase the breathing rate, and (ii) responsive to the breathing rate being above a second threshold, to include in the coaching indication an instruction to decrease the breathing rate.

7. The athletic coaching system of claim 5, wherein the computer is further configured to calculate the cadence of the user based on $M_{move}$, and to perform at least one of the following: (i) responsive to the cadence being below a first threshold, to include in the coaching indication an instruction to increase the cadence, and (ii) responsive to the cadence being above a second threshold, to include in the coaching indication an instruction to decrease the cadence.

8. The athletic coaching system of claim 5, wherein the computer is further configured to calculate a value indicative of exhale durations of the user based on $TH_{RBN}$, and to include in the coaching indication an instruction to increase the exhale durations responsive to determining that the exhale durations are below a threshold.

9. The athletic coaching system of claim 5, wherein the computer is further configured to generate feature values based on data comprising $TH_{RBN}$ and $M_{move}$, and to utilize a model to calculate, based on the feature values, a value indicative of whether the change is needed.

10. The athletic coaching system of claim 1, wherein the computer is further configured to calculate a target breathing rate based on data comprising at least one of $TH_{RBN}$ and $M_{move}$, and to include in the coaching indication breathing cues that correspond to the target breathing rate.

11. The athletic coaching system of claim 10, wherein the computer is further configured to receive a value indicative of a heart rate (HR) of the user, and to calculate the target breathing rate based on HR (in addition to at least one of $TH_{RBN}$ and $M_{move}$).

12. The athletic coaching system of claim 10, wherein the computer is further configured to calculate a current breathing rate based on $TH_{RBN}$, and to calculate first and second thresholds; wherein the first threshold is below the target breathing rate and second threshold is above the target breathing rate, and responsive to the current breathing rate being below the first threshold or above the second threshold, the computer instructs the user interface to start providing the breathing cues or to increase intensity of provided breathing cues.

13. The athletic coaching system of claim 10, wherein the breathing cues comprise auditory cues that have a frequency that corresponds to the target breathing rate.

14. The athletic coaching system of claim 1, wherein the coaching indication is indicative of synchronization of a breathing pattern of the user with a sequence of movements of the user.

15. The athletic coaching system of claim 14, wherein sequence of movements of the user corresponds to a pressing motion of weights or a barbell, and the coaching indication indicates to inhale in the concentric phase of the press and exhale in the eccentric phase of the press.

16. The athletic coaching system of claim 14, wherein sequence of movements of the user corresponds to swinging a racket in order to hit a ball with the racket, and the coaching indication indicates to exhale while hitting the ball.

17. The athletic coaching system of claim 14, wherein sequence of movements of the user corresponds to making a drive shot in golf, and the coaching indication indicates to: exhale at address, inhale during the backswing, and exhale again on the downswing.

18. The athletic coaching system of claim 14, wherein the computer is further configured to determine whether the user did not breathe in an appropriate pattern while performing the certain movement sequence; and wherein responsive to determining that the user did not breathe in the appropriate pattern, the computer is further configured to notify the user thereof via a user interface.

19. The athletic coaching system of claim 14, wherein the computer is further configured to generate feature values based on $TH_{RBN}$ and $M_{move}$ and to utilize a model to calculate, based on the feature values, a value indicative of whether the breathing pattern was synchronized with the sequence of movements; wherein the model was trained based on data comprising: a first set of previous $TH_{RBN}$ and $M_{move}$ of one or more users, taken while performing the sequence of movements and breathing in a pattern that is synchronized with the sequence of movements, and a second set of previous $TH_{RBN}$ and $M_{move}$ of the one or more users while performing the sequence of movements and breathing in a pattern that is not synchronized with the sequence of movements.

20. The athletic coaching system of claim 14, wherein $M_{move}$ comprise values acquired with at least one of an accelerometer and a gyroscope, which are disposed in an object carried by the user or a garment worn by the user.

\* \* \* \* \*